United States Patent
Petluri et al.

(10) Patent No.: US 12,225,650 B2
(45) Date of Patent: Feb. 11, 2025

(54) DYNAMIC DISPLAY LIGHTING SYSTEMS WITH BIOACTIVE LIGHTING

(71) Applicant: KORRUS, INC., Los Angeles, CA (US)

(72) Inventors: Raghuram L. V. Petluri, Los Angeles, CA (US); Paul Kenneth Pickard, Los Angeles, CA (US)

(73) Assignee: KORRUS, INC., Los Angeles, CA (US)

(*) Notice: Subject to any disclaimer, the term of this patent is extended or adjusted under 35 U.S.C. 154(b) by 46 days.

(21) Appl. No.: 17/738,562

(22) Filed: May 6, 2022

(65) Prior Publication Data

US 2022/0272820 A1 Aug. 25, 2022

Related U.S. Application Data

(63) Continuation of application No. PCT/US2020/059701, filed on Nov. 9, 2020.
(Continued)

(51) Int. Cl.
*H05B 47/17* (2020.01)
*H05B 45/20* (2020.01)
*H05B 47/195* (2020.01)

(52) U.S. Cl.
CPC .......... *H05B 47/17* (2020.01); *H05B 45/20* (2020.01); *H05B 47/195* (2020.01)

(58) Field of Classification Search
CPC ...... H05B 47/17; H05B 45/20; H05B 47/195; A61N 5/0618; A61N 2005/0626; A61N 2005/0642; A61N 2005/0648; A61N 2005/0651; A61N 2005/0659; A61N 2005/0663; A61M 2021/0027; A61M 2021/0044; A61M 2205/3303; A61M 2205/3306; A61M 2205/332; A61M 2205/3358; A61M 2205/3368;
(Continued)

(56) References Cited

U.S. PATENT DOCUMENTS 6,350,275 B1 2/2002 Vreman
9,532,434 B2 12/2016 Keith
(Continued)

FOREIGN PATENT DOCUMENTS

WO 2019139637 7/2019
WO 2019140306 7/2019
(Continued)

OTHER PUBLICATIONS

Alkozei, A. et al., "Acute exposure to blue wavelength light during memory consolidation improces verbal memory performance," PLOS One, Sep. 2017, 11 pages.
(Continued)

*Primary Examiner* — Daniel D Chang
(74) *Attorney, Agent, or Firm* — FisherBroyles LLP

(57) ABSTRACT

A display system for displaying digital content includes one or more LED-based lighting channels adapted to generate a first light output in a first operational mode at a first circadian stimulating energy (CSE), and a second light output in a second operational mode, the second light output associated with a second CSE, and a long red near infrared energy (LRNE) output in a third operating mode.

15 Claims, 47 Drawing Sheets

Related U.S. Application Data

(60) Provisional application No. 62/933,283, filed on Nov. 8, 2019, provisional application No. 62/933,267, filed on Nov. 8, 2019, provisional application No. 62/933,237, filed on Nov. 8, 2019, provisional application No. 62/933,224, filed on Nov. 8, 2019, provisional application No. 62/933,245, filed on Nov. 8, 2019.

(58) Field of Classification Search
CPC .. A61M 2205/3375; A61M 2205/3553; A61M 2205/3584; A61M 2205/3592; A61M 2205/505; A61M 2205/80; A61M 2205/8206; A61M 2209/088; A61M 2230/06; A61M 2230/205; A61M 2230/30; A61M 2230/42; A61M 2230/50; A61M 2230/63; A61M 2230/65; A61M 21/00; A61M 21/02
See application file for complete search history.

(56) References Cited

U.S. PATENT DOCUMENTS

| | | |
|---|---|---|
| 9,719,660 B1 | 8/2017 | Petluri |
| 2013/0140988 A1* | 6/2013 | Maxik .................. A61N 5/0618 315/294 |
| 2014/0303547 A1 | 10/2014 | Loupis |
| 2015/0234108 A1 | 8/2015 | Harley, Jr. |
| 2018/0132329 A1 | 5/2018 | Yan |

FOREIGN PATENT DOCUMENTS

| | | | |
|---|---|---|---|
| WO | 2019140309 | 7/2019 | |
| WO | 2019140327 | 7/2019 | |
| WO | WO-2019140327 A2 * | 7/2019 | ........... G09G 3/2003 |

OTHER PUBLICATIONS

Arjmandi, N., et al. (2018). "Can Light Emitted from Smartphone Screens and Taking Selfies Cause Premature Aging and Wrinkles?" Journal of Biomedical and Physical Engineering 8(4), 447-452.

Avci, P. et al. (2013). Low-level Laser (Light) Therapy (LLLT) in Skin: Stimulating, Healing, Restoring. Semin Cutan Medical Surgery (32)(1), 41-52.

Brassoliatti, P. et al. (2018). Photobiomodulation on Critical Bone Defects of Rat Calvaria: A Systematic Review. Lasers in Medical Science 33(9), 1841-1848.

Commission Internationale de l'Éclairage. 1995. Technical Report: Method of Measuring and Specifying Colour Rendering Properties of Light Sources, CIE No. 13.3-1995. Vienna, Austria: Commission Internationale de l'Éclairage, 22 pages.

Commonly-owned U.S. Appl. No. 62/712,191 filed Jul. 30, 2018, entitled "Switchable Systems for White Light with High Color Rendering and Biological Effects," 94pp.

Commonly-owned U.S. Appl. No. 62/757,664, filed Nov. 8, 2018, entitled "Two-Channel Tunable Lighting Systems With Controllable Equivalent Melanopic Lux and Correlated Color Temperature Outputs," 103pp.

Commonly-owned U.S. Appl. No. 62/757,672, filed Nov. 8, 2018, entitled "Switchable Systems for White Light With High Color Rendering and Biological Effects", 150pp.

Figueiro et al.; "Designing with Circadian Stimulus"; Illuminating Engineering Society; Oct. 2016; p. 31-34.

Gupta, A.K., Mays, et al. (2018). Efficacy of Non-Surgical Treatments for Androgenetic Alopecia: A Systematic Review and Network Meta-Analysis. Journal of The European Academy of Dermatology and Venereology 32(12), 2112-2125.

Hamblin, M.R. (2017). Mechanisms and Applications of the Anti-Inflammatory Effects of Photobiomodulation. AIMS Biophysics 4(3), 337-361.

Hennessy, M., & Hamblin, M. (2017). Photobiomodulation and the Brain: A New Paradigm. Journal of Optics 19(1): 013003.

Hye Oh et al., "Healthy, natural, efficient and tunable lighting: four-package white LEDs for optimizing the circadian effect, color quality and vision performance," Light: Science & Applications 3.2 (2014); 23pp.

International Search Report mailed Mar. 30, 2021, in International Application No. PCT/US2020/059701, 4 pages.

Kwok-Fai, et al. (2014). Effects of Low Laser Treatment on the Survival of Axotomized Retinal Ganglion Cells in Adult Hamsters. Neural Regeneration Research 9(21), 1863-1869.

Lucas et al, "Measuring and using light in the melanopsin age," Trends in Neurosciences, Jan. 2014, vol. 37, No. 1, 9pp.

Olmo-Aguado, S.,et al. (2016). "Red Light of the Visual Spectrum Attenuates Cell Death in Culture and Retinal Ganglion Cell Death in Situ." Acta Ophthalmologica 94, e481-e49.

Rea et al., "Modelling the spectral sensitivity of the human circadian system," Lighting Research and Technology, 2011; 0: 1-12 (abstract only).

Stern, M. et al., "Blue light exposure decreases systolic blood pressure, arterial stiffness, and improves endothelial function in humans," European Journal of Preventative Cardiology, Sep. 2018, 9 pages.

Thapan et al. "An action spectrum for melatonin suppression: evidence for a novel non-rod, non-cone photoreceptor system in humans"; Journal of Physiology; vol. 535.1; 2001; p. 261-267.

Tosini, G., et al. (2016). "Effects of Blue Light on the Circadian System and Eye Physiology." Molecular Vision: Biology and Genetics in Vision Research 22, 61-72.

Vandersee, S., et al. (2015). "Blue-Violet Light Irradiation Dose Dependently Decreases Carotenoids in Human Skin, Which Indicates the Generation of Free Radicals." Oxidative Medicine and Cellular Longevity doi: 10.1155/2015/579675.

Written Opinion of the International Searching Authority mailed Mar. 30, 2021, in International Application No. PCT/US2020/059701, 10 pages.

\* cited by examiner

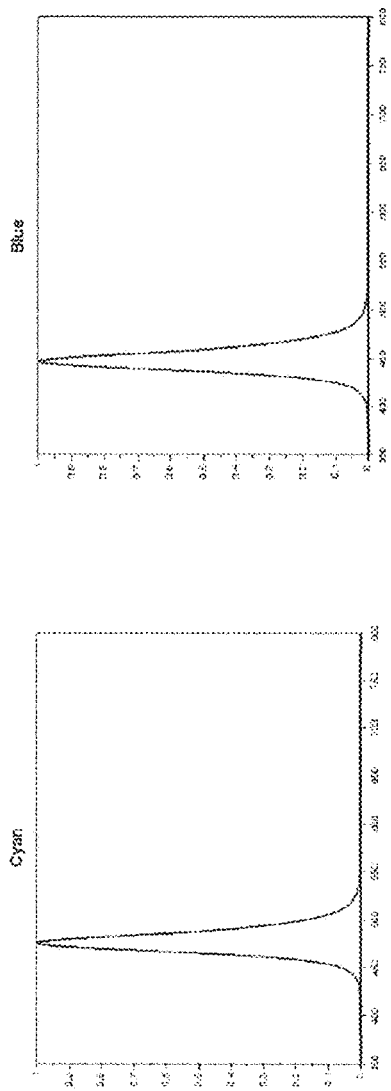
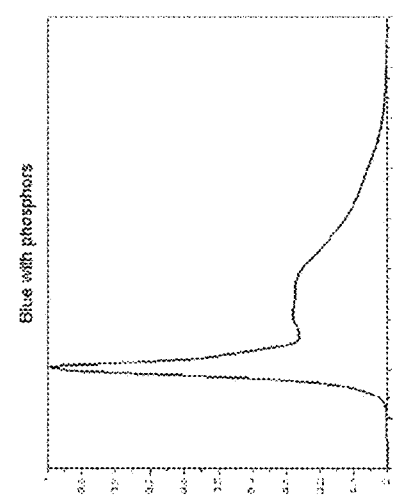
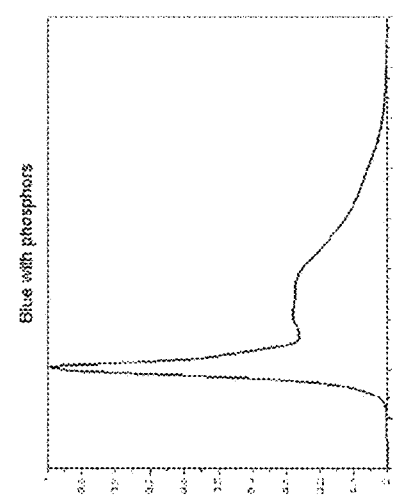
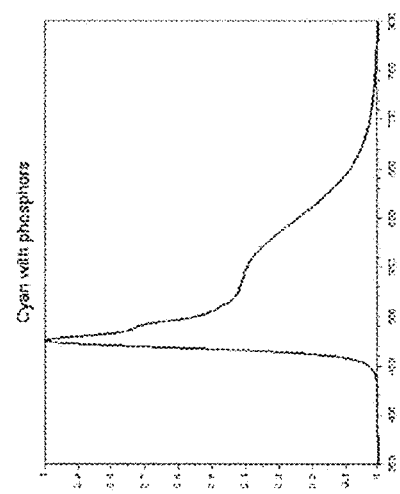
FIG. 3A
FIG. 3B
FIG. 3C
FIG. 3D

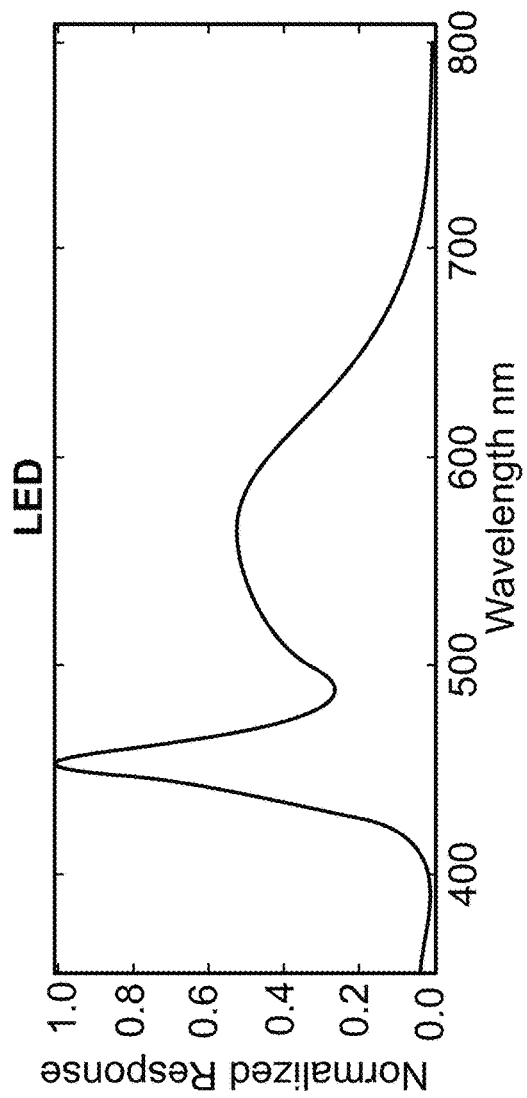
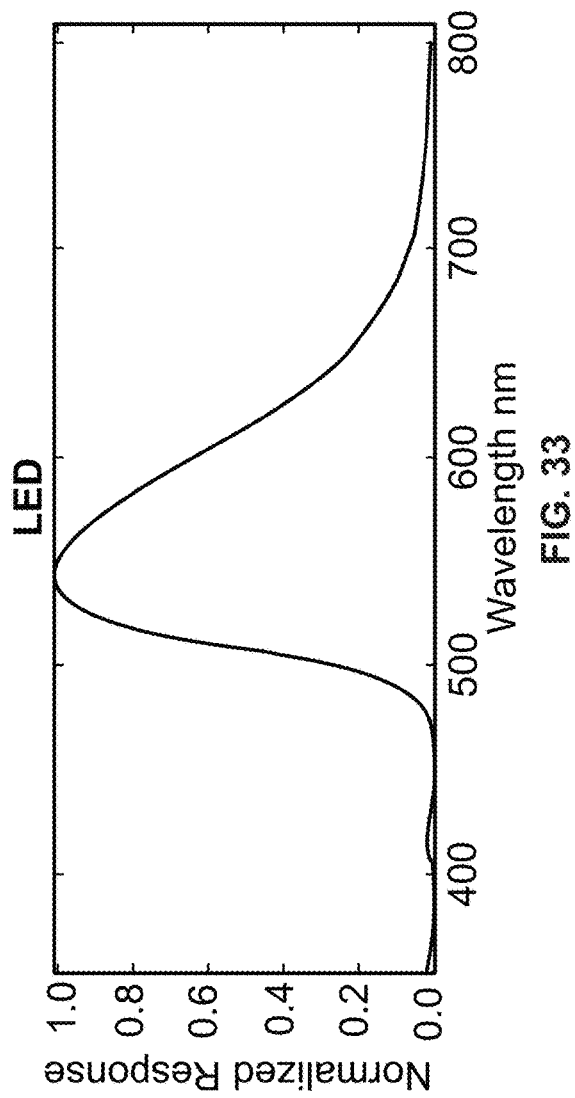

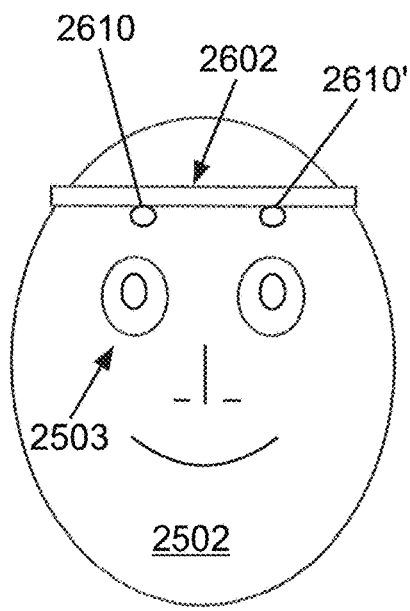
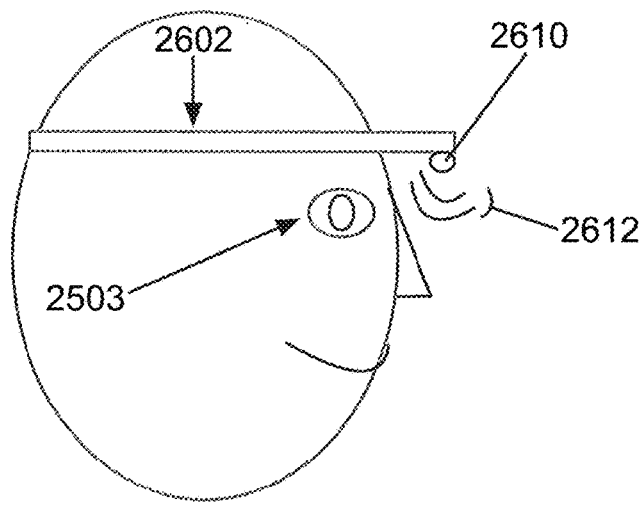
FIG. 48A  FIG. 48B
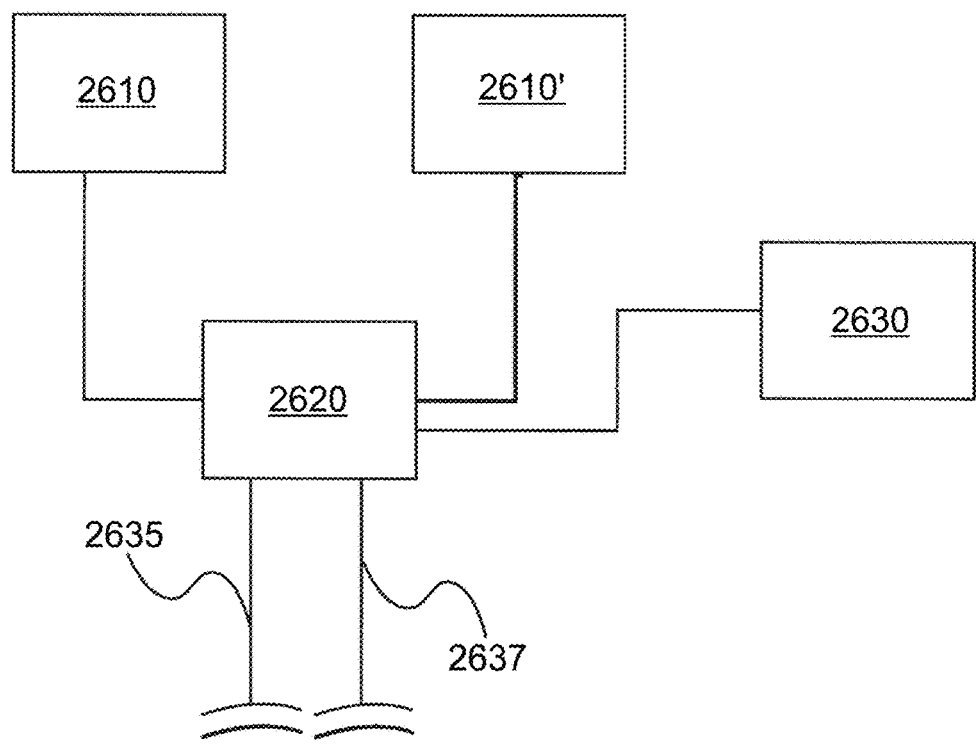
FIG. 49

DYNAMIC DISPLAY LIGHTING SYSTEMS WITH BIOACTIVE LIGHTING

CROSS REFERENCE TO RELATED APPLICATIONS

This application is a continuation of PCT/US2020/059701, filed Nov. 9, 2020, which claims the benefit of U.S. Provisional Patent Appl. No. 62/933,283, filed Nov. 8, 2019, U.S. Provisional Patent Appl. No. 62/933,224, filed Nov. 8, 2019, U.S. Provisional Patent Appl. No. 62/933,237, filed Nov. 8, 2019, U.S. Provisional Patent Appl. No. 62/933,245, filed Nov. 8, 2019 and U.S. Provisional Patent Appl. No. 62/933,267, filed Nov. 8, 2019, the entire disclosures of which are incorporated herein by reference.

FIELD OF THE DISCLOSURE

This disclosure is in the field bioactive digital display devices. In particular, the disclosure relates to devices for use in, and methods of, providing bioactive lighting systems for use in bioactive display systems that can provide controllable biological effects.

BACKGROUND

A wide variety of light emitting devices are known in the art including, for example, incandescent light bulbs, fluorescent lights, and semiconductor light emitting devices such as light emitting diodes ("LEDs").

Displays for digital content can rely on arrays of pixels that produce individual color points. Displays can be backlit with a white light source, which can be LED-based, and then filtered at the pixel-level to produce colored pixels as desired. Alternatively, displays that are not based on backlighting with white light and filtering downstream can include LEDs at the pixel-level that directly emit light at each colored pixel.

There are a variety of resources utilized to describe the light produced from a light emitting device, one commonly used resource is 1931 CIE (Commission Internationale de l'Éclairage) Chromaticity Diagram. The 1931 CIE Chromaticity Diagram maps out the human color perception in terms of two CIE parameters x and y. The spectral colors are distributed around the edge of the outlined space, which includes all of the hues perceived by the human eye. The boundary line represents maximum saturation for the spectral colors, and the interior portion represents less saturated colors including white light. The diagram also depicts the Planckian locus, also referred to as the black body locus (BBL), with correlated color temperatures, which represents the chromaticity coordinates (i.e., color points) that correspond to radiation from a black-body at different temperatures. Illuminants that produce light on or near the BBL can thus be described in terms of their correlated color temperatures (CCT). These illuminants yield pleasing "white light" to human observers, with general illumination typically utilizing CCT values between 1,800K and 10.000K.

Color rendering index (CRI) is described as an indication of the vibrancy of the color of light being produced by a light source. In practical terms, the CRI is a relative measure of the shift in surface color of an object when lit by a particular lamp as compared to a reference light source, typically either a black-body radiator or the daylight spectrum. The higher the CRI value for a particular light source, the better that the light source renders the colors of various objects it is used to illuminate.

Color rendering performance may be characterized via standard metrics known in the art. Fidelity Index (Rf) and the Gamut Index (Rg) can be calculated based on the color rendition of a light source for 99 color evaluation samples ("CES"). The 99 CES provide uniform color space coverage, are intended to be spectral sensitivity neutral, and provide color samples that correspond to a variety of real objects. Rf values range from 0 to 100 and indicate the fidelity with which a light source renders colors as compared with a reference illuminant. In practical terms, the Rf is a relative measure of the shift in surface color of an object when lit by a particular lamp as compared to a reference light source, typically either a black-body radiator or the daylight spectrum. The higher the Rf value for a particular light source, the better that the light source renders the colors of various objects it is used to illuminate. The Gamut Index Rg evaluates how well a light source saturates or desaturates the 99 CES compared to the reference source.

LEDs have the potential to exhibit very high power efficiencies relative to conventional incandescent or fluorescent lights. Most LEDs are substantially monochromatic light sources that appear to emit light having a single color. Thus, the spectral power distribution of the light emitted by most LEDs is tightly centered about a "peak" wavelength, which is the single wavelength where the spectral power distribution or "emission spectrum" of the LED reaches its maximum as detected by a photo-detector. LEDs typically have a full-width half-maximum wavelength range of about 10 nm to 30 nm, comparatively narrow with respect to the broad range of visible light to the human eye, which ranges from approximately from 380 nm to 800 nm.

In order to use LEDs to generate white light, lighting systems have been provided that include two or more LEDs that each emit a light of a different color. The different colors combine to produce a desired intensity and/or color of white light. For example, by simultaneously energizing red, green and blue LEDs, the resulting combined light may appear white, or nearly white, depending on, for example, the relative intensities, peak wavelengths and spectral power distributions of the source red, green and blue LEDs. The aggregate emissions from red, green, and blue LEDs typically provide poor color rendering for general illumination applications due to the gaps in the spectral power distribution in regions remote from the peak wavelengths of the LEDs.

White light may also be produced by utilizing one or more luminescent materials such as phosphors to convert some of the light emitted by one or more LEDs to light of one or more other colors. The combination of the light emitted by the LEDs that is not converted by the luminescent material(s) and the light of other colors that are emitted by the luminescent material(s) may produce a white or near-white light.

LED lamps have been provided that can emit white light with different CCT values within a range. Such lamps utilize two or more LEDs, with or without luminescent materials, with respective drive currents that are increased or decreased to increase or decrease the amount of light emitted by each LED. By controllably altering the power to the various LEDs in the lamp, the overall light emitted can be tuned to different CCT values. The range of CCT values that can be provided with adequate color rendering values and efficiency is limited by the selection of LEDs.

The spectral profiles of light emitted by white artificial lighting can impact circadian physiology, alertness, and cognitive performance levels. Bright artificial light can be used in a number of therapeutic applications, such as in the treatment of seasonal affective disorder (SAD), certain sleep problems, depression, jet lag, sleep disturbances in those with Parkinson's disease, the health consequences associated with shift work, and the resetting of the human circadian clock. Artificial lighting may change natural processes, interfere with melatonin production, or disrupt the circadian rhythm. Blue light may have a greater tendency than other colored light to affect living organisms through the disruption of their biological processes which can rely upon natural cycles of daylight and darkness. Exposure to blue light late in the evening and at night may be detrimental to one's health. Some blue or royal blue light within lower wavelengths can have hazardous effects to human eyes and skin, such as causing damage to the retina.

Red light has been shown to have some potential benefits to biological systems and operations.

Significant challenges remain in providing LED lamps that can provide white light across a range of CCT values while simultaneously achieving high efficiencies, high luminous flux, good color rendering, and acceptable color stability. It is also a challenge to provide lighting apparatuses that can provide desirable lighting performance while addressing for the control of circadian stimulating energy (CSE) performance.

SUMMARY

In accordance with an exemplary and non-limiting embodiment, a display system for displaying digital content comprises one or more LED-based lighting channels adapted to generate a first light output in a first operational mode at a first circadian stimulating energy (CSE), and a second light output in a second operational mode, the second light output associated with a second CSE, and a long red near infrared energy (LRNE) output in a third operating mode.

In accordance with an exemplary and non-limiting embodiment, a panel system for displaying digital content comprise one or more LED-based lighting channels adapted to generate a first circadian stimulating energy (CSE) blue light output in a first operational mode, one or more LED-based lighting channels adapted to generate a second circadian stimulating energy which provides a second CSE blue light output in a second operational mode wherein the second CSE blue light output comprises less CSE blue light than the first CSE blue light output and one or more LED-based lighting channels adapted to generate a long red and near infrared (LRNE) red light output in a third operational mode.

In accordance with an exemplary and non-limiting embodiment, a method to supply aliquots of bioactive illumination comprises providing a wearable device configured to selectively direct aliquots illumination from at least one illumination source towards the eyes of a user, providing a first lighting channel affixed to the portable device having a first illumination in the long red and near infrared energy (LRNE) range of wavelengths, providing a power supply and providing a controller connected to the power supply, the controller configured to be in signal communication with the first lightning channel to selectively apply power thereto, wherein the control system is configured to selectively switch the first lighting channel on and wherein switching comprises at least on/off and intensity of the first lighting channel to provide a bioactive exposure.

In accordance with an exemplary and non-limiting embodiment, a bioactive lighting system comprises a first lighting channel configured to produce a first white light having a first color point and a first spectral power distribution, a second lighting channel configured to produce a second white light having a second color point and a second spectral power distribution, a third lighting channel configured to produce a third white light having a third color point and a third spectral power distribution and a control system configured to independently change the intensity of each of the first, second and third lighting channel, wherein at least two of the channels combined together to form a light effecting bio-physiological functions, wherein the control system is further configured to change the intensity of each of the lighting channels to provide light with a color point at a plurality of points along a predefined path near the black body locus in the 1931 CIE Chromaticity Diagram, and wherein the first spectral power distribution has a first circadian-stimulating energy (CSE) characteristic, the second spectral power distribution has a second circadian-stimulating energy (CSE) characteristic, and the third spectral power distribution has a long red near infrared energy (LRNE) energy characteristic.

In accordance with an exemplary and non-limiting embodiment, a semiconductor light emitting device comprises a plurality of LED strings, with each LED string comprising one or more LEDs having an associated luminophoric medium, wherein the plurality of LED strings together with their associated luminophoric mediums form a plurality of channels, the plurality of channels comprising at least one of long red near infrared (LRNE) red, blue, short-blue-pumped cyan, and long-blue-pumped cyan channels each producing unsaturated color points on the 1931 CIE Chromaticity diagram and a control circuit is configured to adjust a color point of an unsaturated light that results from a combination of the light produced from the plurality of LED strings within a 7-step MacAdam ellipse around any point on a black body locus having a correlated color temperature between 1800K and 10000K.

The general disclosure and the following further disclosure are exemplary and explanatory only and are not restrictive of the disclosure, as defined in the appended claims. Other aspects of the present disclosure will be apparent to those skilled in the art in view of the details as provided herein. In the figures, like reference numerals designate corresponding parts throughout the different views. All callouts and annotations are hereby incorporated by this reference as if fully set forth herein.

DRAWINGS

The summary, as well as the following detailed description, is further understood when read in conjunction with the appended drawings. For the purpose of illustrating the disclosure, there are shown in the drawings exemplary implementations of the disclosure; however, the disclosure is not limited to the specific methods, compositions, and devices disclosed. In addition, the drawings are not necessarily drawn to scale. In the drawings.

Figure 4:
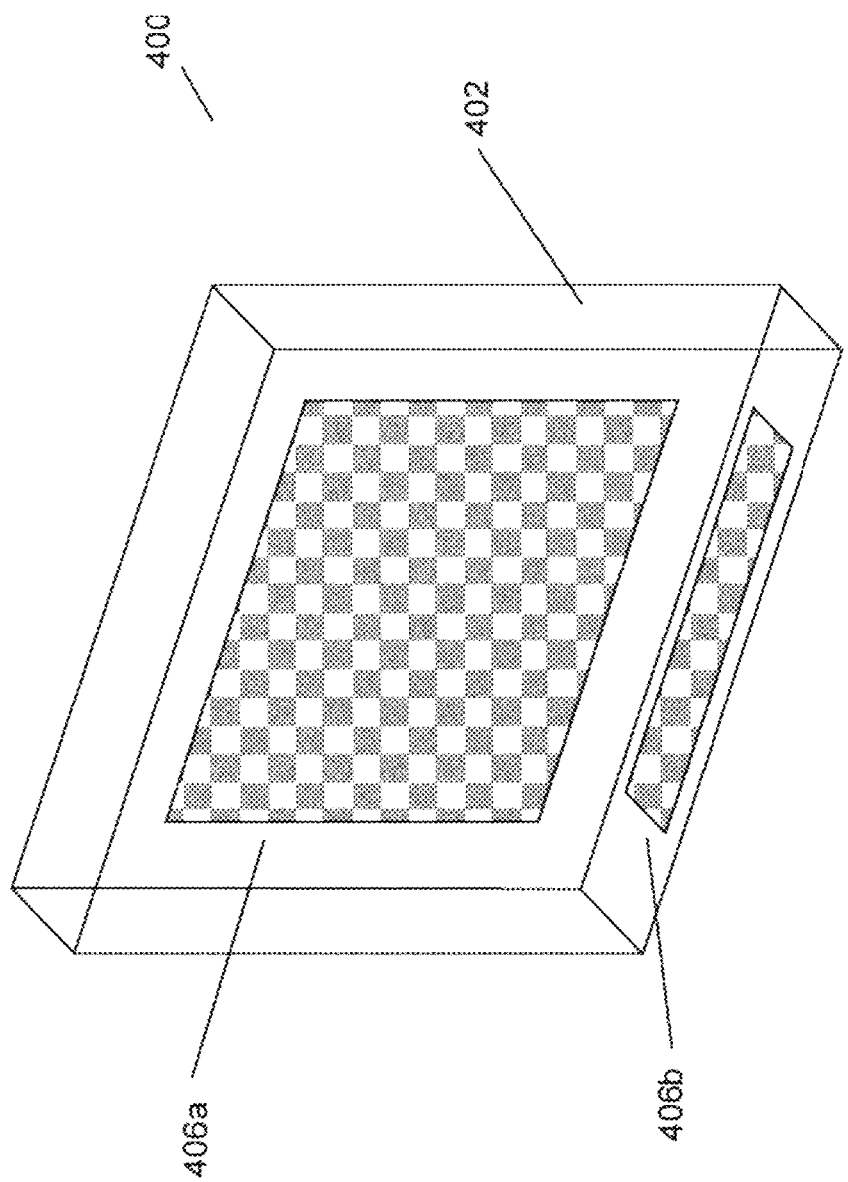
Figure 5:
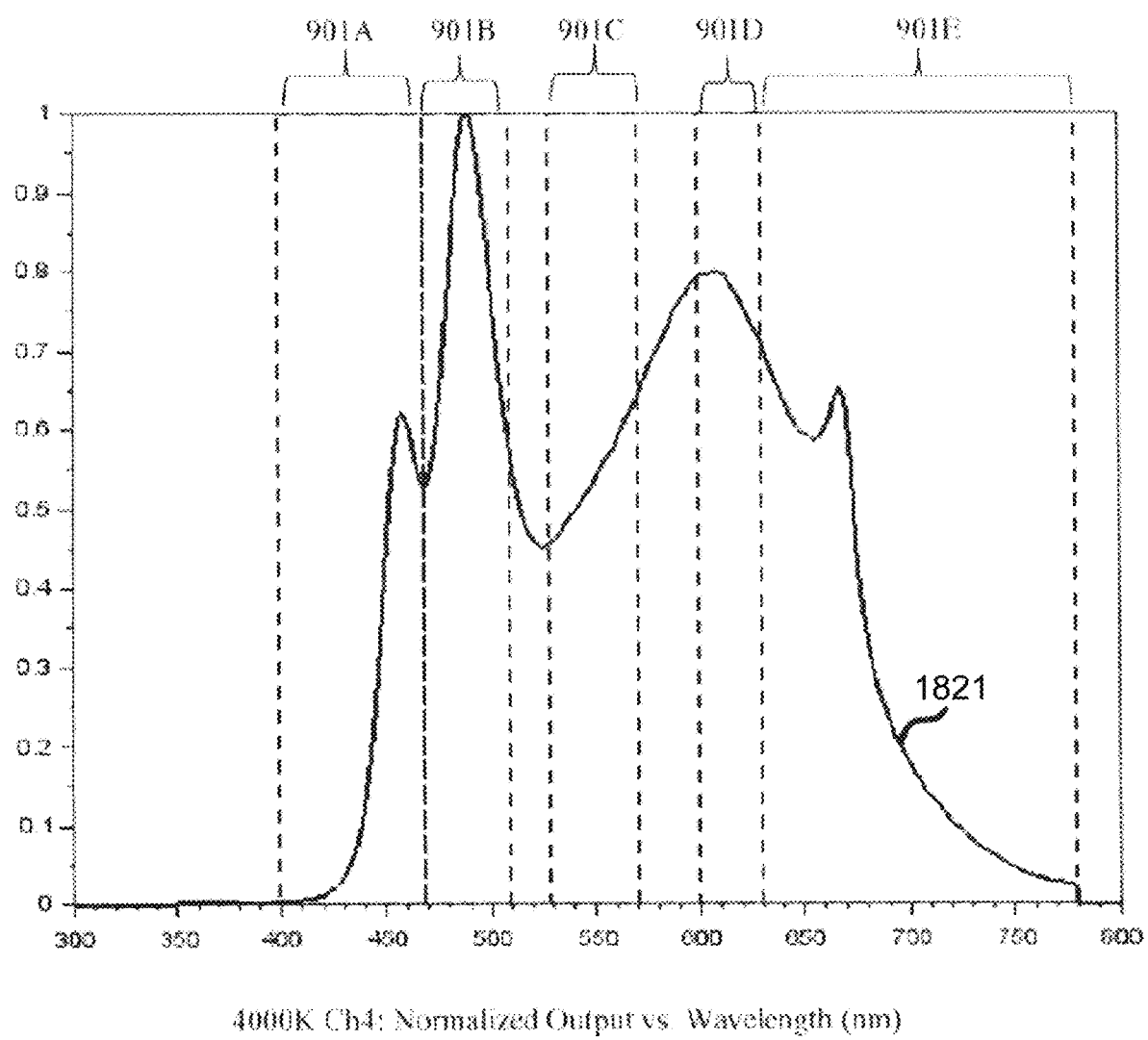
Figure 6:
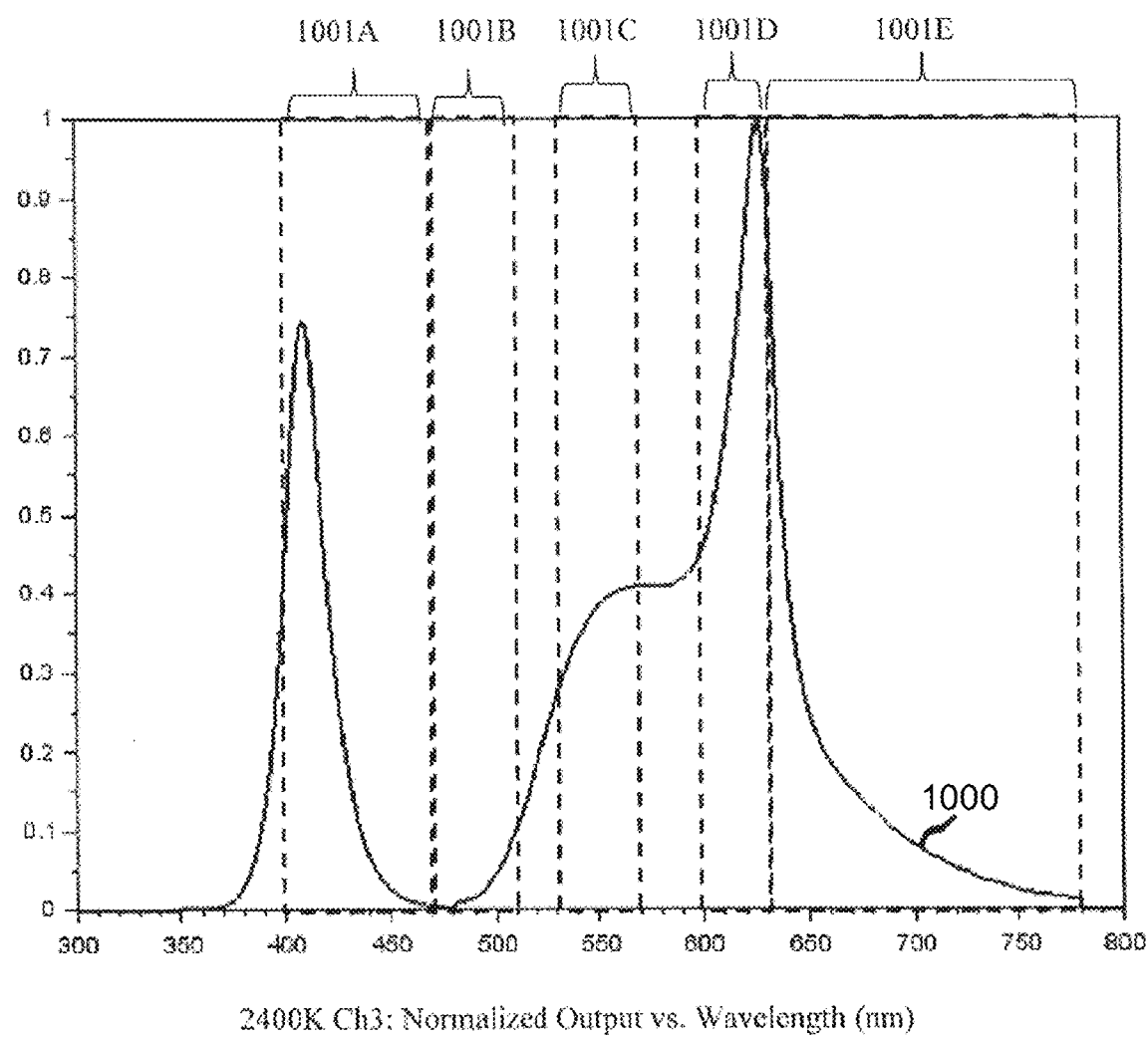
Figure 7:
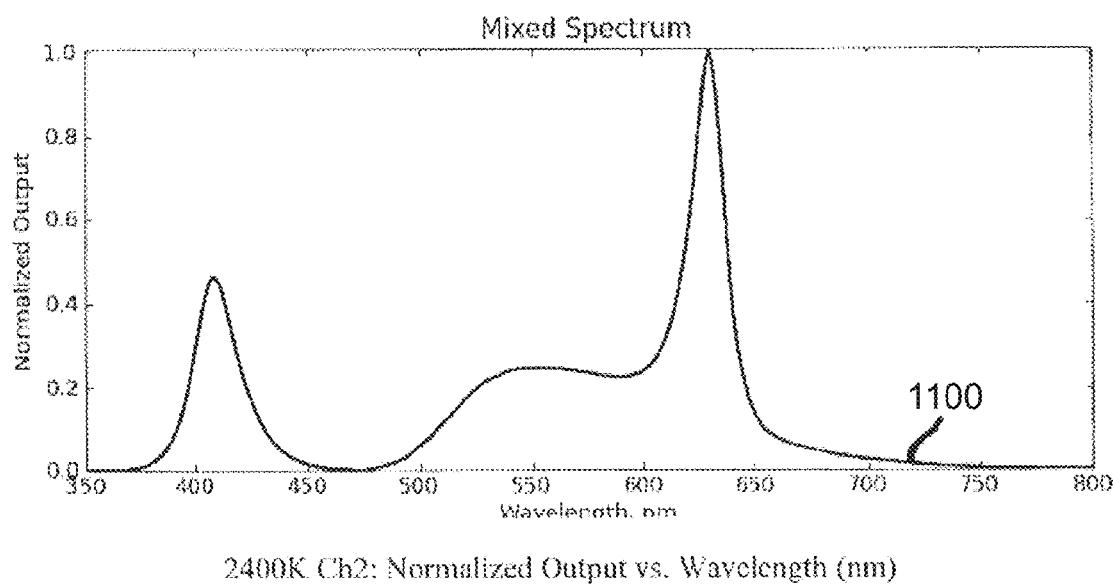
Figure 8:
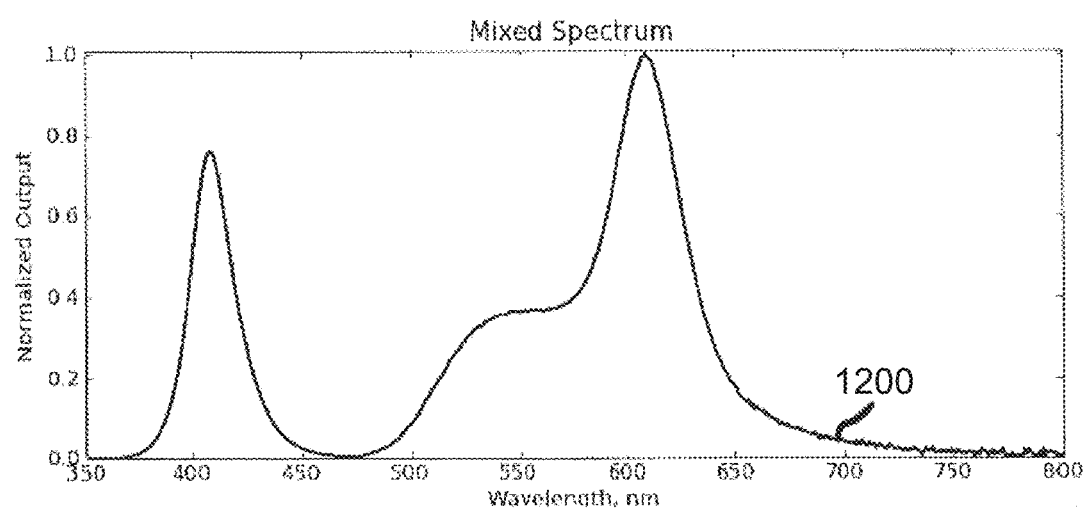
Figure 9:
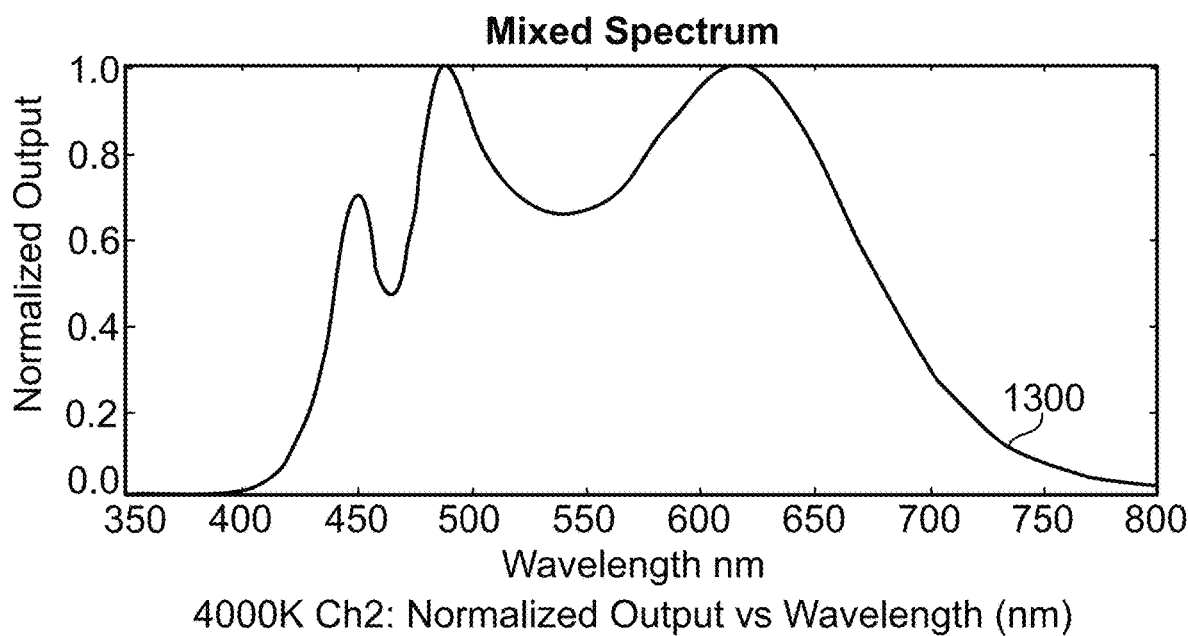
Figure 10:
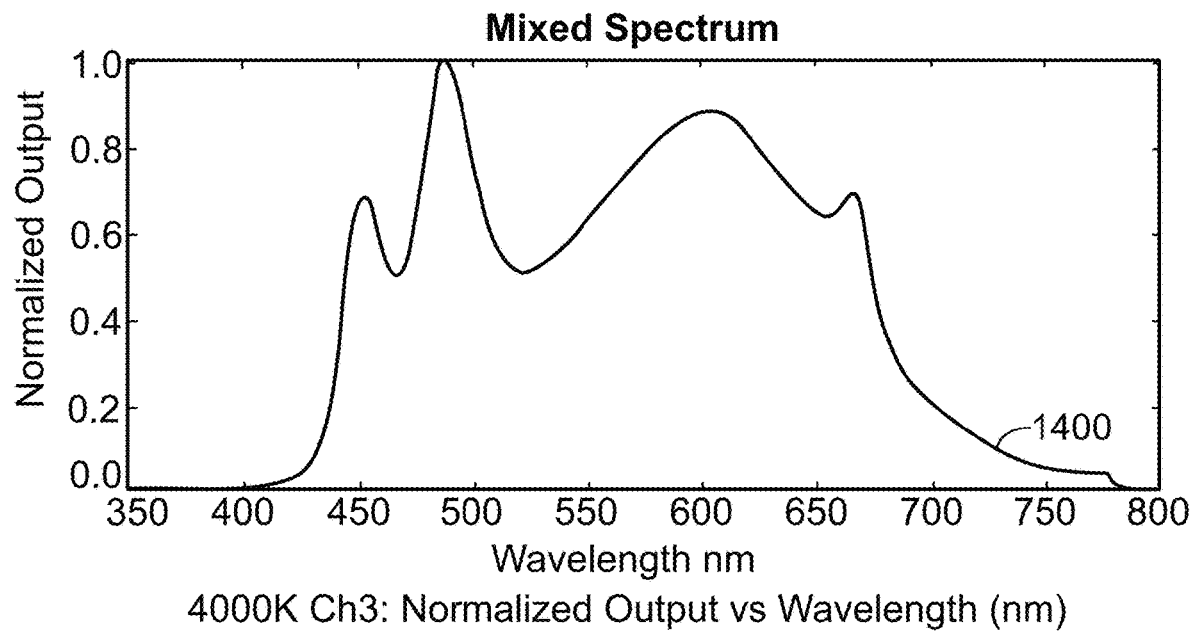
Figure 11:
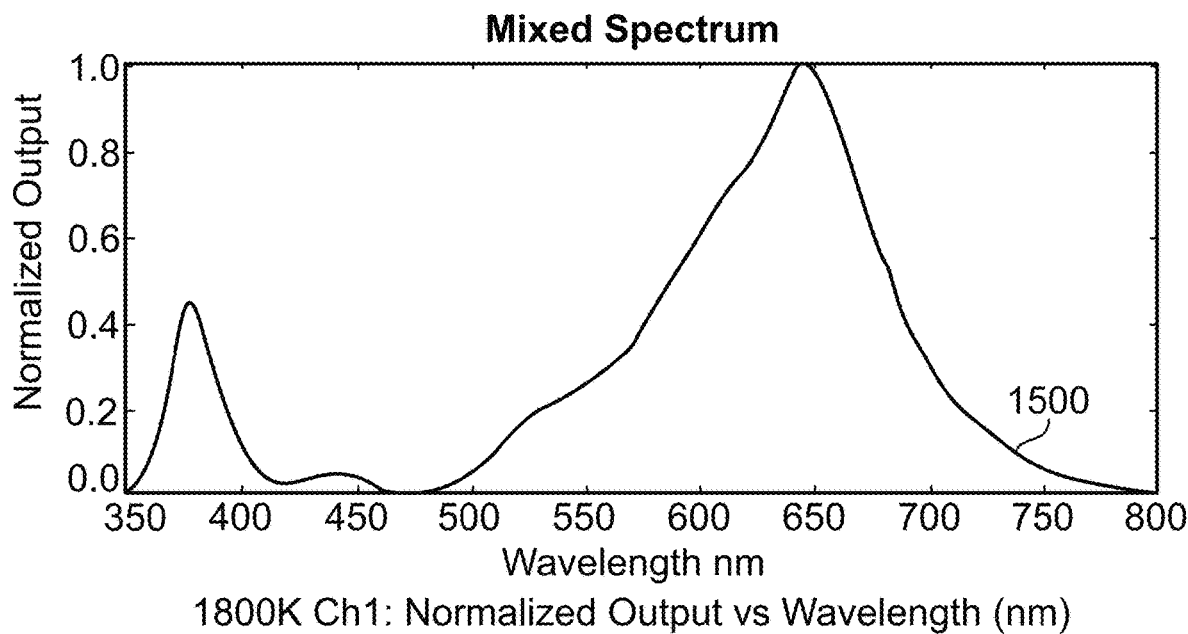
Figure 12:
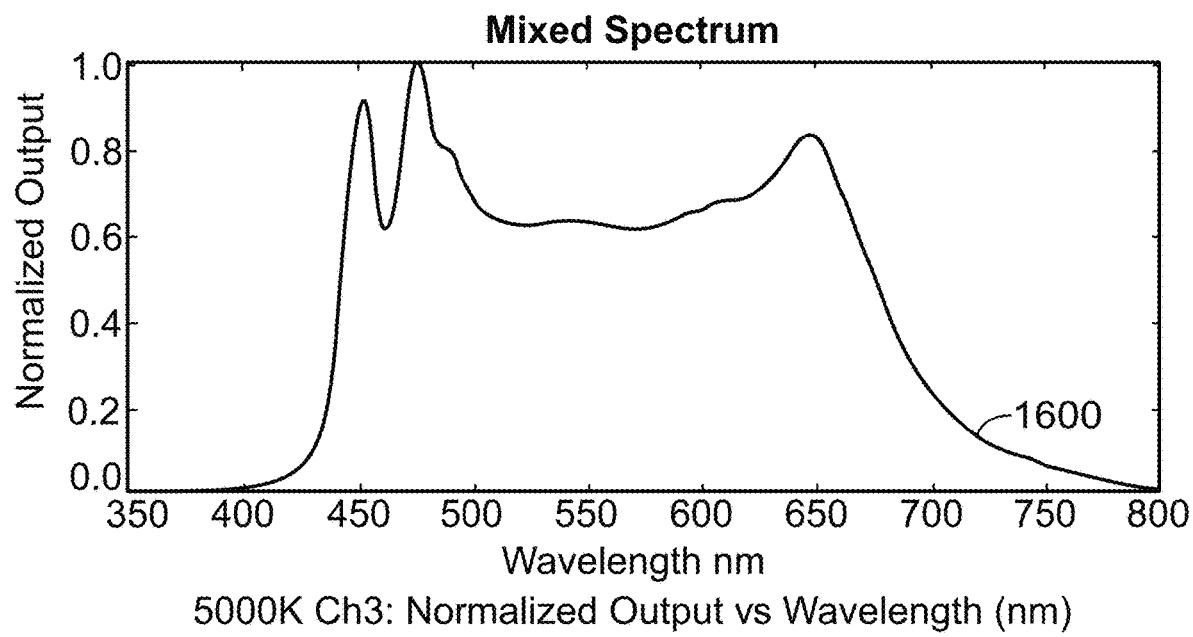
Figure 13:
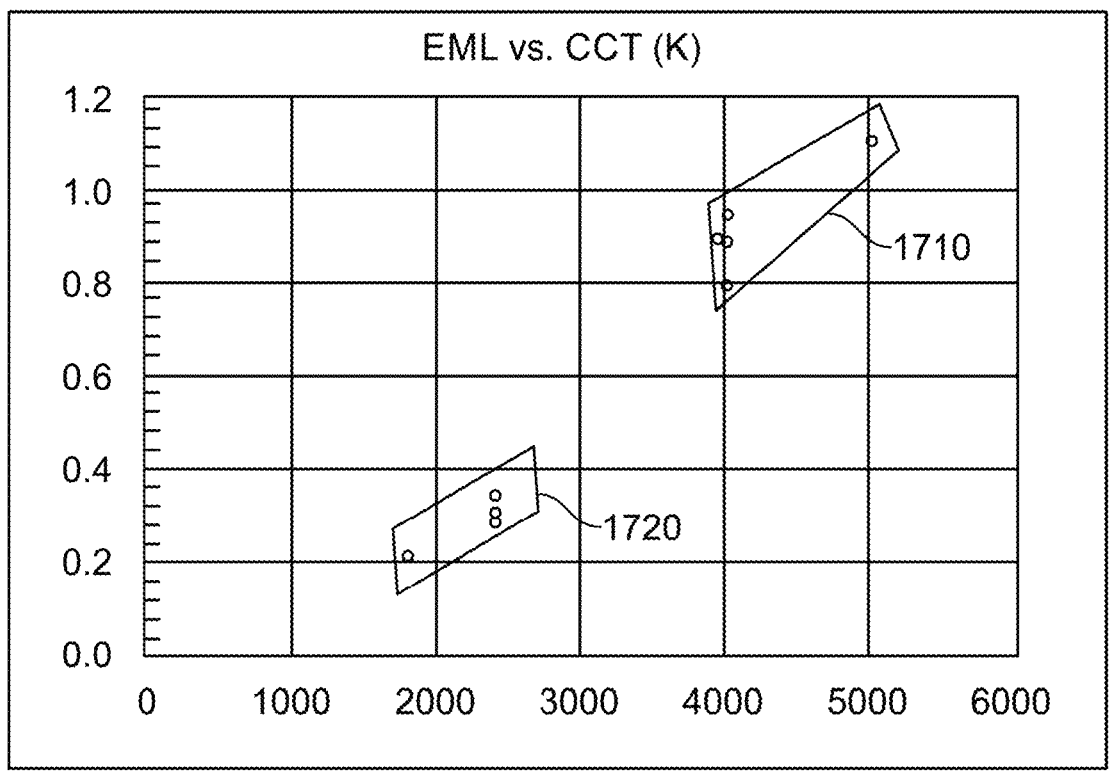
Figure 14:
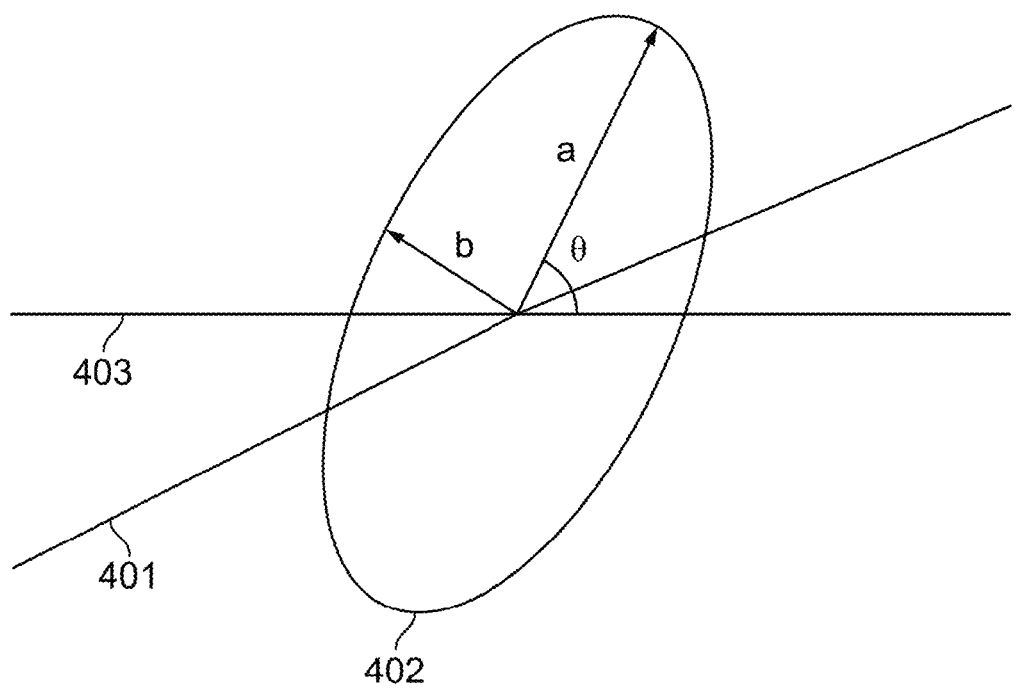
Figure 15:
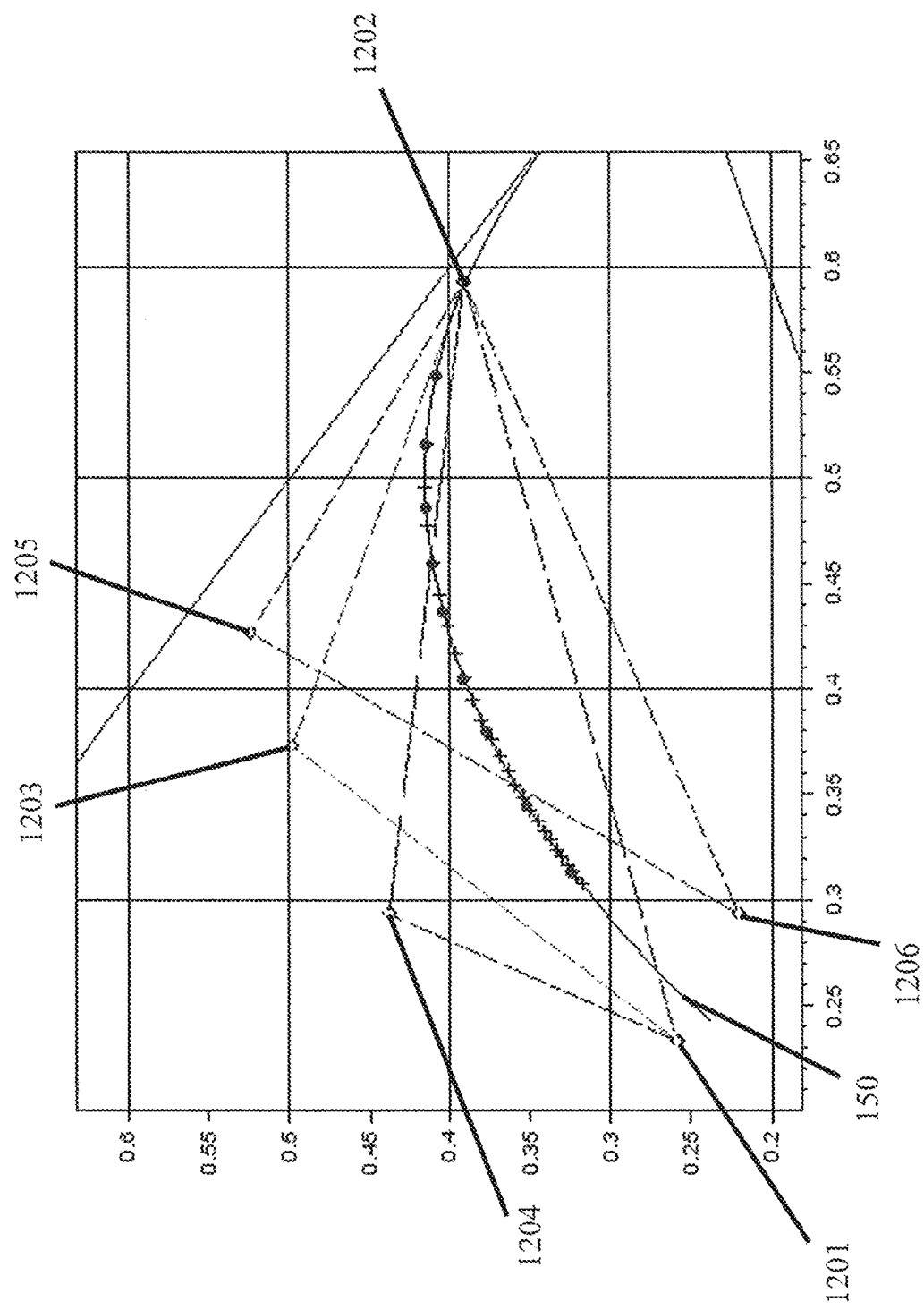
Figure 16:
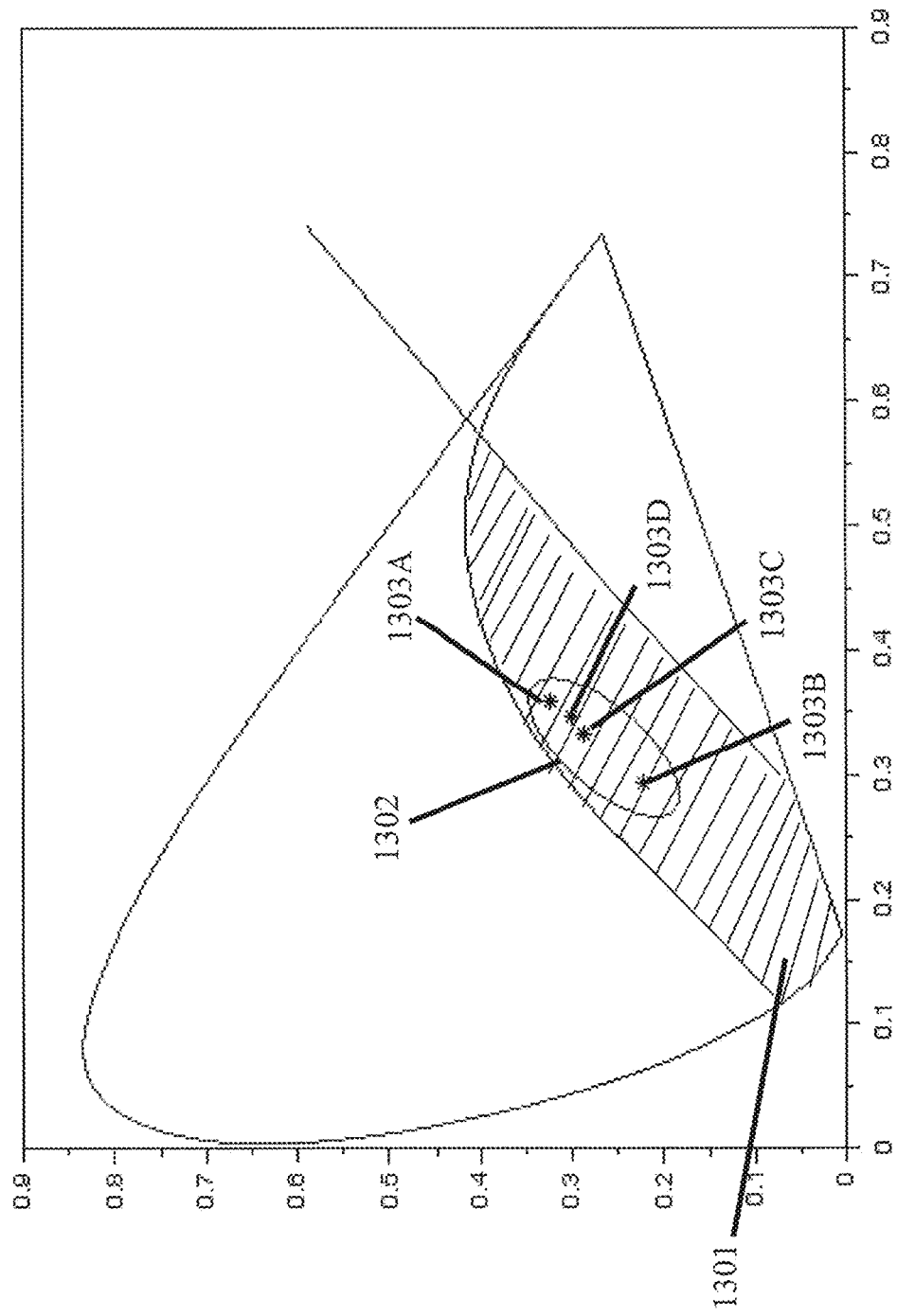
Figure 17:
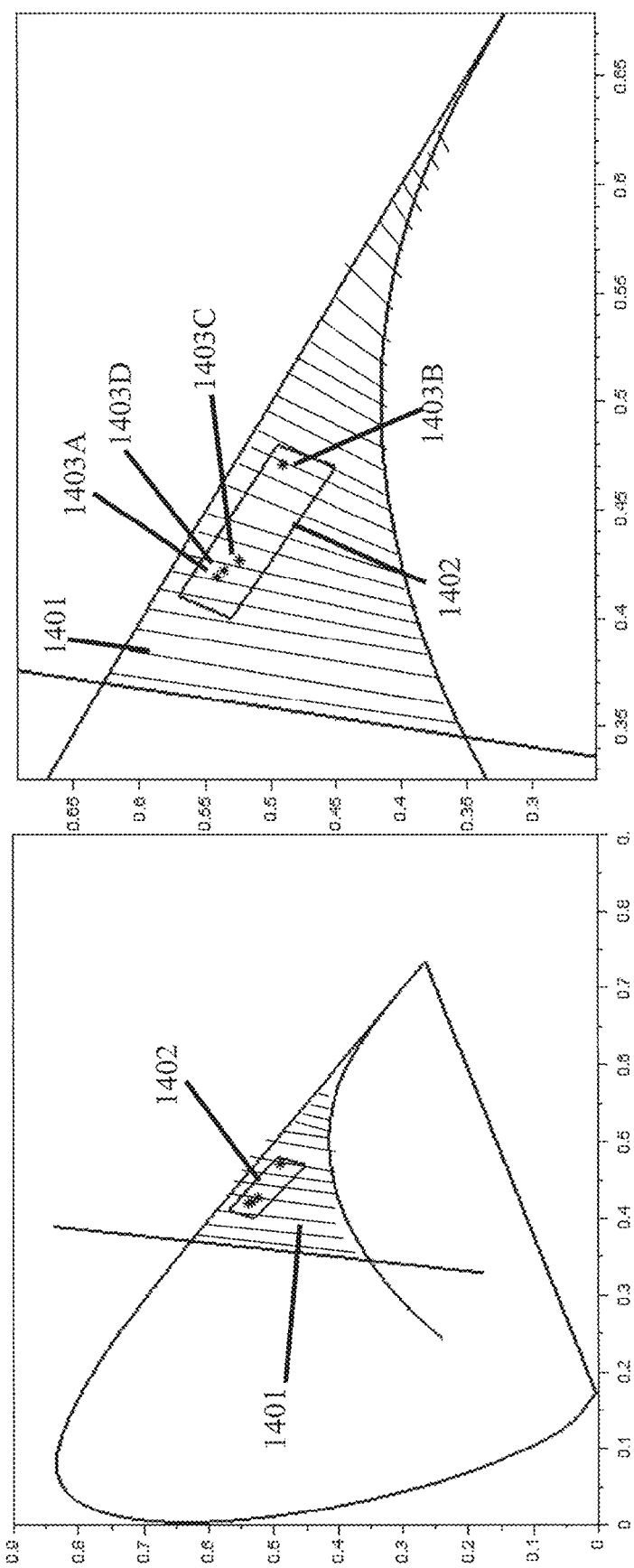
Figure 18:
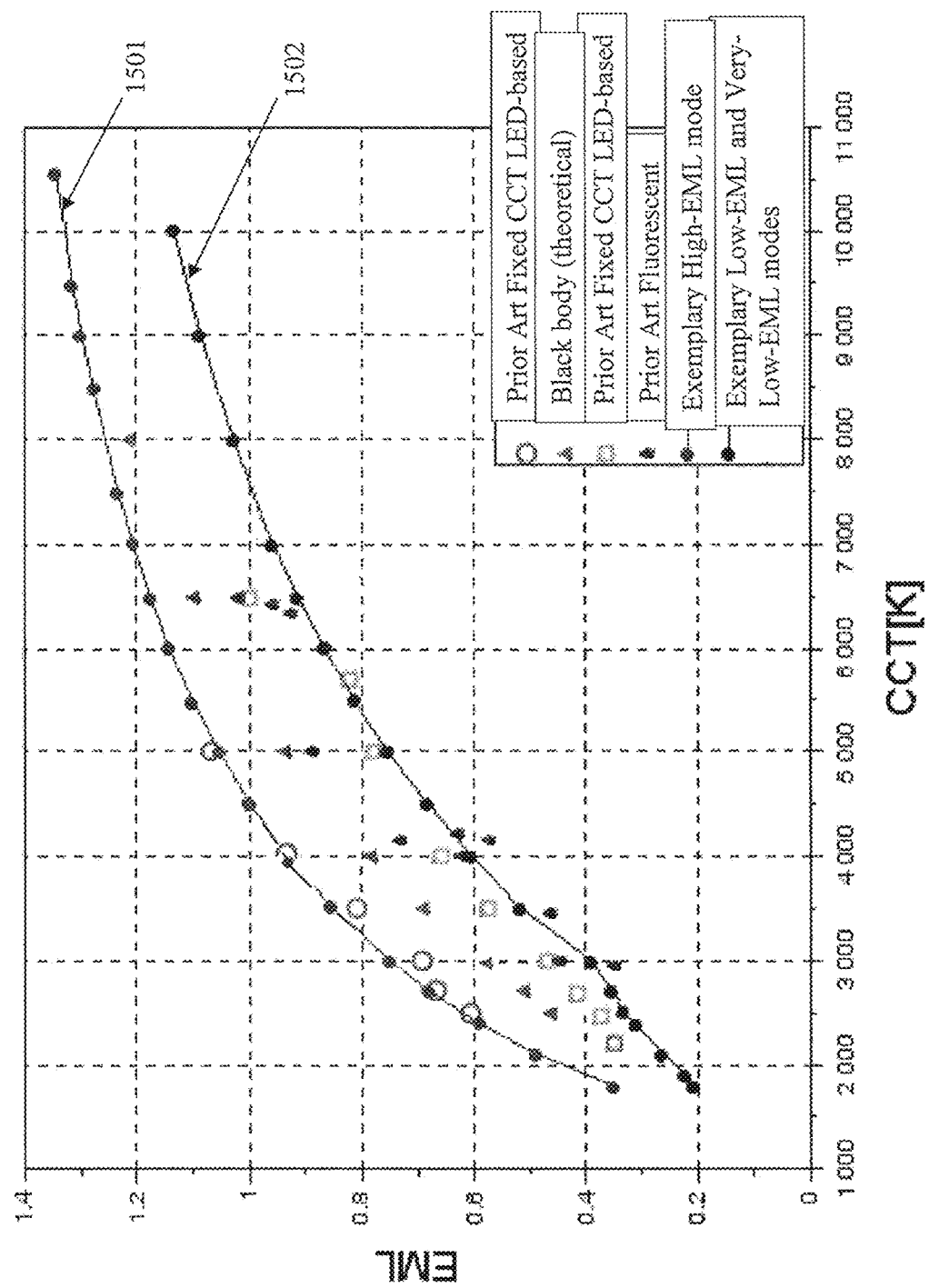
Figure 19:
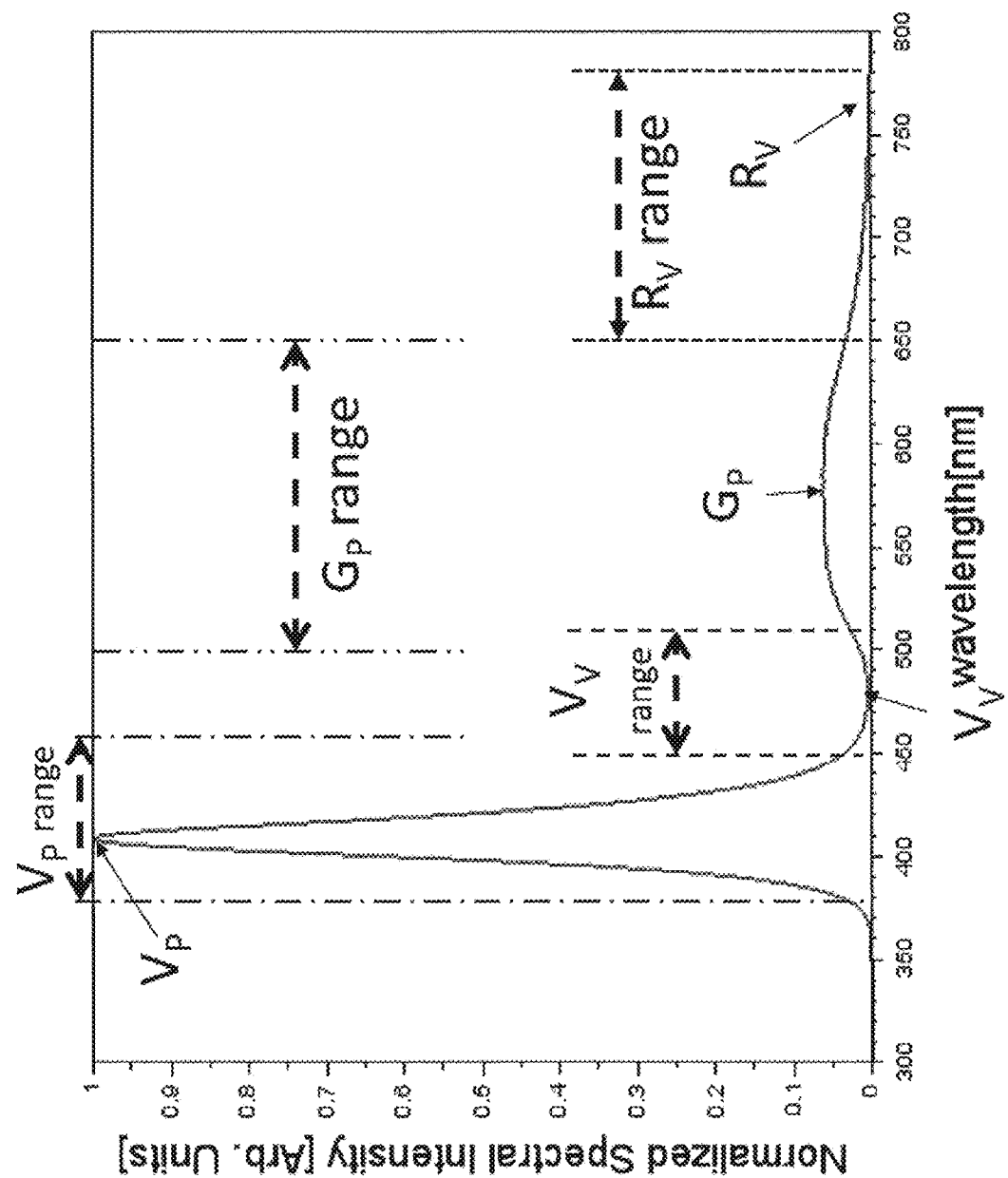
Figure 20:
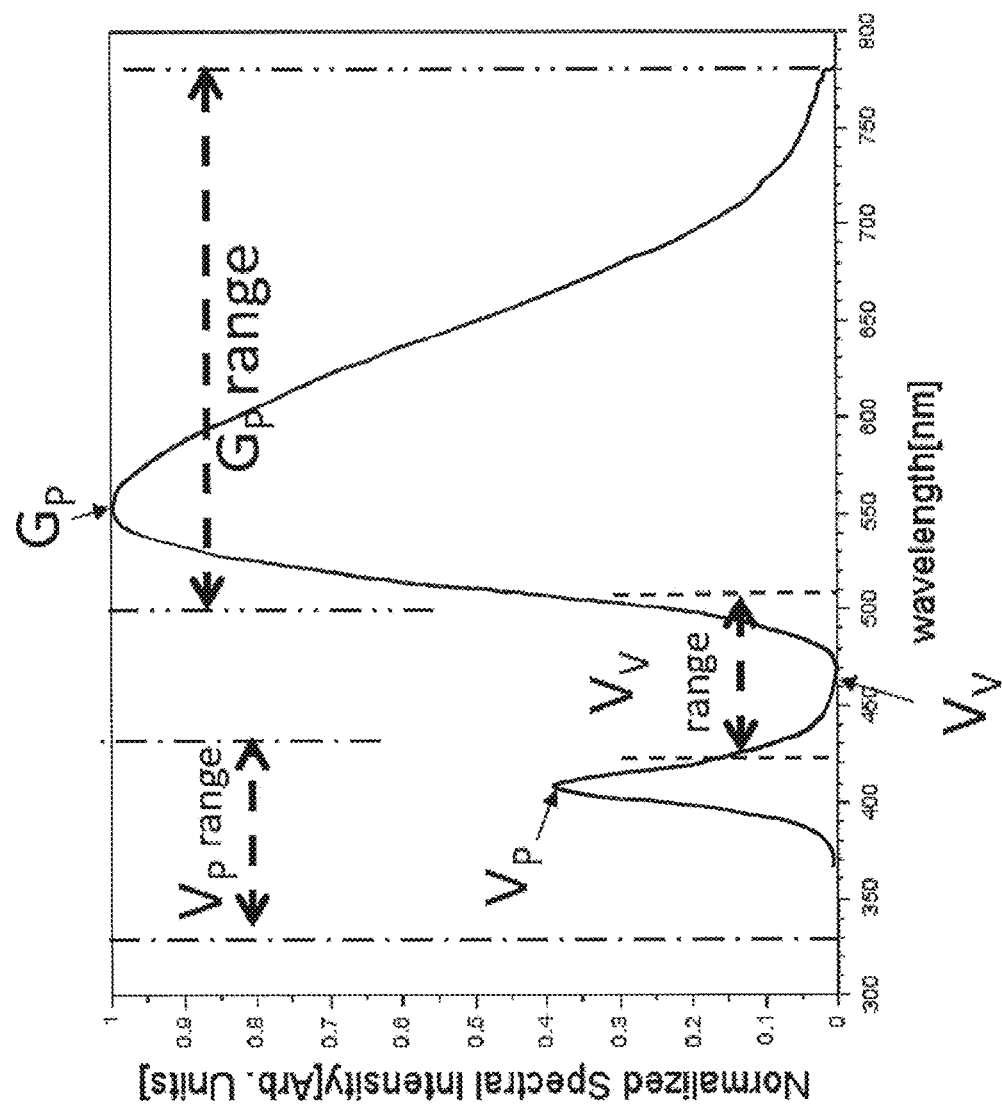
Figure 21:
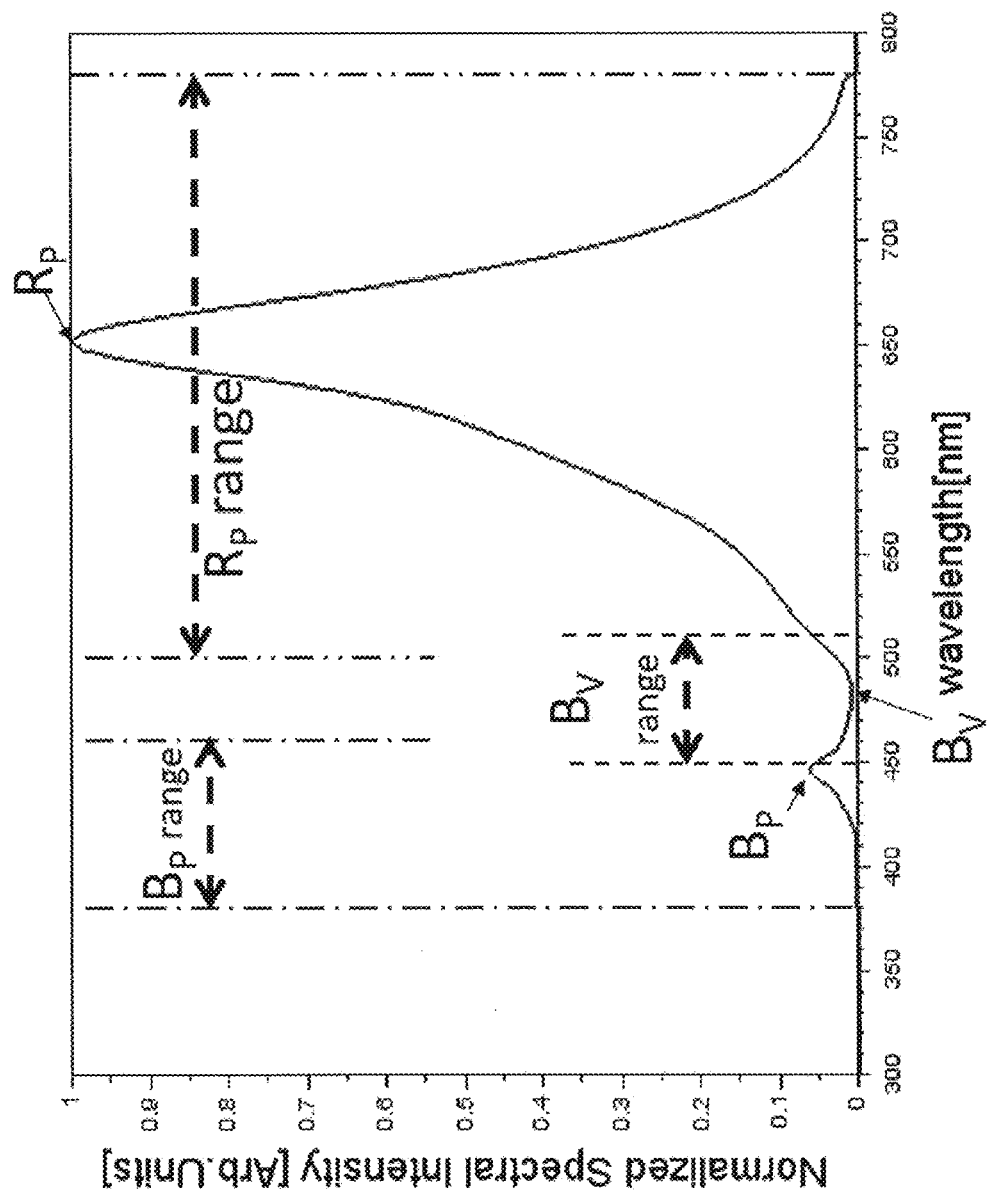
Figure 22A:
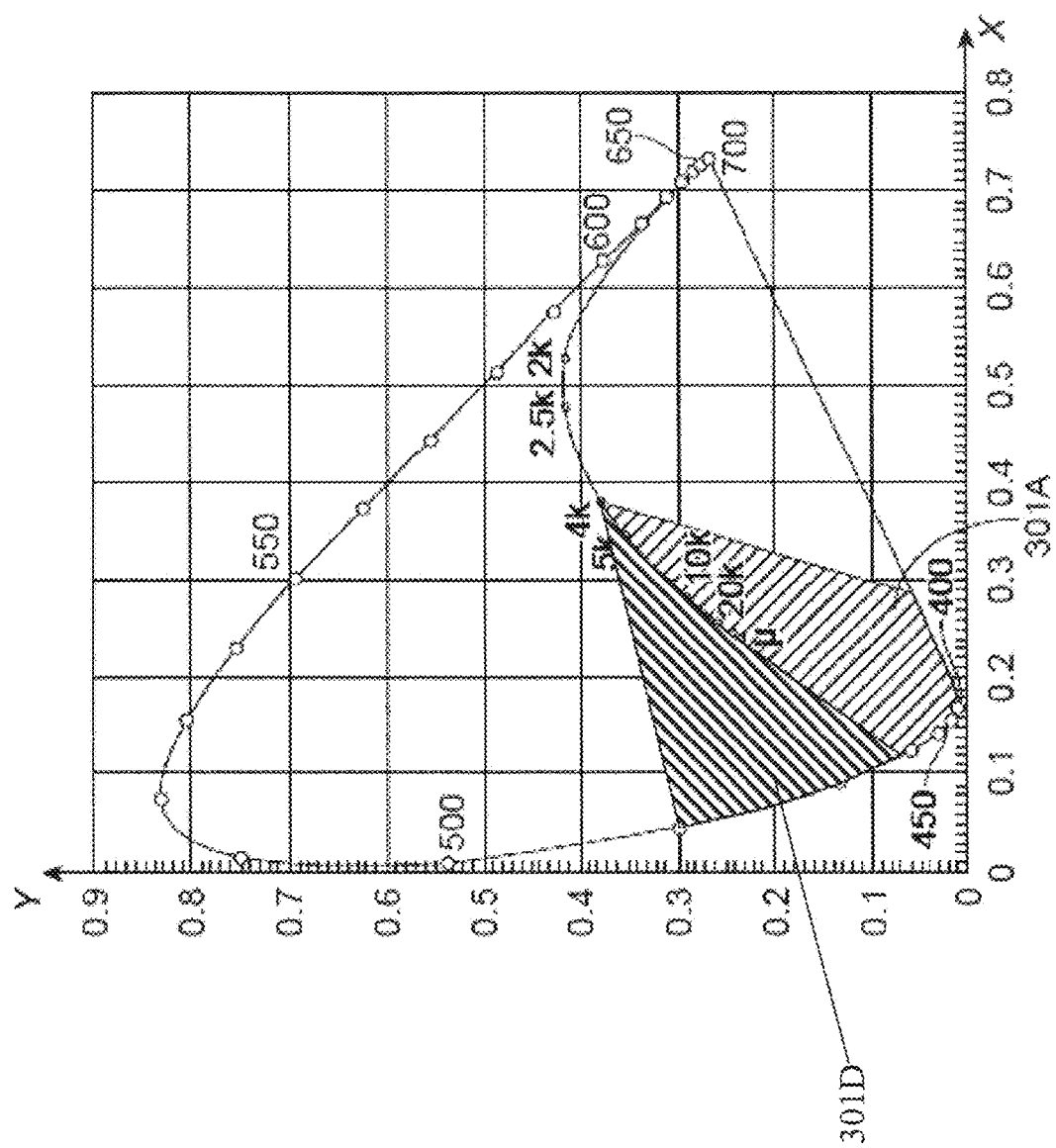
Figure 22B:
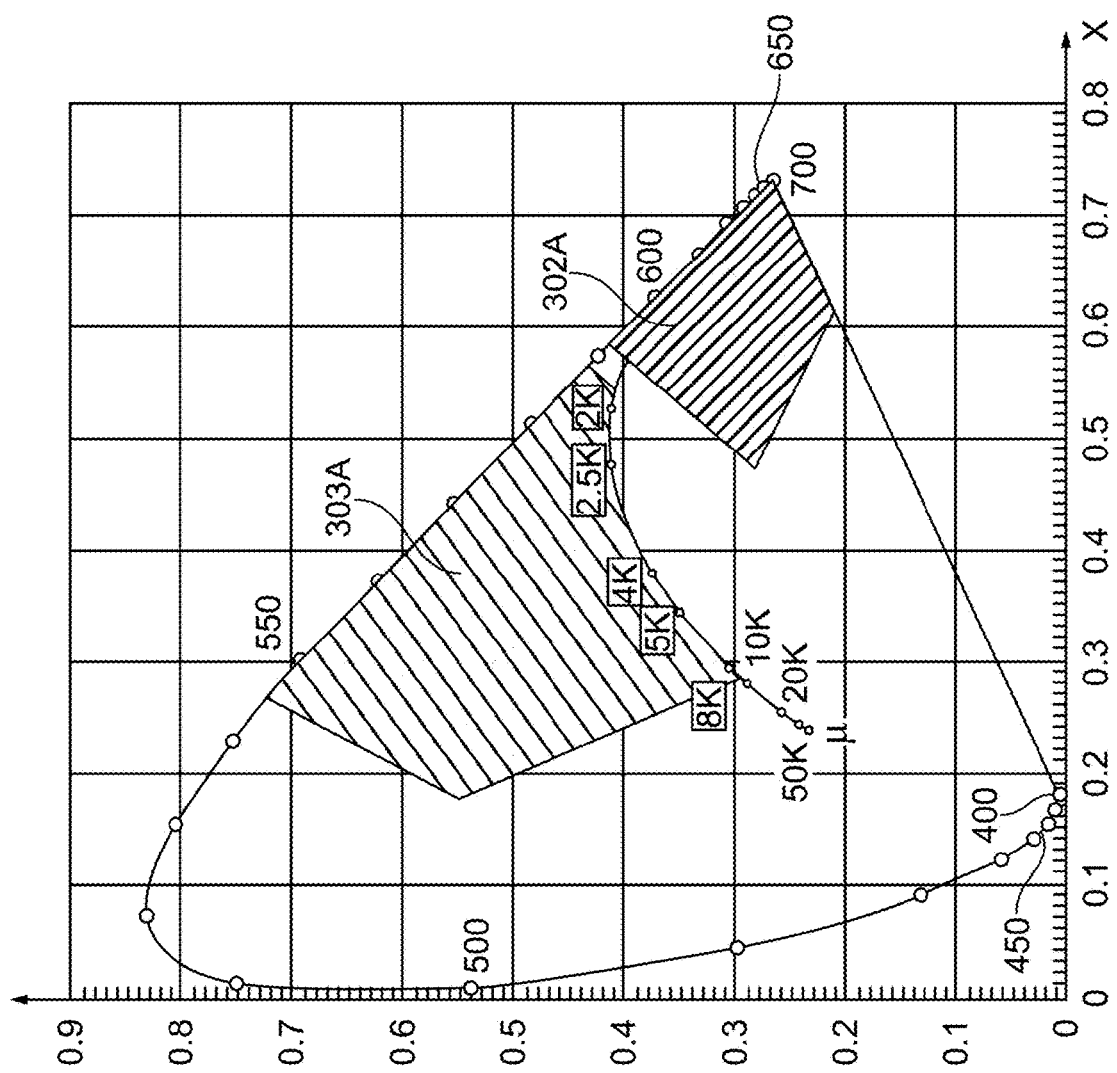
Figure 23:
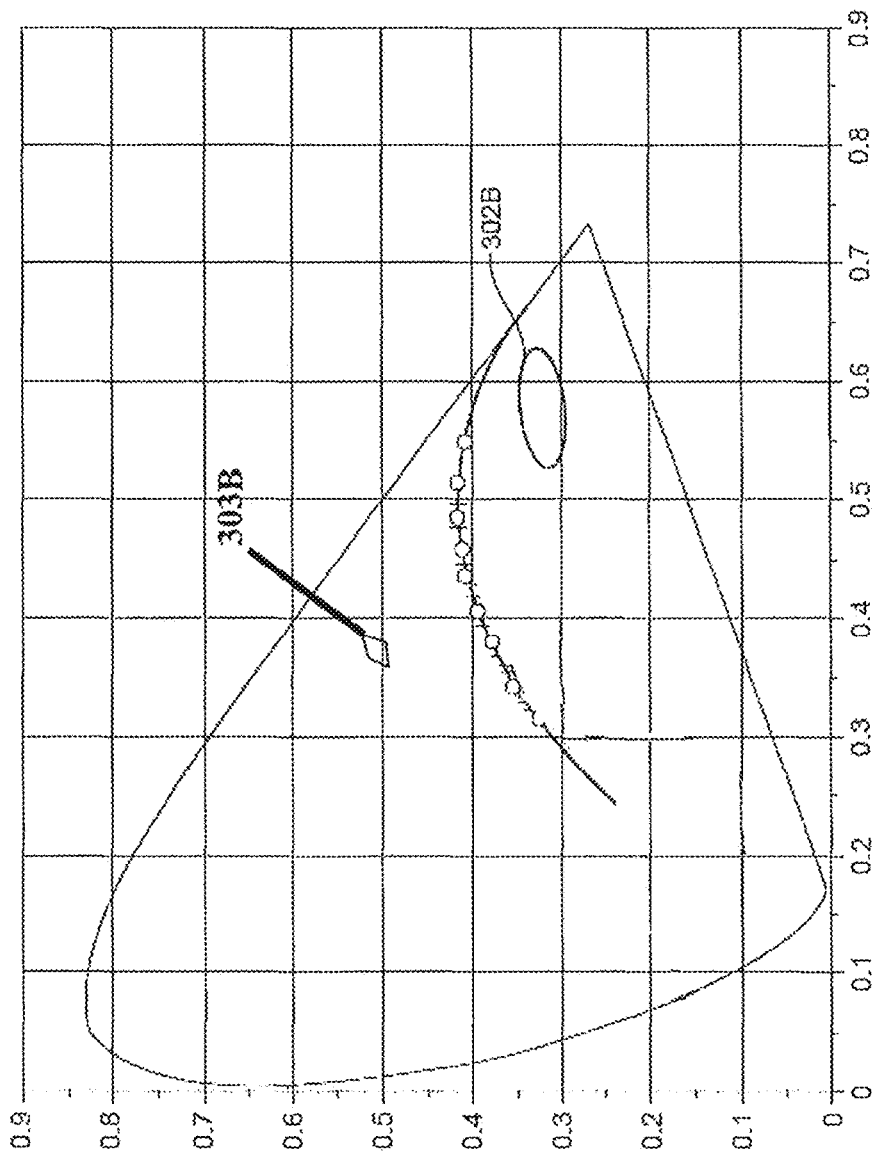
Figure 24:
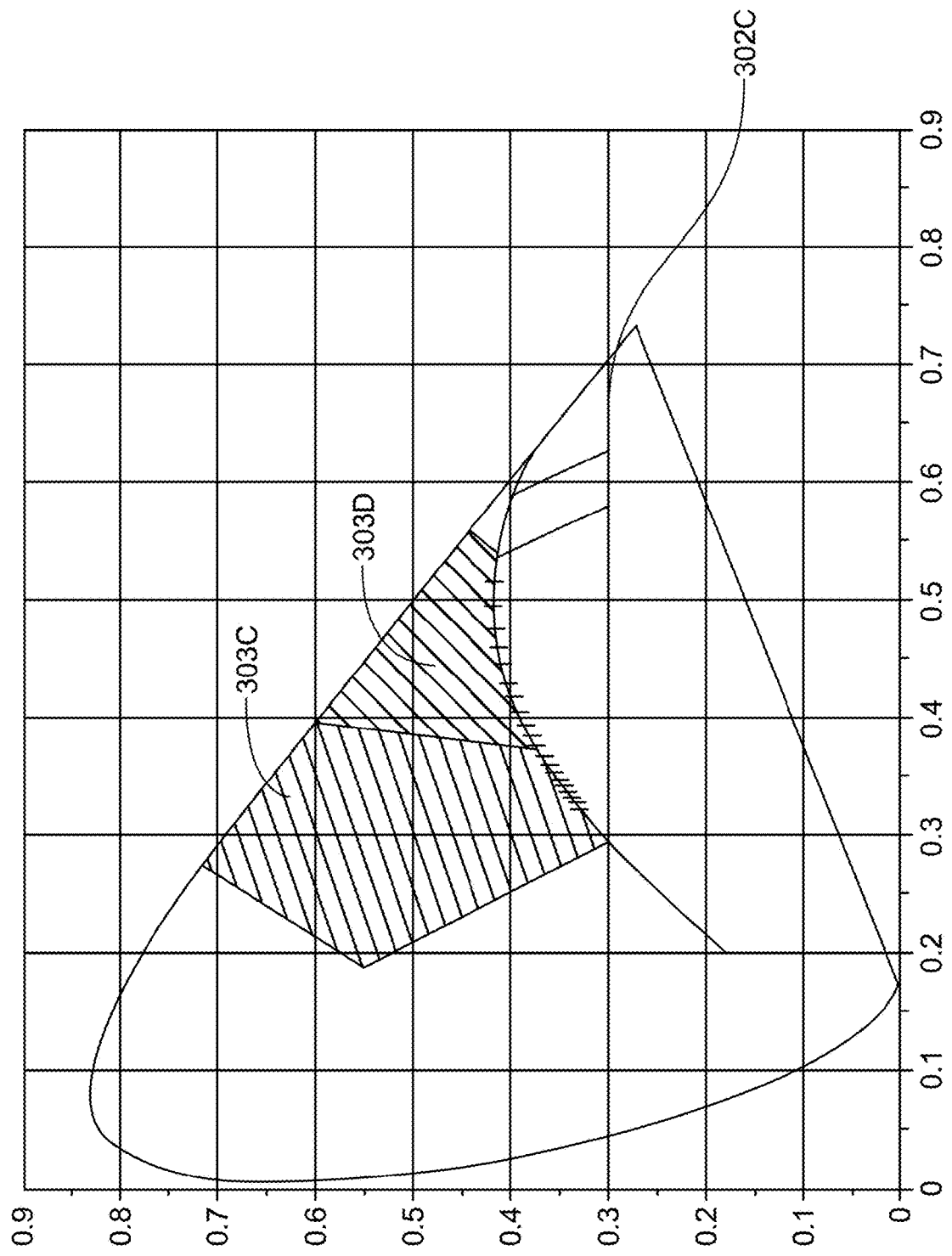
Figure 25:
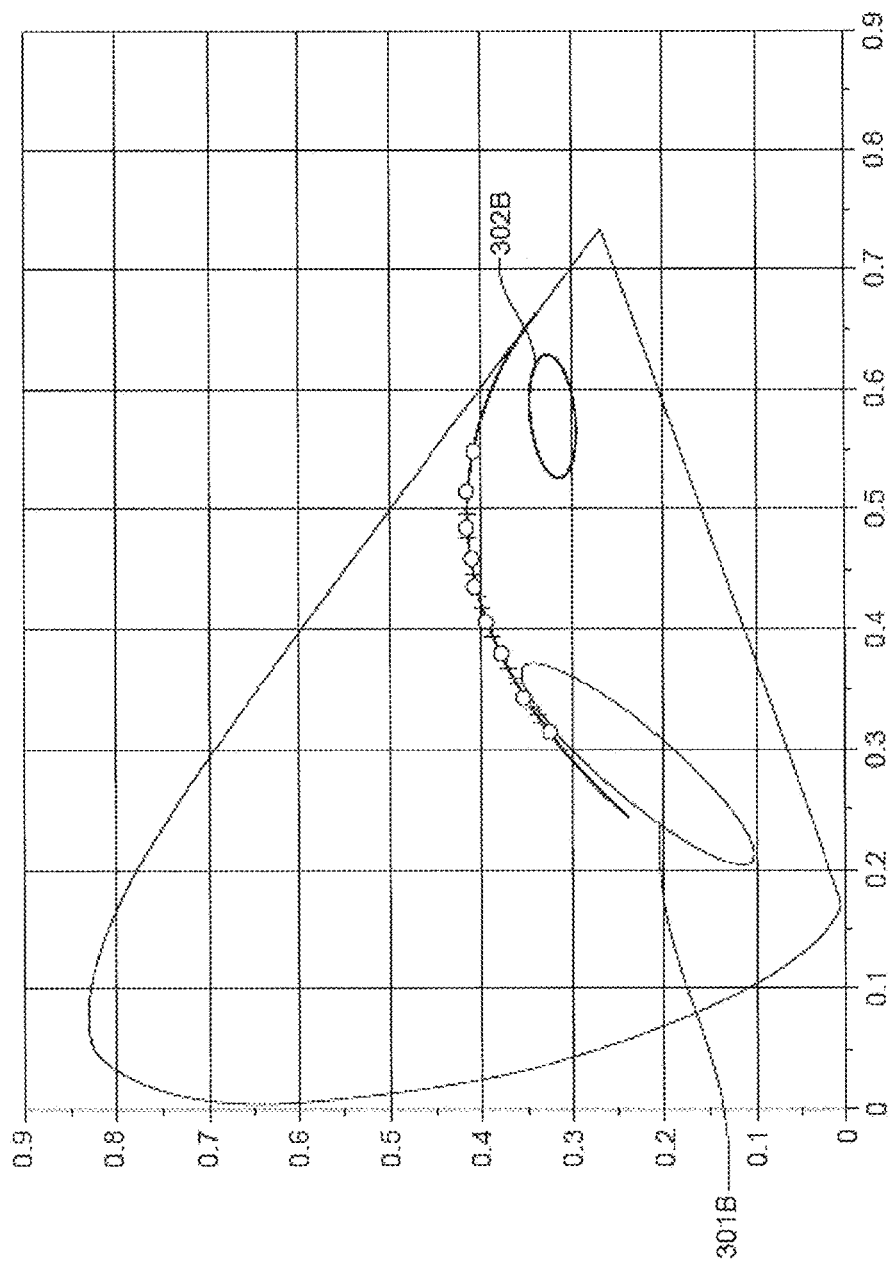
Figure 26:
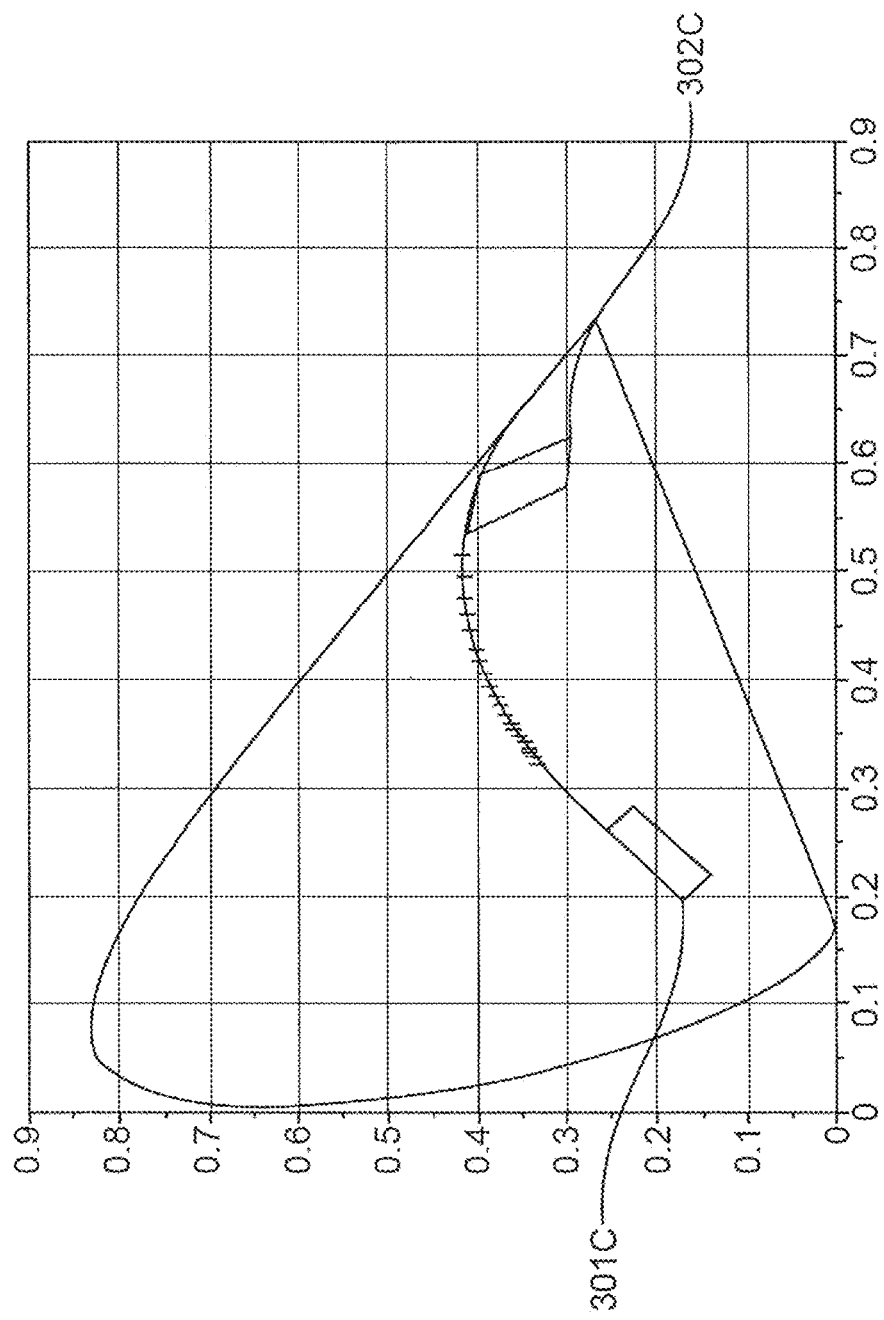
Figure 27:
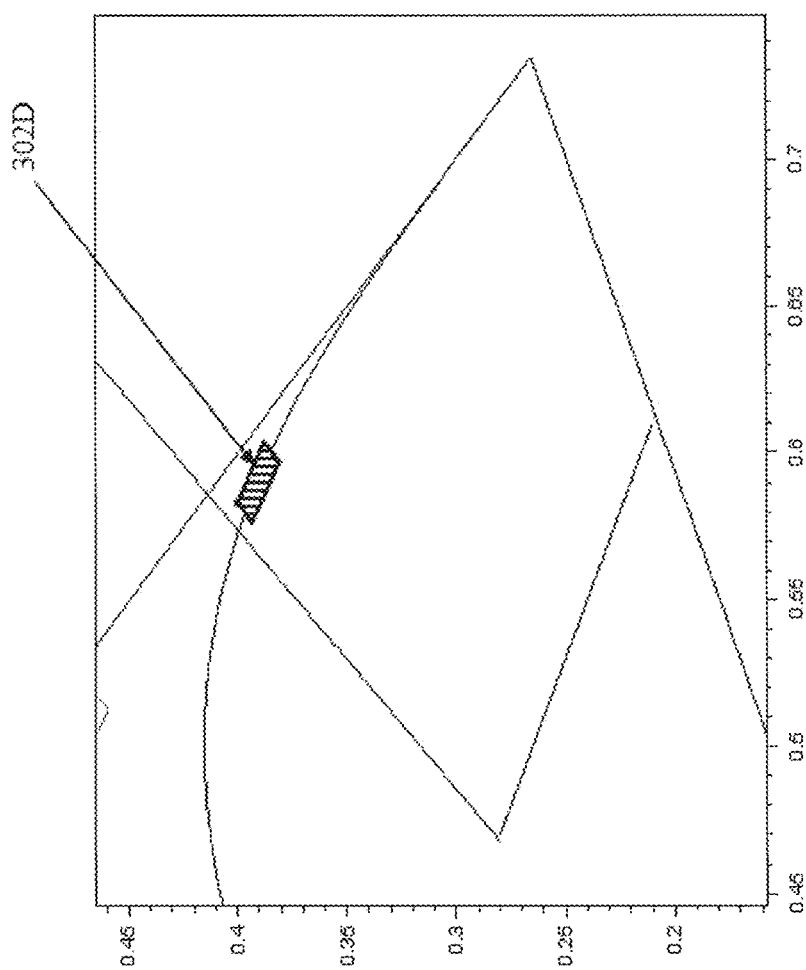
Figure 28:
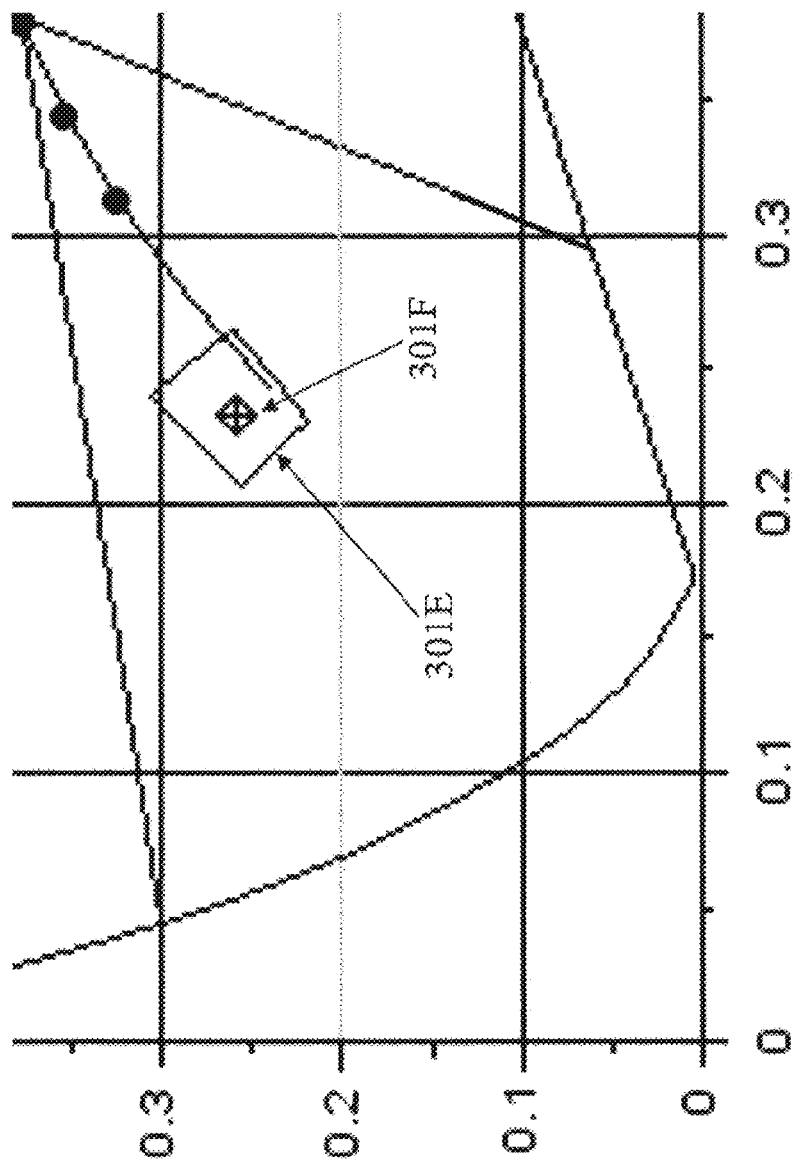

FIGS. 3a, 3b, 3c, and 3d illustrates aspects of display systems according to the present disclosure, including spectral power distributions for some exemplary lighting channels;

FIG. 4 illustrates aspects of display systems according to the present disclosure;

FIG. 5 illustrates some aspects of display systems according to the present disclosure, including aspects of spectral power distributions for light generated by components of the devices;

FIG. 6 illustrates some aspects of display systems according to the present disclosure, including aspects of spectral power distributions for light generated by components of the devices;

FIG. 7 illustrates some aspects of display systems according to the present disclosure, including aspects of spectral power distributions for light generated by components of the devices;

FIG. 8 illustrates some aspects of display systems according to the present disclosure, including aspects of spectral power distributions for light generated by components of the devices;

FIG. 9 illustrates some aspects of display systems according to the present disclosure, including aspects of spectral power distributions for light generated by components of the devices;

FIG. 10 illustrates some aspects of display systems according to the present disclosure, including aspects of spectral power distributions for light generated by components of the devices;

FIG. 11 illustrates some aspects of display systems according to the present disclosure, including aspects of spectral power distributions for light generated by components of the devices;

FIG. 12 illustrates some aspects of display systems according to the present disclosure, including aspects of spectral power distributions for light generated by components of the devices;

FIG. 13 illustrates some aspects of display systems according to the present disclosure, including aspects of spectral power distributions for light generated by components of the devices;

FIG. 14 illustrates some aspects of display systems according to the present disclosure, including some suitable color ranges for light generated by components of the devices FIG. 15 illustrates some aspects of display systems according to the present disclosure, including some suitable color points for light generated by components of the display systems;

FIG. 16 illustrates some aspects of display systems according to the present disclosure, including some suitable color ranges for light generated by components of the display systems;

FIG. 17A and FIG. 17B illustrate some aspects of display systems according to the present disclosure, including some suitable color ranges for light generated by components of the display systems;

FIG. 18 illustrates some aspects of display systems according to the present disclosure in comparison with some prior art and some theoretical light sources, including some light characteristics of white light generated by display systems in various operational modes;

FIG. 19 illustrates some aspects of display systems according to the present disclosure, including aspects of spectral power distributions for light generated by components of the display systems;

FIG. 20 illustrates some aspects of display systems according to the present disclosure, including aspects of spectral power distributions for light generated by components of the display systems;

FIG. 21 illustrates some aspects of display systems according to the present disclosure, including aspects of spectral power distributions for light generated by components of the display systems;

FIGS. 22A-22B illustrate some aspects of display systems according to the present disclosure, including some suitable color ranges for light generated by components of the display systems;

FIG. 23 illustrates some aspects of display systems according to the present disclosure, including some suitable color ranges for light generated by components of the display systems;

FIG. 24 illustrates some aspects of display systems according to the present disclosure, including some suitable color ranges for light generated by components of the display systems;

FIG. 25 illustrates some aspects of display systems according to the present disclosure, including some suitable color ranges for light generated by components of the display systems;

FIG. 26 illustrates some aspects of display systems according to the present disclosure, including some suitable color ranges for light generated by components of the display systems;

FIG. 27 illustrates some aspects of display systems according to the present disclosure, including some suitable color ranges for light generated by components of the display systems; and FIG. 28 illustrates some aspects of display systems according to the present disclosure, including some suitable color ranges for light generated by components of the display systems.

Figure 29:
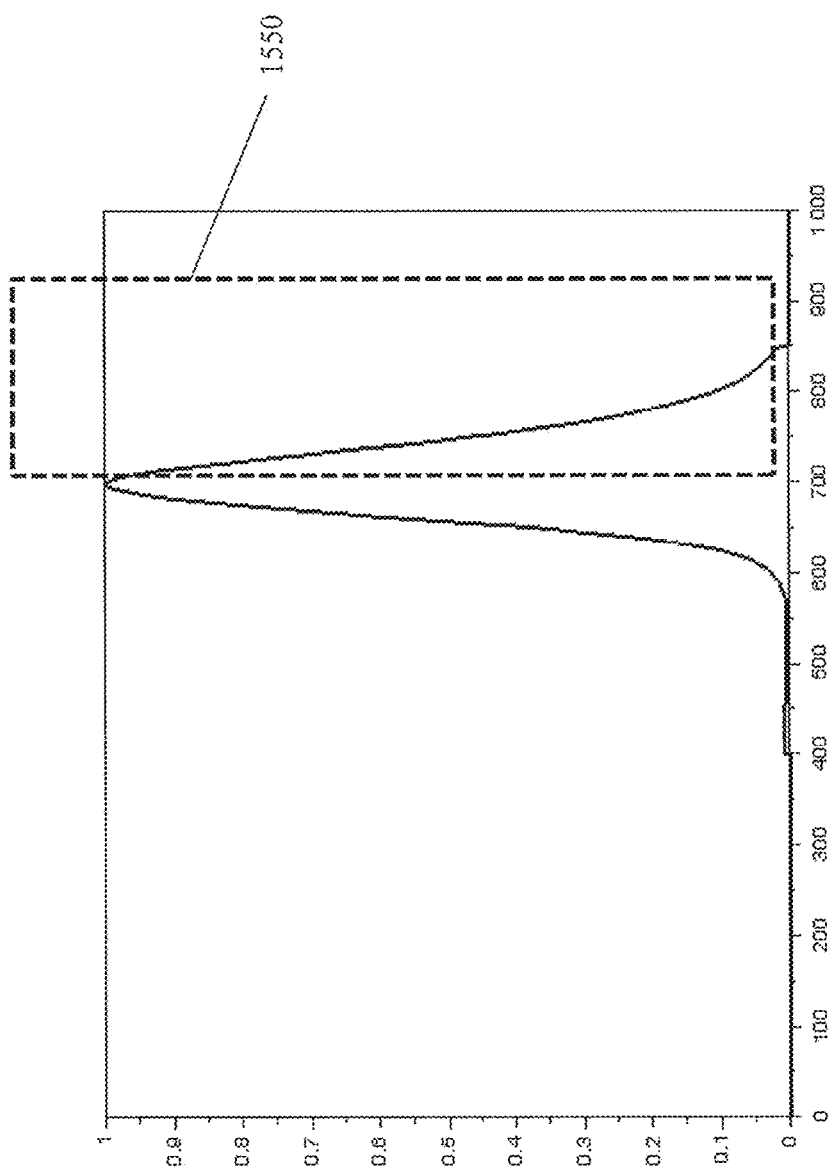

FIG. 29 illustrates some aspects of light emitting devices according to the present disclosure, including aspects of LRNE spectral power distributions for light generated by components of the devices.

Figure 30:
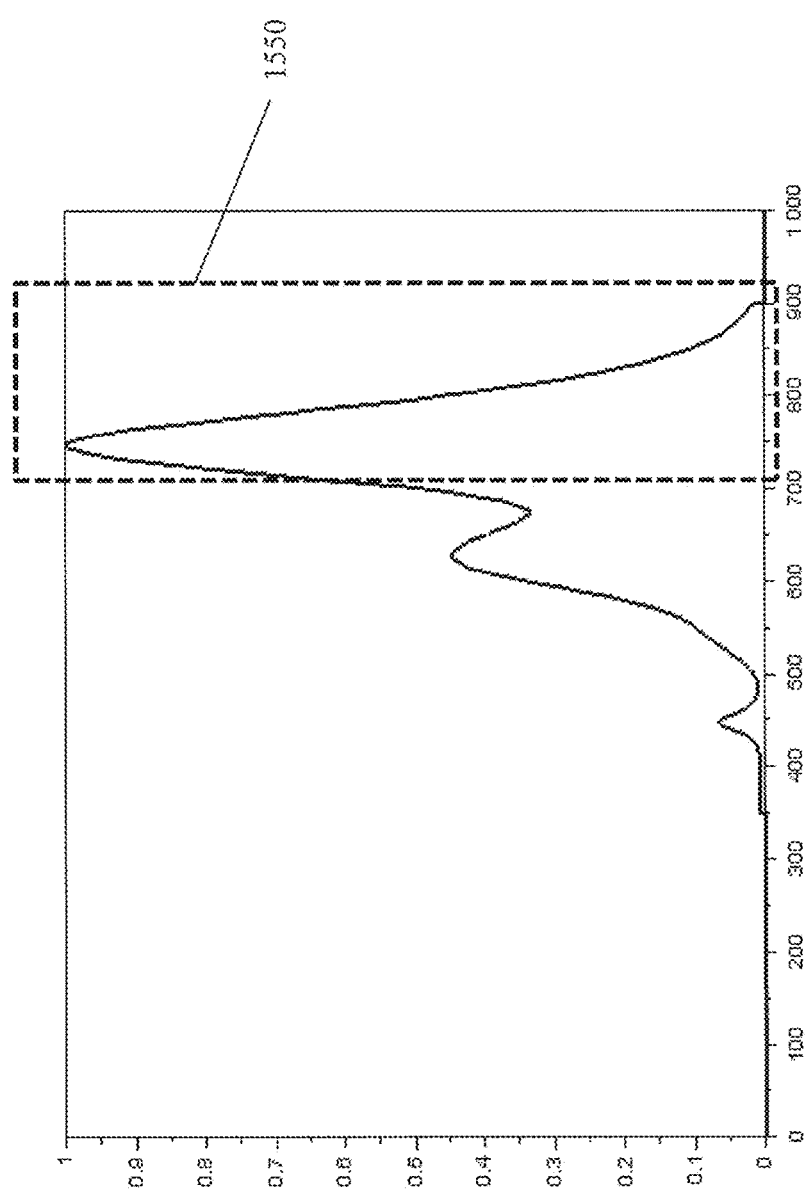

FIG. 30 illustrates some aspects of light emitting devices according to the present disclosure, including aspects of LRNE spectral power distributions for light generated by components of the devices.

Figure 31:
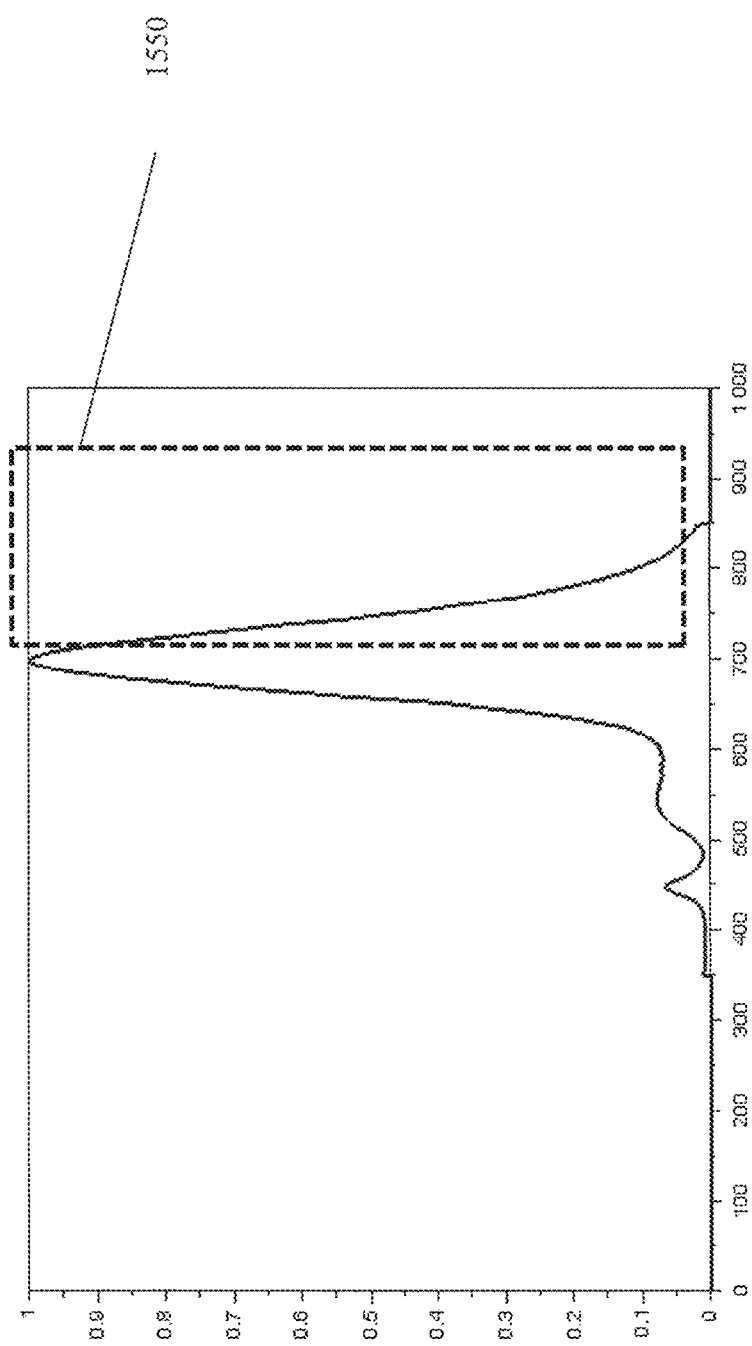

FIG. 31 illustrates some aspects of light emitting devices according to the present disclosure, including aspects of LRNE spectral power distributions for light generated by components of the devices.

Figure 34:
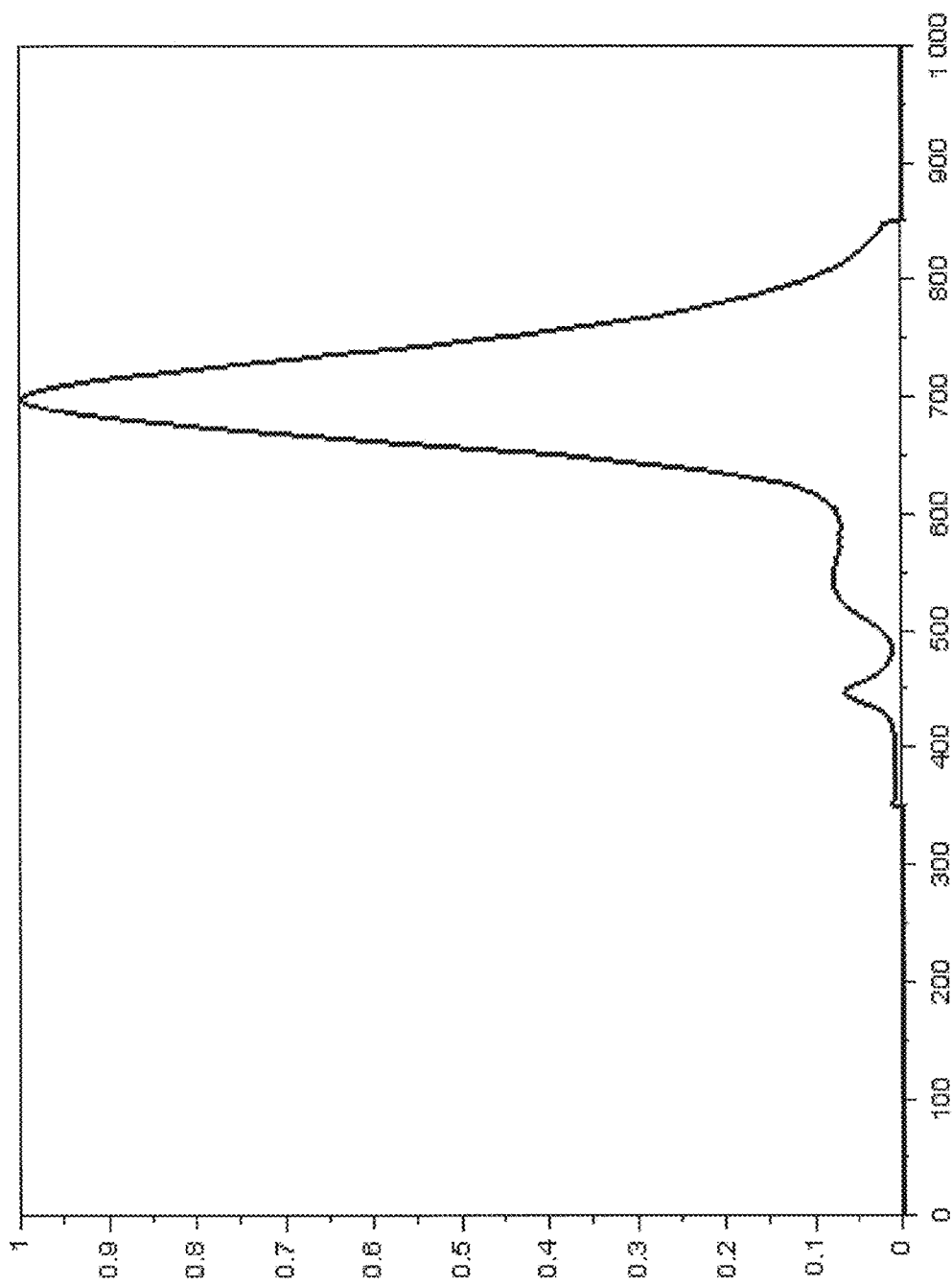
Figure 35:
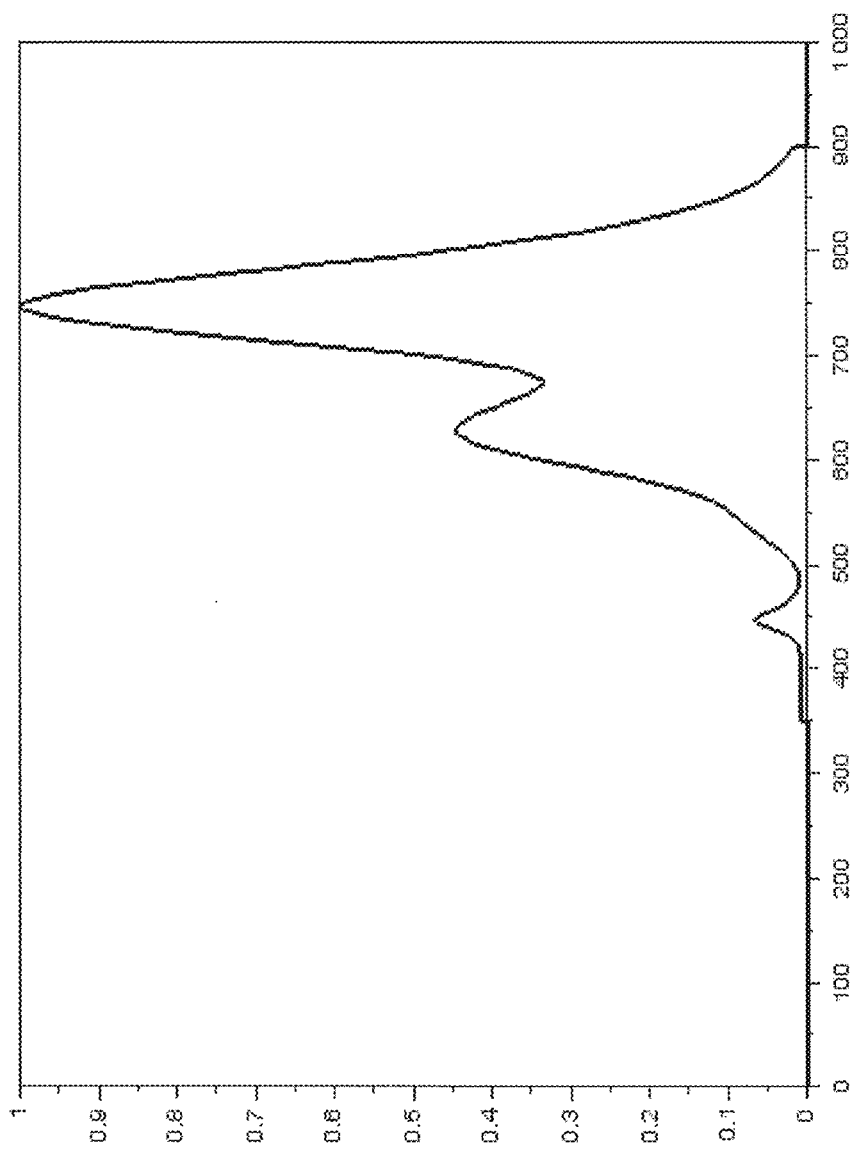
Figure 36:
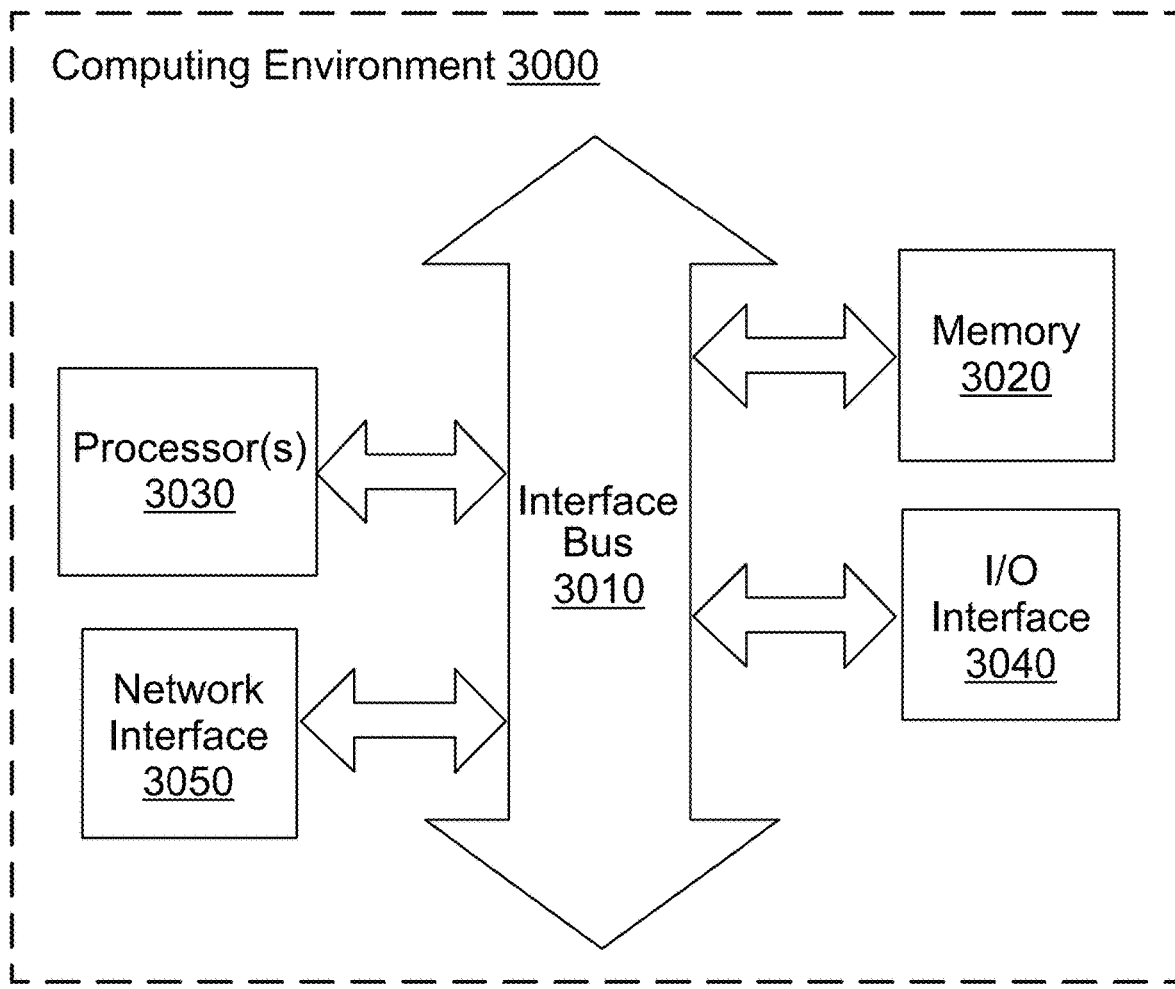
Figure 37:
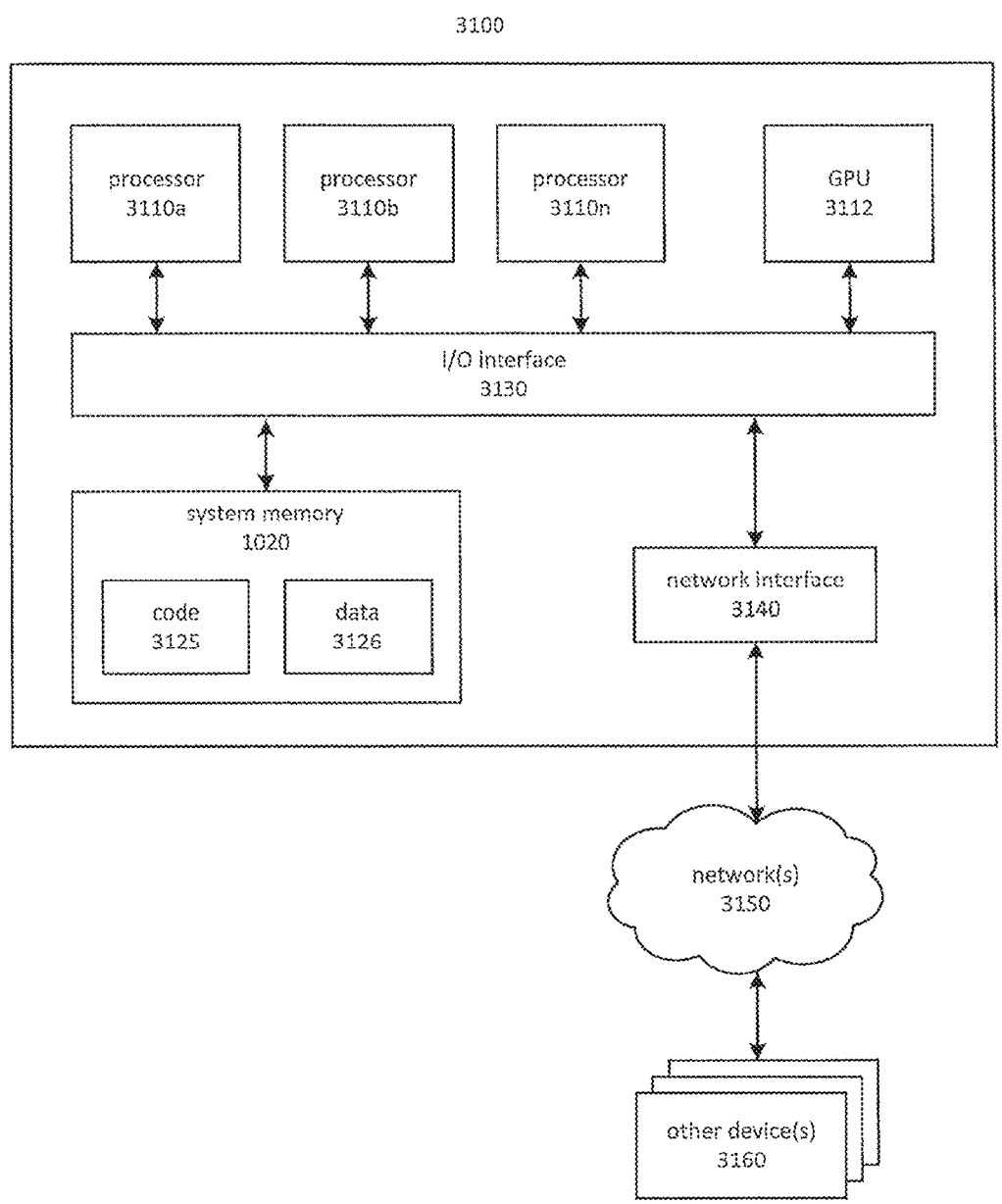
Figure 38:
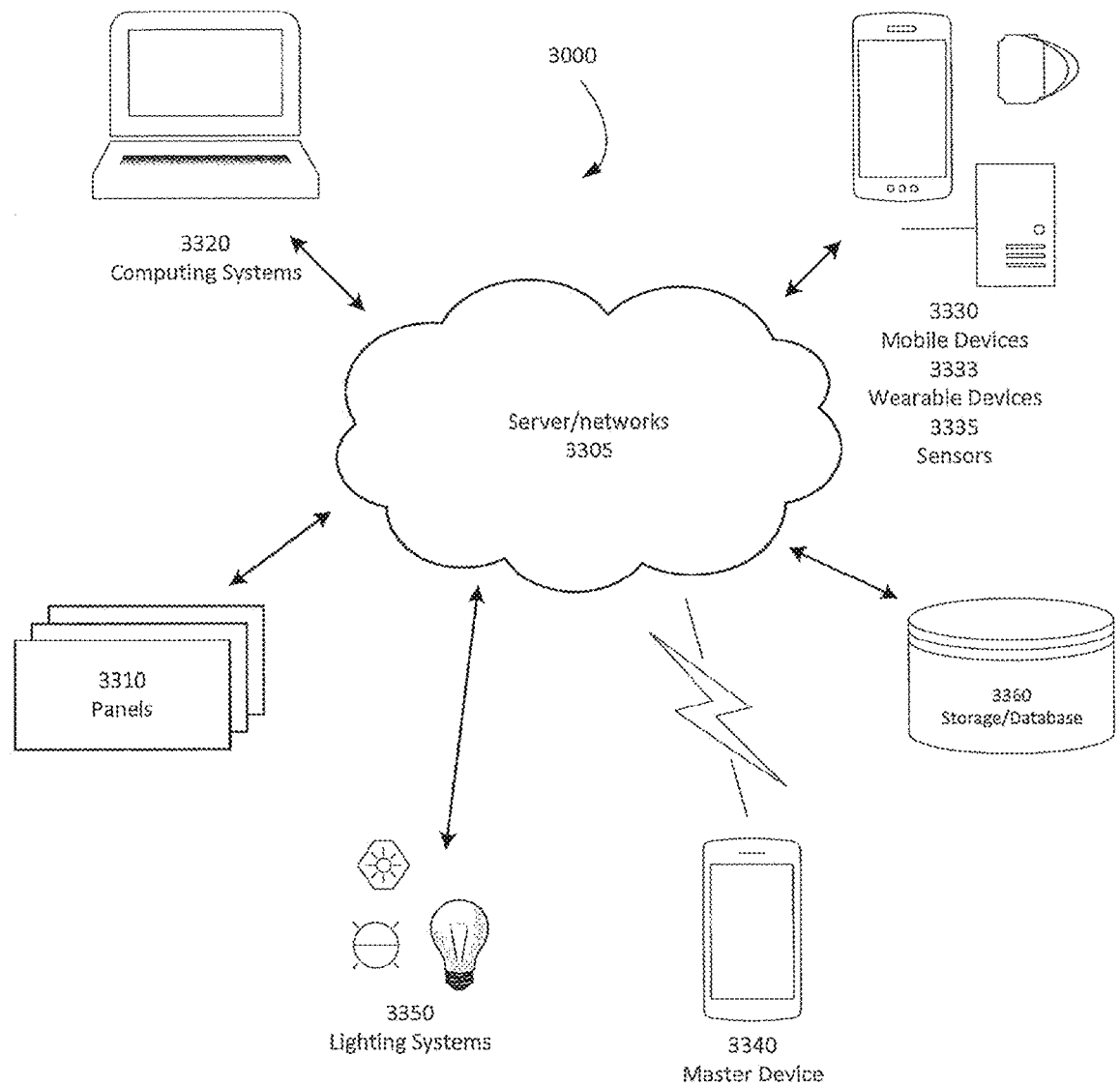

FIG. 32 illustrates some aspects of display systems according to the present disclosure, including aspects of spectral power distributions for light generated by components of the display systems;

FIG. 33 illustrates some aspects of display systems according to the present disclosure, including aspects of spectral power distributions for light generated by components of the display systems;

FIG. 34 illustrates some aspects of display systems according to the present disclosure, including aspects of spectral power distributions for light generated by components of the display systems;

FIG. 35 illustrates some aspects of display systems according to the present disclosure, including aspects of spectral power distributions for light generated by components of the display systems;

FIG. 36 depicts aspects of control of the bioactive illumination;

FIG. 37 is a block diagram of computing systems and methods of control of bioactive illumination; and, FIG. 38 is an overview of a bioactive illumination control systems and methods.

Figure 39:
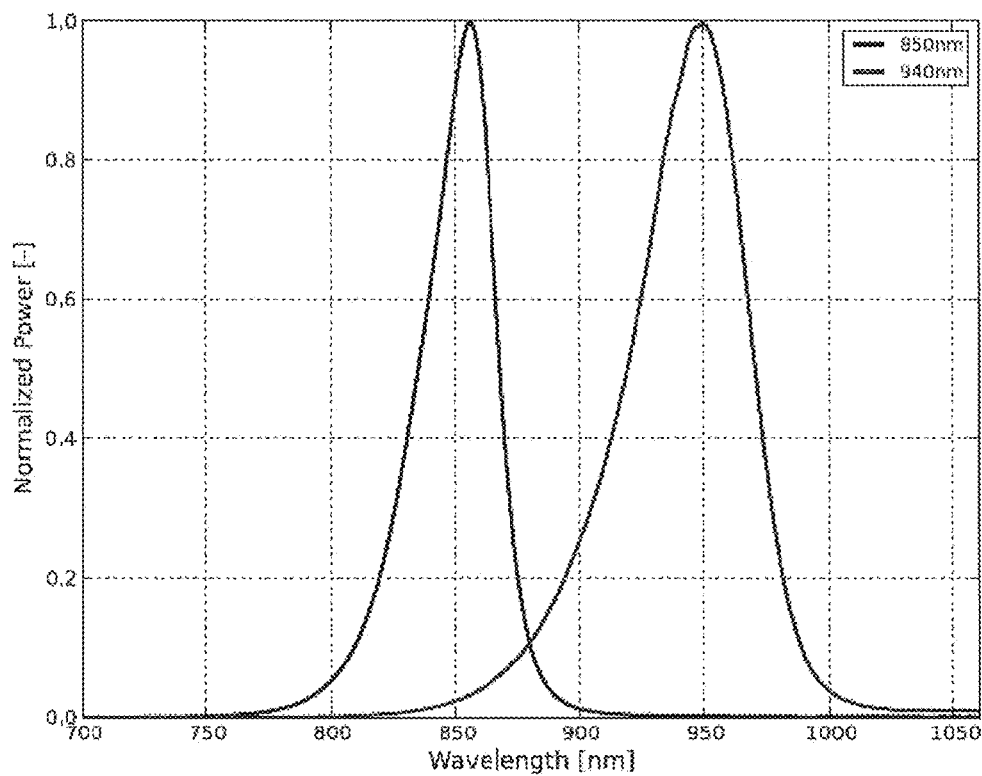

FIG. 39 illustrates some aspects of LRNE spectral power distributions for light generated by components of display systems according to the present disclosure.

Figure 40:
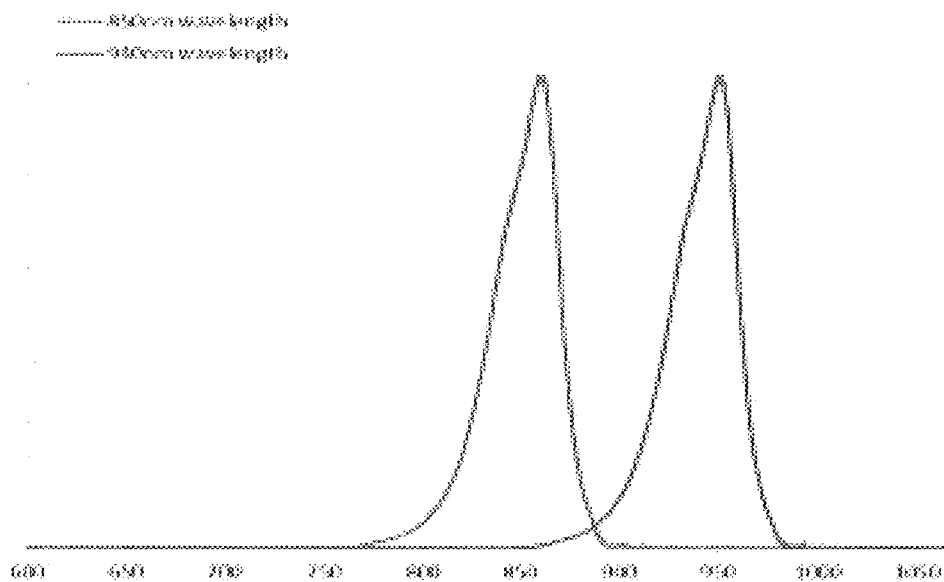

FIG. 40 illustrates some aspects of LRNE spectral power distributions for light generated by components of display systems according to the present disclosure.

Figure 41:
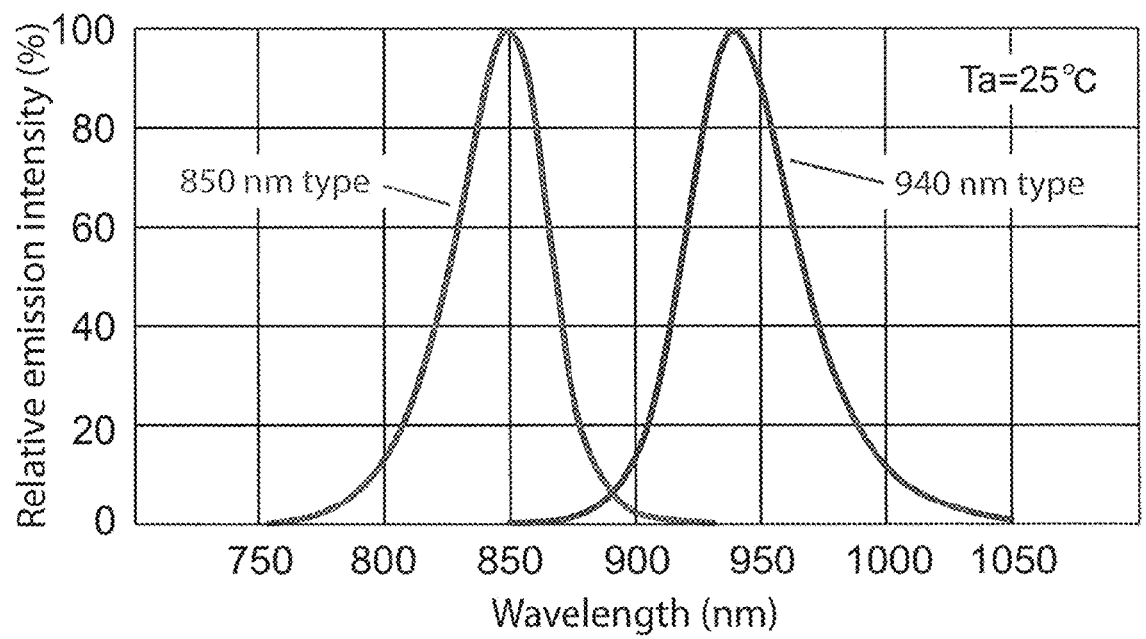

FIG. 41 illustrates some aspects of LRNE spectral power distributions for light generated by components of display systems according to the present disclosure.

Figure 42:
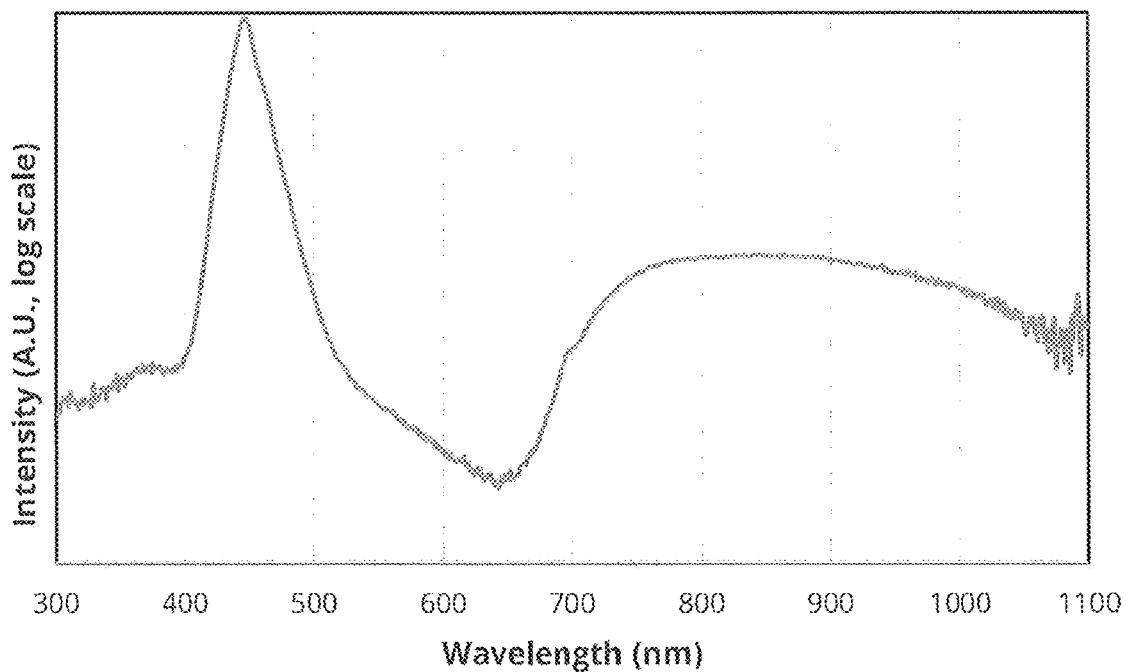

FIG. 42 illustrates some aspects of LRNE spectral power distributions for light generated by components of display systems according to the present disclosure.

Figure 43:
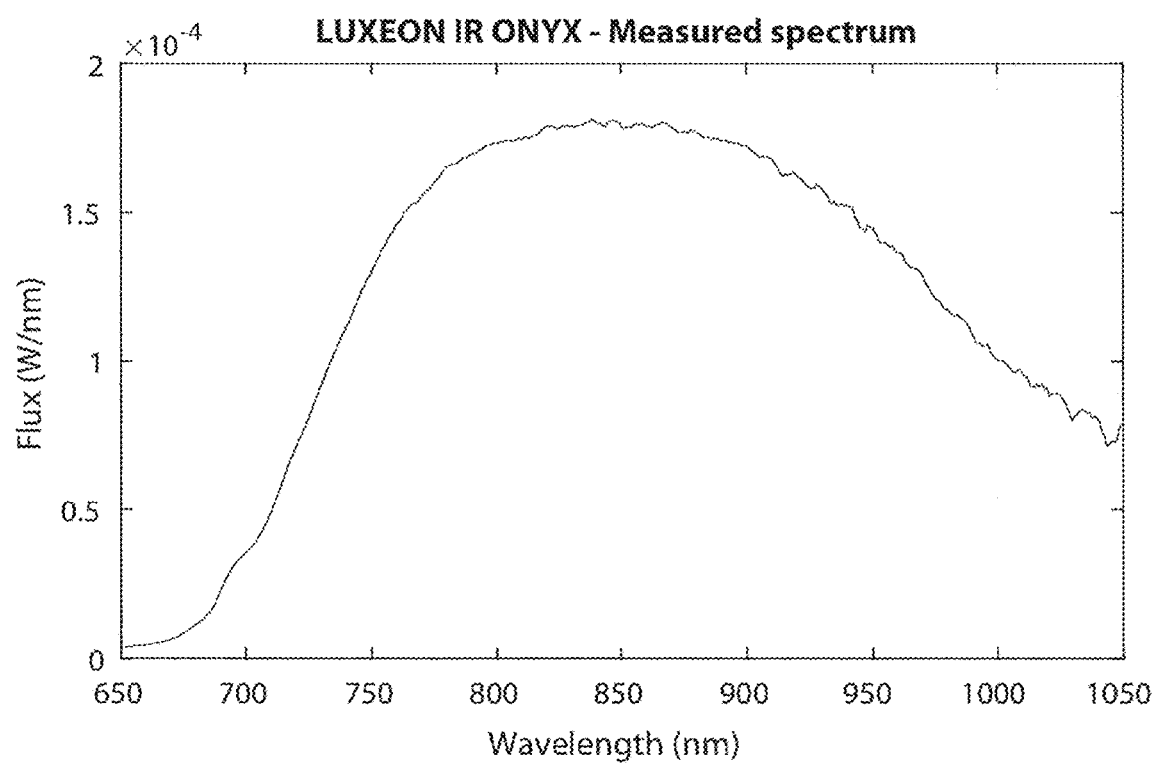

FIG. 43 illustrates some aspects of LRNE spectral power distributions for light generated by components of display systems according to the present disclosure.

Figure 44:
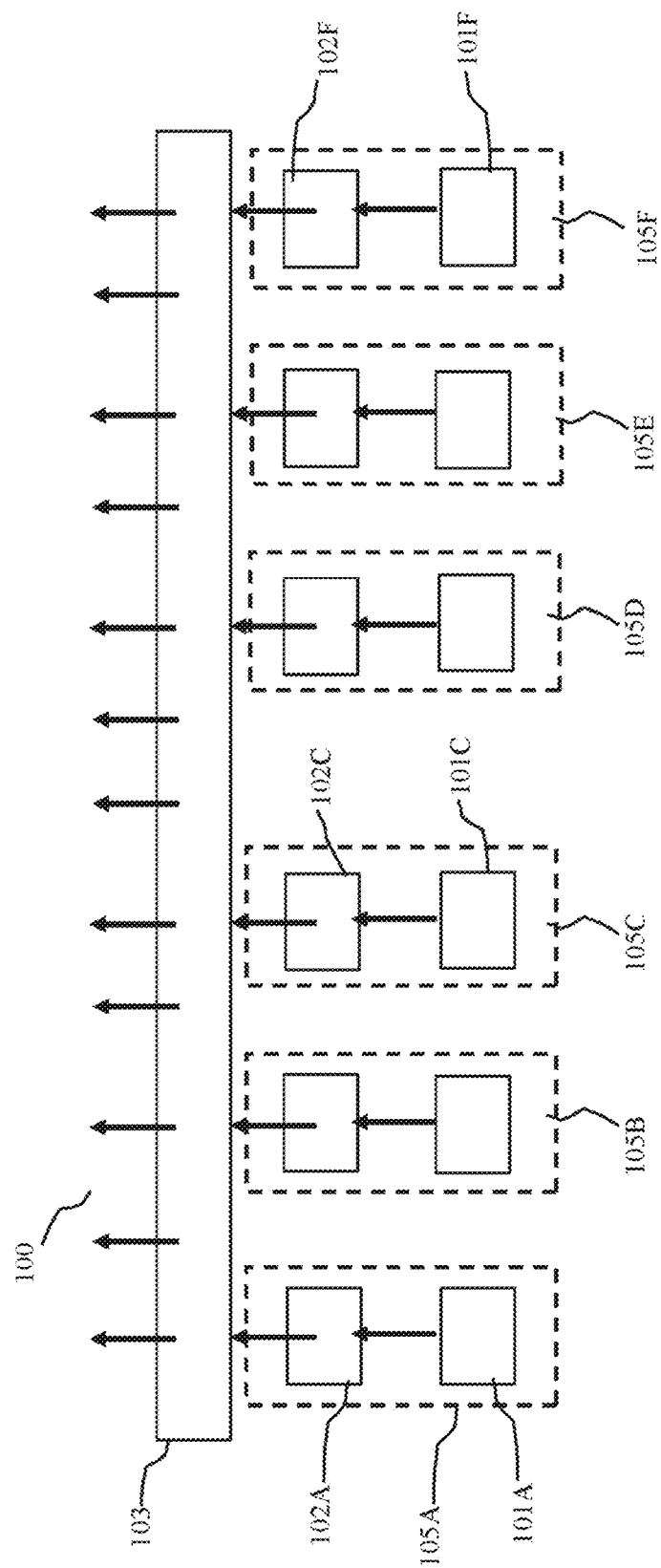
Figure 45:
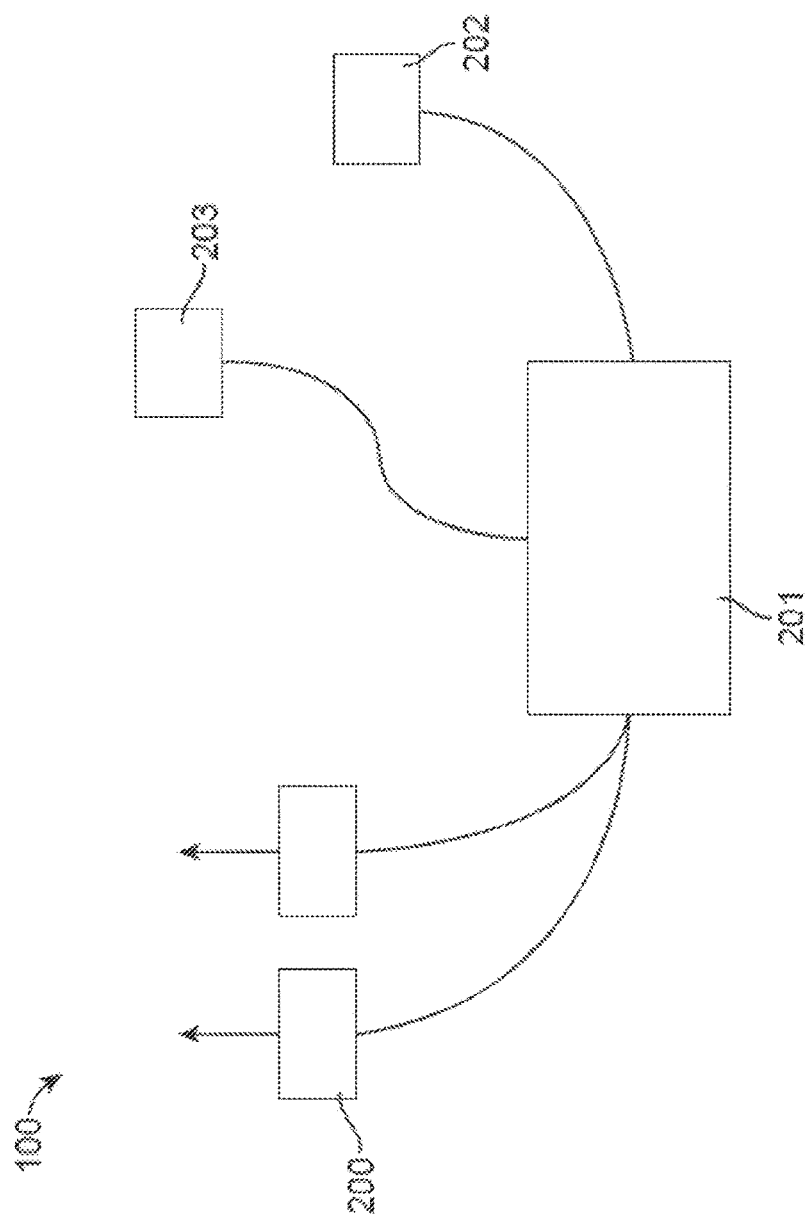
Figure 46:
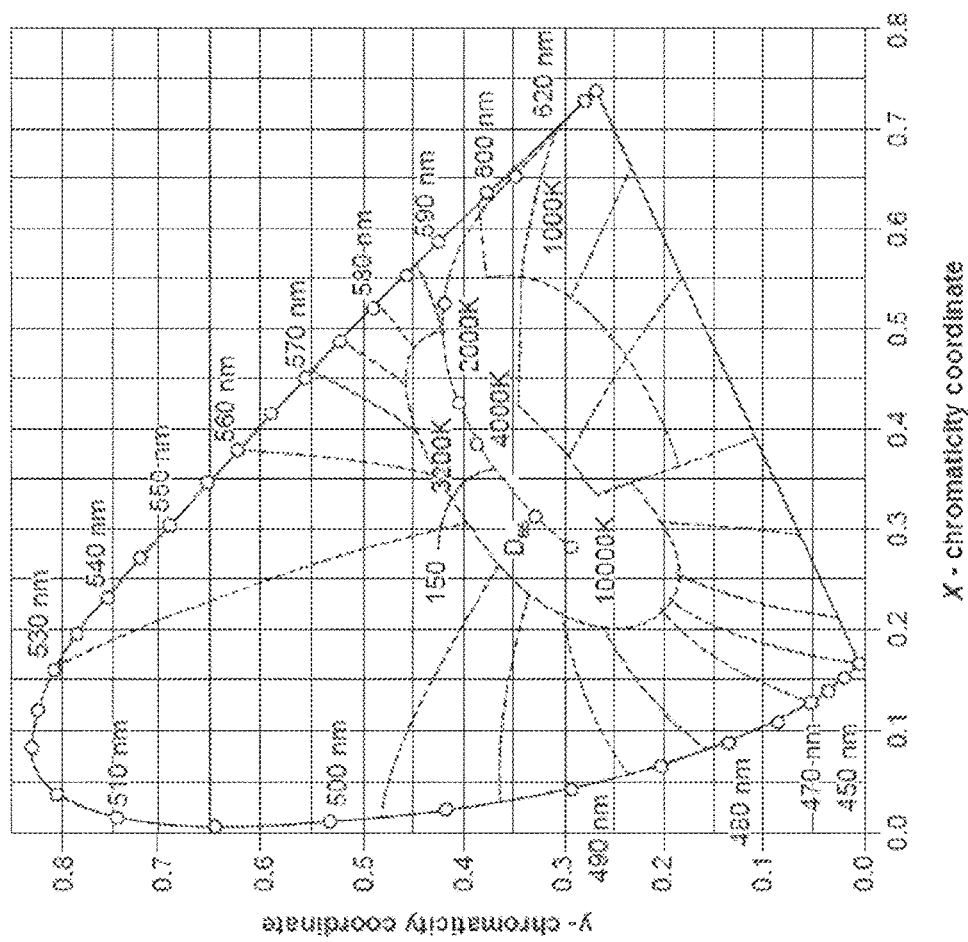
Figure 47:
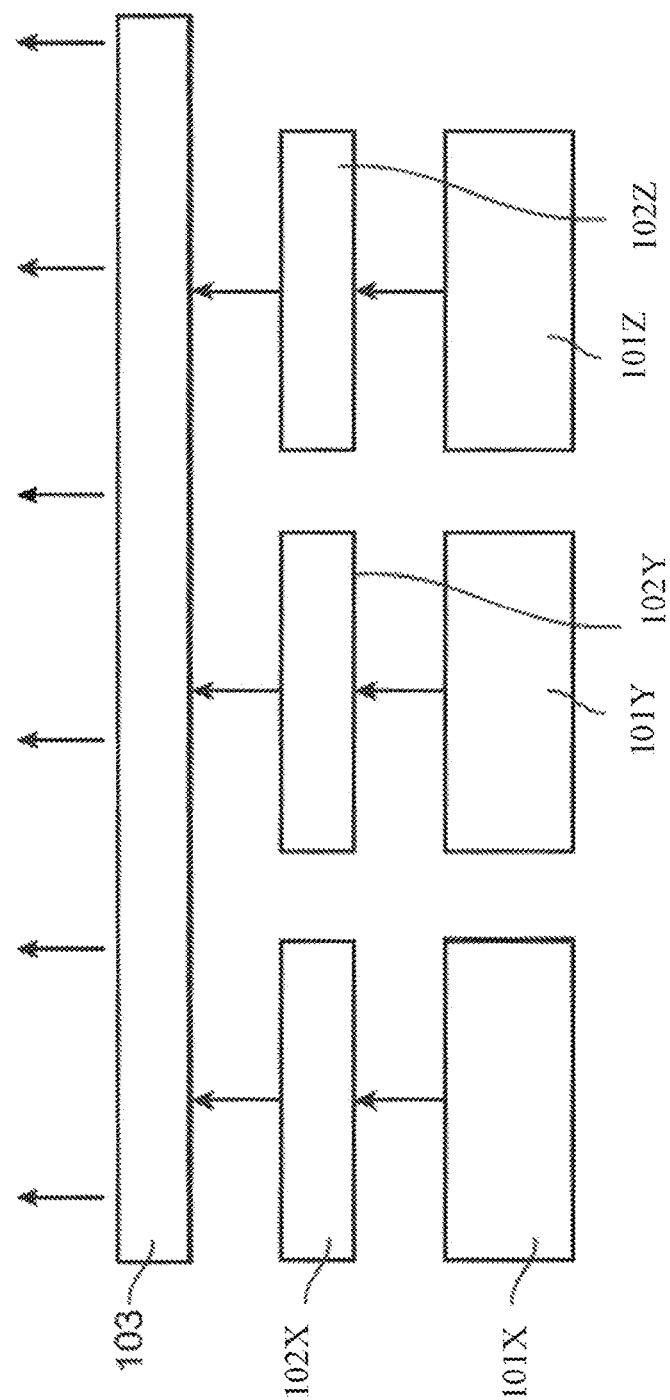

FIG. 44 illustrates aspects of light emitting devices according to the present disclosure;

FIG. 45 illustrates aspects of light emitting devices according to the present disclosure;

FIG. 46 depicts a graph of a 1931 CIE Chromaticity Diagram illustrating the location of the Planckian locus;

FIG. 47 illustrates aspects of light emitting devices according to the present disclosure:

FIGS. 48A and 48B illustrate a simplified wearable bioactive lighting system and device.

FIG. 49 illustrates aspects of a simplified control system for wearable bioactive lighting systems and devices.

Figure 50A:
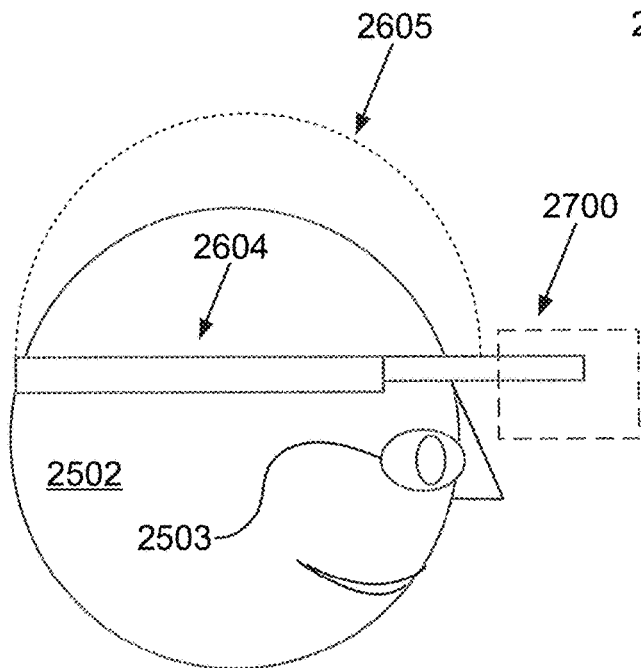

FIG. 50A illustrates aspects of a wearable bioactive lighting systems and devices.

FIGS. 50B through 50F illustrate exemplars of supports of FIG. 50A of a wearable bioactive lighting systems and devices.

FIGS. 51A through 51D illustrate aspects of a wearable bioactive lighting systems and devices.

Figure 52:
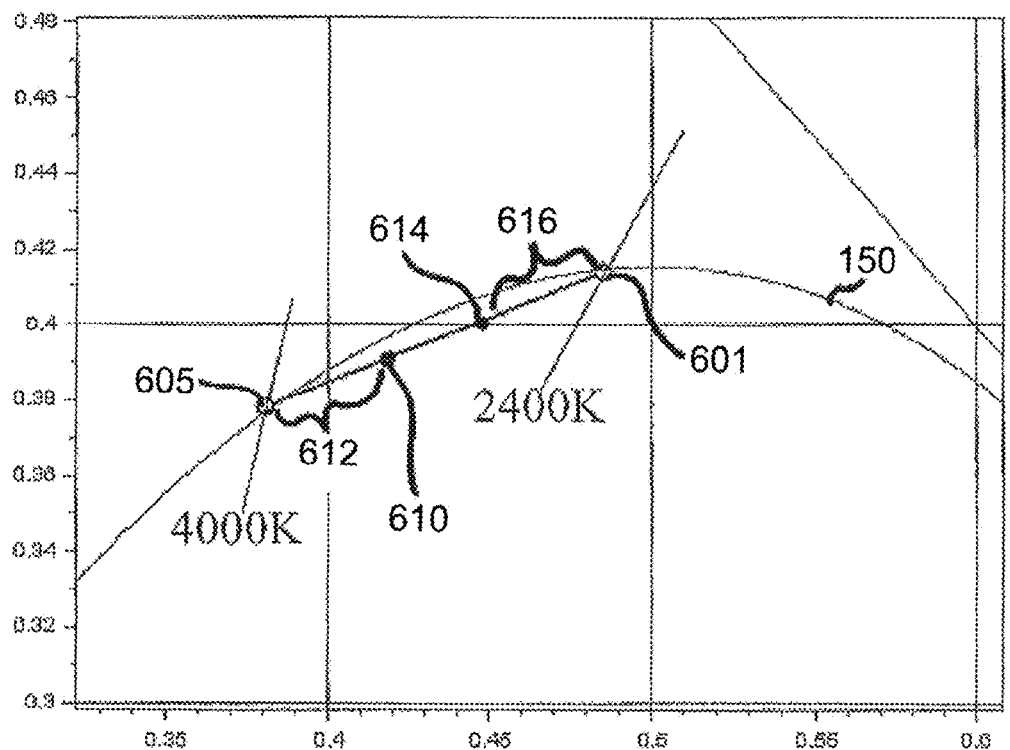
Figure 53:
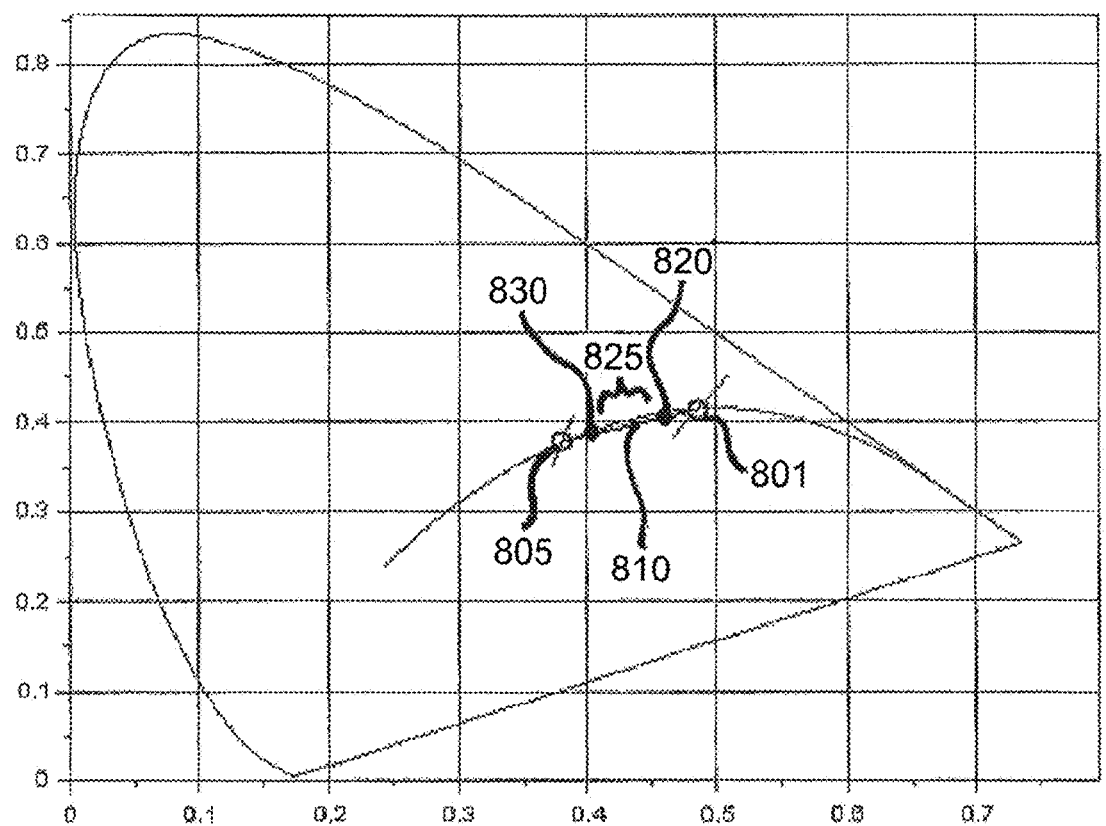
Figure 54:
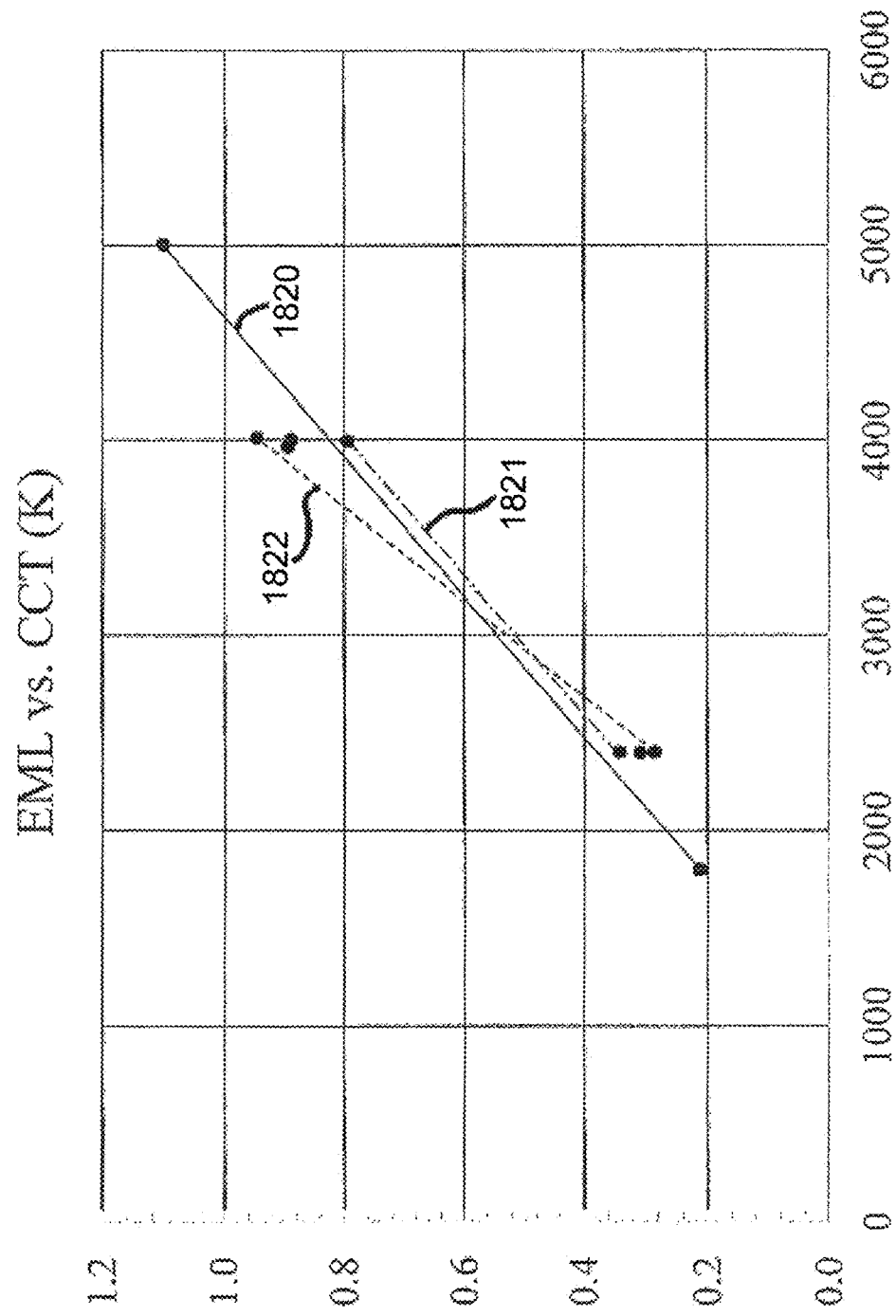

FIG. 52 illustrates some aspects of lighting systems according to the present disclosure;

FIG. 53 illustrates some aspects of lighting systems according to the present disclosure:

FIG. 54 illustrates some aspects of lighting systems according to the present disclosure;

All descriptions and callouts in the Tables and Figures are hereby incorporated by this reference as if fully set forth herein.

FURTHER DISCLOSURE

The present disclosure may be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular exemplars by way of example only and is not intended to be limiting of the claimed disclosure. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another exemplar includes from the one particular value and/or to the other particular value. Similarly, when values are expressed as approximations, by use of the antecedent "about." it will be understood that the particular value forms another exemplar. All ranges are inclusive and combinable.

The term "circadian-stimulating energy characteristics" refers to any characteristics of a spectral power distribution that may have biological effects on a subject. In some aspects, the circadian-stimulating energy characteristics of aspects of the lighting systems of this disclosure can include one or more of CS, CLA, EML, BLH, CER, CAF, LEF, circadian power, circadian flux, and the relative amount of power within one or more particular wavelength ranges. Circadian-stimulating energy may be referred to as "CSE". The application of CSE to biological systems in doses, amount, aliquots and volumes may be referred to as CSE therapy.

Benefits of Blue Light

Exposure to blue light including CSE affects various bio-physiological and psychological functions of the human body and may be called "bioactive". Many of these effects are beneficial. For instance, a region of what is commonly called the blue wavelength region of light may improve memory performance and cognitive function. Exposure to blue wavelength light during memory consolidation has been shown to improve subsequent delayed memory recall when compared to placebo wavelength light exposure. Alkozei, A., Smith R., Dailey N. S., Bajaj S., & Killgore W. D. S. (2017). Acute Exposure to a quantity, volume, aliquot or dose of a specific Blue Wavelength Light During Memory Consolidation Improves Verbal Memory Performance. *PLoS ONE* 12(9), 1-11. Additionally, blue wavelength light may decrease blood pressure, increase blood flow, and improve overall endothelial function. Full body irradiation with blue light has been shown to promote release nitric oxide from the skin into circulating blood. As a result, systolic blood pressure and vascular resistance have been shown to decrease. Stem, M. et al. (2018). Blue Light Exposure Decreases Systolic Blood Pressure, Arterial Stiffness, and Improves Endothelial Function in Humans. *European Journal of Preventive Cardiology* 0(00), 1-9.

Challenges of Blue Light.

In some instances exposure to a quantity of blue light may be involved in damage in human eyes. Blue Light Hazard (BLH) is a known risk and the measure of BLH provides a measure of potential for a photochemical induced retinal injury that results from radiation exposure. Such exposure is one factor which has been linked to photoreceptor damage. It has been reported that the blue light appears to decrease Adenosine Triphosphate (ATP) energy production in retinal ganglion cells. This has a negative effect on mitochondrial function and oxidative stress which has been shown to decrease survival of ganglion cells. Tosini, G., Ferguson, I., & Tsubota, K. (2016). Effects of Blue Light on the Circadian System and Eye Physiology. *Molecular Vision: Biology and Genetics in Vision Research* 22, 61-72. As ganglion cells play a major role in synchronizing circadian rhythms, their destruction inhibits the eye's ability to determine length-of-day and length-of-night. Retinal ganglion cell death further leads to impaired vision. There is also increasing evidence that excessive blue light exposure may cause damage in human skin; it may contribute to wrinkles, worsening skin laxity, and pigmentation issues. Arjmandi, N., Mortazavi G. H., Zarei, S., Faraz M., & Mortazavi, S. A R. (2018). Can Light Emitted from Smartphone Screens and Taking Selfies Cause Premature Aging and Wrinkles? *Journal of Biomedical and Physical Engineering* 8(4), 447-452. When blue light penetrates the skin it can damage DNA, leading to inflammation, the breakdown of healthy collagen and elastin, and hyperpigmentation. Vandersee, S., Beyer, M., Lademann, J., & Darvin, M. E. (2015). Blue-Violet Light Irradiation Dose Dependently Decreases Carotenoids in Human Skin, Which Indicates the Generation of Free Radicals. *Oxidative Medicine and Cellular Longevity*. doi: 10.1155/2015/579675. It is also reported that excessive blue light at night negatively affects the human body's natural sleep cycle. Blue light, which inhibits melatonin production, reduces both quantity and quality of sleep.

Benefits of Long Red and Near IR.

Blue light is not the only light in the visible spectrum that can be used to affect bio-physiological functions and/or psychological functions (also referred to herein as "bioactive") of the human body. Recent studies indicate that therapy which may include doses of long red and near-IR: Long Red typically with a spectrum of >625 nms to <700 nms with peak wavelengths >640-670 nm and Near-Infrared typical ranges from >700 nms and <1400 nm (with typical peak wavelengths: 850 nm, 940 nm, 1064 nm) may affect bio-physiological functions and are also described herein as "bioactive" they may improve eye health, skin health, hair growth, and cognitive function. The spectral sensitivity corresponding to the human eye can be considered to be based on the color-matching functions of the 1931 Standard Observer (XYZ tristimulus values for CIE 1931 2° color-matching), which show that the effect of light above 700 nm on color perception to be substantially negligible. In other words, it will have no significant impact on the overall (ccx, ccy) color point on the 1931 CIE Chromaticity Diagram of emitted light from a lighting system. Emissions of Long Red and Near-Infrared may be referred to collectively as Long Red and Near-Infrared Energy (LRNE). How the human eye perceives red, long red and near infrared in a given individual may vary based on a plethora of factors including but not limited to age, stimulation of eye before exposure, eye health and health in general. Accordingly, there will be an overlap between the end of long red and the beginning of near infrared. Those of ordinary skill in the art and the skilled artisan will recognize variation is narrow and does not create substantial uncertainty in the terms. Hence the terminology LRNE is encompasses the entirety of both long red and near-infrared.

Additionally, LRNE may be beneficial by reducing, limiting, counteracting or ameliorating some of the negative effects associated with excessive blue light exposure. Disclosed herein are methods and systems to provide therapeutic doses of LRNE either to address a biological condition or as a prophylactic or health supplement means to limit or prevent at least one of an emotional, neurological, immune, and biological condition or system. "Bioactive Exposure" refers to one or both of LRNE and CSE and directing at least one of LRNE and CSE at a biological system which may be a specific organ or any part of the body.

The Bioactive Exposure may be controlled by a control system (described herein, see e.g., FIG. 38 whereby at least one controller, e.g., a computing device receives inputs including fixed, variable and dynamically changing from a variety of sources and the processor associated with the system and method applies at least one of LRNE and CSE in accordance with said control system. Control input data is at least one of input by: users, server, database, derived from a decisioning engine and collected by at least one sensor. The inputs are provided to a processor via signal communication. The processor may be local to the therapeutic device, remote from the therapeutic device or the processing may take place both locally and remote from the therapeutic device. Control systems disclosed herein may adjust the amount and timing of aliquots of bioactive Exposure. The control of aliquots and frequency in response to input may be used to dynamically adjust the therapeutic or health supplement application of one or more of CSE and LRNE to users. Dynamic adjustment of Bioactive Exposure to a user may be viewed as personalized whereby data harvested from sensors in the lighting installation environment as well as sensors that reflect information about users, such as one or more of physiological sensors (including wearable devices, such as armbands, wrist bands, chest bands, glasses, clothing, and the like), sensors on various devices used by a user, ambient sensors, and the like. The control system may have modules within the platform which may connect to or integrate with data sources of information about users as described below. The frequency of the LRNE and CSE are controllable and the range of emission spans constant on to micro-pulses of less than a tenth of a second. Light pulses can be used to provide Bioactive Exposure. Such pulse may have a duration of less than 100 ms, with a frequency between 10 Hz and 0.5 mHz and have been shown to have a bioactive effect, such pulses may vary from a single pulse up to 400,000 pulses.

Disclosed herein are additional methods and systems to provide Bioactive Exposure as one of a supplement and therapeutic dose of LRNE to:

A. Lessen the effect of age-related macular degeneration by stimulating mitochondria in retinal ganglion eye cells to produce more ATP energy. (Calaza, K. C., Kam, J. H., Hogg, C., & Jeffery G. (2015) and *Neurobiology of Aging* 36, 2869-2876.) The increase in ATP production has been shown to slow the decline in vision associated with aging. LRNE may additionally improve the effects of glaucoma, a condition that destroys ganglion eye cells, by protecting the cornea and the retina. (Olmo-Aguado, S., Núñez-Álvarez, C., & Osborne, N. N. (2016). Red Light of the Visual Spectrum Attenuates Cell Death in Culture and Retinal Ganglion Cell Death in Situ. *Acta Ophthalmologica* 94, e481-e491).

B. Address a biological condition or as a prophylactic or supplement means to limit or prevent a biological condition. Examples include but are not limited to, to prevent fluid build-up in the front of the eye, a main complication of glaucoma known to result in cell death of ganglion cells. LRNE has been shown to prevent the death of retinal ganglion cells when the optic nerve has been damaged, thereby preventing vision loss that would otherwise occur. (Kwok-Fai, S., Leung. M. C. P., & Cui, Q. (2014). Effects of Low Laser Treatment on the Survival of Axotomized Retinal Ganglion Cells in Adult Hamsters. *Neural Regeneration Research* 9(21), 1863-1869.)

C. improve skin health and appearance by the application of LRNE therapy. LRNE can reduce acute and chronic inflammation by increasing blood flow to damaged tissues. (Hamblin, M. R. (2017). Mechanisms and Applications of the Anti-Inflammatory Effects of Photobiomodulation. *AIMS Biophysics* 4(3), 337-361.) LRNE may be applied to increase natural collagen production, resulting in younger, healthier looking skin. Rats that were exposed to doses of LRN experienced an increase in collagen synthesis and neoformed bone. Brassoliatti, P. et al. (2018). Photobiomodulation on Critical Bone Defects of Rat Calvaria: A Systematic Review. *Lasers in Medical Science* 33(9), 1841-1848. Patients dealing with acne or depigmentation conditions, such as vitiligo, may benefit from undergoing LRN therapy, as it can control sebum production (which leads to acne), and it can stimulate melanocyte proliferation (which enhances skin re-pigmentation). Skin that has been wounded, burned, or scarred also repairs more rapidly if it is exposed to LRN, as red light significantly increases tensile strength and wound contraction while decreasing inflammation. Avci, P. et al. (2013). Low-level Laser (Light) Therapy (LLLT) in Skin: Stimulating, Healing, Restoring. *Semin Cutan Medical Surgery* (32)(1), 41-52.

D. A myriad of other bio-physiological function are impacted by LRNEs, including but not limited to, hair growth and cognitive function. LRNE therapy may be used in conjunction with or as an alternative treatment to hormone regulating drugs typically used to treat hair loss. LRNE exposure has been shown to be a treatment in terms of hair regrowth. Gupta. A. K., Mays, et al. (2018). Efficacy of Non-Surgical Treatments for Androgenetic Alopecia: A Systematic Review and Network Meta-Analysis. *Journal of The European Academy of Dermatology and Venereology* 32(12), 2112-2125. Research has also demonstrated that LRNE exposure may lead to improved cognitive function with few side effects. In one study, those exposed to LRNE experienced quicker reaction times, better memory, a more positive mood, and the ability to learn new information faster. These beneficial effects on the human brain may be related to LRNE's increasing cerebral blood flow and oxygen availability and boost ATP energy production. Hennessy, M., & Hamblin, M. (2017). Photobiomodulation and the Brain: A New Paradigm. *Journal of Optics* 19(1):013003.

E. LRNE therapy may be able to counteract, limit or ameliorate the negative effects from excessive CSE and blue light exposure. When humans absorb natural blue light from the sun, they also absorb natural red light from the sun-together the two provide numerous health benefits. However, an overload of artificial blue light such as CSE by itself may be determinantal. This damage can be mitigated through LRN exposure. Balancing and/or controlling an exposure of both artificial blue light and LRNE support wellness benefits similar to those that flow from natural, sunlight exposure.

It is to be appreciated that certain features of the disclosure which are, for clarity, described herein in the context of separate exemplar, may also be provided in combination in a single exemplary implementation. Conversely, various features of the disclosure that are, for brevity, described in the context of a single exemplary implementation, may also be provided separately or in any subcombination. Further, reference to values stated in ranges include each and every value within that range.

The 1931 CIE Chromaticity diagram is a two-dimensional chromaticity space in which every visible color is represented by a point having x- and y-coordinates, also referred to herein as (ccx, ccy) coordinates. Fully saturated (monochromatic) colors appear on the outer edge of the diagram, while less saturated colors (which represent a combination of wavelengths) appear on the interior of the diagram. The term "saturated", as used herein, means having a purity of at least 85%, the term "purity" having a well-known meaning to persons skilled in the art, and procedures for calculating purity being well-known to those of skill in the art. The Planckian locus, or black body locus (BBL), is known to those of skill in the art and follows the color an incandescent black body would take in the chromaticity space as the temperature of the black body changes from about 1000K to 10,000 K. The black body locus goes from deep red at low temperatures (about 1000 K) through orange, yellowish white, white, and finally bluish white at very high temperatures. The temperature of a black body radiator corresponding to a particular color in a chromaticity space is referred to as the "correlated color temperature." In general, light corresponding to a correlated color temperature (CCT) of about 2700 K to about 6500 K is considered to be "white" light. In particular, as used herein, "white light" generally refers to light having a chromaticity point that is within a 10-step MacAdam ellipse of a point on the black body locus having a CCT between 2700K and 6500K. However, it will be understood that tighter or looser definitions of white light can be used if desired. For example, white light can refer to light having a chromaticity point that is within a seven step MacAdam ellipse of a point on the black body locus having a CCT between 2700K and 6500K. The distance from the black body locus can be measured in the CIE 1960 chromaticity diagram, and is indicated by the symbol Auv, or DUV or duv as referred to elsewhere herein. If the chromaticity point is above the Planckian locus the DUV is denoted by a positive number; if the chromaticity point is below the locus, DUV is indicated with a negative number. If the DUV is sufficiently positive, the light source may appear greenish or yellowish at the same CCT. If the DUV is sufficiently negative, the light source can appear to be purple or pinkish at the same CCT. Observers may prefer light above or below the Planckian locus for particular CCT values, and light above or below the Planckian locus may be more or less suitable for use in displaying digital content on display systems in different settings or operational modes. DUV calculation methods are well known by those of ordinary skill in the art and are more fully described in ANSI C78.377. American National Standard for Electric Lamps-Specifications for the Chromaticity of Solid State Lighting (SSL) Products, which is incorporated by reference herein in its entirety for all purposes. The CIE Standard Illuminant D65 illuminant is intended to represent average daylight and has a CCT of approximately 6500K and the spectral power distribution is described more fully in Joint ISO/CIE Standard, ISO 10526:1999/CIE 5005/E-1998, CIE Standard Illuminants for Colorimetry, which is incorporated by reference herein in its entirety for all purposes.

The color points described in the present disclosure can be within color-point ranges defined by geometric shapes on the 1931 CIE Chromaticity Diagram that enclose a defined set of ccx, ccy color coordinates. It should be understood that any gaps or openings in any described or depicted boundaries for color-point ranges should be closed with straight lines to connect adjacent endpoints in order to define a closed boundary for each color-point range.

The light emitted by a light source may be represented by a point on a chromaticity diagram, such as the 1931 CIE chromaticity diagram, having color coordinates denoted (ccx, ccy) on the X-Y axes of the diagram. A region on a chromaticity diagram may represent light sources having similar chromaticity coordinates.

The ability of a light source to accurately reproduce color in illuminated objects can be characterized using the color rendering index ("CRI"), also referred to as the CIE Ra value. The Ra value of a light source is a modified average of the relative measurements of how the color rendition of an illumination system compares to that of a reference black-body radiator or daylight spectrum when illuminating eight reference colors R1-R8. Thus, the Ra value is a relative measure of the shift in surface color of an object when lit by a particular lamp. The Ra value equals 100 if the color coordinates of a set of test colors being illuminated by the illumination system are the same as the coordinates of the same test colors being irradiated by a reference light source of equivalent CCT. For CCTs less than 5000K, the reference illuminants used in the CRI calculation procedure are the SPDs of blackbody radiators; for CCTs above 5000K, imaginary SPDs calculated from a mathematical model of daylight are used. These reference sources were selected to approximate incandescent lamps and daylight, respectively.

Daylight generally has an Ra value of nearly 100, incandescent bulbs have an Ra value of about 95, fluorescent lighting typically has an Ra value of about 70 to 85, while monochromatic light sources have an Ra value of essentially zero. Light sources for general illumination applications with an Ra value of less than 50 are generally considered very poor and are typically only used in applications where economic issues preclude other alternatives. The calculation of CIE Ra values is described more fully in Commission Internationale de l'Éclairage. 1995. *Technical Report: Method of Measuring and Specifying Colour Rendering Properties of Light Sources*, CIE No. 13.3-1995. Vienna, Austria: Commission Internationale de l'Éclairage, which is incorporated by reference herein in its entirety for all purposes. In addition to the Ra value, a light source can also be evaluated based on a measure of its ability to render a saturated red reference color R9, also known as test color sample 9 ("TCS09"), with the R9 color rendering value ("R9 value"). Light sources can also be evaluated based on a measure of ability to render additional colors R10-R15, which include realistic colors like yellow, green, blue, Caucasian skin color (R13), tree leaf green, and Asian skin color (R15), respectively. Light sources can further be evaluated by calculating the gamut area index ("GAI"). Connecting the rendered color points from the determination of the CIE Ra value in two dimensional space will form a gamut area. Gamut area index is calculated by dividing the gamut area formed by the light source with the gamut area formed by a reference source using the same set of colors that are used for CRI. GAI uses an Equal Energy Spectrum as the reference source rather than a black body radiator. A gamut area index related to a black body radiator ("GAIBB") can be calculated by using the gamut area formed by the blackbody radiator at the equivalent CCT to the light source.

The ability of a light source to accurately reproduce color in illuminated objects can be characterized using the metrics described in *IES Method for Evaluating Light Source Color Rendition*, Illuminating Engineering Society, Product ID: TM-30-15 (referred to herein as the "TM-30-15 standard"), which is incorporated by reference herein in its entirety for all purposes. The TM-30-15 standard describes metrics including the Fidelity Index (Rf) and the Gamut Index (Rg) that can be calculated based on the color rendition of a light source for 99 color evaluation samples ("CES"). The 99 CES provide uniform color space coverage, are intended to be spectral sensitivity neutral, and provide color samples that correspond to a variety of real objects. Rf values range from 0 to 100 and indicate the fidelity with which a light source renders colors as compared with a reference illuminant. Rg values provide a measure of the color gamut that the light source provides relative to a reference illuminant. The range of Rg depends upon the Rf value of the light source being tested. The reference illuminant is selected depending on the CCT. For CCT values less than or equal to 4500K, Planckian radiation is used. For CCT values greater than or equal to 5500K, CIE Daylight illuminant is used. Between 4500K and 5500K a proportional mix of Planckian radiation and the CIE Daylight illuminant is used, according to the following equation:

$$S_{r,M}(\lambda, T_t) = \frac{5500 - T_t}{1000} S_{r,P}(\lambda, T_t) + \left(1 - \frac{5500 - T_t}{1000}\right) S_{r,D}(\lambda, T_t),$$

where $T_t$ is the CCT value, $S_{r,M}(\lambda,T_t)$ is the proportional mix reference illuminant, $S_{r,P}(\lambda,T_t)$ is Planckian radiation, and $S_{r,D}(\lambda,T_t)$ is the CIE Daylight illuminant.

Circadian illuminance (CLA) is a measure of circadian effective light, spectral irradiance distribution of the light incident at the cornea weighted to reflect the spectral sensitivity of the human circadian system as measured by acute melatonin suppression after a one-hour exposure, and CS, which is the effectiveness of the spectrally weighted irradiance at the cornea from threshold (CS=0.1) to saturation (CS=0.7). The values of CLA are scaled such that an incandescent source at 2856K (known as CIE Illuminant A) which produces 1000 lux (visual lux) will produce 1000 units of circadian lux (CLA). CS values are transformed CLA values and correspond to relative melotonian suppression after one hour of light exposure for a 2.3 mm diameter pupil during the mid-point of melotonian production. CS is calculated from $$CS = 0.7\left(1 - \frac{1}{1 + \left(\frac{CLA}{355.7}\right)^{\wedge 1.126}}\right).$$

The calculation of CLA is more fully described in Rea et al., "Modelling the spectral sensitivity of the human circadian system," Lighting Research and Technology, 2011; 0: 1-12, and Figueiro et al., "Designing with Circadian Stimulus", October 2016, LD+A Magazine, Illuminating Engineering Society of North America, which are incorporated by reference herein in its entirety for all purposes. Figueiro et al. describe that exposure to a CS of 0.3 or greater at the eye, for at least one hour in the early part of the day, is effective for stimulating the circadian system and is associated with better sleep and improved behavior and mood.

Equivalent Melanopic Lux (EML) provides a measure of photoreceptive input to circadian and neurophysiological light responses in humans, as described in Lucas et al., "Measuring and using light in the melanopsin age." Trends in Neurosciences, January 2014, Vol. 37, No. 1, pages 1-9, which is incorporated by reference herein in its entirety, including all appendices, for all purposes. Melanopic lux is weighted to a photopigment with λmax 480 nm with pre-receptoral filtering based on a 32 year old standard observer, as described more fully in the Appendix A, Supplementary Data to Lucas et al. (2014), User Guide: Irradiance Toolbox (Oxford 18 Oct. 2013). University of Manchester. Lucas Group, which is incorporated by reference herein in its entirety for all purposes. EML values are shown in the tables and Figures herein as the ratio of melanopic lux to luminous flux, with luminous flux considered to be 1000 lumens. It can be desirable for biological effects on users to provide illumination having higher EML in the morning, but lower EML in the late afternoon and evening.

Blue Light Hazard (BLH) provides a measure of potential for a photochemical induced retinal injury that results from radiation exposure. Blue Light Hazard is described in IEC/EN 62471, Photobiological Safety of Lamps and Lamp Systems and Technical Report IEC/TR 62778: Application of IEC 62471 for the assessment of blue light hazard to light sources and luminaires, which are incorporated by reference herein in their entirety for all purposes. A BLH factor can be expressed in (weighted power/lux) in units of $\mu W/cm^2/lux$.

In some aspects the present disclosure relates to lighting devices and methods to provide light having particular vision energy and circadian energy performance. Many figures of merit are known in the art, some of which are described in Ji Hye Oh, Su Ji Yang and Young Rag Do, "Healthy, natural, efficient and tunable lighting: four-package white LEDs for optimizing the circadian effect, color quality and vision performance," Light: Science & Applications (2014) 3: e141-e149, which is incorporated herein in its entirety, including supplementary information, for all purposes. Luminous efficacy of radiation ("LER") can be calculated from the ratio of the luminous flux to the radiant flux ($S(\lambda)$), i.e. the spectral power distribution of the light source being evaluated, with the following equation:

$$LER\left(\frac{lm}{W}\right) = 683\left(\frac{lm}{W}\right)\frac{\int V(\lambda)S(\lambda)d\lambda}{\int S(\lambda)d\lambda}.$$

Circadian efficacy of radiation ("CER") can be calculated from the ratio of circadian luminous flux to the radiant flux, with the following equation:

$$CER\left(\frac{blm}{W}\right) = 683\left(\frac{blm}{W}\right)\frac{\int C(\lambda)S(\lambda)d\lambda}{\int S(\lambda)d\lambda}.$$

Circadian action factor ("CAF") can be defined by the ratio of CER to LER, with the following equation:

$$\left(\frac{blm}{lm}\right) = \frac{CER\left(\frac{blm}{W}\right)}{LER\left(\frac{lm}{W}\right)}.$$

The term "blm" refers to biolumens, units for measuring circadian flux, also known as circadian lumens. The term "lm" refers to visual lumens. $V(\lambda)$ is the photopic spectral luminous efficiency function and $C(\lambda)$ is the circadian spectral sensitivity function. The calculations herein use the circadian spectral sensitivity function. $C(\lambda)$, from Gall et al., Proceedings of the CIE Symposium 2004 on Light and Health: Non-Visual Effects, 30 Sep.-2 Oct. 2004; Vienna, Austria 2004. CIE: Wien, 2004, pp 129-132, which is incorporated herein in its entirety for all purposes. By integrating the amount of light (milliwatts) within the circadian spectral sensitivity function and dividing such value by the number of photopic lumens, a relative measure of melatonin suppression effects of a particular light source can be obtained. A scaled relative measure denoted as melatonin suppressing milliwatts per hundred lumens may be obtained by dividing the photopic lumens by 100. The term "melatonin suppressing milliwatts per hundred lumens" consistent with the foregoing calculation method is used throughout this application and the accompanying figures and tables. The melatonin suppression index (MSI) of a light source can be calculated from the ratio of the integration of cross product constant lumen spectrum of lamp with melatonin suppression action spectrum in wavelength range 380 nm to 780 nm to the integration of cross product of constant lumen spectrum of Day light spectrum at 6500K with melatonin suppression action spectrum in 380 nm to 780 nm region. The function melatonin suppression action spectrum, "MSAS" or $M(\lambda)$, is defined by Thapan K, "An action spectrum for melatonin suppression: evidence for a novel non-rod, non-cone photoreceptor system in humans", Journal of Physiology, 2001, 535: 261-267, which is incorporated herein for all purposes.

The ability of a light source to provide illumination that allows for the clinical observation of cyanosis is based upon the light source's spectral power density in the red portion of the visible spectrum, particularly around 660 nm. The cyanosis observation index ("COI") is defined by AS/NZS 1680.2.5 Interior Lighting Part 2.5: Hospital and Medical Tasks, Standards Australia, 1997 which is incorporated by reference herein in its entirety, including all appendices, for all purposes. COI is applicable for CCTs from about 3300K to about 5500K, and is preferably of a value less than about 3.3. If a light source's output around 660 nm is too low a patient's skin color may appear darker and may be falsely diagnosed as cyanosed. If a light source's output at 660 nm is too high, it may mask any cyanosis, and it may not be diagnosed when it is present. COI is a dimensionless number and is calculated from the spectral power distribution of the light source. The COI value is calculated by calculating the color difference between blood viewed under the test light source and viewed under the reference lamp (a 4000 K Planckian source) for 50% and 100% oxygen saturation and averaging the results. The lower the value of COI, the smaller the shift in color appearance results under illumination by the source under consideration.

The ability of a light source to accurately reproduce color in illuminated objects can be characterized by the Television Lighting Consistency Index ("TLCI-2012" or "TLCI") value Qa, as described fully in EBU Tech 3355, Method for the Assessment of the Colorimetric Properties of Luminaires, European Broadcasting Union ("EBU"), Geneva, Switzerland (2014), and EBU Tech 3355-si, An Introduction to Spectroradiometry, which are incorporated by reference herein in their entirety, including all appendices, for all purposes. The TLCI compares the test light source to a reference luminaire, which is specified to be one whose chromaticity falls on either the Planckian or Daylight locus and having a color temperature which is that of the CCT of the test light source. If the CCT is less than 3400 K, then a Planckian radiator is assumed. If the CCT is greater than 5000 K, then a Daylight radiator is assumed. If the CCT lies between 3400 K and 5000 K, then a mixed illuminant is assumed, being a linear interpolation between Planckian at 3400 K and Daylight at 5000 K. Therefore, it is necessary to calculate spectral power distributions for both Planckian and Daylight radiators. The mathematics for both operations is known in the art and is described more fully in CIE Technical Report 15:2004, Colorimetry $3^{rd}$ ed., International Commission on Illumination (2004), which is incorporated herein in its entirety for all purposes.

Displays

Aspects of the present inventions relate to display systems that are adapted to produce and display color(s) at the pixel level that can be used to help in inducing and/or regulating a circadian rhythm cycle in a person looking at the displays or otherwise proximate the display. The display systems may be computer displays or television displays. The lighting system for the display systems pixels may be arranged to produce colors of the pixels in the display that effect the circadian rhythm over the course of time. The lighting system may be adapted to generate a circadian stimulating energy (CSE) blue frequency of light (e.g. cyan, energy at and/or near 485 nm) that causes activity associated with 'waking' the person through the circadian cycle (e.g. effecting, causing, or maintaining a wakeful and alert state in the viewer by enabling melatonin suppression by exciting the Intrinsically photosensitive retinal ganglion cells (ipRGCs)). It may also be adapted to reduce the circadian-inducing blue frequency over time to reduce the 'waking' effect. The lighting system may further be adapted with two or more separate blue frequencies such that either or both may be used to generate the blue in the pixels of the display. One of the blue frequencies may be a standard blue color (e.g. substantial energy around approximately 450 nm, a narrow band emission around approximately 450 nm) such that the display pixel generates standard display colors and another blue frequency may be a circadian-inducing blue (e.g. a cyan emission, substantial energy around approximately 485 nm, a narrow or broad band emission around approximately 485 nm) that is designed to effect the circadian rhythm in a more significant way by waking the person. With such a display, the display pixel colors can be changed from standard colors to represent colors accurately, according to display color standards, to display colors that are similar but not necessarily standard colors to generate an effect of the person's circadian rhythm. While the non-standard blue pixels may not be standard and may not display computer generated content in accordance with a standard color pallet, in many situations the colors may be acceptable by a user because the colors may still be acceptable while also inducing a circadian rhythm to awaken the person while using the display in the special color mode.

The CSE blue may have significant energy at a longer wavelength than the typical blue used in a display. The inventors have appreciated that longer wavelengths in the blue and cyan regions (e.g. wavelengths between the typical display blue and typical display green) can be used to both generate acceptable colors in the computer-generated content and also have a greater effect on a person's circadian rhythm. In some embodiments, the energy may be provided in a narrow band (e.g. a typical LED narrow band emission spectra with a maximum energy between 460 nm and 500 nm, 460 nm and 480 nm, 470 nm and 480 nm, or 490 nm and 500 nm). In embodiments, the energy may be more broadly spread (e.g. through the use of a phosphor or quantum dot structure) such that there is significant energy produced in the region between 460 nm and 500 nm. In such broad width systems the maximum energy may or may not fall within the 460 nm to 500 nm region. For example, the peak may be at or near the typical display blue of 450 nm and also have significant energy in the 460 nm to 500 nm region. The significant energy may be an intensity of more than 10%, 20%, 30%, 40%, or 50% of the maximum energy. That significant energy may fall within the regions of 460 and 470 nm, 470 nm and 480 nm, or 490 nm and 500 nm for example.

A computer display according to the principles of the present inventions may include a micro-LED array where the micro-LED array includes a pixel array formed of micro-LEDs including red, green and blue generating LEDs. In embodiments, the blue LED may be a circadian rhythm inducing blue LED (as described herein). If only three colors are arranged in the pixel array, the circadian-inducing blue for the pixel may not fall within the standard color gamut for the display but will generally generate acceptable colors while effecting the circadian rhythm. In embodiments, the pixel array includes two different color generating blue LEDs, one with a standard color for the display and one that may not be within the standard color gamut for display but that is adapted to affect the circadian rhythm to induce a waking effect. This arrangement would include four colors per pixel in the pixel array of the micro-LED array. In embodiments, the computer display includes only a portion of micro-LEDs with the circadian rhythm effecting blue. The micro-LED pixels may be built with different color generating LEDs, white LEDs with filters, LEDs with phosphors, etc.

In some embodiments, the CSE blue microLED may have a narrow emission characteristic where substantially all of the energy is produced over 120 nm or so and having a full width at half maximum (FWHM) of about 40 nm. FIG. 3a illustrates and example spectral power distribution of such a microLED. In embodiments, the circadian-inducing blue microLED may have a broader emission characteristic. FIG. 3c illustrates one such example spectral power distribution. The broader emission may be developed by adding a phosphor to the microLED system, by using a number of narrow band emission microLEDs, etc. In embodiments, a filter may be associated with the microLED. For example, the desired blue color point may include an emission band that is broader than is achievable through a single narrow emission microLED so a phosphor or multiple narrow band LEDs may be used to broaden the emission and then a filter may be used to cut the broader emission down to the desired amount.

A standard color computer display may use a blue LED with a narrow emission characteristic, such as is illustrated in FIG. 3b. In some embodiments, the standard blue may be replaced with a broader band blue, such as is illustrated in FIG. 3d, to add some cyan to the emission (i.e. slightly longer wavelength energy). This configuration may also include a filter to cut the long tail but maintain some emission in the circadian blue emission region.

Aspects of a computer display in some implementations may include an LCD backlit pixel array. Generally, an LCD backlit display has a backlight that generates a broadband of colors (e.g. white LEDs, white fluorescent) or one that generates narrow bands of color (e.g. red, green, and blue LEDs). Manufactures have typically adopted an arrangement where the backlight is a broadband white LED based system and each pixel of the LCD array is associated with a colored filter (e.g. red, green and blue) to produce the full color gamut for each pixel of the display. In some embodiments, the LCD pixel array includes filters to produce three colors per pixel based on a backlighting system that produces white light. The pixel filters filter the white light into red, green and blue. The backlight also generally produces a constant amount of light and the LCD's at each sub pixel color are changed to regulate the intensity of the color of the sub pixel (e.g. 256 steps based on a polarization setting at the sub pixel level). In embodiments, the blue filter is adapted to transmit light that is more effective at effecting the circadian rhythm (e.g. 485 nm). In embodiments, each pixel includes a fourth filter for a fourth sub pixel color. The fourth pixel uses a circadian blue pass filter such that light transmitting the sub pixel filter effects the circadian cycle in a more significant way than light passing through a standard blue filter in the pixel array. With the fourth filter configuration, the display may be set to use one and/or the other color of blue to form the blue in the pixels.

In some embodiments, the backlight produces red, green and blue in a sequence and only one LCD is used per pixel position such that the one LCD will turn on in sequence with the desired corresponding required color for the pixel. The sequential lighting system may than include a circadian-inducing blue color to affect the circadian rhythm. The sequential lighting system may further include two different colors of blue (e.g. standard blue and circadian blue) and the sequence cycles through all four colors. In embodiments, the circadian blue color may or may not be included in every cycle of the sequence. Reducing the number of cycles involves may have an effect on the perceived combined color of the pixel and of the effect of the circadian rhythm.

In some embodiments of the LCD configuration(s), the backlight may be modified to include enhanced emission at the circadian blue region. For example, a cyan LED may be included in the backlight itself such that it produces enough emission in the circadian blue region that it can generate adequate color for display and effect on the person's circadian rhythm. The backlight may include a broadband emission source (e.g. as illustrated in FIG. 3c) or a narrow emission source (e.g. as illustrated in FIG. 3a) for this purpose. The filter associated with the circadian blue pixels can then be adjusted to transmit the desired bandwidth of light in the region. Traditionally, the backlights used in a display do not produce much emission in this desired region so changing the lighting system to include more emission in this region may be desirable.

A computer display according to aspects of some implementations may include an OLED pixel array where the OLED array includes a pixel array formed of OLED sub pixels. The OLEDs may include red, green and blue generating OLEDs. In some embodiments, the OLEDs may produce white light and include filters to pass only the particular color desired for the sub pixel. In embodiments, the blue OLED or filter may be adapted to produce a circadian rhythm inducing blue color. If only three colors are arranged in the pixel array, the blue for the pixel may not fall within the standard color for the display but will generally generate acceptable colors while effecting the circadian rhythm. In embodiments, the pixel array may include two different color blue OLEDs, one with a standard color for the display and one that may not be within the standard color gamut for display but that is adapted to affect the circadian rhythm wake cycle. This arrangement would include four colors per pixel in the pixel array of the OLED array. In embodiments, the computer display includes only a portion of OLEDs with the circadian rhythm effecting blue.

In some embodiments, the OLED may produce a broadband of light in the region and be filtered. In embodiments, the circadian-inducing OLED may produce a narrow band emission and possibly be filtered or not.

In some implementations aspects relate to the inclusion of more than three standard colors in a computer display pixel array. The more than three colors may include the addition of a color(s) that is intended to provide a bioactive display that is switchable between a standard color gamut and a modified color gamut. The modification to the pixel colors may be adapted to produce pixel colors that can affect a person's physiological and psychological functions while maintaining the display as an effective computer display for the presentation of digital content. A control system, computer processor associated with the display may be used, either automatically (e.g. based on sensed conditions, based on time of day, based on a schedule) or through a user interface, to switch between the two modes. Such a system may also be operated in a mode where both a standard blue and circadian blue are operated simultaneously or through a rapid switching mode (e.g. pulse width modulation to regulate the apparent intensity of each one). The modified color pixel array is bioactive and may be regulated by the control system and/or a computer system to determine dose or aliquot of light of a particular characteristic or mode by a change the pixel colors over time to assist in regulating the person's circadian cycle or other physiological and psychological functions.

In some implementations the red spectrum may be positioned in the long red near infrared energy (LRNE) region. In some instances the system may switch between the two modes. Such a system may also be operated in a mode where both a standard red and LRNE red are operated simultaneously or through a rapid switching mode (e.g. pulse width modulation to regulate the apparent intensity of each one). The modified color pixel array is bioactive and may be regulated by the control system. In some instances red in the LRNE non-visible region also referred to as near infrared may be used simultaneously or through a rapid switching mode with red or long red. Spectral power distributions shown in FIGS. 29-31. Region 1550 represents LRNE emissions which are considered by CIE standards previously noted to be outside the visual spectrum of humans The control system may further operate based on data sources that describe the user of the display (e.g. wearable sensors, sleep sensors, as described herein).

Figure 1:
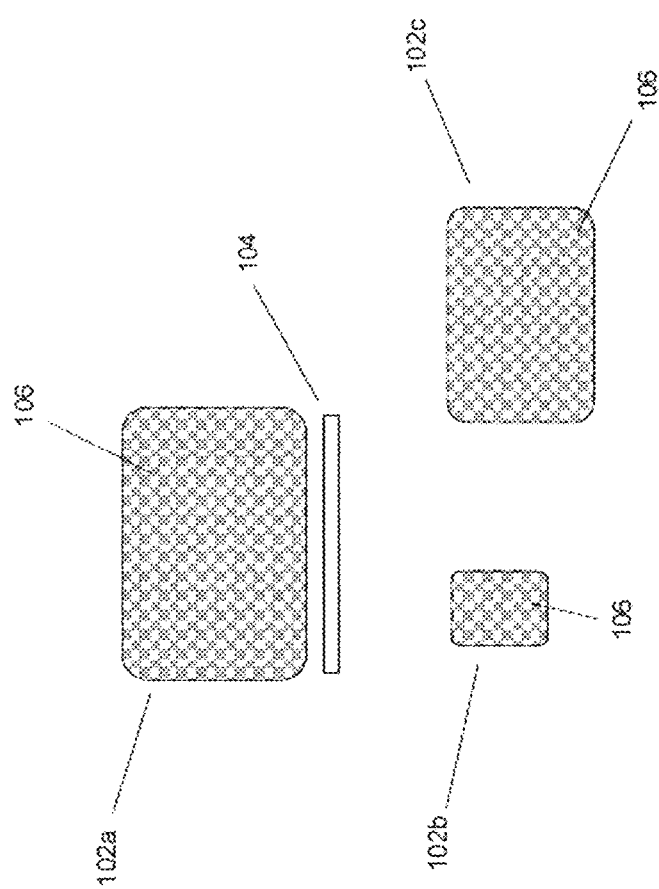
FIG. 1 illustrates aspects of display systems according to the present disclosure.

FIG. 1 illustrates some examples of computer displays 102 in various configurations. Each of the configurations includes an array of pixels 106 positioned and controlled to display computer-generated content. One configuration is a desktop computer display 102*a*. The desktop configuration includes a peripheral 104 (e.g. keyboard, mouse, drawing pad, Bluetooth connected device, WiFi connected device). The desktop, or any other configuration, may receive data from personal devices (e.g. a user's fitbit, sleep sensor) and adjust the color and/or intensity of the light emitted by the pixels 106. Device 102*b* is a small touch screen device (e.g. phone, pda). Device 102*c* is a tablet device, which may have a touch screen. The display could also be a television, which may be an Internet device, radio receiver device, cable TV device, satellite TV device, etc.

Figure 2:
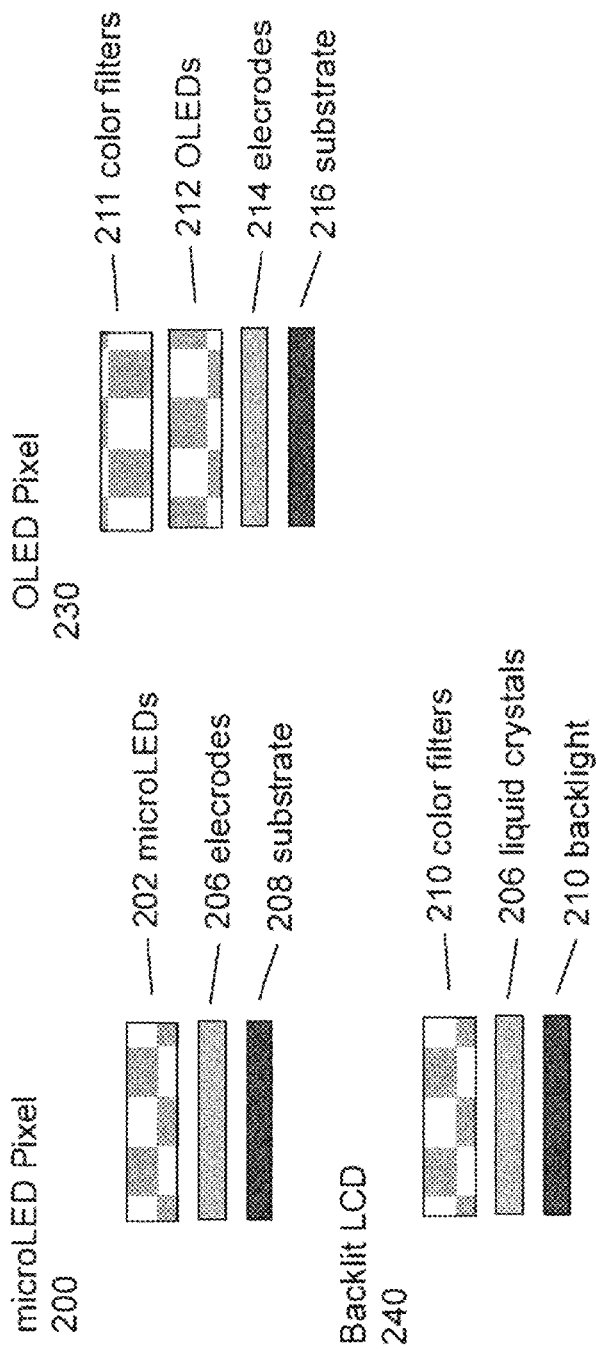
FIG. 2 illustrates aspects of display systems according to the present disclosure, including aspects of lighting systems therein.

FIG. 2 illustrates various examples of bioactive lighting pixel constructions that may be built into a display in accordance with the principles of the present inventions. These examples are simplified examples of the basic construction of the various display technologies at a pixel level. The three examples presented are the microLED 200, OLED 230, and backlit LCD 240. Each of these examples uses a pixel technology that generates light at the pixel level that is outside of the normal display color gamut and at a color point or frequency that is known to affect a person's circadian rhythm and other physiological and psychological functions.

A microLED based computer display may be based on an array of microLED pixels 200. Each micoLED pixel 200 in the area of the display may include different color producing microLEDs 200, electrodes 208 to power and control each microLED in each pixel, and a substrate 208. Each of the microLEDs may emit light of a particular color based on the materials used in the construction of the microLED. As a secondary example, the microLED(s) may be arranged to irradiate a phosphor for color conversion or they may be arranged to transmit light through a filter. In embodiments, the microLEDs in the pixel may be red, green and circadian blue. The circadian blue may be a blue outside of the normal blue gamut that is used in a display. It may be a blue with spectral characteristics of the circadian lighting systems disclosed herein. In a configuration where only three colors are included in the pixel, the color gamut of the display may always be outside of the standard display gamut. This may be acceptable to a user that is less concerned about the exact color of displayed content and more concerned with receiving a light that effects the user's circadian rhythm while still having reasonable colors produced. In another embodiment, the pixel may include four colors: red, green, standard display blue and circadian blue. This configuration lends itself to a control system that can switch between the standard blue and the circadian blue. The circadian blue may be used in the morning hours, for example, and then the display may switch to the standard blue in later hours. In yet later hours, the standard blue may be turned down to further reduce the stimulation of the circadian rhythm. The two blues may fade in and out in a synchronized fashion. Both may be on at one time to reduce the circadian blue as the system transitions to the standard blue. In some implementations described herein the red spectrum may be positioned in the long red near infrared energy (LRNE) region. In some instances the system may switch between the two modes. Such a system may also be operated in a mode where both a standard red and LRNE red are operated simultaneously or through a rapid switching mode (e.g. pulse width modulation to regulate the apparent intensity of each one). The modified color is bioactive and may be regulated by the control system. In some instances red in the LRNE non-visible region also referred to as near infrared may be used simultaneously or through a rapid switching mode with red or long red. The LRNE may be applied in doses or aliquots based on sensor data or other inputs to the control systems. Such LRNE may be used as a health supplement based controls systems. Application of LRNE may also be coordinated with a measure of CSE received by a user over a period of time as a counter effect of excessive CSE. Application of LRNE may also be controlled, at least in part, by physiological measures of the user including but not limited to data harvested from sensors associated with or information about users, such as one or more of physiological sensors. An OLED based computer display may be based on an array of OLED pixels 230. The OLED pixel 230 may have three separately controllable OLEDs 212 in each pixel. Each one may emit a similar color (e.g. white) and each one may be optically associated with a different colored filter 211 to generate red, green and circadian blue. In an alternate construction, each OLED emitter may generate its own color (e.g. through a different material, through a phosphor conversion). Each OLED pixel may be constructed with electrodes 214 to power and control each color and a substrate 216. In embodiments, the color set includes a circadian blue (e.g. as described herein). In embodiments, the color set has only three colors, including the circadian blue, and the display produces colors outside of the standard display color gamut. In embodiments, the color set has four colors, including a standard blue and a circadian blue, such that a control system could choose which blue to activate and control as described herein. In some implementations the red spectrum may be positioned in the long red near infrared energy (LRNE) region. In some instances the system may switch between the two modes. Such a system may also be operated in a mode where both a standard red and LRNE red are operated simultaneously or through a rapid switching mode (e.g. pulse width modulation to regulate the apparent intensity of each one). The modified color is bioactive and may be regulated by the control system. In some instances red in the LRNE non-visible region also referred to as near infrared may be used simultaneously or through a rapid switching mode with red or long red. The LRNE may be applied in doses or aliquots based on sensor data or other inputs to the control systems. Such LRNE may be used as a health supplement based controls systems. Application of LRNE may also be coordinated with a measure of CSE received by a user over a period of time. Application of LRNE may also be controlled, at least in part, by physiological measures of the user including but not limited to data harvested from sensors associated with or information about users, such as one or more of physiological sensors.

As shown schematically in FIG. 2, in certain implementations backlit LCD based computer displays may be based on an array of backlit LCD pixels 240. The construction of the LCD display may include liquid crystals 206 for multiple channels at each pixel where each liquid crystal in the pixel is associated with a filter that filters the light from a backlight 210. In this configuration, the backlight 210 makes white light and the filters cut the white light into a particular color, generally red, green and blue. In embodiments, the blue filter in the color filter layer 210 is a circadian blue color filter. In embodiments, the filter layer 210 includes two blue filters, associated with two separate liquid crystals: one for circadian blue and one for the standard display blue. In embodiments, the color set includes a circadian blue (e.g. as described herein). In embodiments, the filter color set has only three colors, including the circadian blue, and the display produces colors outside of the standard display color gamut. In embodiments, the filter color set has four colors, including a standard blue and a circadian blue, such that a control system could choose which blue to activate and control. In some implementations the red spectrum may be positioned in the long red near infrared energy (LRNE) region. In some instances the system may switch between the two modes. Such a system may also be operated in a mode where both a standard red and LRNE red are operated simultaneously or through a rapid switching mode (e.g. pulse width modulation to regulate the apparent intensity of each one). The modified color is bioactive and may be regulated by the control system. In some instances red in the LRNE non-visible region also referred to as near infrared may be used simultaneously or through a rapid switching mode with red or long red. The LRNE may be applied in doses or aliquots based on sensor data or other inputs to the control systems. Such LRNE may be used as a health supplement based controls systems. Application of LRNE may also be coordinated with a measure of CSE received by a user over a period of time. Application of LRNE may also be controlled, at least in part, by physiological measures of the user including but not limited to data harvested from sensors associated with or information about users, such as one or more of physiological sensors.

In embodiments, the LCD pixels may be arranged with a backlight 210 that sequentially cycles through separate colors and the liquid crystal layer in this arrangement may only have one liquid crystal per pixel and it may not include a filter layer. As the backlight sequences through its colors the liquid crystal can be turned on to emit the correct color. By quickly cycling through the colors the user's eye can integrate the color and perceive it as a combined color. For example, leaving the liquid crystal in the 'on' or transmit mode and cycling very quickly between red and blue of equal intensity can cause the person to perceive the pixel as purple. In such a construction, the backlight 210 may include a circadian blue emitter(s). In some embodiments, the backlight 210 includes standard display blue and a circadian blue. In some embodiments, the backlight 210 includes standard display red and a visible LRNE red. In some embodiments, the backlight 210 includes standard display red and a non-visible LRNE red. In some embodiments, the backlight 210 includes standard display red a visible LRNE red and a non-visible LRNE red. In some embodiments, the backlight 210 includes one of a standard display blue and a circadian blue emitter, a standard display red and a visible LRNE red. In some embodiments, the backlight 210 includes one of a standard display blue and a circadian blue emitter, standard display red and a non-visible LRNE red. In some embodiments, the backlight 210 includes one of a standard display blue and a circadian blue emitter, standard display red a visible LRNE red and a non-visible LRNE red.

Another aspect of the present inventions relates to a computer display edge lighting system or peripheral. An edge lighting system may surround the computer display and emit light that effects the circadian rhythm of a person using or proximate the computer display. The edge lighting system may include a lighting system similar to the display lighting systems described herein or a panel lighting system as described herein. The edge lighting system may be coordinated with the pixels of the display (e.g. through a computer system associated with both devices). It may otherwise be controlled separately (e.g. as described herein).

FIG. 4 illustrates an example of a bioactive panel 400 in accordance with the principles of the present inventions. The panel may be any number of shapes and sizes and have mechanical features such that it can be mounted in a number of ways and integrated into a number of other systems. It may also be lit and/or emit light in a number of ways. As illustrated, the lighting system(s) 406 in the panel may be mounted along an edge 406b, on a back plane 406a, or otherwise. The panel may further include a transmissive or partially transmissive surface and/or internal optical systems to manipulate the light from the panel (e.g. a diffuser or baffles).

A bioactive panel may also be controlled to create lighting effects that are soothing to a person (e.g. bio-mimicking effects). These effects may simulate the flicker of light on water, flicker of a candle, light being effected as it passes around and through leaves of a tree moving in the wind, etc. Subtle intensity, color and directionality variations could be introduced in a planar distributed source of light to recreate similar effects. These effects may be generated by controlling the lighting system 400 itself and/or through a controllable optical system.

Types of Circadian Lighting Systems for Display Systems

Lighting systems that may be used in display systems in accordance with the principles of the present inventions include, for example, 2-channel, 3-channel, 4-channel, 5-channel, or 6-channel LED-based color-tuning systems. Individual channels within the multi-channel systems may have particular color points and spectral power distributions for the light output generated by the channel. As used herein, the term "channel" refers to all the components in a light-generating pathway from an LED (microLED, OLED) through any filtering or other components until the light exits the display system.

In some implementations, 2-channel systems can be used having two w % bite light channels. The two white light channels can be those described more fully in U.S. Provisional Patent Application No. 62/757,664, filed Nov. 8, 2018, entitled "Two-Channel Tunable Lighting Systems with Controllable Equivalent Melanopic Lux and Correlated Color Temperature Outputs," and International Patent Application No. PCT/US2019/013356, filed Jan. 11, 2019, entitled "Two-Channel Tunable Lighting Systems With Controllable Equivalent Melanopic Lux And Correlated Color Temperature Outputs" the entirety of which is incorporated herein for all purposes.

White Light Channels

In some aspects, the present disclosure provides for display systems that incorporate two white lighting channels, which can be referred to herein as a first lighting channel and a second lighting channel. The white lighting channels can be used to backlight a display system that utilizes color filtering in order to generate a digital display.

First Lighting Channels

In some aspects, the present disclosure provides first lighting channels for use in lighting systems. The first lighting channels can have first color points with CCT values between about 4000K and about 6500K. In some implementations, the first color point can have a CCT of about 4000K. In certain implementations, the first color point can have a CCT of about 4000K, about 4100K, about 4200K, about 4300K, about 4400K, about 4500K, about 4600K, about 4700K, about 4800K, about 4900K, about 5000K, about 5100K, about 5200K, about 5300K, about 5400K, about 5500K, about 5600K, about 5700K, about 5800K, about 5900K, about 6000K, about 6100K, about 6200K, about 6300K, about 6400K, or about 6500K.

In some implementations, the first lighting channel can have one or more LEDs having an emission with a first peak wavelength of between about 440 nm and about 510 nm. In certain implementations, the first lighting channel can have one or more LEDs having an emission with a first peak wavelength of about 450 nm.

In some implementations, the first lighting channel can have a first color point with a CCT value of about 4000K. The first lighting channel can have a first color point with a color-point range 304A can be defined by a polygonal region on the 1931 CIE Chromaticity Diagram defined by the following ccx, ccy color coordinates: (0.4006, 0.4044), (0.3736, 0.3874), (0.3670, 0.3578), (0.3898, 0.3716), which correlates to an ANSI C78.377-2008 standard 4000K nominal CCT white light with target CCT and tolerance of 3985±275K and target duv and tolerance of 0.001±0.006, as more fully described in American National Standard ANSI C78.377-2008, "Specifications for the Chromaticity of Solid State Lighting Products." National Electrical Manufacturers Association, American National Standard Lighting Group, which is incorporated herein in its entirety for all purposes. In some implementations, suitable color-point ranges for the first color point can be described as MacAdam ellipse color ranges in the 1931 CIE Chromaticity Diagram color space, as illustrated schematically in FIG. 14, which depicts a color-point range 402, the black body locus 401, and a line 403 of constant ccy coordinates on the 1931 CIE Chromaticity Diagram. In FIG. 14, MacAdam ellipse ranges are described with major axis "a", minor axis "b", and ellipse rotation angle θ relative to line 403. In some implementations, the color-point range for the first color point can be range 304B, an embodiment of color range 402, and can be defined as a single 5-step MacAdam ellipse with center point (0.3818, 0.3797) with a major axis "a" of 0.01565, minor axis "b" of 0.00670, with an ellipse rotation angle θ of 52.70°, shown relative to a line 403. In some implementations, the color-point range for the first color point can be range 304C, an embodiment of color range 402, and can be defined as a single 3-step MacAdam ellipse with center point (0.3818, 0.3797) with a major axis "a" of 0.00939, minor axis "b" of 0.00402, with an ellipse rotation angle θ of 53.7°, shown relative to a line 403. In further implementations, the first color point can be within the color-point ranges described in Table 57 for the selected boundary for each nominal CCT value. In other implementations, the color-point range for the first color point can be a region on the 1931 CIE Chromaticity Diagram defined by a polygon connecting the (ccx, ccy) coordinates (0.0.3670, 0.3575), (0.3737, 0.3875), (0.4007, 0.4047), and (0.3898, 0.3720). In yet further implementations, the color-point range for the first color point can be a region on the 1931 CIE Chromaticity Diagram defined by a 4-step MacAdam ellipse centered at 3985K CCT and duv=+0.9845. In other implementations, the color-point range for the first color point can be a region on the 1931 CIE Chromaticity Diagram defined by a polygon connecting the (ccx, ccy) coordinates (0.3703, 0.3590), (0.3851, 0.3679), (0.3942, 0.3972), and (0.3769, 0.3864).

In some implementations, the first lighting channel can have certain spectral power distributions. Some aspects of some exemplary first lighting channels are shown in Table 44. Aspects of the spectral power distributions for the exemplary first lighting channels shown in Table 44 and an average of the exemplary first lighting channels (shown as "Exemplary 1st channels avg") are provided in Tables 46, 48, 50, 52, and 53, which show the ratios of spectral power within wavelength ranges, with an arbitrary reference wavelength range selected for each exemplary first lighting channel or average thereof and normalized to a value of 100.0, except for Table 53, in which the values are normalized to a value of 1.000. In certain implementations, the first lighting channel can have a first spectral power distribution with spectral power in one or more of the wavelength ranges other than the reference wavelength range increased or decreased within 30% greater or less, within 20% greater or less, within 10% greater or less, or within 5% greater or less than the values shown in Tables 46, 48, 50, 52, and 53. In some implementations, the first lighting channel can have a spectral power distribution that falls between the minimum (shown as "min") and maximum (shown as "max") values in each of the wavelength ranges as shown in one or more of the Tables 46, 48, 50, 52, and 53. In further implementations, the first lighting channel can have a spectral power distribution that falls between values 5% less, 10% less, 20% less, or 30% less than the minimum (shown as "min") and values 5% more, 10% more, 20% more, or 30% more than the maximum (shown as "max") values in each of the wavelength ranges as shown in one or more of the Tables 46, 48, 50, 52, and 53. FIGS. 5, 9, 10, 12 and 29-31 depict aspects of first spectral power distributions for the exemplary first lighting channels described herein. FIG. 12 depicts a spectral power distribution 1600 for the exemplary lighting channel "5000K Ch1" listed in Table 44 and further characterized elsewhere herein. FIG. 10 depicts a spectral power distribution 1400 for the exemplary lighting channel "40(0K Ch3" listed in Table 44 and further characterized elsewhere herein. FIG. 9 depicts a spectral power distribution 1300 for the exemplary lighting channel "4000K Ch2" listed in Table 44 and further characterized elsewhere herein. FIG. 9 depicts a spectral power distribution 900 for the exemplary lighting channel "4000K Ch4" listed in Table 44 and further characterized elsewhere herein. FIG. 5 further depicts some exemplary wavelength ranges 901A, 901B. 901C, 901D, and 901E, which correspond to the wavelength ranges shown in Table 53. As shown in Table 53, in some implementations, first lighting channels may have particular spectral power values within one or more of wavelength ranges 901A, 901B, 901C, 901D, and 901E, or other wavelength ranges not depicted in FIG. 5 or shown in Table 53 but described elsewhere herein.

In some aspects, the first lighting channel can have a first white light having a first color point with a CCT and EML value that falls within a range of possible pairings of CCT and EML values, also referred to herein as a CCT-EML range. A suitable CCT-EML range 1710 for first lighting channels of the present disclosure is shown graphically in FIG. 13, which also shows exemplary point pairings of CCT and EML for the exemplary first lighting channels shown in Table 3. Tables 1 and 2 show CCT and EML values for color points generated by some commercially available fixed-CCT LED-driven white light systems having Ra values of approximately 80.

In further aspects of the present disclosure, the lighting systems can provide an EML slope against CCT difference for the first lighting channels and the second lighting channels, also referred to herein as "EML slope." EML slope against CCT difference between pairings of the exemplary first and second lighting channels shown in Table 3 are shown in Table 13, with the slope values shown per 1000K for ease of reading. Some exemplary EML slope lines 1820, 1821, and 1822 are shown graphically in FIG. 54 for pairings for some pairings of the exemplary first lighting channels and second lighting channels listed in Table 3. In some implementations, the EML slope can be between about 0.25 and about 0.45, about 0.30 and about 0.42, about 0.35 and about 0.42, about 0.38 and about 0.42, between about 0.40 and about 0.42, or between about 0.33 and about 0.40. In further implementations, the EML slope can be about 0.25, about 0.26, about 0.27, about 0.28, about 0.29, about 0.30, about 0.31, about 0.32, about 0.33, about 0.34, about 0.35, about 0.36, about 0.37, about 0.38, about 0.39, about 0.40, about 0.41, about 0.42, about 0.43, about 0.44, or about 0.45.

Second Lighting Channels

In some aspects, the present disclosure provides second lighting channels for use in lighting systems. The second lighting channels can have second color points with CCT values between about 1800K and about 2700K. In some implementations, the first color point can have a CCT of about 2400K. In some implementations, the first color point can have a CCT of about 1800K, about 1900K, about 2000K, about 2100K, about 2200K, about 2300K, about 2400K, about 2500K, about 2600K, or about 2700K.

In some implementations, the second lighting channel can have one or more LEDs having an emission with a second peak wavelength of between about 380 nm and about 420 nm. In certain implementations, the second lighting channel can have one or more LEDs having an emission with a second peak wavelength of about 410 nm. In some aspects, the use of a different peak wavelength for the LEDs in the second lighting channel in comparison to the LEDs in the first lighting channel can contribute to the desired performance of the lighting systems of the disclosure.

In some implementations of the present disclosure, the second lighting channel can produce light having a second color point within a suitable color-point range. In certain implementations, the second color point can be within the color-point ranges described in Table 57 for the selected boundary for each nominal CCT value. In some implementations, the second color point can be within a color-point range defined by a region bounded by a polygon connecting the (ccx, ccy) coordinates on the 1931 CIE Chromaticity Diagram of (0.4593, 0.3944), (0.5046, 0.4007), (0.5262 0.4381), and (0.4813 0.4319). In further implementations, the second color point can be within a color-point range defined by a region bounded by a 4-step MacAdam ellipse centered at 2370K CCT value and duv=−0.3. In yet further implementations, the second color point can be within a color-point range defined by a region bounded by a polygon connecting the (ccx, ccy) coordinates on the 1931 CIE Chromaticity Diagram of (0.4745, 0.4025), (0.4880, 0.4035), (0.5036, 0.4254), (0.4880, 0.4244).

In some implementations, the second lighting channel can have certain spectral power distributions. Some aspects of some exemplary second lighting channels are shown in Table 44. Aspects of the spectral power distributions for the exemplary second lighting channels shown in Table 44 and an average of the exemplary second lighting channels (shown as "Exemplary 2nd channels avg") are provided in Tables 45, 47, 49, 51, and 53, which show the ratios of spectral power within wavelength ranges, with an arbitrary reference wavelength range selected for each exemplary second lighting channel or average thereof and normalized to a value of 100.0, except for Table 53, in which the values are normalized to a value of 1.000. In certain implementations, the second lighting channel can have a spectral power distribution with spectral power in one or more of the wavelength ranges other than the reference wavelength range increased or decreased within 30% greater or less, within 20% greater or less, within 10% greater or less, or within 5% greater or less than the values shown in one or more of Tables 45, 47, 49, 51, and 53. In some implementations, the second lighting channel can have a spectral power distribution that falls between the minimum (shown as "min") and maximum (shown as "max") values in each of the wavelength ranges as shown in one or more of the Tables 45, 47, 49, 51, and 53. In further implementations, the second lighting channel can have a spectral power distribution that falls between values 5% less, 10% less, 20% less, or 30% less than the minimum (shown as "min") and values 5% more, 10% more, 20% more, or 30% more than the maximum (shown as "max") values in each of the wavelength ranges as shown in one or more of the Tables 45, 47, 49, 51, and 53. FIG. 7 depicts a spectral power distribution 1100 for the exemplary lighting channel "2400K Ch2" listed in Table 44 and further characterized elsewhere herein. FIG. 8 depicts a spectral power distribution 1200 for the exemplary lighting channel "2400K Ch3" listed in Table 44 and further characterized elsewhere herein. FIG. 11 depicts a spectral power distribution 1500 for the exemplary lighting channel "1800K Ch1" listed in Table 44 and further characterized elsewhere herein. FIG. 6 depicts a spectral power distribution 1000 for the exemplary lighting channel "2400K Ch3" listed in Table 44 and further characterized elsewhere herein. FIG. 6 further depicts some exemplary wavelength ranges 1001A, 1001B, 1001C, 1001D, and 1001E, which correspond to the wavelength ranges shown in Table 53. As shown in Table 53, in some implementations, second lighting channels may have particular spectral power values within one or more of wavelength ranges 1001A, 1001B, 1001C, 1001D, and 1001E, or other wavelength ranges not depicted in FIG. 6 or shown in Table 12 but described elsewhere herein.

Colored Lighting Channels

In some implementations, the 3-channel BIOACTIVE LED-based color-tuning systems can include channels as described in U.S. Provisional Patent Application No. 62/712,182 filed Jul. 30, 2018, and U.S. Provisional Patent Application No. 62/757,672, filed Nov. 8, 2018, entitled "Switchable Systems for White Light with High Color Rendering and Biological Effects," which is incorporated herein in its entirety for all purposes.

In some implementations, the bioactive 4-channel, 5-channel, and 6-channel LED-based color tuning systems can include channels as described more fully in U.S. Provisional Patent Application No. 62/757,672, filed Nov. 8, 2018, entitled "Switchable Systems for White Light with High Color Rendering and Biological Effects," which is incorporated herein in its entirety for all purposes.

In some implementations, bioactive display systems can comprise standard lighting channels for red, blue, and green color points used in digital display systems known to those of skill in the art, such as those described herein and shown in FIG. 3b, and additional lighting channels each comprising a cyan lighting channel with an output with a color point in a cyan color region. The standard lighting channels may have light emissions with substantially all of the spectral energy distribution contained within a wavelength range of about 120 nm a full width at half maximum (FWHM) of about 40 nm. In certain implementations, the cyan lighting channel may include cyan lighting elements and channels as described in International Patent Application No. PCT/US2018/020792, filed Mar. 2, 2018, as short-blue-pumped cyan channels driven by LEDs having peak wavelengths of between about 430 nm to about 460 nm (referred to as "green" therein) and long-blue-pumped cyan channels driven by LEDs having peak wavelengths ranging from about 460 nm to about 485 nm (referred to as "cyan" therein). In further implementations, the cyan lighting channel may include cyan lighting elements and channels as described in U.S. Provisional Application No. 62/757,672, filed Nov. 8, 2018, as long-blue-pumped cyan and short-blue-pumped cyan. In some implementations, the display systems can comprise at least one lighting channel that comprises a short-blue-pumped cyan channel and at least one lighting channel that comprises a long-blue-pumped cyan channel.

In some implementations, the cyan light channels can have spectral power distributions. Tables 1-4 show the ratios of spectral power within wavelength ranges, with an arbitrary reference wavelength range selected for each color range and normalized to a value of 100.0. In certain implementations, the spectral power distribution of a cyan light channel falls between minimum and maximum values in particular wavelength ranges relative to an arbitrary reference wavelength range. In some implementations, the short-blue-pumped cyan can fall within the values between Short-blue-pumped cyan minimum 1 and Short-blue-pumped cyan maximum 1 in the wavelength ranges shown in Table 1, Table 2, or both Tables 1 and 2. In other implementations, the short-blue-pumped cyan can fall within the values between Short-blue-pumped cyan minimum 1 and Short-blue-pumped cyan maximum 2 in the wavelength ranges shown in Table 1. In some implementations, the Long-Blue-Pumped Cyan lighting channel can produce light with spectral power distribution that falls within the values between Long-Blue-Pumped Cyan minimum 1 and Long-Blue-Pumped Cyan maximum 1 in the wavelength ranges shown in Table 1, Table 2, or both Tables 1 and 2. Tables 3 and 4 show the ratios of spectral power within wavelength ranges, with an arbitrary reference wavelength range selected for the short-blue-pumped cyan color range and normalized to a value of 100.0, for a short-blue-pumped cyan channel that may be used in some implementations of the disclosure. The exemplary Short-blue-pumped cyan Channel 1 has a ccx, ccy color coordinate shown in Table 5. In certain implementations, the short-blue-pumped cyan channel can have a spectral power distribution with spectral power in one or more of the wavelength ranges other than the reference wavelength range increased or decreased within 30% greater or less, within 20% greater or less, within 10% greater or less, or within 5% greater or less than the values shown in Table 3 or 4. In some implementations, the long-blue-pumped cyan channel can produce cyan light having certain spectral power distributions. Tables 3 and 4 shows ratios of spectral power within wavelength ranges, with an arbitrary reference wavelength range selected for the long-blue-pumped cyan color range and normalized to a value of 100.0, for several non-limiting embodiments of the long-blue-pumped cyan channel. The exemplary Long-blue-pumped cyan Channel 1 has a ccx, ccy color coordinate Shown in Table 5. In certain implementations, the long-blue-pumped cyan channel can have a spectral power distribution with spectral power in one or more of the wavelength ranges other than the reference wavelength range increased or decreased within 301% greater or less, within 20% greater or less, within 10% greater or less, or within 5% greater or less than the values shown in Table 3 and 4.

Blue Channels

In some implementations of the present disclosure, lighting systems can include bioactive blue channels that produce light with a blue color point that falls within a blue color range. In certain implementations, suitable blue color ranges can include blue color ranges 301A-F. FIG. 22A depicts a blue color range 301A defined by a line connecting the ccx, ccy color coordinates of the infinity point of the Planckian locus (0.242, 0.24) and (0.12, 0.068), the Planckian locus from 4000K and infinite CCT, the constant CCT line of 4000K, the line of purples, and the spectral locus. FIG. 22A also depicts a blue color range 301D defined by a line connecting (0.3806, 0.3768) and (0.0445, 0.3), the spectral locus between the monochromatic point of 490 nm and (0.12, 0.068), a line connecting the ccx, ccy color coordinates of the infinity point of the Planckian locus (0.242, 0.24) and (0.12, 0.068), and the Planckian locus from 4000K and infinite CCT. The blue color range may also be the combination of ranges 301A and 301D together. FIG. 25 depicts a blue color range 301B can be defined by a 60-step MacAdam ellipse at a CCT of 20000K, 40 points below the Planckian locus. FIG. 26 depicts a blue color range 301C that is defined by a polygonal region on the 1931 CIE Chromaticity Diagram defined by the following ccx, ccy color coordinates: (0.22, 0.14). (0.19, 0.17), (0.26, 0.26), (0.28, 0.23). FIG. depicts blue color ranges 301E and 301F. Blue color range 301E is defined by lines connecting (0.231, 0.218), (0.265, 0.260), (0.2405, 0.305), and (0.207, 0.256).

TABLE 1

Spectral Power Distribution for Wavelength Ranges (nm)

| | 380 < $\lambda \le$ 420 | 420 < $\lambda \le$ 460 | 460 < $\lambda \le$ 500 | 500 < $\lambda \le$ 540 | 540 < $\lambda \le$ 580 | 580 < $\lambda \le$ 620 | 620 < $\lambda \le$ 660 | 660 < $\lambda \le$ 700 | 700 < $\lambda \le$ 740 | 740 < $\lambda \le$ 780 |
|---|---|---|---|---|---|---|---|---|---|---|
| Blue minimum 1 | 0.3 | 100.0 | 0.8 | 15.2 | 25.3 | 26.3 | 15.1 | 5.9 | 1.7 | 0.5 |
| Blue maximum 1 | 110.4 | 100.0 | 196.1 | 61.3 | 59.2 | 70.0 | 80.2 | 22.1 | 10.2 | 4.1 |
| Red minimum 1 | 0.0 | 10.5 | 0.1 | 0.1 | 2.2 | 36.0 | 100.0 | 2.2 | 0.6 | 0.3 |
| Red maximum 1 | 2.0 | 1.4 | 3.1 | 7.3 | 22.3 | 59.8 | 100.0 | 61.2 | 18.1 | 5.2 |
| Short-blue-pumped cyan minimum 1 | 3.9 | 100.0 | 112.7 | 306.2 | 395.1 | 318.2 | 245.0 | 138.8 | 39.5 | 10.3 |
| Short-blue-pumped cyan maximum 1 | 130.6 | 100.0 | 553.9 | 2660.6 | 4361.9 | 3708.8 | 2223.8 | 712.2 | 285.6 | 99.6 |
| Short-blue-pumped cyan maximum 2 | 130.6 | 100.0 | 553.9 | 5472.8 | 9637.9 | 12476.9 | 13285.5 | 6324.7 | 1620.3 | 344.7 |
| Long-blue-pumped cyan minimum 1 | 0.0 | 0.0 | 100.0 | 76.6 | 38.0 | 33.4 | 19.6 | 7.1 | 2.0 | 0.6 |
| Long-blue-pumped cyan maximum 1 | 1.8 | 36.1 | 100.0 | 253.9 | 202.7 | 145.0 | 113.2 | 63.1 | 24.4 | 7.3 |

TABLE 2

| | Spectral Power Distribution for Wavelength Ranges (nm) | | | |
|---|---|---|---|---|
| | 380 < λ ≤ 500 | 500 < λ ≤ 600 | 600 < λ ≤ 700 | 700 < λ ≤ 780 |
| Blue minimum 1 | 100.0 | 27.0 | 19.3 | 20.5 |
| Blue maximum 1 | 100.0 | 74.3 | 46.4 | 51.3 |
| Red minimum 1 | 100.0 | 51.4 | 575.6 | 583.7 |
| Red maximum 1 | 100.0 | 2332.8 | 8482.2 | 9476.2 |
| Short-blue-pumped cyan minimum 1 | 100.0 | 279.0 | 170.8 | 192.8 |
| Short-blue-pumped cyan maximum 1 | 100.0 | 3567.4 | 4366.3 | 4696.6 |
| Long-blue-pumped cyan minimum 1 | 100.0 | 155.3 | 41.1 | 43.5 |
| Long-blue-pumped cyan maximum 1 | 100.0 | 503.0 | 213.2 | 243.9 |

TABLE 3

| | Spectral Power Distribution for Wavelength Ranges (nm) | | | | | | | | | | |
|---|---|---|---|---|---|---|---|---|---|---|---|
| Exemplary Color Channels | 380 < λ ≤ 400 | 400 < λ ≤ 420 | 420 < λ ≤ 440 | 440 < λ ≤ 460 | 460 < λ ≤ 480 | 480 < λ ≤ 500 | 500 < λ ≤ 520 | 520 < λ ≤ 540 | 540 < λ ≤ 560 | 560 < λ ≤ 580 | 580 < λ ≤ 600 |
| Blue Channel 1 | 0.1 | 1.2 | 20.6 | 100 | 49.2 | 35.7 | 37.2 | 36.7 | 33.4 | 26.5 | 19.8 |
| Red Channel 1 | 0.0 | 0.3 | 1.4 | 1.3 | 0.4 | 0.9 | 4.2 | 9.4 | 15.3 | 26.4 | 45.8 |
| Short-Blue-Pumped Cyan Channel 1 | 0.2 | 1.2 | 8.1 | 22.2 | 17.5 | 46.3 | 88.2 | 98.5 | 100.0 | 90.2 | 73.4 |
| Long-Blue-Pumped Cyan Channel 1 | 0.0 | 0.1 | 0.7 | 9.9 | 83.8 | 100 | 75.7 | 65.0 | 62.4 | 55.5 | 43.4 |
| Blue Channel 2 | 0.4 | 2.5 | 17.2 | 100 | 60.9 | 30.9 | 29.3 | 30.2 | 28.6 | 24.3 | 20.7 |
| Red Channel 2 | 0.1 | 0.4 | 1.1 | 3.4 | 3.6 | 2.7 | 5.9 | 11.0 | 16.9 | 28.1 | 46.8 |
| Short-Blue-Pumped Cyan Channel 2 | 0.5 | 0.6 | 3.4 | 13.5 | 16.6 | 47.2 | 83.7 | 95.8 | 100.0 | 95.8 | 86.0 |
| Long-Blue-Pumped Cyan Channel 2 | 0.1 | 0.2 | 1.0 | 9.1 | 54.6 | 100.0 | 99.6 | 75.7 | 65.5 | 56.8 | 48.9 |

| | Spectral Power Distribution for Wavelength Ranges (nm) | | | | | | | | | |
|---|---|---|---|---|---|---|---|---|---|---|
| Exemplary Color Channels | 600 < λ ≤ 620 | 620 < λ ≤ 640 | 640 < λ ≤ 660 | 660 < λ ≤ 680 | 680 < λ ≤ 700 | 700 < λ ≤ 720 | 720 < λ ≤ 740 | 740 < λ ≤ 760 | 760 < λ ≤ 780 | 780 < λ ≤ 800 |
| Blue Channel 1 | 14.4 | 10.6 | 7.6 | 4.7 | 2.6 | 1.4 | 0.7 | 0.4 | 0.2 | 0.0 |
| Red Channel 1 | 66.0 | 87.0 | 100.0 | 72.5 | 42.0 | 22.3 | 11.6 | 6.1 | 3.1 | 0.0 |
| Short-Blue-Pumped Cyan Channel 1 | 57.0 | 48.1 | 41.4 | 27.0 | 15.1 | 7.9 | 4.0 | 2.1 | 1.0 | 0.0 |
| Long-Blue-Pumped Cyan Channel 1 | 30.9 | 21.5 | 14.5 | 8.5 | 4.5 | 2.4 | 1.3 | 0.7 | 0.3 | 0.0 |
| Blue Channel 2 | 18.5 | 16.6 | 13.6 | 9.5 | 6.0 | 3.5 | 2.0 | 1.2 | 0.8 | 0.0 |
| Red Channel 2 | 68.9 | 92.6 | 100.0 | 73.9 | 44.5 | 24.7 | 13.1 | 6.8 | 3.5 | 0.0 |
| Short-Blue-Pumped Cyan Channel 2 | 76.4 | 74.6 | 68.3 | 46.1 | 26.1 | 14.0 | 7.2 | 3.6 | 1.8 | 0.0 |
| Long-Blue-Pumped Cyan Channel 2 | 41.3 | 33.3 | 24.1 | 15.8 | 9.4 | 5.4 | 3.0 | 1.7 | 1.1 | 0.0 |

TABLE 4

| | Spectral Power Distribution for Wavelength Ranges (nm) | | | | | | | | | |
|---|---|---|---|---|---|---|---|---|---|---|
| Exemplary Color Channels | 380 < λ ≤ 420 | 420 < λ ≤ 460 | 460 < λ ≤ 500 | 500 < λ ≤ 540 | 540 < λ ≤ 580 | 580 < λ ≤ 620 | 620 < λ ≤ 660 | 660 < λ ≤ 700 | 700 < λ ≤ 740 | 740 < λ ≤ 780 |
| Red Channel 1 | 0.2 | 1.4 | 0.7 | 7.3 | 22.3 | 59.8 | 100.0 | 61.2 | 18.1 | 4.9 |
| Red Channel 2 | 1.8 | 4.2 | 2.7 | 7.2 | 19.3 | 59.1 | 100.0 | 59.5 | 20.4 | 5.9 |
| Blue Channel 1 | 1.1 | 100.0 | 70.4 | 61.3 | 49.7 | 28.4 | 15.1 | 6.0 | 1.7 | 0.5 |
| Blue Channel 2 | 25.7 | 100.0 | 69.4 | 31.6 | 38.7 | 38.3 | 33.7 | 14.9 | 5.6 | 2.0 |
| Short-Blue-Pumped Cyan Channel 1 | 0.7 | 15.9 | 33.5 | 98.2 | 100.0 | 68.6 | 47.1 | 22.1 | 6.3 | 1.7 |
| Short-Blue-Pumped Cyan Channel 2 | 30.3 | 100.0 | 313.2 | 1842.7 | 2770.2 | 2841.2 | 2472.2 | 1119.1 | 312.7 | 77.8 |

TABLE 4-continued

Spectral Power Distribution for Wavelength Ranges (nm)

| Exemplary Color Channels | 380 < λ ≤ 420 | 420 < λ ≤ 460 | 460 < λ ≤ 500 | 500 < λ ≤ 540 | 540 < λ ≤ 580 | 580 < λ ≤ 620 | 620 < λ ≤ 660 | 660 < λ ≤ 700 | 700 < λ ≤ 740 | 740 < λ ≤ 780 |
|---|---|---|---|---|---|---|---|---|---|---|
| Long-blue-pumped cyan Channel 1 | 0.0 | 5.8 | 100.0 | 76.6 | 64.1 | 40.4 | 19.6 | 7.1 | 2.0 | 0.6 |
| Long-blue-pumped cyan Channel 2 | 0.4 | 5.3 | 100.0 | 165.3 | 105.4 | 77.0 | 49.0 | 22.7 | 8.1 | 2.3 |

TABLE 5

| Exemplary Color Channels | ccx | ccy | LED pump peak wavelength |
|---|---|---|---|
| Red Channel 1 | 0.5932 | 0.3903 | 450-455 nm |
| Blue Channel 1 | 0.2333 | 0.2588 | 450-455 nm |
| Long-Blue-Pumped Cyan Channel 1 | 0.2934 | 0.4381 | 505 nm |
| Short-Blue-Pumped Cyan Channel 1 | 0.373 | 0.4978 | 450-455 nm |
| Violet Channel 1 | 0.3585 | 0.3232 | 380 nm |
| Violet Channel 2 | 0.3472 | 0.3000 | 400 nm |
| Violet Channel 3 | 0.2933 | 0.2205 | 410 nm |
| Violet Channel 4 | 0.3333 | 0.2868 | 420 nm |
| Violet Channel 5 | | | 400 nm |
| Yellow Channel 1 | 0.4191 | 0.5401 | 380 nm |
| Yellow Channel 2 | 0.4218 | 0.5353 | 400 nm |
| Yellow Channel 3 | 0.4267 | 0.5237 | 410 nm |
| Yellow Channel 4 | 0.4706 | 0.4902 | 420 nm |
| Yellow Channel 5 | | | 400 nm |
| Yellow Channel 6 | | | 410 nm |

In certain implementations, the cyan lighting channels described herein, including short-blue-pumped cyan channels and long-blue-pumped cyan channels as described herein, can generate light outputs with cyan color points that fall within a cyan color range. In certain implementations, suitable cyan color ranges can include cyan color ranges 303A-E, which can be seen in FIGS. 22B, 23, and 24. Cyan color range 303A is defined by a line connecting the ccx, ccy color coordinates (0.18, 0.55) and (0.27, 0.72), the constant CCT line of 9000K, the Planckian locus between 9000K and 1800K, the constant CCT line of 1800K, and the spectral locus on the 1931 CIE Chromaticity Diagram. A cyan color range 303B can be defined by the region bounded by lines connecting (0.360, 0.495), (0.371, 0.518), (0.388, 0.522), and (0.377, 0.499). A cyan color range 303C is defined by a line connecting the ccx, ccy color coordinates (0.18, 0.55) and (0.27, 0.72), the constant CCT line of 9000K, the Planckian locus between 9000K and 4600K, the constant CCT line of 4600K, and the spectral locus. A cyan color range 303D is defined by the constant CCT line of 4600K, the spectral locus, the constant CCT line of 1800K, and the Planckian locus between 4600K and 1800K. In some implementations, the long-blue-pumped cyan channel can provide a color point within a cyan color region 303E defined by lines connecting (0.497, 0.469), (0.508, 0.484), (0.524, 0.472), and (0.513, 0.459).

In some implementations, the LEDs in the cyan color channels can be LEDs with peak emission wavelengths at or below about 535 nm. In some implementations, the LEDs emit light with peak emission wavelengths between about 360 nm and about 535 nm. In some implementations, the LEDs in the cyan color channels can be formed from InGaN semiconductor materials. In some implementations, the LEDs used in the long-blue-pumped cyan channels can be LEDs having peak emission wavelengths between about 360 nm and about 535 nm, between about 380 nm and about 520 nm, between about 470 nm and about 505 nm, about 480 nm, about 470 nm, about 460 nm, about 455 nm, about 450 nm, or about 445 nm. In certain implementations, the LEDs used in long-blue-pumped cyan channels can have a peak wavelength between about 460 nm and 515 nm. In some implementations, the LEDs in the long-blue-pumped cyan channels can include one or more LUXEON Rebel Blue LEDs (LXML-PB01, LXML-PB02) of color bins 1, 2, 3, 4, or 5, which have peak wavelengths ranging from 460 nm to 485 nm, or LUXEON Rebel Cyan LEDs (LXML-PE01) of color bins 1, 2, 3, 4, or 5, which have peak wavelengths raving from 460 nm to 485 nm. In some implementations, the short-blue-pumped cyan channels can have LEDs having a peak wavelength between about 405 nm and about 485 nm, between about 430 nm and about 460 nm, between about 430 nm and about 455 nm, between about 430 nm and about 440 nm, between about 440 nm and about 450 nm, between about 440 nm and about 445 nm, or between about 445 nm and about 450 nm. The LEDs used in the short-blue-pumped cyan channels may have full-width half-maximum wavelength ranges of between about 10 nm and about 30 nm. In some preferred implementations, the short-blue-pumped cyan channels can include one or more LUXEON Z Color Line royal blue LEDs (product code LXZ1-PR01) of color bin codes 3, 4, 5, or 6, one or more LUXEON Z Color Line blue LEDs (LXZ1-PB01) of color bin code 1 or 2, or one or more LUXEON royal blue LEDs (product code LXML-PR01 and LXML-PR02) of color bins 3, 4, 5, or 6 (Lumileds Holding B.V., Amsterdam, Netherlands).

Yellow Channels

In some implementations of the present disclosure, lighting systems can include yellow channels that produce light with a yellow color point that falls within a yellow color range. Non-limiting FIGS. 17A and 17B depicts some aspects of suitable yellow color ranges for implementations of yellow channels of the present disclosure. In some implementations, the yellow channels can produce light having a yellow color point that falls within a yellow color range 1401, with boundaries defined on the 1931 CIE Chromaticity Diagram of the constant CCT line of 5000K from the Planckian locus to the spectral locus, the spectral locus, and the Planckian locus from 5000K to 550K. In certain implementations, the yellow channels can produce light having a yellow color point that falls within a yellow color range 1402, with boundaries defined on the 1931 CIE Chromaticity Diagram by a polygon connecting (ccx, ccy) coordinates of (0.47, 0.45), (0.48, 0.495), (0.41, 0.57), and (0.40, 0.53). In some implementations, the yellow channels can produce light having a color point at one of the exemplary yellow color points 1403A-D shown in FIG. 17B and described more fully elsewhere herein.

Violet Channels

In some implementations of the present disclosure, lighting systems can include violet channels that produce light with a violet color point that falls within a violet color range. Non-limiting FIG. 16 depicts some aspects of suitable violet color ranges for implementations of violet channels of the present disclosure. In some implementations, the violet channels can produce light having a violet color point that falls within a violet color range 1301, with boundaries defined on the 1931 CIE Chromaticity Diagram of the Planckian locus between 1600K CCT and infinite CCT, a line between the infinite CCT point on the Planckian locus and the monochromatic point of 470 nm on the spectral locus, the spectral locus between the monochromatic point of 470 nm and the line of purples, the line of purples from the spectral locus to the constant CCT line of 1600K, and the constant CCT line of 1600K between the line of purples and the 1600K CCT point on the Planckian locus. In certain implementations, the violet channels can produce light having a violet color point that falls within a violet color range 1302, with boundaries defined on the 1931 CIE Chromaticity Diagram by a 40-step MacAdam ellipse centered at 6500K CCT with DUV=−40 points. In some implementations, the violet channels can produce light having a color point at one of the exemplary violet points 1303A-D shown in FIG. 16 and described more fully elsewhere herein.

Red Channels

In some implementations of the present disclosure, lighting systems can include bioactive red channels that produce light with a red color point that falls within a red color range. In certain implementations, suitable red color ranges can include red color ranges 302A-D. FIG. 22B depicts a red color range 302A defined by the spectral locus between the constant CCT line of 1600K and the line of purples, the line of purples, a line connecting the ccx, ccy color coordinates (0.61, 0.21) and (0.47, 0.28), and the constant CCT line of 1600K bioactive LRNE is within that range. FIG. 23 depicts some suitable color ranges for some implementations of the disclosure. FIG. 25 shows a red color range 302B that can be defined by a 20-step MacAdam ellipse at a CCT of 1200K, 20 points below the Planckian locus. FIG. 24 depicts some further color ranges suitable for some implementations of the disclosure. A red color range 302C is defined by a polygonal region on the 1931 CIE Chromaticity Diagram defined by the following ccx, ccy color coordinates: (0.53, 0.41), (0.59, 0.39), (0.63, 0.29), (0.58, 0.30). In FIG. 26, a red color range 302C is depicted and can be defined by a polygonal region on the 1931 CIE Chromaticity Diagram defined by the following ccx, ccy color coordinates: (0.53, 0.41), (0.59, 0.39), (0.63, 0.29), (0.58, 0.30). FIG. 27 depicts a red color range 302D defined by lines connecting the ccx, ccy coordinates (0.576, 0.393), (0.583, 0.400), (0.604, 0.387), and (0.597, 0.380).

Long Red and Near Infrared Channel

In some aspects, the present disclosure relates to long red and near infrared lighting channels that can provide long red and near infrared energy ("LRNE"). Long red and near infrared channels can provide one or both of Visible LRNE and Non-Visible LRNE. Visible LRNE refers to light having spectral power in wavelengths between about 625 nm and about 700 nm. Non-Visible LRNE refers to light having spectral power in wavelengths greater than or equal to about 700 nm. The Long Red and Near Infrared Channels, also referred to as LRNE channels or LRNE lighting channels, of the present disclosure can be part of one or more red channels involved in color-tuning and providing white light, or as separate channel that can be operated independently of color-tuning or color-rendering requirements. In some implementations an additional LRNE channel includes the non-visible region of the LRNE also referred to as near infrared. Although the near infrared may not be visually perceived as red, such a channel can provide benefits of LRNE as described above. In FIGS. 29-31, Region 1550 represents LRNE emissions which are considered by most to be outside the visual spectrum of humans. FIG. 29 depicts the emission spectrum of an exemplary nitride long-red phosphor, Long-Red Phosphor 700 nm, excited by violet or blue light wavelengths between about 380 nm and about 490 nm. In certain implementations red nitride phosphors having peak wavelengths between about 675 nm and about 775 nm can be included in one or more red channels or long-red channels. Aspects of exemplary phosphors that may be suitable for use in LRNE channels of the present disclosure are shown in Tables 61-63.

FIG. 30 shows aspects of the spectral power distribution of an exemplary LRNE lighting channel, LRNE Channel B, with further details shown in Tables 7-9 below. Three phosphor materials can be provided in a luminophoric medium associated with an LED string in LRNE Channel B, and in some implementations the phosphor materials can include a YAG phosphor, a red phosphor with emission peak at about 630 nm, and a red phosphor with an emission peak at about 750 nm.

FIG. 31 shows aspects of the spectral power distribution of an exemplary LRNE lighting channel, LRNE Channel A, with further details show in Tables 7-9 below. Three phosphor materials can be provided in a luminophoric medium associated with an LED string in LRNE Channel A, and in some implementations the phosphor materials can include a YAG phosphor, a red phosphor with emission peak at about 630 nm, and a red phosphor with an emission peak at about 700 nm.

In some implementations, the LRNE channels can produce red light having certain spectral power distributions. Tables 7-9 shows the ratios of spectral power within wavelength ranges, with an arbitrary reference wavelength range selected and normalized to a value of 100.0, for LRNE channels that may be used in some implementations of the disclosure. In some implementations, the LRNE channels can have a spectral power distribution that falls within the ranges between the Exemplary LRNE Channel Minimum and the Exemplary LRNE Channel Maximum in the wavelength ranges shown in Tables 7-9. In certain implementations, the LRNE channels of the disclosure can have a spectral power distribution with spectral power in one or more of the wavelength ranges other than the reference wavelength range increased or decreased within 30% greater or less, within 20% greater or less, within 10% greater or less, or within 5% greater or less than the values shown in Tables 7-9 for LRNE Channels A-B and the Exemplary LRNE Channel Average.

FIGS. 39-43 show aspects of some suitable commercially available LED systems that can be used in the LRNE channels of the present disclosure. FIG. 39 shows the emission spectra of some the LUXEON IR 2720 Line of products from Lumileds (Lumileds Holding B.V., Amsterdam, Netherlands). The peak wavelength of the LUXEON® IR 2720 LED series can be selected from between about 840 nm and about 965 nm as desired for bioactive effects. FIG. 40 shows the emission spectra of some of the SST-10-IR product line from Luminus (Luminus, Inc., Sunnyvale, California, USA). Peak wavelengths of 850 nm or 940 nm can be selected. FIG. 41 shows the emission spectra of some 850 nm and 940 nm type LEDs available from Vision Light Tech (Vision Light Tech, Protonenlaan 22, 5405 NE UDEN, The Netherlands). FIG. 42 shows the spectral power characteristics of LUXEON IR ONYX product from Lumileds (Lumileds Holding B.V., Amsterdam, Netherlands). FIG. 43 shows the emission spectra that can be isolated via a Long Pass (LP) filter (such as MidOpt LP920 (Midwest Optical Systems, Inc., 322 Woodwork Lane, Palatine, IL 60067 USA)). Between the spectra shown in FIGS. 42 and 43, the LP filter cuts the short wavelength part of the spectrum susceptible to being seen by the human eye. In other implementations, LP filters with higher or lower wavelength thresholds for cut-off can be selected to isolate the spectral power in wavelength ranges as desired for LRNE bioactive effects.

Spectral Power Distributions of Colored Channels:

In implementations utilizing LEDs that emit substantially saturated light at wavelengths between about 360 nm and about 535 nm, the display systems can include suitable recipient luminophoric mediums for each LED in order to produce light having color points within the suitable blue color ranges 301A-F, red color ranges 302A-D, cyan color ranges 303A-E, violet color ranges 1301, 1302, and yellow color ranges 1401, 1402 described herein. The light emitted by each lighting channel (from each LED string, i.e., the light emitted from the LED(s) and associated recipient luminophoric medium together) can have a suitable spectral power distribution ("SPD") having spectral power with ratios of power across the visible wavelength spectrum from about 380 nm to about 780 nm or across the visible, near-visible, and non-visible wavelength spectrum from about 320 nm to about 1000 nm. While not wishing to be bound by any particular theory, it is speculated that the use of such LEDs in combination with recipient luminophoric mediums to create unsaturated light within the suitable color ranges 301A-F, 302A-D, 303A-E, 1301, 1302, 1401, and 1402 provides for improved color rendering performance for white light across a predetermined range of CCTs from a single display systems. Further, while not wishing to be bound by any particular theory, it is speculated that the use of such LEDs in combination with recipient luminophoric mediums to create unsaturated light within the suitable color ranges 301A-F, 302A-D, 303A-E, 1301, 1302, 1401, and 1402 provides for improved light rendering performance, providing higher EML performance along with color-rendering performance, for white light across a predetermined range of CCTs from a single display systems. Some suitable ranges for spectral power distribution ratios of the lighting channels of the present disclosure are shown in Tables 1-4 and 7-15. The Tables show the ratios of spectral power within wavelength ranges, with an arbitrary reference wavelength range selected for each color range and normalized to a value of 100.0 except where indicated otherwise.

In some implementations, the lighting channels of the present disclosure can each product a colored light that falls between minimum and maximum values in particular wavelength ranges relative to an arbitrary reference wavelength range. Tables 1, 2, and 7-15 show some exemplary minimum and maximum spectral power values for the blue, red, long-red near infrared (LRNE), short-blue-pumped cyan, long-blue-pumped cyan, yellow, and violet channels of the disclosure. In certain implementations, the blue lighting channel can produce light with spectral power distribution that falls within the values between Blue minimum 1 and Blue maximum 1 in the wavelength ranges shown in Table 1, Table 2, or both Tables 1 and 2. In some implementations, the red lighting channel can produce light with spectral power distribution that falls within the values between Red minimum 1 and Red maximum 1 in the wavelength ranges shown in Table 1, Table 2, or both Tables 1 and 2. In some implementations, the red channel can produce red light having a spectral power distribution that falls within the ranges between the Exemplary Red Channels Minimum and the Exemplary Red Channels Maximum in the wavelength ranges shown in one or more of Tables 7-9. In some implementations, the short-blue-pumped cyan can fall within the values between Short-blue-pumped cyan minimum 1 and Short-blue-pumped cyan maximum 1 in the wavelength ranges shown in Table 1, Table 2, or both Tables 1 and 2. In other implementations, the short-blue-pumped cyan can fall within the values between Short-blue-pumped cyan minimum 1 and Short-blue-pumped cyan maximum 2 in the wavelength ranges shown in Table 1. In some implementations, the Long-Blue-Pumped Cyan lighting channel can produce light with spectral power distribution that falls within the values between Long-Blue-Pumped Cyan minimum 1 and Long-Blue-Pumped Cyan maximum 1 in the wavelength ranges shown in Table 1, Table 2, or both Tables 1 and 2. In some implementations, the yellow channel can produce yellow light having a spectral power distribution that falls within the ranges between the Exemplary Yellow Channels Minimum and the Exemplary Yellow Channels Maximum in the wavelength ranges shown in one or more of Tables 13-15. In some implementations, the violet channel can produce violet light having a spectral power distribution that falls within the ranges between the Exemplary Violet Channels Minimum and the Exemplary Violet Channels Maximum in the wavelength ranges shown in one or more of Tables 10-12. While not wishing to be bound by any particular theory, it is speculated that because the spectral power distributions for generated light with color points within the blue, long-blue-pumped cyan, short-blue-pumped cyan, yellow, and violet color ranges contains higher spectral intensity across visible wavelengths as compared to lighting apparatuses and methods that utilize more saturated colors, this allows for improved color rendering for test colors other than R1-R8. International Patent Application No. PCT/US2018/020792, filed Mar. 2, 2018, discloses aspects of some additional red, blue, short-pumped-blue (referred to as "green" therein), and long-pumped-blue (referred to as "cyan" therein) channel elements that may be suitable for some implementations of the present disclosure, the entirety of which is incorporated herein for all purposes.

In some implementations, the short-blue-pumped cyan channel can produce cyan light having certain spectral power distributions. Tables 3 and 4 show the ratios of spectral power within wavelength ranges, with an arbitrary reference wavelength range selected for the short-blue-pumped cyan color range and normalized to a value of 100.0, for a short-blue-pumped cyan channel that may be used in some implementations of the disclosure. The exemplary Short-blue-pumped cyan Channel 1 has a ccx, ccy color coordinate shown in Table 5. In certain implementations, the short-blue-pumped cyan channel can have a spectral power distribution with spectral power in one or more of the wavelength ranges other than the reference wavelength range increased or decreased within 30% greater or less, within 20% greater or less, within 10% greater or less, or within 5% greater or less than the values shown in Table 3 or 4.

In some implementations, the long-blue-pumped cyan channel can produce cyan light having certain spectral power distributions. Tables 3 and 4 shows ratios of spectral power within wavelength ranges, with an arbitrary reference wavelength range selected for the long-blue-pumped cyan color range and normalized to a value of 100.0, for several non-limiting embodiments of the long-blue-pumped cyan channel. The exemplary Long-blue-pumped cyan Channel 1 has a ccx, ccy color coordinate Shown in Table 5. In certain implementations, the long-blue-pumped cyan channel can have a spectral power distribution with spectral power in one or more of the wavelength ranges other than the reference wavelength range increased or decreased within 30% greater or less, within 20% greater or less, within 10% greater or less, or within 5% greater or less than the values shown in Table 3 and 4.

In some implementations, the red channel can produce red light having certain spectral power distributions. Tables 3-4 and 7-9 show the ratios of spectral power within wavelength ranges, with an arbitrary reference wavelength range selected for the red color range and normalized to a value of 100.0, for red lighting channels which may be LRNE channels that may be used in some implementations of the disclosure. The exemplary Red Channel 1 has a ccx, ccy color coordinate of (0.5932, 0.3903). In certain implementations, the red channel can have a spectral power distribution with spectral power in one or more of the wavelength ranges other than the reference wavelength range increased or decreased within 30% greater or less, within 20% greater or less, within 10% greater or less, or within 5% greater or less than the values shown in Tables 3-4 and 7-9 for Red Channels 1-11, Long-Red Channels A-B (for the LRNE spectrum), the Exemplary Long-Red Channel Average, and the Exemplary Red Channels Average.

In some implementations, the blue channel can produce blue light having certain spectral power distributions. Tables 3 and 4 show the ratios of spectral power within wavelength ranges, with an arbitrary reference wavelength range selected for the blue color range and normalized to a value of 100.0, for a blue channel that may be used in some implementations of the disclosure. Exemplary Blue Channel 1 has a ccx, ccy color coordinate of (0.2333, 0.2588). In certain implementations, the blue channel can have a spectral power distribution with spectral power in one or more of the wavelength ranges other than the reference wavelength range increased or decreased within 30% greater or less, within 20% greater or less, within 10% greater or less, or within 5% greater or less than the values shown in Tables 3 and 4.

In some implementations, the yellow channel can have certain spectral power distributions. Tables 13-15 show the ratios of spectral power within wavelength ranges, with an arbitrary reference wavelength range selected and normalized to a value of 100.0 for exemplary yellow lighting channels, Yellow Channels 1-6. Table 5 shows some aspects of the exemplary yellow lighting channels for some implementations of the disclosure. In certain implementations, the yellow channel can have a spectral power distribution with spectral power in one or more of the wavelength ranges other than the reference wavelength range increased or decreased within 30'% greater or less, within 20% greater or less, within 10% greater or less, or within 5% greater or less than the values shown in one or more of Tables 13-15 for Yellow Channels 1-6 and the Exemplary Yellow Channels Average.

In some implementations, the violet channel can have certain spectral power distributions. Tables 13-15 show the ratios of spectral power within wavelength ranges, with an arbitrary reference wavelength range selected and normalized to a value of 100.0 for exemplary violet lighting channels, Violet Channels 1-5. Table 5 shows some aspects of the exemplary violet lighting channels for some implementations of the disclosure. In certain implementations, the violet channel can have a spectral power distribution with spectral power in one or more of the wavelength ranges other than the reference wavelength range increased or decreased within 30% greater or less, within 20% greater or less, within 10% greater or less, or within 5% greater or less than the values shown in one or more of Tables 12-15 for one or more of Violet Channels 1-6 and the Exemplary Violet Channels Average.

In some implementations, the lighting channels of the present disclosure can each product a colored light having spectral power distributions having particular characteristics. In certain implementations, the spectral power distributions of some lighting channels can have peaks, points of relatively higher intensity, and valleys, points of relatively lower intensity that fall within certain wavelength ranges and have certain relative ratios of intensity between them.

Tables 38 and 39 and FIG. 19 show some aspects of exemplary violet lighting channels for some implementations of the disclosure. In certain implementations, a Violet Peak ($V_P$) is present in a range of about 380 nm to about 460 nm. In further implementations, a Violet Valley ($V_V$) is present in a range of about 450 nm to about 510 nm. In some implementations, a Green Peak ($G_P$) is present in a range of about 500 nm to about 650 nm. In certain implementations, a Red Valley ($R_V$) is present in a range of about 650 nm to about 780 nm. Table 38 shows the relative intensities of the peaks and valleys for exemplary violet lighting channels of the disclosure, with the $V_P$ values assigned an arbitrary value of 1.0 in the table. The wavelength at which each peak or valley is present is also shown in Table 38. Table 39 shows the relative ratios of intensity between particular pairs of the peaks and valleys of the spectral power distributions for exemplary violet lighting channels and minimum, average, and maximum values thereof. In certain implementations, the violet channel can have a spectral power distribution with the relative intensities of $V_V$, $G_P$, and $R_V$ increased or decreased within 30% greater or less, within 20% greater or less, within 10% greater or less, or within 5% greater or less than the values shown in Table 38 for one or more of Violet Channels 1-5 and the Exemplary Violet Channels Average. In some implementations, the violet channel can produce violet light having a spectral power distribution with peak and valley intensities that fall between the Exemplary Violet Channels Minimum and the Exemplary Violet Channels Maximum shown in Table 38. In further implementations, the violet channel can produce violet light having a spectral power distribution with relative ratios of intensity between particular pairs of the peak and valley intensities that fall between the Exemplary Violet Channels Minimum and the Exemplary Violet Channels Maximum values shown in Table 39. In certain implementations, the violet channel can have a spectral power distribution with the relative ratios of intensity between particular pairs of the peak and valley intensities increased or decreased within 30% greater or less, within 20% greater or less, within 10% greater or less, or within 5% greater or less than the relative ratio values shown in Table 39 for one or more of Violet Channels 1-5 and the Exemplary Violet Channels Average.

Tables 40 and 41 and FIG. 20 show some aspects of exemplary yellow lighting channels for some implementations of the disclosure. In certain implementations, a Violet Peak ($V_P$) is present in a range of about 330 nm to about 430 nm. In further implementations, a Violet Valley ($V_V$) is present in a range of about 420 nm to about 510 nm. In some implementations, a Green Peak ($G_P$) is present in a range of about 500 nm to about 780 nm. Table 40 shows the relative intensities of the peaks and valleys for exemplary yellow lighting channels of the disclosure, with the $G_P$ values assigned an arbitrary value of 1.0 in the table. The wavelength at which each peak or valley is present is also shown in Table 40. Table 41 shows the relative ratios of intensity between particular pairs of the peaks and valleys of the spectral power distributions for exemplary yellow lighting channels and minimum, average, and maximum values thereof. In certain implementations, the yellow channel can have a spectral power distribution with the relative intensities of $V_P$ and $V_V$ increased or decreased within 30% greater or less, within 20% greater or less, within 10% greater or less, or within 5% greater or less than the values for one or more of Yellow Channels 1-6 and the Exemplary Yellow Channels Average shown in Table 40. In some implementations, the yellow channel can produce yellow light having a spectral power distribution with peak and valley intensities that fall between the Exemplary Yellow Channels Minimum and the Exemplary Yellow Channels Maximum shown in Table 40. In further implementations, the yellow channel can produce yellow light having a spectral power distribution with relative ratios of intensity between particular pairs of the peak and valley intensities that fall between the Exemplary Yellow Channels Minimum and the Exemplary Yellow Channels Maximum values shown in Table 41. In certain implementations, the yellow channel can have a spectral power distribution with the relative ratios of intensity between particular pairs of the peak and valley intensities increased or decreased within 30% greater or less, within 20% greater or less, within 10% greater or less, or within 5% greater or less than the relative ratio values for one or more of Yellow Channels 1-6 and the Exemplary Yellow Channels Average shown in Table 41.

Tables 42, 43, and 61-63 and FIG. 21, FIGS. 29-35 show some aspects of exemplary red lighting channels (including both visible and non-visible LRNE) for some implementations of the disclosure. In certain implementations, a Blue Peak (BP) is present in a range of about 380 nm to about 460 nm. In further implementations, a Blue Valley ($B_V$) is present in a range of about 450 nm to about 510 nm. In some implementations, a Red Peak ($R_P$) is present in a range of about 500 nm to about 780 nm. Table 42 shows the relative intensities of the peaks and valleys for exemplary red lighting channels of the disclosure, with the $R_P$ values assigned an arbitrary value of 1.0 in the table. The wavelength at which each peak or valley is present is also shown in Table 42. Table 43 shows the relative ratios of intensity between particular pairs of the peaks and valleys of the spectral power distributions for exemplary red lighting channels and minimum, average, and maximum values thereof. In certain implementations, the red channel can have a spectral power distribution with the relative intensities of BP and By increased or decreased within 30% greater or less, within 20% greater or less, within 10% greater or less, or within 5% greater or less than the values for one or more of Red Channels 1, 3-6, and 9-17 and the Exemplary Red Channels Average shown in Table 42. In some implementations, the red channel can produce red light having a spectral power distribution with peak and valley intensities that fall between the Exemplary Red Channels Minimum and the Exemplary Red Channels Maximum shown in Table 42. In further implementations, the red channel can produce red light having a spectral power distribution with relative ratios of intensity between particular pairs of the peak and valley intensities that fall between the Exemplary Red Channels Minimum and the Exemplary Red Channels Maximum values shown in Table 43. In certain implementations, the red channel can have a spectral power distribution with the relative ratios of intensity between particular pairs of the peak and valley intensities increased or decreased within 30% greater or less, within 20% greater or less, within 10% greater or less, or within 5% greater or less than the relative ratio values for one or more of Red Channels 1, 3-6, and 9-17 and the Exemplary Red Channels Average shown in Table 43.

Luminescent Materials and Luminophoric Mediums

Blends of luminescent materials can be used in luminophoric mediums having the desired saturated color points when excited by their respective LED strings including luminescent materials such as those disclosed in co-pending U.S. Pat. No. 9,719,660 issued Aug. 1, 2017, entitled "Compositions for LED Light Conversions", the entirety of which is hereby incorporated by this reference as if fully set forth herein. Traditionally, a desired combined output light can be generated along a tie line between the LED string output light color point and the saturated color point of the associated recipient luminophoric medium by utilizing different ratios of total luminescent material to the encapsulant material in which it is incorporated. Increasing the amount of luminescent material in the optical path will shift the output light color point towards the saturated color point of the luminophoric medium. In some instances, the desired saturated color point of a recipient luminophoric medium can be achieved by blending two or more luminescent materials in a ratio. The appropriate ratio to achieve the desired saturated color point can be determined via methods known in the art. Generally speaking, any blend of luminescent materials can be treated as if it were a single luminescent material, thus the ratio of luminescent materials in the blend can be adjusted to continue to meet a target CIE value for LED strings having different peak emission wavelengths. Luminescent materials can be tuned for the desired excitation in response to the selected LEDs used in the LED strings, which may have different peak emission wavelengths within the range of from about 360 nm to about 535 nm. Suitable methods for tuning the response of luminescent materials are known in the art and may include altering the concentrations of dopants within a phosphor, for example. In some implementations of the present disclosure, luminophoric mediums can be provided with combinations of two types of luminescent materials. The first type of luminescent material emits light at a peak emission between about 515 nm and about 590 nm in response to the associated LED string emission. The second type of luminescent material emits at a peak emission between about 590 nm and about 700 nm in response to the associated LED string emission. In some instances, the luminophoric mediums disclosed herein can be formed from a combination of at least one luminescent material of the first and second types described in this paragraph. In implementations, the luminescent materials of the first type can emit light at a peak emission at about 515 nm, 525 nm, 530 nm, 535 nm, 540 nm, 545 nm, 550 nm, 555 nm, 560 nm, 565 nm, 570 nm, 575 nm, 580 nm, 585 nm, or 590 nm in response to the associated LED string emission. In preferred implementations, the luminescent materials of the first type can emit light at a peak emission between about 520 nm to about 555 nm. In implementations, the luminescent materials of the second type can emit light at a peak emission at about 590 nm, about 595 nm, 600 nm, 605 nm, 610 nm, 615 nm, 620 nm, 625 nm, 630 nm, 635 nm, 640 nm, 645 nm, 650 nm, 655 nm, 670 nm, 675 nm, 680 nm, 685 nm, 690 nm, 695 nm, or 700 nm in response to the associated LED string emission. In preferred implementations, the luminescent materials of the first type can emit light at a peak emission between about 600 nm to about 670 nm. Some exemplary luminescent materials of the first and second type are disclosed elsewhere herein and referred to as Compositions A-F. Table 6 shows aspects of some exemplar luminescent materials and properties.

Blends of Compositions A-F can be used in luminophoric mediums having desired saturated color points when excited by respective LED strings in the lighting channels of the disclosure. In some implementations, one or more blends of one or more of Compositions A-F can be used to produce luminophoric mediums. In some preferred implementations, one or more of Compositions A, B, and D and one or more of Compositions C, E, and F can be combined to produce luminophoric mediums. In some preferred implementations, the encapsulant for luminophoric mediums comprises a matrix material having density of about 1.1 mg/mm3 and refractive index of about 1.545 or from about 1.4 to about 1.6. In some implementations, Composition A can have a refractive index of about 1.82 and a particle size from about 18 micrometers to about 40 micrometers. In some implementations, Composition B can have a refractive index of about 1.84 and a particle size from about 13 micrometers to about 30 micrometers. In some implementations, Composition C can have a refractive index of about 1.8 and a particle size from about 10 micrometers to about 15 micrometers. In some implementations, Composition D can have a refractive index of about 1.8 and a particle size from about 10 micrometers to about 15 micrometers. Suitable phosphor materials for Compositions A, B, C, and D are commercially available from phosphor manufacturers such as Mitsubishi Chemical Holdings Corporation (Tokyo, Japan), Intematix Corporation (Fremont, CA), EMD Performance Materials of Merck KGaA (Darmstadt, Germany), and PhosphorTech Corporation (Kennesaw, GA).

TABLE 6

| Designator | Exemplary Material(s) | Density (g/mL) | Emission Peak (nm) | FWHM (nm) | Emission Peak Range (nm) | FWHM Range (nm) |
|---|---|---|---|---|---|---|
| Composition "A" | Luag: Cerium doped lutetium aluminum garnet ($Lu_3Al_5O_{12}$) | 6.73 | 535 | 95 | 530-540 | 90-100 |
| Composition "B" | Yag: Cerium doped yttrium aluminum garnet ($Y_3Al_5O_{12}$) | 4.7 | 550 | 110 | 545-555 | 105-115 |
| Composition "C" | a 650 nm-peak wavelength emission phosphor: Europium doped calcium aluminum silica nitride ($CaAlSiN_3$) | 3.1 | 650 | 90 | 645-655 | 85-95 |
| Composition "D" | a 525 nm-peak wavelength emission phosphor: GBAM:$BaMgAl_{10}O_{17}$:Eu | 3.1 | 525 | 60 | 520-530 | 55-65 |
| Composition "E" | a 630 nm-peak wavelength emission quantum dot: any semiconductor quantum dot material of appropriate size for desired emission wavelengths | 5.1 | 630 | 40 | 625-635 | 35-45 |
| Composition "F" | a 610 nm-peak wavelength emission quantum dot: any semiconductor quantum dot material of appropriate size for desired emission wavelengths | 5.1 | 610 | 40 | 605-615 | 35-45 |

Luminescent materials can include phosphors, scintillators, day glow tapes, nanophosphors, inks that glow in visible spectrum upon illumination with light, semiconductor quantum dots, or combinations thereof. In some implementations, the luminescent materials may comprise phosphors comprising one or more of the following materials: $BaMg_2Al_{16}O_{27}$:$Eu^{2+}$, $BaMg_2Al_{16}O_{27}$:$Eu^{2+}$, $Mn^{2+}$, $CaSiO_3$: Pb,Mn, $CaWO_4$:Pb, $MgWO_4$, $Sr_5Cl(PO_4)_3$:$Eu^{2+}$, $Sr_2P_2O_7$:$Sn^{2+}$, $Sr_6P_5BO_{20}$:Eu, $Ca_5F(PO_4)_3$:Sb, $(Ba,Ti)_2P_2O_7$:Ti, $Sr_5F(PO_4)_3$:Sb,Mn, $(La,Ce,Tb)PO_4$:Ce,Th, $(Ca,Zn,Mg)_3(PO_4)_2$:Sn, $(Sr,Mg)_3(PO_4)_2$:Sn, $Y_2O_3$:$Eu^{3+}$, $Mg_4(F)GeO_6$:Mn, $LaMgAl_{11}O_{19}$:Ce, $LaPO_4$:Ce, $SrAl_{12}O_{19}$:Ce, $BaSi_2O_5$:Pb, $SrB_4O_7$:Eu, $Sr_2MgSi_2O_7$:Pb, $Gd_2O_2S$:Tb, $Gd_2O_2S$:Eu, $Gd_2O_2S$:Pr, $Gd_2O_2S$:Pr,Ce,F, $Y_2O_2S$:Tb, $Y_2O_2S$:Eu, $Y_2O_2S$:Pr, $Zn(0.5)Cd(0.4)S$:Ag, $Zn(0.4)Cd(0.6)S$:Ag, $Y_2SiO_5$:Ce, $YAlO_3$:Ce, $Y_3(Al,Ga)_5O_{12}$:Ce, CdS:In, ZnO:Ga, ZnO:Zn, (Zn,Cd)S:Cu,Al, ZnCdS:Ag,Cu, ZnS:Ag, ZnS:Cu, NaI:Tl, CsI:Tl, $^6$LiF/ZnS:Ag, $^6$LiF/ZnS:Cu,Al,Au, ZnS:Cu,Al, ZnS:Cu,Au,Al, $CaAlSiN_3$:Eu, $(Sr,Ca)AlSiN_3$:Eu, $(Ba,Ca,Sr,Mg)_2SiO_4$:Eu, $Lu_3Al_5O_{12}$:Ce, $Eu^{3+}(Gd_{0.9}Y_{0.1})_3Al_5O_{12}$:$Bi^{3+}$,$Tb^{3+}$, $Y_3Al_{15}O_{12}$:Ce, $(La,Y)_3Si_6Nn$:Ce, $Ca_2AlSi_3O_2N_5$:$Ce^{3+}$, $Ca_2AlSi_3O_2N_5$:$Eu^{2+}$, $BaMgAl_{10}O_{17}$:Eu, $Sr_5(PO_4)_3Cl$:Eu, $(Ba,Ca,Sr,Mg)_2SiO_4$:Eu, $Si_{6-z}Al_zN_{8-z}O_z$:Eu (wherein 0<z≤4.2); $M_3Si_6O_2N_2$:Eu (wherein M=alkaline earth metal element), $(Mg,Ca,Sr,Ba)Si_2O_2N_2$:Eu, $Sr_4Al_{14}O_{25}$:Eu, $(Ba,Sr,Ca)Al_2O_4$:Eu, $(Sr,Ba)Al_2Si_2O_8$:Eu, $(Ba,Mg)_2SiO_4$:Eu, $(Ba,Sr,Ca)_2(Mg, Zn)Si_2O_7$:Eu, $(Ba, Ca,Sr,Mg)_9(Sc,Y,Lu,Gd)_2(Si,Ge)_6O_{24}$:Eu, $Y_2SiO_5$:CeTb, $Sr_2P_2O_7$—$Sr_2B_2O_5$:Eu, $Sr_2Si_3O_8$-$2SrCl_2$:Eu, $Zn_2SiO_4$:Mn, $CeMgAl_{11}O_{19}$:Tb, $Y_3Al_5O_{12}$:Tb, $Ca_2Ys(SiO_4)_6O_2$:Tb, $La_3Ga_5SiO_{14}$:Tb, $(Sr,Ba,Ca)Ga_2S_4$:Eu,Tb,Sm, $Y_3(Al,Ga)_5O_{12}$:Ce, $(Y,Ga,Tb,La,Sm,Pr,Lu)_3(Al,Ga)_5O_{12}$:Ce, $Ca_3Sc_2Si_3O_{12}$:Ce, $Ca_3(Sc,Mg, Na,Li)$_2$Si$_3$O$_{12}$:Ce, CaSc$_2$O$_4$:Ce, Eu-activated β-Sialon, SrAl$_2$O$_4$:Eu, (La,Gd,Y)$_2$O$_2$S:Tb, CeLaPO$_4$:Tb, ZnS:Cu,Al, ZnS:Cu,Au,Al, (Y,Ga,Lu,Sc,La)BO$_3$:Ce,Tb, Na$_2$Gd$_2$B$_2$O$_7$: Ce,Tb, (Ba,Sr)$_2$(Ca,Mg,Zn)B$_2$O$_6$:K,Ce,Tb, Ca$_8$Mg(SiO$_4$)$_4$Cl$_2$:Eu,Mn, (Sr,Ca,Ba)(Al,Ga,In)$_2$S$_4$:Eu, (Ca,Sr)$_8$(Mg,Zn)(SiO$_4$)$_4$Cl$_2$:Eu,Mn, M$_3$Si$_6$O$_9$N$_4$:Eu, Sr$_5$Al$_5$Si$_{21}$O$_2$N$_{35}$:Eu, Sr$_3$Si$_{13}$Al$_3$N$_{21}$O$_2$:Eu, (Mg,Ca,Sr,Ba)$_2$Si$_5$N$_8$:Eu, (La,Y)$_2$O$_2$S:Eu, (Y,La,Gd,Lu)$_2$O$_2$S:Eu, Y(V,P)O$_4$:Eu, (Ba,Mg)$_2$SiO$_4$:Eu,Mn, (Ba,Sr,Ca,Mg)$_2$SiO$_4$:Eu,Mn, LiW$_2$O$_8$:Eu, LiW$_2$O$_8$:Eu,Sm, Eu$_2$W$_2$O$_9$, Eu$_2$W$_2$O$_9$:Nb and Eu$_2$W$_2$O$_9$: Sm, (Ca,Sr)S:Eu, YAlO$_3$:Eu, Ca$_2$Y$_8$(SiO$_4$)$_6$O$_2$:Eu, LiY$_9$(SiO$_4$)$_6$O$_2$:Eu, (Y,Gd)$_3$Al$_5$O$_{12}$:Ce, (Tb,Gd)$_3$Al$_5$O$_{12}$:Ce, (Mg,Ca,Sr,Ba)$_2$Si$_5$(N,O)$_8$:Eu, (Mg,Ca,Sr,Ba)Si(N,O)$_2$:Eu, (Mg,Ca,Sr,Ba)AlSi(N,O)$_3$:Eu, (Sr,Ca,Ba,Mg)$_{10}$(PO$_4$)Cl$_2$: Eu, Mn,Eu,Ba$_3$MgSi$_2$O$_8$:Eu,Mn, (Ba,Sr,Ca,Mg)$_3$(Zn,Mg)Si$_2$O$_8$:Eu,Mn, (k-x)MgO.xAF$_2$.GeO$_2$:yMn$^{4+}$ (wherein k=2.8 to 5, x=0.1 to 0.7, y=0.005 to 0.015, A=Ca, Sr, Ba, Zn or a mixture thereof), Eu-activated α-Sialon, (Gd,Y,Lu,La)$_2$O$_3$:Eu, Bi, (Gd,Y,Lu,La)$_2$O$_2$S:Eu,Bi, (Gd,Y,Lu,La)VO$_4$:Eu, Bi, SrY$_2$S$_4$:Eu,Ce, CaLa$_2$S$_4$:Ce,Eu, (Ba,Sr,Ca)MgP$_2$O$_7$:Eu, Mn, (Sr,Ca,Ba,Mg,Zn)$_2$P$_2$O$_7$:Eu,Mn, (Y,Lu)$_2$WO$_6$:Eu,Ma, (Ba,Sr,Ca)$_x$Si$_y$N$_z$:Eu,Ce (wherein x, y and z are integers equal to or greater than 1),(Ca,Sr,Ba,Mg)$_{10}$(PO$_4$)$_6$(F,Cl,Br,OH):Eu,Mn, ((Y,Lu,Gd,Tb)$_{1-x-y}$Sc$_x$Ce$_y$)$_2$(Ca,Mg)(Mg,Zn)$_{2+r}$Si$_{z-q}$Ge$_q$O$_{12-δ}$, SrAlSi$_4$N$_7$, Sr$_2$Al$_2$Si$_9$O$_2$N$_{14}$:Eu, M$^1_a$M$^2_b$M$^3_c$O$_d$ (wherein M$^1$=activator element including at least Ce, M$^2$=bivalent metal element, M$^3$=trivalent metal element, 0.0001≤a≤0.2, 0.8≤b≤1.2, 1.6≤c≤2.4 and 3.2≤d≤4.8), Al$_{2+x}$M$_y$Mn$_z$F$_n$ (wherein A=Na and/or K; M=Si and Al, and −1≤x≤1, 0.9≤y+z≤1.1, 0.001≤z≤0.4 and 5≤n≤7), KSF/KSNAF, or (La$_{1-x-y}$, Eu$_x$, Ln$_y$)$_2$O$_2$S (wherein 0.02≤x≤0.50 and 0≤y≤0.50, Ln=Y$^{3+}$, Gd$^{3+}$, Lu$^{3+}$, Sc$^{3+}$, Sm$^{3+}$ or Er$^{3+}$). In some preferred implementations, the luminescent materials may comprise phosphors comprising one or more of the following materials: CaAlSiN$_3$:Eu, (Sr,Ca)AlSiN$_3$:Eu, BaMgAl$_{10}$O$_{17}$:Eu, (Ba,Ca,Sr,Mg)$_2$SiO$_4$: Eu, β-SiAlON, Lu$_3$Al$_5$O$_{12}$:Ce, Eu$^{3+}$(Cd$_{0.9}$Y$_{0.1}$)$_3$Al$_5$O$_{12}$: Bi$^{3+}$,Tb$^{3+}$, Y$_3$Al$_5$O$_{12}$:Ce, La$_3$Si$_6$N$_{11}$:Ce, (La,Y)$_3$Si$_6$N$_{11}$:Ce, Ca$_2$AlSi$_3$O$_2$N$_5$:Ce$^{3+}$, Ca$_2$AlSi$_3$O$_2$N$_5$:Ce$^{3+}$,Eu$^{2+}$, Ca$_2$AlSi$_3$O$_2$N$_5$:Eu$^{2+}$, BaMgAl$_{10}$O$_{17}$:Eu$^{2+}$, Sr$_{4.5}$Eu$_{0.5}$(PO$_4$)$_3$Cl, or M$^1_a$M$^2_b$M$^3_c$O$_d$ (wherein M$^1$=activator element comprising Ce, M$^2$=bivalent metal element, M$^3$=trivalent metal element, 0.0001≤a≤0.2, 0.8≤b≤1.2, 1.6≤c≤2.4 and 3.2≤d≤4.8). In further preferred implementations, the luminescent materials may comprise phosphors comprising one or more of the following materials: CaAlSiN$_3$:Eu, BaMgAl$_{10}$O$_{17}$:Eu, Lu$_3$Al$_5$O$_{12}$:Ce, or Y$_3$Al$_5$O$_{12}$:Ce.

In certain implementations, LRNE emissions can be generated with one or more luminescent materials that generate emissions with wavelengths between about 625 nm and about 1400 nm. In some implementations, the luminescent materials can comprise phosphors comprising one or more of the materials listed above. FIG. 29 shows an emission profile for an exemplary long-red phosphor, referred to herein as Long-Red Phosphor 700 nm, having a peak emission wavelength of about 700 nm suitable for some implementations. In certain implementations, an exemplary long-red phosphor, referred to herein as Long-Red Phosphor 675 nm, having a peak emission wavelength of about 675 nm can be used. Some aspects of the spectral power distributions of the emissions for Long-Red Phosphor 700 nm and Long-Red Phosphor 675 nm are shown in Tables 61-63.

In yet further implementations, the luminescent materials can comprise phosphors comprising one or more of the following materials excited by light at about 273 nm: LiAlO$_2$:Fe$^{3+}$ (peak at 770 nm), CdS:Ag$^+$,Cl$^-$ (peak at 800 nm), ZnSbGaTe:Cr$^{3+}$,Nd$^{3+}$ (peak at 845 nm), La$_3$In$_2$Ga$_3$O$_{12}$:Cr, Dy$^3$ (peak at 905 nm), BaGd$_2$ZnO$_5$:Yb$^{3+}$ (peak at 979 nm) and Ba(GdY)$_2$ZnO$_5$:Yb$^{3+}$ (peak at 979 nm). In further implementations, the luminescent materials can comprise chemically modified versions of these phosphors having excitation bands overlapping with violet or blue LED wavelengths.

In certain implementations, the luminophoric mediums can include luminescent materials that comprise one or more quantum materials. Throughout this specification, the term "quantum material" means any luminescent material that includes: a quantum dot; a quantum wire: or a quantum well. Some quantum materials may absorb and emit light at spectral power distributions having narrow wavelength ranges, for example, wavelength ranges having spectral widths being within ranges of between about 25 nanometers and about 50 nanometers. In examples, two or more different quantum materials may be included in a lumiphor, such that each of the quantum materials may have a spectral power distribution for light emissions that may not overlap with a spectral power distribution for light absorption of any of the one or more other quantum materials. In these examples, cross-absorption of light emissions among the quantum materials of the lumiphor may be minimized. Throughout this specification, the term "quantum dot" means: a nanocrystal made of semiconductor materials that are small enough to exhibit quantum mechanical properties, such that its excitons are confined in all three spatial dimensions. Throughout this specification, the term "quantum wire" means: an electrically conducting wire in which quantum effects influence the transport properties. Throughout this specification, the term "quantum well" means: a thin layer that can confine (quasi-)particles (typically electrons or holes) in the dimension perpendicular to the layer surface, whereas the movement in the other dimensions is not restricted.

Circadian-Inducing Blue Properties

In some aspects, the bioactive circadian-inducing blue light in the display systems can have circadian-stimulating energy (CSE) characteristics that lead to biological effects in users. The circadian-inducing blue, and overall light emissions including the circadian-inducing blue, can have a first circadian-stimulating energy characteristic related to the associated first spectral power distribution of the circadian-inducing blue or overall light emissions, while light emissions from the non-circadian-inducing blue and related overall light emissions can have a second circadian-stimulating energy characteristic related to the associated second spectral power distribution of the circadian-inducing blue or overall light emissions.

In certain implementations, the first circadian-stimulating energy characteristic and the second circadian-stimulating energy characteristic can be the percentage of the spectral power in the associated first spectral power distribution and the second spectral power distribution, respectively, between a first wavelength value and a second wavelength value, forming a particular wavelength range therein greater than the first wavelength value and less than or equal to the second wavelength value. In some instances, the first and second circadian-stimulating energy characteristics can be one or more of the percentage of spectral power in the wavelength ranges of 470 nm<λ≤480 nm, 480 nm<λ≤490 nm, and 490 nm<λ≤500 nm in comparison to the total energy from 320 nm<λ≤800 nm in the first and second spectral power distributions respectively. In some implementations, the percentage of spectral power in the wavelength ranges of 470 nm<λ≤480 nm in comparison to the total energy from 320 nm<λ≤800 nm of the first spectral power distribution can be between about 2.50 and about 6.00, between about 3.00 and about 5.50, between about 3.00 and about 4.00, between about 3.50 and about 4.00, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, or about 6.0. In certain implementations, the percentage of spectral power in the wavelength ranges of 480 nm<$\lambda$≤490 nm in comparison to the total energy from 320 nm<$\lambda$≤800 nm in the first spectral power distribution can be between about 4.0 and about 6.5, between about 4.5 and about 5.5, between about 4.4 and about 4.6, between about 5.2 and about 5.8, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, or about 6.5. In some implementations, the percentage of spectral power in the wavelength ranges of 490 nm<$\lambda$≤500 nm in comparison to the total energy from 320 nm<$\lambda$≤800 nm in the first spectral power distribution can be between about 3.5 and about 6.0, between about 4.0 and about 5.0, between about 4.5 and about 5.5, between about 4.5 and about 5.0, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, or about 6.0. In some implementations, the percentage of spectral power in the wavelength ranges of 470 nm<$\lambda$≤480 nm in comparison to the total energy from 320 nm<$\lambda$≤800 nm in the second spectral power distribution can be between about 0.025 and about 0.080, between about 0.030 and about 0.060, between about 0.050 and about 0.070, between about 0.050 and about 0.060, about 0.025, about 0.030, about 0.035, about 0.040, about 0.045, about 0.050, about 0.055, about 0.56, about 0.57, about 0.58, about 0.59, about 0.060, about 0.61, about 0.62, about 0.63, about 0.64, about 0.065, about 0.66, about 0.67, about 0.68, about 0.69, about 0.070, about 0.075, or about 0.080. In certain implementations, the percentage of spectral power in the wavelength ranges of 480 nm<$\lambda$≤490 nm in comparison to the total energy from 320 nm<$\lambda$≤800 nm in the second spectral power distribution can be between about 0.10 and about 0.30, between about 0.10 and about 0.15, between about 0.20 and about 0.25, between about 0.13 and about 0.24, about 0.10, about 0.11, about 0.12, about 0.13, about 0.14, about 0.15, about 0.016, about 0.17, about 0.18, about 0.19, about 0.20, about 0.21, about 0.22, about 0.23, about 0.24, about 0.25, about 0.26, about 0.27, about 0.28, about 0.29, or about 0.30. In some implementations, the percentage of spectral power in the wavelength ranges of 490 nm<$\lambda$≤500 nm in comparison to the total energy from 320 nm<$\lambda$≤800 nm in the second spectral power distribution can be between about 0.25 and about 0.75, between about 0.25 and about 0.40, between about 0.55 and about 0.70, between about 0.30 and about 0.35, about 0.25, about 0.26, about 0.27, about 0.28, about 0.29, about 0.30, about 0.31, about 0.32, about 0.33, about 0.34, about 0.35, about 0.36, about 0.37, about 0.38, about 0.39, about 0.40, about 0.41, about 0.42, about 0.43, about 0.44, about 0.45, about 0.46, about 0.47, about 0.48, about 0.49, about 0.50, about 0.51, about 0.52, about 0.53, about 0.54, about 0.55, about 0.56, about 0.57, about 0.58, about 0.59, about 0.60, about 0.61, about 0.62, about 0.63, about 0.64, about 0.65, about 0.66, about 0.67, about 0.68, about 0.69, about 0.70, about 0.71, about 0.72, about 0.73, about 0.74, or about 0.75.

In further aspects of the present disclosure, the first and second circadian-stimulating energy characteristics can relate to spectral energy within particular wavelength ranges. In some implementations, spectral energy concentrations within particular wavelength ranges can lead to biological effects by providing photostimulation to intrinsically photosensitive retinal ganglion cells (ipRGCs), which express melanopsin, a photopigment that can respond to light directly, and can be associated with non-image-forming functions such as circadian photoentrainment and pupil-size control in addition to some image-forming functions, ipRGCs are sensitive to light at wavelengths between about 400 nm and about 600 nm, with a peak sensitivity and response to light with wavelengths around 480 nm to 490 nm. In certain implementations, the first circadian-stimulating energy characteristic and the second circadian-stimulating energy characteristic can be the percentage of the spectral power in the first spectral power distribution and the second spectral power distribution, respectively, between a first wavelength value and a second wavelength value, forming a particular wavelength range therein greater than the first wavelength value and less than or equal to the second wavelength value. In some implementations, the first wavelength value can be about 400 nm, about 410 nm, about 420 nm, about 430 nm, about 440 nm, about 450 nm, about 460 nm, about 470 nm, about 480 nm, about 490 nm, about 500 nm, about 510 nm, about 520 nm, about 530 nm, about 540 nm, about 550, about 560 nm, about 570 nm, about 580 nm, about 590 nm, or about 600 nm. In some implementations, the second wavelength value can be about 410 nm, about 420 nm, about 430 nm, about 440 nm, about 450 nm, about 460 nm, about 470 nm, about 480 nm, about 490 nm, about 500 nm, about 510 nm, about 520 nm, about 530 nm, about 540 nm, about 550, about 560 nm, about 570 nm, about 580 nm, about 590 nm, about 600 nm, or about 610 nm. In certain implementations, the first wavelength value can be 440 nm and the second wavelength value can be 490 nm, with the particular wavelength range being 440<$\lambda$≤490 nm, as shown for values for the exemplary first and second lighting channels shown in Table 3, which shows the percent spectral energy in the range 440<$\lambda$≤490 nm in comparison to the total spectral energy in the range 380<$\lambda$≤780 nm. In further implementations, other first and second wavelength values can be selected for the first circadian-stimulating energy characteristic and the second circadian-stimulating energy characteristic of the percentages of the spectral power in the first spectral power distribution and the second spectral power distribution between the first and second wavelength values, including but not limited to wavelength ranges (in nm) from about 400 to about 410, about 410 to about 420, about 420 to about 430, about 430 to about 440, about 440 to about 450, about 450 to about 460, about 460 to about 470, about 470 to about 480, about 480 to about 490, about 490 to about 500, about 500 to about 510, about 510 to about 520, about 520 to about 530, about 530 to about 540, about 540 to about 550, or about 550 to about 560.

In certain implementations, one or more of the circadian-stimulating energy characteristics of the lighting systems can be EML values of the first, second, and third white light. In some aspects of the present disclosure, the lighting systems can provide a ratio of a first EML value of the first spectral power distribution to a second EML value of the second spectral power distribution. In some implementations, the ratio of the first EML value to the second EML value can be between about 2.0 and about 5.5, between about 3.0 and about 5.0, between about 2.8 and about 3.8, between about 2.6 and about 3.3, between about 4.0 and about 5.5, between about 4.5 and about 5.5, between about 5.5 and about 6.5, between about 6.5 and about 7.5, between about 7.5 and about 8.5, between about 8.5 and about 9.5, between about 2.0 and about 10.0, between about 3.0 and about 10.0, between about 4.0 and about 10.0, between about 5.0 and about 10.0, between about 6.0 and about 10.0, between about 7.0 and about 10.0, between about 8.0 and about 10.0, or between about 9.0 and about 10.0. In further implementations, the ratio of the first EML value to the second EML value can be about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6, about 6.1, about 6.2, about 6.3, about 6.4, about 6.5, about 6.6, about 6.7, about 6.8, about 6.9, about 7, about 7.1, about 7.2, about 7.3, about 7.4, about 7.5, about 7.6, about 7.7, about 7.8, about 7.9, about 8, about 8.1, about 8.2, about 8.3, about 8.4, about 8.5, about 8.6, about 8.7, about 8.8, about 8.9, about 9, about 9.1, about 9.2, about 9.3, about 9.4, about 9.5, about 9.6, about 9.7, about 9.8, about 9.9, or about 10.0.

In certain implementations, the first spectral power distribution has a first circadian-stimulating energy characteristic, and the second spectral power distribution has a second circadian-stimulating energy characteristic. In some implementations, the first circadian-stimulating energy characteristic can be a first percentage, the first percentage comprising the percentage of the spectral power between 380 nm and 780 nm in the first spectral power distribution between 440 nm and 490 nm. In certain implementations, the second circadian-stimulating energy characteristic can be a second percentage, the second percentage comprising the percentage of the spectral power between 380 nm and 780 nm in the second spectral power distribution between 440 nm and 490 nm. In certain implementations of the lighting systems of the present disclosure, the first percentage can be between about 15% and about 25%, between about 16% and about 22%, about 16%, about 17%, about 18%, about 19%, about 20%, about 21%, about 22%, about 23%, about 24%, or about 25%. In further implementations of the lighting systems of the present disclosure, the second percentage can be between about 0.9% and about 1.05%, between about 0.85% and about 0.95%, between about 0.85% and about 0.90%, between about 0.90% and about 0.95%, about 0.90%, about 0.91%, about 0.92%, about 0.93%, about 0.94%, about 0.95%, about 0.96%, about 0.97%, about 0.98%, about 0.99%, about 1.00%, about 1.01%, about 1.02%, about 1.03%, about 1.04%, or about 1.05%. In some implementations, the lighting systems can have a ratio of the first percentage to the second percentage of between about 13 and about 30, between about 15 and about 25, between about 20 and about 25, between about 20 and about 30, between about 18 and about 22, about 13, about 14, about 15, about 16, about 17, about 18, about 19, about 20, about 21, about 22, about 23, about 24, about 25, about 26, about 27, about 28, about 29, or about 30.

LRNE Properties

In some aspects, the bioactive LRNE red light in the display systems can have long red near infrared energy characteristics that lead to biological effects in users. The LRNE and overall light emissions including the LRNE can have a first LRNE energy characteristic related to the associated first spectral power distribution of the long red portion of the LRNE or overall light emissions.

The LRNE and overall light emissions including the LRNE can have a second LRNE energy characteristic related to the associated second spectral power distribution of the near infrared portion of the LRNE or overall light emissions.

As illustrated in FIG. 38, various lighting systems and control system embodiments may be implemented in accordance with the present invention. Several devices and examples are discussed below, but it will be appreciated that the present invention is not limited to those particular configurations, and may be applied to any combination of devices, computing systems, control systems, data centers, structures, and the like.

An integrated control system can connect one or more external systems, input, and information to provide bioactive lighting, as discussed herein, through a plurality of devices, systems, and modalities. In various examples, the control system may communicate over one or more computing systems using one or more servers and networks 3305 in communication with one another (e.g., network, Bluetooth, wired, wireless communication, etc.).

In embodiments, lighting systems associated with each device may be managed by a master device 3340, which can communicate various lighting levels, timing, and configuration, for example, to achieve the desired bioactive lighting. Such levels may vary based on one or more of time of day, intended effect of the lighting, individual preferences, capabilities of the device, feedback mechanisms, sensor input, and more.

As illustrated in FIG. 38, control systems may comprise a variety of devices, including but not limited to panels and panel systems 3310, computing systems 3320, laptops, mobile devices 3330, wearable devices 3333, sensors 3335, lighting systems 3350 including but not limited to home, office, vehicle, and industrial lighting systems. The master device 3340 may be a mobile device, computing systems, as discussed further below, and may be manually managed, automated, incorporated with machine learning, located in the cloud, and more.

In an example, lighting systems that may be used in a bioactive computer display system and/or bioactive panel system 3310 in accordance with the principles of the present inventions may be controlled over time to supplement, treat or otherwise effect biological system and cycles of an exposed user throughout the day in different ways. The lighting systems may be automatically, semi-automatically or manually adjusted. The lighting systems may be adjusted based on sensor data, activity data, social media data, etc.

In embodiments, as the panel 3310 systems are installed in the environment of a lighting installation, networking features automatically engage upon powering up one or more the panel systems, and the panel systems may automatically commission themselves, such as by connecting to an overall control platform and/or to other panel systems. Thus, the panel systems in an installation may self-commission and self-configure to create a network connection between the panel systems in the environment and a remote operator (such as in the cloud). The panel systems may configure in a master/slave, ring, mesh, or peer-to-peer network, by which autonomous control features may be engaged in the environment. In embodiments, remote control features may be engaged using the network connection to the platform or other remote operators.

In embodiments, networked communication can be used among components in the control system 3310 in a deployed lighting installation that includes panel systems. Once installed and commissioned, control of the lighting installation may be handed over to an operator of a platform, such as a building owner, occupant, landlord, tenant, or the like. In embodiments, handoff may include using identity and authentication features, such as using keys, passwords, or the like that allow operation of the lighting installation by permitted users. In embodiments, a remote-control interface of the platform may be used by an operator for remote operation of the lighting installation. The remote-control interface may use a lighting project data structure as a source of knowledge about the properties, configurations, control capabilities, and other elements of a lighting installation, so that the same platform used for the design of the lighting installation may be used to control the lighting installation. The remote-control interface may include operational guidance features, such as guiding users through the operation of a lighting installation.

In embodiments, an autonomous control system may be provided for a lighting installation that includes panel systems of the present disclosure, by which the lighting installation may control various features of the lighting system, such as based on information collected locally in the environment, such as from one or more sensors 3330. For example, the autonomous control system may automatically adjust control parameters for a light source, including but not limited to panel systems, to achieve improved adherence to the overall specifications for a lighting installation, may adjust timing variables based on detected usage patterns in a space, may adjust lighting properties based on changes in a space (such as changes in colors paints, carpet and fabrics), and the like.

Under operation, the lighting installation may include an operational feedback system, configured to collect information about the lighting installation, which may include interfaces for soliciting and receiving user feedback (such as regarding satisfaction with the installation or indicating desired changes) and which may include a sensor system 3330, e.g., a lighting installation sensor system, such as including light sensors, motion sensors, temperature sensors, and others to collect information about the actual lighting conditions in the environment, activities of occupants within the environment, and the like. Information collected by the lighting installation sensor system may be relayed to a validation system of the lighting platform, such as for validation that an installation is operating as designed, including by comparison of light properties at various locations in the environment with the specifications and requirements provided in the lighting design environment, such as reflected in the lighting project data structure. In embodiments, the variances from the specifications and requirements may be provided to the autonomous control system and/or the remote-control system, so that adjustments may be made, either autonomously or by a local or remote operator of the lighting installation, to enable adjustments (such as to colors, intensities, color temperatures, beam directions, and other factors), such as to cause the lighting installation to better meet the specifications and requirements. The operational feedback system may also capture feedback that leads to revisiting the lighting design in the lighting design environment, which may induce further iteration, resulting in changes to control parameters for the panel systems, as well as automated ordering of additional or substitute panel systems, with updated installation and operational guidance.

In embodiments, remote control may enable field programmable lighting systems, such as for transitional environments like museums (where art objects change regularly), stores (where merchandise shifts) and the like as well as for customizable environments (such as personalizing lighting in a hotel room according to a specification for a guest (which may include having the guest select an aesthetic filter) or personalized lighting for a workstation for an employee in an office setting. Such features may enable the lighting installation to change configurations (such as among different aesthetic filters) for multi-use environments, multi-tenant environments, and the like where lighting conditions may need to change substantially over time.

In embodiments, a lighting system may include navigation features, such as being associated with beacons, where the lighting system interacts with one or more devices to track users within a space. The panel systems and their locations may be associated with a map, such as the map of the lighting space in the design environment. The map may be provided from the lighting design environment to one or more other location or navigation systems, such that locations of panel systems may be used as known locations or points of interest within a space.

In some embodiments, the lighting installation may be designed for an operation that is coordinated with one or more external systems, e.g., lighting, panel, and computer systems, which may serve as inputs to the lighting installation, such as music, video and other entertainment content (such as to coordinate lighting with sound). Inputs may include voice control inputs, which may include systems for assessing tone or mood from vocal patterns, such as to adjust lighting based on the same.

Types of User Interfaces and Control Systems for the Control of the Circadian Lighting Lighting systems that may be used in a bioactive computer display system in accordance with the principles of the present disclosure may be controlled over time to affect a person's circadian cycle, and other physiological functions and/or psychological functions throughout the day in different ways. Modes include controlled application or reduction of CSE and application or reduction of LRNE. The lighting systems may be automatically or manually adjusted. The lighting systems may be adjusted based on sensor data, activity data, social media data, etc.

In embodiments, as the display systems are installed in the environment of a lighting installation, networking features automatically engage upon powering up one or more the display systems, and the display systems may automatically commission themselves, such as by connecting to an overall control platform and/or to other display systems. Thus, the display systems in an installation may self-commission and self-configure to create a network connection between the display systems in the environment and a remote operator (such as in the cloud). The display systems may configure in a master/slave, ring, mesh, or peer-to-peer network, by which autonomous control features may be engaged in the environment. In embodiments, remote control features may be engaged using the network connection to the platform or other remote operators.

In embodiments, networked communication can be used among components in a deployed lighting installation that includes display systems. Once installed and commissioned, control of the lighting installation may be handed over to an operator of a platform, such as a building owner, occupant, landlord, tenant, or the like. In embodiments, handoff may include using identity and authentication features, such as using keys, passwords, or the like that allow operation of the lighting installation by permitted users. In embodiments, a remote-control interface of the platform may be used by an operator for remote operation of the lighting installation. The remote-control interface may use a lighting project data structure as a source of knowledge about the properties, configurations, control capabilities, and other elements of a lighting installation, so that the same platform used for the design of the lighting installation may be used to control the lighting installation. The remote-control interface may include operational guidance features, such as guiding users through the operation of a lighting installation.

In embodiments, an autonomous control system may be provided for a lighting installation that includes display systems of the present disclosure, by which the lighting installation may control various features of the lighting system, such as based on information collected locally in the environment, such as from one or more sensors. For example, the autonomous control system may automatically adjust control parameters for a light source, including but not limited to display systems, to achieve improved adherence to the overall specifications for a lighting installation, may adjust timing variables based on detected usage patterns in a space, may adjust lighting properties based on changes in a space (such as changes in colors paints, carpet and fabrics), and the like.

Under operation, the lighting installation may include an operational feedback system, configured to collect information about the lighting installation, which may include interfaces for soliciting and receiving user feedback (such as regarding satisfaction with the installation or indicating desired changes) and which may include a lighting installation sensor system, such as including light sensors, motion sensors, temperature sensors, and others to collect information about the actual lighting conditions in the environment, activities of occupants within the environment, and the like. Information collected by the lighting installation sensor system may be relayed to a validation system of the lighting platform, such as for validation that an installation is operating as designed, including by comparison of light properties at various locations in the environment with the specifications and requirements provided in the lighting design environment, such as reflected in the lighting project data structure. In embodiments, the variances from the specifications and requirements may be provided to the autonomous control system and/or the remote-control system, so that adjustments may be made, either autonomously or by a local or remote operator of the lighting installation, to enable adjustments (such as to colors, intensities, color temperatures, beam directions, and other factors), such as to cause the lighting installation to better meet the specifications and requirements. The operational feedback system may also capture feedback that leads to revisiting the lighting design in the lighting design environment, which may induce further iteration, resulting in changes to control parameters for the display systems, as well as automated ordering of additional or substitute display systems, with updated installation and operational guidance.

In embodiments, remote control may enable field programmable lighting systems, such as for transitional environments like museums (where art objects change regularly), stores (where merchandise shifts) and the like as well as for customizable environments (such as personalizing lighting in a hotel room according to a specification for a guest (which may include having the guest select an aesthetic filter) or personalized lighting for a workstation for an employee in an office setting. Such features may enable the lighting installation to change configurations (such as among different aesthetic filters) for multi-use environments, multi-tenant environments, and the like where lighting conditions may need to change substantially over time.

In embodiments, a lighting system may include navigation features, such as being associated with beacons, where the lighting system interacts with one or more devices to track users within a space. The display systems and their locations may be associated with a map, such as the map of the lighting space in the design environment. The map may be provided from the lighting design environment to one or more other location or navigation systems, such that locations of display systems may be used as known locations or points of interest within a space.

In embodiments, the lighting installation may be designed for an operation that is coordinated with one or more external systems, which may serve as inputs to the lighting installation, such as music, video and other entertainment content (such as to coordinate lighting with sound). Inputs may include voice control inputs, which may include systems for assessing tone or mood from vocal patterns, such as to adjust lighting based on the same.

In embodiments, inputs may also include inputs from wearable devices, such as enabling adjustment of lighting control parameters (autonomously or with remote or local control features) based on physiological factors, such as ones indicating health conditions, emotional states, moods, or the like. Inputs from wearable devices may be used in the operational feedback system, such as to measure reactions to lighting conditions (such as to enable automated adjustment of a lighting installation), as well as to measure impacts on mood, health conditions, energy, wellness factors, and the like.

In embodiments, the platform may be configured to change settings or parameters for a lighting installation (including but not limited to display systems of the present disclosure, such as by using a custom tuning system) based on a variety of real time data, with a view to having the lighting installation, including display systems included therein, best suit its environment in a dynamic way. In embodiments, data may be obtained that serves as an indicator of the emotional state or the stress level of an environment, and the lighting installation may respond accordingly to that state or stress level. In embodiments, data about the environment may be collected by a wearable device, such as a smartwatch, armband, or the like; for example, data may be collected on acceleration, location, ambient light characteristics, and heart rate, among other possibilities. In embodiments, the data may be provided to the platform for analysis, including using machine learning, such as to observe physiological indicators of stress, mood, or the like under given lighting conditions. The analysis may enable model-based controls (such as where a given mood or state of the users in a room are linked to a set of control parameters appropriate for that state). In embodiments, machine learning may be used; for example, over time, by variation of parameters for lighting objects and fixtures (such as color, color temperature, illumination patterns, lighting distributions, and many others), a machine learning system may, using feedback on outcomes based at least in part on physiological data and other data collected by a wearable device, select and/or promotion lighting installation parameters that improve various measures of stress, mood, satisfaction, or the like. This may occur in real time under control of a machine learning system based on the current conditions of users or the environment. In embodiments, data collected at least in part by a physiological monitor or wearable device may be used as an input to processing logic on a lighting object that changes lighting levels or other parameters to accommodate the 'emotional state' of the users in an environment where the lighting object is located. In embodiments, there is memory that retains and manages function with no appreciable drain on the battery.

In embodiments, inputs may include systems that take data harvested from sensors in the lighting installation environment as well as sensors that reflect information about users, such as one or more of physiological sensors (including wearable devices, such as armbands, wrist bands, chest bands, glasses, clothing, and the like), sensors on various devices used by a user, ambient sensors, and the like. These may include sensing one or more of temperature, pressure, ambient lighting conditions, localized lighting conditions, lighting spectrum characteristics, humidity, UV light, sound, particles, pollutants, gases (e.g., oxygen, carbon dioxide, carbon monoxide and radon), radiation, location of objects or items, motion (e.g., speed, direction and/or acceleration). Where one or more wearable or physiological sensors are used, they may sense one or more of a person's temperature, blood pressure, heart rate, oxygen saturation, activity type, activity level, galvanic skin response, respiratory rate, cholesterol level (including HDL, LDL and triglyceride), hormone or adrenal levels (e.g., Cortisol, thyroid, adrenaline, melatonin, and others), histamine levels, immune system characteristics, blood alcohol levels, drug content, macro and micro nutrients, mood, emotional state, alertness, sleepiness, and the like.

In embodiments, the platform may connect to or integrate with data sources of information about users, such as including social networks (Facebook™, LinkedIn™, Twitter™, and the like, sources of medical records (23&Me™ and the like), productivity, collaboration and/or calendaring software (Google™, Outlook™, scheduling apps and the like), information about web browsing and/or shopping activity, activity on media streaming services (Netflix™, Spotify™, YouTube™, Pandora™ and the like), health record information and other sources of insight about the preferences or characteristics of users of the space of a lighting installation, including psychographic, demographic and other characteristics.

In embodiments, the platform may use information from sources that indicate patterns, such as patterns involving periods of time (daily patterns, weekly patterns, seasonal patterns, and the like), patterns involving cultural factors or norms (such as indicating usage patterns or preferences in different regions), patterns relating to personality and preferences, patterns relating to social groups (such as family and work group patterns), and the like. In embodiments, the platform may make use of the data harvested from various sources noted above to make recommendations and/or to optimize (such as automatically, under computer control) the design, ordering, fulfillment, deployment and/or operation of a lighting installation, such as based on understanding or prediction of user behavior. This may include recommendation or optimization relating to achieving optimal sleep time and duration, setting optimal mealtimes, satisfying natural light exposure requirements during the day, and maintaining tolerable artificial light exposure levels (such as during night time). In embodiments, the platform may anticipate user needs and optimize the lighting installation to enhance productivity, alertness, emotional well-being, satisfaction, safety and/or sleep. In further embodiments, the platform may control one or more display systems of the present disclosure in accordance with the user needs of the environment based on this information.

In embodiments, the platform may store a space utilization data structure that indicates, over time, how people use the space of the lighting installation, such as indicating what hallways are more trafficked, and the like. This may inform understanding of a space, such as indicating what is an entry, what is a passage, what is a workspace, and the like, which may be used to suggest changes or updates to a lighting design. In embodiments, sensors may be used to collect and read where people have been in the space, such as using one or more video cameras, IR sensors, microwave sensors. LIDAR, ultrasound or the like. In embodiments, the platform may collect and read what adjustments people have made, such as task lamp activation and other activities that indicate how a lighting fixture is used by an individual in a space. By way of these examples, aggregate usage information may be used to optimize a lighting design and adjust other lighting designs. Based on these factors, a space may be dynamically adjusted, and the lighting model for an installation may be updated to reflect the actual installation.

In embodiments, control capabilities of the display systems may include dynamic configuration of control parameters, such as providing a dimming curve for a light source, including but not limited to a display system of the present disclosure, that is customized to the preferences of a designer or other user. This may include a selection from one or more modes, such as ones described elsewhere herein that have desired effects on mood or aesthetic factors, that have desired health effects, that meet the functional requirements, or the like.

In order to truly achieve circadian action, prolonged exposure may be required, however, a melanopic flux may, in many embodiments, need to be at least 10:1 and in further embodiments, may need to be 20:1, 50:1, 100:1, or a greater ratio. It will be appreciated in light of the disclosure that most conventional systems simply adjust from a warm CCT to a cool CCT, which may only provide a 2:1 or 3:1 ratio of melanopic flux, which may not be enough to provide health benefits. In embodiments, the platform may include spectral tuning targets for display systems of the present disclosure that may optimize this ratio based on local installation environments. These targets, along with adjustments intensity of light (e.g., 4:1) may provide a higher ratio, such as a 10:1 ratio or greater, and thus provide greater melanopic flux ratios.

In a second mode and either in combination with the above mode or not, the platform may support an ability to shift the bias of light in a room. In embodiments, controlled variation of one or more display systems of the present disclosure in a lighting environment can contribute to generating a lighting bias typical of being outside.

In embodiments, various other programmable modes may be provided, such as display system settings where using different combinations of color light sources to achieve a given mixed color output may be optimized for efficacy, efficiency, color quality, health impact (e.g., circadian action), or to satisfy other requirements. In embodiments, the programmable modes may also include programmable dimming curves, color tuning curves, and the like (such as allowing various control interfaces, such as extra-low voltage (ELV) controllers or voltage-based dimmers to affect fixture colors, such as where a custom tuning curve provides a start point, an end point and a dimming and/or color tuning path in response to a level of dimming). In embodiments, programmable modes may use conventional tuning mechanisms, such as simple interpolation systems (which typically use two or three white color LEDs) are dimmable on a zero to ten-volt analog system, and have a second voltage-based input for adjusting the CCT of a fixture between warm and cool CCTs. The display systems as described herein can provide for tunable ranges of color points at various x, y coordinates on the 1931 CIE chromaticity diagram. Because of the wide range of potential white or non-white colors produced by the display systems, they may be controlled by the platform that may specify a particular x, y coordinate on the CIE diagram. Lighting control protocols like DMX™ and Dali 2.0™ may achieve this result.

In embodiments, a programmable color curve for an LED driver may be input, such as through an interface of the platform, or through a desktop software interface, a mobile phone, a tablet app, or the like, that enables a user to define a start and stop point to a color tuning curve and to specify how it will be controlled by a secondary input, such as a voltage-based input (e.g., a 0 to 10-volt input) to the fixture. These may include pre-defined curves, as well as the ability to set start, end, and waypoints to define custom curves. For example, an exemplary color curve can have a starting point around 8000K biased above the black body curve, with the color curve crossing the black body around 2700K, and finishing around 1800K below the black body curve. Similarly, another exemplary curve could be programmed such that the start was 4000K well above the black body, with the end being 4000K well below the black body. By way of these examples, any adjustment would be in hue only, not CCT. Further examples may include a curve that never produces a white color, such as starting in the purple and finishing in orange. In any of these cases, these curves may be programmed into display systems via the interface of the platform, the desktop, mobile phone or tablet. In embodiments, the curves may be designed, saved, and then activated, such as using the secondary (supplemental) 0 to 10-volt input.

In embodiments, a three-channel warm dim mode may be used, such as that described more fully in U.S. Provisional Patent Application No. 62/712,182 filed Jul. 30, 2018, which is incorporated herein in its entirety for all purposes, for target applications where the "fully on" CCT falls between 3000K and 2500K. By way of these examples, as the fixture dims (via ELV control or in response to the 0 to 10-volt input) the CCT may be gradually decreased to between 2500K and 1800K. In certain embodiments, the hue adjustment may all occur below the black body curve. Alternative embodiments may use a cyan channel as described elsewhere herein, either long-blue-pumped cyan or short-blue-pumped cyan, and a red channel as described elsewhere herein, plus a 4000K white channel as described elsewhere herein to achieve a warm dimming mode that allows for adjustment both above and below the black body curve. In some embodiments of the three-channel warm dim mode, the white channel can have a color point within a 7-step MacAdam ellipse around any point on the black body locus having a correlated color temperature between about 3500K and about 6500K.

In some aspects, the present disclosure provides lighting systems that can be operated in a plurality of lighting modes. In certain implementations, the lighting systems of the present disclosure can output white light at color points along a predetermined path within a 7-step MacAdam ellipse around any point on the black body locus having a correlated color temperature between 1800K and 10000K. In other implementations, the lighting systems can be configured to output white light at color points along a predetermined path within a 7-step MacAdam ellipse around any point on the black body locus having a correlated color temperature within a portion of the range of 1800K and 10000K. In certain implementations, lighting systems can be operated in a very-low-EML mode to produce white light having CCT from about 1800K to about 3500K. In some implementations, the lighting systems can be operated in a low-EML mode to produce white light having CCT from about 1800K to about 3500K or from about 1800K to about 10000K. In some implementations, lighting systems can be operated in a high-EML mode to produce white light having CCT from about 1800K to about 10000K. In some implementations, the lighting systems can be operated in a high-CRI mode to produce white light having CCT from about 1800K to about 10000K. In some implementations, the lighting systems can be operated in a highest-CRI mode to produce white light having CCT from about 1800K to about 10000K. In certain implementations, the operation of the lighting systems of the present disclosure in a high-EML mode can be used to produce white light at a plurality of points with CCT and EML corresponding to the curve 1501 of FIG. 18. In some implementations, the operation of the lighting systems of the present disclosure in a low-EML mode can be used to produce white light at a plurality of points with CCT and EML corresponding to at least a portion of the curve 1502 of FIG. 18. In some implementations, the operation of the lighting systems of the present disclosure in a very-low-EML mode can be used to produce white light at a plurality of points with CCT and EMIL corresponding to at least a portion of the curve 1502 of FIG. 18.

In some aspects, the lighting systems of the present disclosure can be used to provide a plurality of white light points at different CCT values and with different EML values. It can be desirable to provide white light with substantially different EML characteristics in order to provide bioactive light configured for a biological effects to users exposed to the lighting systems. In some implementations, the lighting systems can provide a ratio of EML between a first color point produced at around 4000K produced in a High-EML mode and a second color point produced at around 2400K in a Low-EML or Very-Low-EML mode. In certain implementations, the ratio can be about 2.0, about 2.1, about 2.2, about 2.3, about 2.4, about 2.5, about 2.6, about 2.7, about 2.8, about 2.9, or about 3.0. In further implementations, the ratio can be between about 2.7 and about 2.9.

In some aspects, the present disclosure provides semiconductor light emitting devices capable to producing tunable White light through a range of CCT values. In some implementations, devices of the present disclosure can output white light at color points along a predetermined path within a 7-step MacAdam ellipse around any point on the black body locus having a correlated color temperature between 1800K and 10000K. In some implementations, the semiconductor light emitting devices can comprise first, second, third, and fourth LED strings, with each LED string comprising one or more LEDs having an associated luminophoric medium, wherein the first second, third, and fourth LED strings together with their associated luminophoric mediums can comprise red, blue, short-blue pumped cyan, and long-blue-pumped cyan channels respectively, producing first, second, third, and fourth w1saturated color points within red, blue, short-blue-pumped cyan, and long blue-pumped cyan regions on the 1931 CIE Chromaticity diagram, respectively. In some implementations the devices can further include a control circuit can be configured to adjust a fifth color point of a fifth unsaturated light that results from a combination of the first, second, third, and fourth unsaturated light with the fifth color point falls within a 7-step MacAdam ellipse around any point on the black body locus having a correlated color temperature between 1800K and 10000K. In some implementations the devices can be configured to generate the fifth unsaturated light corresponding to a plurality of points along a predefined path with the light generated at each point having light with Rf greater than or equal to about 88, Rg greater than or equal to about 98 and less than or equal to about 104, or both. In some implementations the devices can be configured to generate the fifth w1saturated light corresponding to a plurality of points along a predefined path with the light generated at each point having light with Ra greater than or equal to about 95 along points with correlated color temperature between about 1800K and 10000K, R9 greater than or equal to about 87 along points with correlated color temperature between about 2000K and about 10000K, or both. In some implementations the devices can be configured to generate the fifth unsaturated light corresponding to a plurality of points along a predefined path with the light generated at each point having light with Rg greater than or equal to 91 along greater than or equal to 90% of the points with correlated color temperature between about 2000K and about 10000K. In some implementations the devices can be configured to generate the fifth unsaturated light corresponding to a plurality of points along a predefined path with the light generated at each point having one or more of EML greater than or equal to about 0.45 along points with correlated color temperature above about 2100K, EML greater than or equal to about 0.55 along points with correlated color temperature above about 2400K, EML greater than or equal to about 0.7 along points with correlated color temperature above about 3000K EML greater than or equal to about 0.9 along points with correlated color temperature above about 4000K, and EML greater than or equal to about 1 1 along points with correlated color temperature above about 6000K. In some implementations the devices can be configured to generate the fifth unsaturated light corresponding to a plurality of points along a predefined path with the light generated at each point having light with R13 greater than or equal to about 97, R15 greater than or equal to about 94, or both. The blue color region can comprise a region on the 1931 CIE Chromaticity Diagram comprising the combination of a region defined by a line connecting the ccx, ccy color coordinates of the infinity point of the Planckian locus (0.242, 0.24) and (0.12, 0.068), the Planckian locus from 4000K and infinite CCT, the constant CCT line of 4000K, the line of purples, and the spectral locus and a region defined by a line connecting (0.3806, 0.3768) and (0.0445, 0.3), the spectral locus between the monochromatic point of 490 nm and (0.12, 0.068), a line connecting the ccx, ccy color coordinates of the infinity point of the Planckian locus (0.242, 0.24) and (0.12, 0.068), and the Planckian locus from 4000K and infinite CCT The blue color region can comprise a region on the 1931 CIE Chromaticity Diagram defined by a line connecting the ccx, ccy color coordinates of the infinity point of the Planckian locus (0.242, 0.24) and (0.12, 0.068), the Planckian locus from 4000K and infinite CCT, the constant CCT line of 4000K, the line of purples, and the spectral locus. The blue color region can comprise a region on the 1931 CIE Chromaticity Diagram defined by a line connecting (0.3806, 0.3768) and (0.0445, 0.3), the spectral locus between the monochromatic point of 490 nm and (0.12, 0.068), a line connecting the ccx, ccy color coordinates of the infinity point of the Planckian locus (0.242, 0.24) and (0.12, 0.068), and the Planckian locus from 4000K and infinite CCT. The blue color region can comprise a region on the 1931 CIE Chromaticity Diagram defined by lines connecting (0.231, 0.218), (0.265, 0.260), (0.2405, 0.305) and (0.207, 0.256). The red color region can comprise a region on the 1931 CIE Chromaticity Diagram defined by the spectral locus between the constant CCT line of 1600K and the line of purples, the line of purples, a line connecting the ccx, ccy color coordinates (0.61, 0.21) and (0.47, 0.28), and the constant CCT line of 1600K. The red color region can comprise a region on the 1931 CIE Chromaticity Diagram defined by lines connecting the ccx, ccy coordinates (0.576, 0.393), (0.583, 0.400), (0.604, 0.387), and (0.597, 0.380). The short-blue-pumped cyan color region, long-blue-pumped cyan color region, or both can comprise a region on the 1931 CIE Chromaticity Diagram defined by a line connecting the ccx, ccy color coordinates (0.18, 0.55) and (0.27, 0.72), the constant CCT line of 9000K, the Planckian locus between 9000K and 1800K, the constant CCT line of J 800K, and the spectral locus. The short-blue-pumped cyan color region, long-blue-pumped cyan color region, or both can comprise a region on the 1931 CIE Chromaticity Diagram defined by a line connecting the ccx, ccy color coordinates (0.18, 0.55) and (0.27, 0.72), the constant CCT line of 9000K, the Planckian locus between 9000K and 4600K, the constant CCT line of 4600K, and the spectral locus. The short-blue pumped cyan color region, long-blue-pumped cyan color region, or both can comprise a region on the 1931 CIE Chromaticity Diagram defined by the constant CCT line of 4600K, the spectral locus, the constant CCT line of 1800K, and the Planckian locus between 4600K and 1800K. The short-blue-pumped cyan color region, long-blue-pumped cyan color region, or both can comprise a region on the 1931 CIE Chromaticity Diagram defined by the region bounded by lines connecting (0.360, 0.495), (0.371, 0.518), (0.388, 0.522), and (0.377, 0.499). The short-blue-pumped cyan color region, long-blue-pumped cyan color region, or both can comprise a region on the J 931 CIE Chromaticity Diagram defined by the region by lines connecting (0.497, 0.469), (0.508, 0.484), (0.524, 0.472), and (0.513, 0.459). In some implementations the spectral power distributions for one or more of the red channel, blue channel, short-blue-pumped cyan channel, and long-blue-pumped cyan channel can fall within the minimum and maximum ranges shown in Tables 1 and 2. In some implementations the red channel can have a spectral power distribution with spectral power in one or more of the wavelength ranges other than the reference wavelength range increased or decreased within 30~"o greater or less, within 20% greater or less, within 10° 10 greater or less, or within 5% greater or less than the values of a red channel shown in Tables 3 and 4. In some implementations the blue channel can have a spectral power distribution with spectral power in one or more of the wavelength ranges other than the reference wavelength range increased or decreased within 30% greater or less, within 20% greater or less, within 10% i greater or less, or within 5% greater or less than the values of a blue channel shm.v11 in Tables 3 and 4. In some implementations the short-blue-pumped cyan channel can have a spectral power distribution with spectral power in one or more of the wavelength ranges other than the reference wavelength range increased or decreased within 30% greater or less, within 20% greater or less, within 10% greater or less, or within 5% greater or less than the values of a short-blue-pumped cyan channel shown in Table 3. In some implementations the long-bluepumped cyan channel can have a spectral power distribution with spectral power in one or more of the wavelength ranges other than the reference wavelength range increased or decreased within 30% greater or less, within 20% greater or less, within 10% greater or less, or within 5% greater or less than the values of a long-blue-pumped cyan channel shown in Table 3. In some implementations one or more of the LEDs in the fourth LED string can have a peak wavelength of between about 480 nm and about 505 nm. In some implementations one or more of the LEDs in the first, second, and third LED strings can have a peak wavelength of between about 430 nm and about 460 nm. In some implementations, the devices can be configured to generate the fifth unsaturated light corresponding to a plurality of points along a predefined path with the light generated at each point having light with BLH factor less than 0.26 µW/cm2/lux. In some implementations, the devices can be configured to generate the fifth unsaturated light corresponding to a plurality of points along a predefined path with the light generated at each point having light with one or more of BLH factor less than or equal to about 0.05 along points with correlated color temperature below about 2100K, BLH factor less than or equal to about 0.065 along points with correlated color temperature below about 2400K, BLH factor less than or equal to about 0.12 along points with correlated color temperature below about 3000K, BLH factor less than or equal to about 0.25 along points with correlated color temperature below about 4000K, and BLH factor less than or equal to about 0.35 along points with correlated color temperature below about 6500K. In some implementations, the devices can be configured to generate the fifth unsaturated light corresponding to a plurality of points along a predefined path with the light generated at each point having light with the ratio of the EML to the BLH factor being greater than or equal to about 2.5, greater than or equal to about 2.6, greater than or equal to about 2.7, greater than or equal to about 2.8, greater than or equal to about 2.9, greater than or equal to about 3.0, greater than or equal to about 3.1, greater than or equal to about 3.2, greater than or equal to about 3.3, greater than or equal to about 3.4, greater than or equal to about 3.5, greater than or equal to about 4.0, greater than or equal to about 4.5, or greater than or equal to about 5.0. Providing a higher ratio of the EML to the BLH factor can be advantageous to provide light that provides desired biological impacts but does not have as much potential for photochemical induced injuries to the retina or skin. In certain implementations, the operation of the lighting systems of the present disclosure in a combination of very-low-EML and low-EML modes can be used to produce white light at a plurality of points with CCT and EML corresponding to the curve 1502 of FIG. 18. In certain embodiments, the display systems of the present disclosure can include a 4-channel color system as described elsewhere herein and in U.S. Provisional Patent Application No. 62/757,672 filed Nov. 8, 2018, and U.S. Provisional Application No. 62/712,191 filed Jul. 30, 2018, the contents of which are incorporated by reference herein in their entirety as if fully set forth herein, includes 3000K to 1800K CCT white color points within its range, a programmable mode may be included within the driver that adjusts color with the dimming percentage as well. In some aspects, this may be similar to a conventional control mode, except that the color control would not be on the secondary 0 to 10-volt channel, but may be activated through the primary 0 to 10-volt input channel or ELV controller. In embodiments, the "starting" color point may be the one when the fixture was "fully on." In embodiments, the "ending" color point may be the one where the fixture is maximally dimmed. It is thus possible to make full range color change, such as purple to orange, which is slaved to the 0 to 10-volt or ELV dimming signal.

In embodiments, an optimized mode may be provided. With a 4-channel color system, there are many ways to create a single x-y point on the CIE diagram. In embodiments, the maximally efficient mode may typically be one that uses the colors that have x, y coordinates closest to the target x, y coordinate. But for best color quality, utilizing a fourth channel (and thereby requiring more light from the color in the opposite "corner") may help provide a desired spectral power distribution. For the maximum melatonin suppression (for systems hoping to mimic circadian lighting), a higher cyan channel content may be required for CCTs of 3500K and above and minimizing cyan and blue content below 3500K. It will be appreciated in light of the disclosure that conventional systems either require expert users to understand the color balances necessary to achieve these effects (who then implement the color balances channel-by-channel) or are designed for maximum efficiency with color quality as a byproduct.

In embodiments, a digital power system is provided herein (including firmware-driven power conversion and LED current control) that controls a multichannel color system, such as a 4-channel color system, and allows for the inclusion of "modes" which may calculate the correct color balance between the various channels to provide optimized outputs. In embodiments, optimization may occur around one or more of efficacy, color quality, circadian effects, and other factors. Other modes are possible, such as optimizing for contrast, particular display requirements. It will be appreciated in light of the disclosure that this is not an exhaustive list but is representative of potential modes that could be engaged through an interface of the platform (or of a mobile, tablet or desktop application) where a color tuning curve may be specified, such that the curve is used to specify an interface between a controller and the Digital PSU in a display system. In embodiments, these modes may account for actual measured colors for each display system and calculate the correct balance of for the chosen modes, such as based on algorithms loaded into the Digital PSU microprocessor.

In embodiments, machine learning may be used, such as based on various feedback measures, such as relating to mood (stated by the user or measured by one or more sensors), noise levels (such as indicating successful utilization of a space based on a desired level of noise), returns on investment (such as where display systems are intended to promote retail merchandise), reported pain levels, measured health levels, performance levels of users (including fitness, wellness, and educational performance, among others), sleep levels, vitamin D levels, melatonin levels, and many others. In embodiments, the lighting installations including the display systems may be operated or controlled based on external information, such as based on seasonal lighting conditions, weather, climate, collective mood indicators (such as based on stock market data, news feeds, or sentiment indices), analyses of social network data, and the like. This may include controlling a system to reflect, or influence, the mood of occupants.

EXAMPLES

General Simulation Method for Examples 1-13, 13A-13N and 35

Display systems having three, four, five, and six LED-string-driven lighting channels with particular color points were simulated. For each device, LED strings and recipient luminophoric mediums with particular emissions were selected, and then white light rendering capabilities were calculated for a select number of representative points on or near the Planckian locus between about 1800K and 10000K. Ra, R9, R13, R15, LER, Rf, Rg, CLA, CS, EML, BLH factor, CAF, CER, COI, and circadian performance values were calculated at each representative point.

The calculations were performed with Scilab (Scilab Enterprises, Versailles, France), LightTools (Synopsis, Inc., Mountain View, CA), and custom software created using Python (Python Software Foundation, Beaverton, OR). Each LED string was simulated with an LED emission spectrum and excitation and emission spectra of luminophoric medium(s). For luminophoric mediums comprising phosphors, the simulations also included the absorption spectrum and particle size of phosphor particles. The LED strings generating combined emissions within blue, short-blue-pumped cyan, and red color regions were prepared using spectra of a LUXEON Z Color Line royal blue LEDs (product code LXZ1-PR01) of color bin codes 3, 4, 5, or 6, one or more LUXEON Z Color Line blue LEDs (LXZ1-PB01) of color bin code 1 or 2, or one or more LUXEON royal blue LEDs (product code LXML-PR01 and LXML-PR02) of color bins 3, 4, 5, or 6 (Lumileds Holding B.V., Amsterdam, Netherlands). The LED strings generating combined emissions with color points within the long-blue-pumped cyan regions were prepared using spectra of LUXEON Rebel Blue LEDs (LXML-PB01, LXML-PB02) of color bins 1, 2, 3, 4, or 5, which have peak wavelengths ranging from 460 nm to 485 nm, or LUXEON Rebel Cyan LEDs (LXML-PE01) of color bins 1, 2, 3, 4, or 5, which have peak wavelengths raving from 460 nm to 485 nm. Similar LEDs from other manufacturers such as OSRAM GmbH and Cree, Inc. could also be used. The LED strings generating combined emissions with color points within the yellow and violet regions were simulated using spectra of LEDs having peak wavelengths of between about 380 nm and about 420 nm, such as one or more 410 nm peak wavelength violet LEDs, one or more LUXEON Z UV LEDs (product codes LHUV-0380-, LHUV-0385-, LHUV-0390-, LHUV-0395-, LHUV-0400-, LHUV-0405-, LHUV-0410-, LHUV-0415-, LHUV-0420-) (Lumileds Holding B.V., Amsterdam, Netherlands), one or more LUXEON UV FC LEDs (product codes LxF3-U410) (Lumileds Holding B.V., Amsterdam, Netherlands), one or more LUXEON UV U LEDs (product code LHUV-0415-) (Lumileds Holding B.V., Amsterdam, Netherlands), for example.

The emission, excitation and absorption curves are available from commercially available phosphor manufacturers such as Mitsubishi Chemical Holdings Corporation (Tokyo, Japan), Intematix Corporation (Fremont, CA), EMD Performance Materials of Merck KGaA (Darmstadt, Germany), and PhosphorTech Corporation (Kennesaw, GA). The luminophoric mediums used in the LED strings were combinations of one or more of Compositions A, B, and D and one or more of Compositions C, E, and F as described more fully elsewhere herein. Those of skill in the art appreciate that various combinations of LEDs and luminescent blends can be combined to generate combined emissions with desired color points on the 1931 CIE chromaticity diagram and the desired spectral power distributions.

Additionally, to any of the examples or simulations described herein a LRNE emission wavelengths of Long Red (>625 to <700 nms with peak wavelengths >640-670 nms) may be added. Further, a Near-Infrared (typical ranges from >700 and <1400 nms (with typical peak wavelengths: 850 nm, 940 nm, 1064 nm)) via LEDs or via a LRNE LED string which is driven by a blue LED utilizing a recipient luminophoric media may be added.

In any of the below examples the red channel may be deployed as one or more LRNE channels only or a red channel with at least one LRNE channel. The LRNE can be used in a method, device or system in conjunction with blue light providing CSE or any blue channel providing or the LRNE may be used independently of CSE or lots of blue.

Example 1

A display system was simulated having four LED strings. A first LED string is driven by a blue LED having peak emission wavelength of approximately 450 nm to approximately 455 nm, utilizes a recipient luminophoric medium, and generates a combined emission of a blue channel having the color point and characteristics of Blue Channel 1 as described above and shown in Tables 3-5. A second LED string is driven by a blue LED having peak emission wavelength of approximately 450 nm to approximately 455 nm, utilizes a recipient luminophoric medium, and generates a combined emission of a red channel having the color point and characteristics of Red Channel 1 as described above and shown in Tables 3-5 and 7-9. A third LED string is driven by a blue LED having peak emission wavelength of approximately 450 nm to approximately 455 nm, utilizes a recipient luminophoric medium, and generates a combined emission of a short-blue-pumped cyan color channel having the color point and characteristics of Short-Blue-Pumped Cyan Channel 1 as described above and shown in Tables 3-5. A fourth LED string is driven by a cyan LED having peak emission wavelength of approximately 505 nm, utilizes a recipient luminophoric medium, and generates a combined emission of a long-blue-pumped cyan channel having the color point and characteristics of Long-Blue-Pumped Cyan Channel 1 as described above and shown in Tables 3-5.

Tables 16-19 shows light-rendering characteristics of the device for a representative selection of white light color points near the Planckian locus. Table 18 shows data for white light color points generated using only the first, second, and third LED strings in high-CRI mode. Table 16 shows data for white light color points generated using all four LED strings in highest-CRI mode. Table 17 shows data for white light color points generated using only the first, second, and fourth LED strings in high-EML mode. Table 19 show performance comparison between white light color points generated at similar approximate CCT values under high-EML mode and high-CRI mode.

Example 2

Further simulations were performed to optimize the outputs of the display system of Example 1. Signal strength ratios for the channels were calculated to generate 100 lumen total flux output white light at each CCT point. The relative lumen outputs for each of the channels is shown, along with the light-rendering characteristics, in Tables 20-22.

Example 3

A display system was simulated having four LED strings. A first LED string is driven by a blue LED having peak emission wavelength of approximately 450 nm to approximately 455 nm, utilizes a recipient luminophoric medium, and generates a combined emission of a blue channel having the color point and characteristics of Blue Channel 1 as described above and shown in Tables 3-5. A second LED string is driven by a blue LED having peak emission wavelength of approximately 450 nm to approximately 455 nm, utilizes a recipient luminophoric medium, and generates a combined emission of a red channel having the color point and characteristics of Red Channel 1 as described above and shown in Tables 3-5 and 7-9. A fifth LED string is driven by a violet LED having peak emission wavelength of about 380 nm, utilizes a recipient luminophoric medium, and generates a combined emission of a yellow color channel having the color point and characteristics of Yellow Channel 1 as described above and shown in Tables 5 and 13-15. A sixth LED string is driven by a violet LED having peak emission wavelength of about 380 nm, utilizes a recipient luminophoric medium, and generates a combined emission of a violet channel having the color point and characteristics of Violet Channel 1 as described above and shown in Tables 5 and 10-12.

Tables 23-24 shows light-rendering characteristics of the device for a representative selection of white light color points near the Planckian locus. Table 23 shows data for white light color points generated using the first, second, fifth, and sixth LED strings, i.e. the blue, red, yellow, and violet channels, in low-EML mode. Table 24 shows data for white light color points generated using the second, fifth, and sixth LED strings, i.e. the red, yellow, and violet channels, in very-low-EML mode.

Example 4

A display system was simulated having four LED strings. A first LED string is driven by a blue LED having peak emission wavelength of approximately 450 nm to approximately 455 nm, utilizes a recipient luminophoric medium, and generates a combined emission of a blue channel having the color point and characteristics of Blue Channel 1 as described above and shown in Tables 3-5. A second LED string is driven by a blue LED having peak emission wavelength of approximately 450 nm to approximately 455 nm, utilizes a recipient luminophoric medium, and generates a combined emission of a red channel having the color point and characteristics of Red Channel 1 as described above and shown in Tables 3-5 and 7-9. A fifth LED string is driven by a violet LED having peak emission wavelength of about 400 nm, utilizes a recipient luminophoric medium, and generates a combined emission of a yellow color channel having the color point and characteristics of Yellow Channel 2 as described above and shown in Tables 5 and 13-15. A sixth LED string is driven by a violet LED having peak emission wavelength of about 400 nm, utilizes a recipient luminophoric medium, and generates a combined emission of a violet channel having the color point and characteristics of Violet Channel 2 as described above and shown in Tables 5 and 10-12.

Tables 25-26 shows light-rendering characteristics of the device for a representative selection of white light color points near the Planckian locus. Table 25 shows data for white light color points generated using the first, second, fifth, and sixth LED strings, i.e. the blue, red, yellow, and violet channels, in low-EML mode. Table 26 shows data for white light color points generated using the second, fifth, and sixth LED strings, i.e. the red, yellow, and violet channels, in very-low-EML mode.

Example 5

A display system was simulated having four LED strings. A first LED string is driven by a blue LED having peak emission wavelength of approximately 450 nm to approximately 455 nm, utilizes a recipient luminophoric medium, and generates a combined emission of a blue channel having the color point and characteristics of Blue Channel 1 as described above and shown in Tables 3-5. A second LED string is driven by a blue LED having peak emission wavelength of approximately 450 nm to approximately 455 nm, utilizes a recipient luminophoric medium, and generates a combined emission of a red channel having the color point and characteristics of Red Channel 1 as described above and shown in Tables 3-5 and 7-9. A fifth LED string is driven by a violet LED having peak emission wavelength of about 410 nm, utilizes a recipient luminophoric medium, and generates a combined emission of a yellow color channel having the color point and characteristics of Yellow Channel 3 as described above and shown in Tables 5 and 13-15. A sixth LED string is driven by a violet LED having peak emission wavelength of about 410 nm, utilizes a recipient luminophoric medium, and generates a combined emission of a violet channel having the color point and characteristics of Violet Channel 3 as described above and shown in Tables 5 and 10-12.

Tables 27-28 shows light-rendering characteristics of the device for a representative selection of white light color points near the Planckian locus. Table 27 shows data for white light color points generated using the first, second, fifth, and sixth LED strings, i.e. the blue, red, yellow, and violet channels, in low-EML mode. Table 28 shows data for white light color points generated using the second, fifth, and sixth LED strings, i.e. the red, yellow, and violet channels, in very-low-EML mode.

Example 6

A display system was simulated having four LED strings. A first LED string is driven by a blue LED having peak emission wavelength of approximately 450 nm to approximately 455 nm, utilizes a recipient luminophoric medium, and generates a combined emission of a blue channel having the color point and characteristics of Blue Channel 1 as described above and shown in Tables 3-5. A second LED string is driven by a blue LED having peak emission wavelength of approximately 450 nm to approximately 455 nm, utilizes a recipient luminophoric medium, and generates a combined emission of a red channel having the color point and characteristics of Red Channel 1 as described above and shown in Tables 3-5 and 7-9. A fifth LED string is driven by a violet LED having peak emission wavelength of about 420 nm, utilizes a recipient luminophoric medium, and generates a combined emission of a yellow color channel having the color point and characteristics of Yellow Channel 4 as described above and shown in Tables 5 and 13-15. A sixth LED string is driven by a violet LED having peak emission wavelength of about 420 nm, utilizes a recipient luminophoric medium, and generates a combined emission of a violet channel having the color point and characteristics of Violet Channel 4 as described above and shown in Tables 5 and 10-12.

Table 29 shows light-rendering characteristics of the device for a representative selection of white light color points near the Planckian locus. Table 29 shows data for white light color points generated using the second, fifth, and sixth LED strings, i.e. the red, yellow, and violet channels, in very-low-EML mode.

Example 7

A display system was simulated having six lighting channels. The six lighting channels are a combination of the lighting channels of Example 1 and Example 3: Blue Channel 1, Red Channel 1, Short-Blue-Pumped Cyan Channel 1, Long-Blue-Pumped Cyan Channel 1, Yellow Chanel 1, and Violet Channel 1. As shown above with reference to Examples 1 and 3, the device can be operated in various operating modes with different combinations of lighting channels. Tables 30-31 show EML and CS values at various nominal CCT values under different operating modes and the % changes that can be achieved by switching between operating modes at the same nominal CCT.

Example 8

A display system was simulated having six lighting channels. The six lighting channels are a combination of the lighting channels of Example 1 and Example 4: Blue Channel 1, Red Channel 1, Short-Blue-Pumped Cyan Channel 1, Long-Blue-Pumped Cyan Channel 1, Yellow Chanel 2, and Violet Channel 2. As shown above with reference to Examples 1 and 4, the device can be operated in various operating modes with different combinations of lighting channels. Tables 32-33 show EML and CS values at various nominal CCT values under different operating modes and the % changes that can be achieved by switching between operating modes at the same nominal CCT.

Example 9

A display system was simulated having six lighting channels. The six lighting channels are a combination of the lighting channels of Example 1 and Example 5: Blue Channel 1, Red Channel 1, Short-Blue-Pumped Cyan Channel 1, Long-Blue-Pumped Cyan Channel 1, Yellow Chanel 3, and Violet Channel 3. As shown above with reference to Examples 1 and 5, the device can be operated in various operating modes with different combinations of lighting channels. Tables 34-35 show EML and CS values at various nominal CCT values under different operating modes and the % changes that can be achieved by switching between operating modes at the same nominal CCT.

Example 10

A display system was simulated having six lighting channels. The six lighting channels are a combination of the lighting channels of Example 1 and Example 6: Blue Channel 1, Red Channel 1, Short-Blue-Pumped Cyan Channel 1, Long-Blue-Pumped Cyan Channel 1, Yellow Chanel 4, and Violet Channel 4. As shown above with reference to Examples 1 and 6, the device can be operated in various operating modes with different combinations of lighting channels. Tables 36-37 show EML and CS values at various nominal CCT values under different operating modes and the % changes that can be achieved by switching between operating modes at the same nominal CCT.

Example 11

In some implementations, the display systems of the present disclosure can comprise three lighting channels as described elsewhere herein. In certain implementations, the three lighting channels comprise a red lighting channel, a yellow lighting channel, and a violet lighting channel. The display systems can be operated in a very-low-EML operating mode in which the red lighting channel, the yellow lighting channel, and the violet lighting channel are used. The display systems can further comprise a control system configured to control the relative intensities of light generated in the red lighting channel, the yellow lighting channel, and the violet lighting channel in order to generate white light at a plurality of points near the Planckian locus between about 4000K and about 1400K CCT.

Example 12

In some implementations, the display systems of the present disclosure can comprise four lighting channels as described elsewhere herein. In certain implementations, the four lighting channels comprise a red lighting channel, a yellow lighting channel, a violet lighting channel, and a blue lighting channel. In some implementations, the display systems can be operated in a very-low-EML operating mode in which the red lighting channel, the yellow lighting channel, and the violet lighting channel are used. In further implementations, the display systems can be operated in a low-EML operating mode in which the blue lighting channel, the red lighting channel, the yellow lighting channel, and the violet lighting channel are used. In certain implementations, the display systems can transition between the low-EML and the very-low-EML operating modes in one or both directions while the display systems are providing white light along a path of color points near the Planckian locus. In further implementations, the display systems can transition between the low-EML and very-low-EML operating modes in one or both directions while the display systems are changing the CCT of the white light along the path of color points near the Planckian locus. In some implementations the low-EML operating mode can be used in generating white light near the Planckian locus with CCT values between about 10000K and about 1800K. In further implementations the very-low-EML operating mode can be used in generating white light near the Planckian locus with CCT values between about 4000K and about 1400K.

Example 13

In some implementations, the display systems of the present disclosure can comprise five lighting channels as described elsewhere herein. In certain implementations, the five lighting channels comprise a red lighting channel, a yellow lighting channel, a violet lighting channel, a blue lighting channel, and a long-blue-pumped cyan lighting channel. In some implementations, the display systems can be operated in a very-low-EML operating mode in which the red lighting channel, the yellow lighting channel, and the violet lighting channel are used. In further implementations, the display systems can be operated in a low-EML operating mode in which the blue lighting channel, the red lighting channel, the yellow lighting channel, and the violet lighting channel are used. In yet further implementations, the display systems can be operated in a high-EML operating mode in which the blue lighting channel, the red lighting channel, and the long-blue-pumped cyan lighting channel are used. In certain implementations, the display systems can transition among two or more of the low-EML, the very-low-EML, and high-EML operating modes while the display systems are providing white light along a path of color points near the Planckian locus. In further implementations, the display systems can transition among two or more of the low-EML, the very-low-EML, and high-EML operating modes while the display systems are changing the CCT of the white light along the path of color points near the Planckian locus. In some implementations the low-EML operating mode can be used in generating white light near the Planckian locus with CCT values between about 10000K and about 1800K. In further implementations the very-low-EML operating mode can be used in generating white light near the Planckian locus with CCT values between about 4000K and about 1400K. In yet further implementations, the high-EML operating mode can be used in generating white light near the Planckian locus with CCT values between about 10000K and about 1800K.

Example 13A

A semiconductor light emitting device was simulated having three LED strings. A first LED string is a commercially available 6500K white LED having a spectral power distribution as shown in FIG. 32. A second LED string is driven by a blue LED having peak emission wavelength of approximately 450 nm to approximately 455 nm, utilizes a recipient luminophoric medium, and generates a combined emission of a LRNE channel having the characteristics of Long-Red (LRNE) Channel A as shown in Tables 7-9. The spectral power distribution for Long-Red Channel A is shown in FIG. 34. Three phosphor materials can be provided in the luminophoric medium for the second LED string, and in some implementations the phosphor materials can include a YAG phosphor, a red phosphor with emission peak at about 630 nm, and a red phosphor with an emission peak at about 700 nm. A third LED string is a commercially available "lime" LED having a spectral power distribution as shown in FIG. 33. Table 64 shows light-rendering characteristics of the device for a representative selection of white light color points near the Planckian locus.

Example 13B

A semiconductor light emitting device was simulated having three LED strings. A first LED string is a commercially available 6500K white LED having a spectral power distribution as shown in FIG. 32. A second LED string is driven by a blue LED having peak emission wavelength of approximately 450 nm to approximately 455 nm, utilizes a recipient luminophoric medium, and generates a combined emission of a long-red (LRNE) channel having the characteristics of Long-Red Channel B as shown in Tables 7-9. The spectral power distribution for Long-Red Channel B is shown in FIG. 35. Three phosphor materials can be provided in the luminophoric medium for the second LED string, and in some implementations the phosphor materials can include a YAG phosphor, a red phosphor with emission peak at about 630 nm, and a red phosphor with an emission peak at about 750 nm. A third LED string is a commercially available "lime" LED having a spectral power distribution as shown in FIG. 33.

Table 65 shows light-rendering characteristics of the device for a representative selection of white light color points near the Planckian locus Example 13C A display system was simulated having four LED strings. A first LED string is driven by a blue LED having peak emission wavelength of approximately 450 nm to approximately 455 nm, utilizes a recipient luminophoric medium, and generates a combined emission of a blue channel having the color point and characteristics of Blue Channel 1 as described above and shown in Tables 3-5. A second LED string generates a combined emission of a red channel having the color point and characteristics of Long-Red Channel A, Red Channel B, or Exemplary Long-Red Channel Average as described above and shown in Tables 7-9. A third LED string is driven by a blue LED having peak emission wavelength of approximately 450 nm to approximately 455 nm, utilizes a recipient luminophoric medium, and generates a combined emission of a short-blue-pumped cyan color channel having the color point and characteristics of Short-Blue-Pumped Cyan Channel 1 as described above and shown in Tables 3-5. A fourth LED string is driven by a cyan LED having peak emission wavelength of approximately 505 nm, utilizes a recipient luminophoric medium, and generates a combined emission of a long-blue-pumped cyan channel having the color point and characteristics of Long-Blue-Pumped Cyan Channel 1 as described above and shown in Tables 3-5.

White light color points can generate using only the first, second, and third LED strings in a high-CRI mode. White light color points can be generated using all four LED strings in a highest-CRI mode. White light color points can be generated using only the first, second, and fourth LED strings in a high-EML mode.

Example 13D

A display system was simulated having four LED strings. A first LED string is driven by a blue LED having peak emission wavelength of approximately 450 nm to approximately 455 nm, utilizes a recipient luminophoric medium, and generates a combined emission of a blue channel having the color point and characteristics of Blue Channel 1 as described above and shown in Tables 3-5. A second LED string generates a combined emission of a red channel having the color point and characteristics of LRNE in Long-Red Channel A, Red Channel B, or Exemplary Long-Red Channel Average as described above and shown in Tables 7-9. A fifth LED string is driven by a violet LED having peak emission wavelength of about 380 nm, utilizes a recipient luminophoric medium, and generates a combined emission of a yellow color channel having the color point and characteristics of Yellow Channel 1 as described above and shown in Tables 5 and 13-15. A sixth LED string is driven by a violet LED having peak emission wavelength of about 380 nm, utilizes a recipient luminophoric medium, and generates a combined emission of a violet channel having the color point and characteristics of Violet Channel 1 as described above and shown in Tables 5 and 10-12.

White light color points can be generated using the first, second, fifth, and sixth LED strings, i.e. the blue, long-red, yellow, and violet channels, in low-EML mode. White light color points can be generated using the second, fifth, and sixth LED strings, i.e. the long-red, yellow, and violet channels, in very-low-EML mode.

Example 13E

A display system was simulated having four LED strings. A first LED string is driven by a blue LED having peak emission wavelength of approximately 450 nm to approximately 455 nm, utilizes a recipient luminophoric medium, and generates a combined emission of a blue channel having the color point and characteristics of Blue Channel 1 as described above and shown in Tables 3-5. A second LED string generates a combined emission of a red channel having the color point and characteristics of LRNE/Long-Red Channel A, Red Channel B, or Exemplary Long-Red Channel Average as described above and shown in Tables 7-9. A fifth LED string is driven by a violet LED having peak emission wavelength of about 400 nm, utilizes a recipient luminophoric medium, and generates a combined emission of a yellow color channel having the color point and characteristics of Yellow Channel 2 as described above and shown in Tables 5 and 13-15. A sixth LED string is driven by a violet LED having peak emission wavelength of about 400 nm, utilizes a recipient luminophoric medium, and generates a combined emission of a violet channel having the color point and characteristics of Violet Channel 2 as described above and shown in Tables 5 and 10-12.

White light color points can be generated using the first, second, fifth, and sixth LED strings, i.e. the blue, long-red, yellow, and violet channels, in low-EML mode. White light color points can be generated using the second, fifth, and sixth LED strings, i.e. the long-red, yellow, and violet channels, in very-low-EML mode.

Example 13F

A display system was simulated having four LED strings. A first LED string is driven by a blue LED having peak emission wavelength of approximately 450 nm to approximately 455 nm, utilizes a recipient luminophoric medium, and generates a combined emission of a blue channel having the color point and characteristics of Blue Channel 1 as described above and shown in Tables 3-5. A second LED string generates a combined emission of a red channel having the color point and characteristics of LRNE described in Long-Red Channel A, Red Channel B, or Exemplary Long-Red Channel Average as described above and shown in Tables 7-9. A fifth LED string is driven by a violet LED having peak emission wavelength of about 410 nm, utilizes a recipient luminophoric medium, and generates a combined emission of a yellow color channel having the color point and characteristics of Yellow Channel 3 as described above and shown in Tables 5 and 13-15. A sixth LED string is driven by a violet LED having peak emission wavelength of about 410 nm, utilizes a recipient luminophoric medium, and generates a combined emission of a violet channel having the color point and characteristics of Violet Channel 3 as described above and shown in Tables 5 and 10-12.

White light color points can be generated using the first, second, fifth, and sixth LED strings, i.e. the blue, long-red, yellow, and violet channels, in low-EML mode. White light color points can be generated using the second, fifth, and sixth LED strings, i.e. the long-red, yellow, and violet channels, in very-low-EML mode.

Example 13G

A display system was simulated having four LED strings. A first LED string is driven by a blue LED having peak emission wavelength of approximately 450 nm to approximately 455 nm, utilizes a recipient luminophoric medium, and generates a combined emission of a blue channel having the color point and characteristics of Blue Channel 1 as described above and shown in Tables 3-5. A second LED string generates a combined emission of a red channel having the color point and characteristics of LRNE in Long-Red Channel A, Red Channel B, or Exemplary Long-Red Channel Average as described above and shown in Tables 7-9. A fifth LED string is driven by a violet LED having peak emission wavelength of about 420 nm, utilizes a recipient luminophoric medium, and generates a combined emission of a yellow color channel having the color point and characteristics of Yellow Channel 4 as described above and shown in Tables 5 and 13-15. A sixth LED string is driven by a violet LED having peak emission wavelength of about 420 nm, utilizes a recipient luminophoric medium, and generates a combined emission of a violet channel having the color point and characteristics of Violet Channel 4 as described above and shown in Tables 5 and 10-12.

White light color points can be generated using the second, fifth, and sixth LED strings, i.e. the long-red, yellow, and violet channels, in very-low-EML mode.

Example 13H

A display system was simulated having six lighting channels. The six lighting channels are a combination of the lighting channels of Example 13C and Example 13E: Blue Channel 1, a long-red channel, Short-Blue-Pumped Cyan Channel 1, Long-Blue-Pumped Cyan Channel 1, Yellow Chanel 1, and Violet Channel 1. As shown above with reference to Examples 13C and 13E, the device can be operated in various operating modes with different combinations of lighting channels.

Example 13I

A display system was simulated having six lighting channels. The six lighting channels are a combination of the lighting channels of Example 13C and Example 13F: Blue Channel 1, a long-red channel, Short-Blue-Pumped Cyan Channel 1, Long-Blue-Pumped Cyan Channel 1, Yellow Chanel 2, and Violet Channel 2. As shown above with reference to Examples 13C and 13F, the device can be operated in various operating modes with different combinations of lighting channels.

Example 13J

A display system was simulated having six lighting channels. The six lighting channels are a combination of the lighting channels of Example 13C and Example 13G: Blue Channel 1, a long-red channel, Short-Blue-Pumped Cyan Channel 1, Long-Blue-Pumped Cyan Channel 1, Yellow Chanel 3, and Violet Channel 3. As shown above with reference to Examples 13C and 13G, the device can be operated in various operating modes with different combinations of lighting channels.

Example 13K

A display system was simulated having six lighting channels. The six lighting channels are a combination of the lighting channels of Example 13C and Example 13H. Blue Channel 1, a long-red channel, Short-Blue-Pumped Cyan Channel 1, Long-Blue-Pumped Cyan Channel 1, Yellow Chanel 4, and Violet Channel 4. As shown above with reference to Examples 13C and 13H, the device can be operated in various operating modes with different combinations of lighting channels.

Example 13L

In some implementations, the display systems of the present disclosure can comprise three lighting channels as described elsewhere herein. In certain implementations, the three lighting channels comprise a long-red lighting channel, a yellow lighting channel, and a violet lighting channel. The display systems can be operated in a very-low-EML operating mode in which the long-red lighting channel, the yellow lighting channel, and the violet lighting channel are used. The display systems can further comprise a control system configured to control the relative intensities of light generated in the long-red lighting channel, the yellow lighting channel, and the violet lighting channel in order to generate white light at a plurality of points near the Planckian locus between about 4000K and about 1400K CCT.

Example 13M

In some implementations, the display systems of the present disclosure can comprise four lighting channels as described elsewhere herein. In certain implementations, the four lighting channels comprise a long-red lighting channel, a yellow lighting channel, a violet lighting channel, and a blue lighting channel. In some implementations, the display systems can be operated in a very-low-EML operating mode in which the long-red lighting channel, the yellow lighting channel, and the violet lighting channel are used. In further implementations, the display systems can be operated in a low-EML operating mode in which the blue lighting channel, the long-red lighting channel, the yellow lighting channel, and the violet lighting channel are used. In certain implementations, the display systems can transition between the low-EML and the very-low-EML operating modes in one or both directions while the display systems are providing white light along a path of color points near the Planckian locus. In further implementations, the display systems can transition between the low-EML and very-low-EML operating modes in one or both directions while the display systems are changing the CCT of the white light along the path of color points near the Planckian locus. In some implementations the low-EML operating mode can be used in generating white light near the Planckian locus with CCT values between about 10000K and about 1800K. In further implementations the very-low-EML operating mode can be used in generating white light near the Planckian locus with CCT values between about 4000K and about 1400K.

Example 13N

In some implementations, the display systems of the present disclosure can comprise five lighting channels as described elsewhere herein. In certain implementations, the five lighting channels comprise a long-red lighting channel, a yellow lighting channel, a violet lighting channel, a blue lighting channel, and a long-blue-pumped cyan lighting channel. In some implementations, the display systems can be operated in a very-low-EML operating mode in which the long-red lighting channel, the yellow lighting channel, and the violet lighting channel are used. In further implementations, the display systems can be operated in a low-EML operating mode in which the blue lighting channel, the long-red lighting channel, the yellow lighting channel, and the violet lighting channel are used. In yet further implementations, the display systems can be operated in a high-EML operating mode in which the blue lighting channel, the long-red lighting channel, and the long-blue-pumped cyan lighting channel are used. In certain implementations, the display systems can transition among two or more of the low-EML, the very-low-EML, and high-EML operating modes while the display systems are providing white light along a path of color points near the Planckian locus. In further implementations, the display systems can transition among two or more of the low-EML, the very-low-EML, and high-EML operating modes while the display systems are changing the CCT of the white light along the path of color points near the Planckian locus. In some implementations the low-EML operating mode can be used in generating white light near the Planckian locus with CCT values between about 10000K and about 1800K. In further implementations the very-low-EML operating mode can be used in generating white light near the Planckian locus with CCT values between about 4000K and about 1400K. In yet further implementations, the high-EML operating mode can be used in generating white light near the Planckian locus with CCT values between about 10000K and about 1800K General Simulation Method for Examples 14-34

Exemplary first and second lighting channels, and lighting systems having pairs of first and second lighting channels, were simulated. The simulated lighting systems can be used to provide one or more white light sources for a backlighting system in the display systems of the present disclosure. For each lighting channel, LED strings and recipient luminophoric mediums with particular emissions were selected, and then spectral power distributions and various light rendering characteristics and circadian-stimulating energy characteristics were calculated. Ra, R9, R13, R15, LER, Rf, Rg, CLA, CS, EML, BLH factor, CAF, CER, COI, GAI, GAI15, GAIBB, and circadian-stimulating energy characteristics were calculated at each representative point. Characteristics and aspects of the spectral power distributions are shown in Tables 3-12 and FIGS. 9-16.

The calculations were performed with Scilab (Scilab Enterprises, Versailles, France), LightTools (Synopsis, Inc., Mountain View, CA), and custom software created using Python (Python Software Foundation, Beaverton, OR). Each lighting channel was simulated with an LED emission spectrum and excitation and emission spectra of luminophoric medium(s). The luminophoric mediums can comprise luminescent compositions of phosphors, quantum dots, or combinations thereof, with simulations performed based on absorption/emission spectrums and particle sizes. The exemplary first lighting channels were simulated using spectra of LEDs having peak wavelengths of between about 440 nm and about 510 nm, such as a 450 nm peak wavelength blue LED, one or more LUXEON Z Color Line royal blue LEDs (product code LXZ1-PR01) of color bin codes 3, 4, 5, or 6 (Lumileds Holding B.V., Amsterdam, Netherlands), one or more LUXEON Z Color Line blue LEDs (LXZ1-PB01) of color bin code 1 or 2 (Lumileds Holding B.V., Amsterdam, Netherlands), one or more LUXEON royal blue LEDs (product code LXML-PR01 and LXML-PR02) of color bins 3, 4, 5, or 6 (Lumileds Holding B.V., Amsterdam, Netherlands), one or more LUXEON Rebel Blue LEDs (LXML-PB01, LXML-PB02) of color bins 1, 2, 3, 4, or 5 (Lumileds Holding B.V., Amsterdam, Netherlands), or one or more LUXEON Rebel Cyan LEDs (LXML-PE01) of color bins 1, 2, 3, 4, or 5 (Lumileds Holding B.V., Amsterdam, Netherlands), for example. The exemplary second lighting channels were simulated using spectra of LEDs having peak wavelengths of between about 380 nm and about 420 nm, such as one or more 410 nm peak wavelength violet LEDs, one or more LUXEON Z UV LEDs (product codes LHUV-0380-, LHUV-0385-, LHUV-0390-, LHUV-0395-, LHUV-0400-, LHUV-0405-, LHUV-0410-, LHUV-0415-, LHUV-0420-) (Lumileds Holding B.V., Amsterdam, Netherlands), one or more LUXEON UV FC LEDs (product codes LxF3-U410) (Lumileds Holding B.V., Amsterdam, Netherlands), one or more LUXEON UV U LEDs (product code LHUV-0415-) (Lumileds Holding B.V., Amsterdam, Netherlands), for example. Similar LEDs from other manufacturers such as OSRAM GmbH and Cree, Inc. that provide a saturated output at the desired peak wavelengths could also be used.

The emission, excitation and absorption curves for phosphors and quantum dots are available from commercial manufacturers such as Mitsubishi Chemical Holdings Corporation (Tokyo, Japan), Intematix Corporation (Fremont, CA), EMD Performance Materials of Merck KGaA (Darmstadt, Germany), and PhosphorTech Corporation (Kennesaw, GA). The luminophoric mediums used in the first and second lighting channels were simulated as combinations of one or more of luminescent compositions as described more fully elsewhere herein. Those of skill in the art appreciate that various combinations of LEDs and luminescent blends can be combined to generate combined emissions with desired color points on the 1931 CIE chromaticity diagram and the desired spectral power distributions.

Example 14

A lighting system was simulated having a first lighting channel having the characteristics shown as "4000K Ch1" in Tables 44, 46, 48, 50, 52, 53, and 56 and a second lighting channel having the characteristics shown as "2400K Ch1" in Tables 44, 45, 47, 49, 51, 53, and 56 and in FIG. 8. The values for EML slope and EML ratio for this pair of first and second lighting channels are shown in Tables 54 and 55. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 15

A lighting system was simulated having a first lighting channel having the characteristics shown as "4000K Ch2" in Tables 44, 46, 48, 50, 52, 53, and 56 and in FIG. 9, and a second lighting channel having the characteristics shown as "2400K Ch1" in Tables 44, 45, 47, 49, 51, 53, and 56 and in FIG. 8. The values for EML slope and EML ratio for this pair of first and second lighting channels are shown in Tables 54 and 55. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 16

A lighting system was simulated having a first lighting channel having the characteristics shown as "4000K Ch3" in Tables 44, 46, 48, 50, 52, 53, and 56 and in FIG. 10, and a second lighting channel having the characteristics shown as "2400K Ch1" in Tables 44, 45, 47, 49, 51, 53, and 56 and in FIG. 8. The values for EML slope and EML ratio for this pair of first and second lighting channels are shown in Tables 54 and 55. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 17

A lighting system was simulated having a first lighting channel having the characteristics shown as "4000K Ch4" in Tables 44, 46, 48, 50, 52, 53, and 56 and in FIG. 5, and a second lighting channel having the characteristics shown as "2400K Ch1" in Tables 44, 45, 47, 49, 51, 53, and 56 and in FIG. 8. The values for EML slope and EML ratio for this pair of first and second lighting channels are shown in Tables 54 and 55. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 18

A lighting system was simulated having a first lighting channel having the characteristics shown as "5000K Ch1" in Tables 44, 46, 48, 50, 52, 53, and 56 and in FIG. 12, and a second lighting channel having the characteristics shown as "2400K Ch1" in Tables 44, 45, 47, 49, 51, 53, and 56 and in FIG. 8. The values for EML slope and EML ratio for this pair of first and second lighting channels are shown in Tables 54 and 55. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 19

A lighting system was simulated having a first lighting channel having the characteristics shown as "4000K Ch1" in Tables 44, 46, 48, 50, 52, 53, and 56 and a second lighting channel having the characteristics shown as "2400K Ch2" in Tables 44, 45, 47, 49, 51, 53, and 56 and in FIG. 7. The values for EML slope and EML ratio for this pair of first and second lighting channels are shown in Tables 54 and 55. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 20

A lighting system was simulated having a first lighting channel having the characteristics shown as "4000K Ch2" in Tables 44, 46, 48, 50, 52, 53, and 56 and in FIG. 9, and a second lighting channel having the characteristics shown as "2400K Ch2" in Tables 44, 45, 47, 49, 51, 53, and 56 and in FIG. 7. The values for EML slope and EML ratio for this pair of first and second lighting channels are shown in Tables 54 and 55. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 21

A lighting system was simulated having a first lighting channel having the characteristics shown as "4000K Ch3" in Tables 44, 46, 48, 50, 52, 53, and 56 and in FIG. 10, and a second lighting channel having the characteristics shown as "2400K Ch2" in Tables 44, 45, 47, 49, 51, 53, and 56 and in FIG. 7. The values for EML slope and EML ratio for this pair of first and second lighting channels are shown in Tables 54 and 55. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 22

A lighting system was simulated having a first lighting channel having the characteristics shown as "4000K Ch4" in Tables 44, 46, 48, 50, 52, 53, and 56 and in FIG. 5, and a second lighting channel having the characteristics shown as "2400K Ch2" in Tables 44, 45, 47, 49, 51, 53, and 56 and in FIG. 7. The values for EML slope and EML ratio for this pair of first and second lighting channels are shown in Tables 54 and 55. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 23

A lighting system was simulated having a first lighting channel having the characteristics shown as "5000K Ch1" in Tables 44, 46, 48, 50, 52, 53, and 56 and in FIG. 12, and a second lighting channel having the characteristics shown as "2400K Ch2" in Tables 44, 45, 47, 49, 51, 53, and 56 and in FIG. 7. The values for EML slope and EML ratio for this pair of first and second lighting channels are shown in Tables 54 and 55. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 24

A lighting system was simulated having a first lighting channel having the characteristics shown as "4000K Ch1" in Tables 44, 46, 48, 50, 52, 53, and 56 and a second lighting channel having the characteristics shown as "2400K Ch3" in Tables 44, 45, 47, 49, 51, 53, and 56 and in FIG. 6. The values for EML slope and EML ratio for this pair of first and second lighting channels are shown in Tables 54 and 55. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 25

A lighting system was simulated having a first lighting channel having the characteristics shown as "4000K Ch2" in Tables 44, 46, 48, 50, 52, 53, and 56 and in FIG. 9, and a second lighting channel having the characteristics shown as "2400K Ch3" in Tables 44, 45, 47, 49, 51, 53, and 56 and in FIG. 6. The values for EML slope and EML ratio for this pair of first and second lighting channels are shown in Tables 54 and 55. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 26

A lighting system was simulated having a first lighting channel having the characteristics shown as "4000K Ch3" in Tables 44, 46, 48, 50, 52, 53, and 56 and in FIG. 10, and a second lighting channel having the characteristics shown as "2400K Ch3" in Tables 44, 45, 47, 49, 51, 53, and 56 and in FIG. 6. The values for EML slope and EML ratio for this pair of first and second lighting channels are shown in Tables 54 and 55. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 27

A lighting system was simulated having a first lighting channel having the characteristics shown as "4000K Ch4" in Tables 44, 46, 48, 50, 52, 53, and 56 and in FIG. 5, and a second lighting channel having the characteristics shown as "2400K Ch3" in Tables 44, 45, 47, 49, 51, 53, and 56 and in FIG. 6. The values for EML slope and EML ratio for this pair of first and second lighting channels are shown in Tables 54 and 55. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 28

A lighting system was simulated having a first lighting channel having the characteristics shown as "5000K Ch1" in Tables 44, 46, 48, 50, 52, 53, and 56 and in FIG. 12, and a second lighting channel having the characteristics shown as "2400K Ch3" in Tables 44, 45, 47, 49, 51, 53, and 56 and in FIG. 6. The values for EML slope and EML ratio for this pair of first and second lighting channels are shown in Tables 54 and 55. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 29

A lighting system was simulated having a first lighting channel having the characteristics shown as "4000K Ch1" in Tables 44, 46, 48, 50, 52, 53, and 56 and a second lighting channel having the characteristics shown as "1800K Ch1" in Tables 44, 45, 47, 49, 51, 53, and 56 and in FIG. 11. The values for EML slope and EML ratio for this pair of first and second lighting channels are shown in Tables 54 and 55. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 30

A lighting system was simulated having a first lighting channel having the characteristics shown as "4000K Ch2" in Tables 44, 46, 48, 50, 52, 53, and 56 and in FIG. 9, and a second lighting channel having the characteristics shown as "1800K Ch1" in Tables 44, 45, 47, 49, 51, 53, and 56 and in FIG. 11. The values for EML slope and EML ratio for this pair of first and second lighting channels are shown in Tables 54 and 55. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 31

A lighting system was simulated having a first lighting channel having the characteristics shown as "4000K Ch3" in Tables 44, 46, 48, 50, 52, 53, and 56 and in FIG. 10, and a second lighting channel having the characteristics shown as "1800K Ch1" in Tables 44, 45, 47, 49, 51, 53, and 56 and in FIG. 11. The values for EML slope and EML ratio for this pair of first and second lighting channels are shown in Tables 54 and 55. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 32

A lighting system was simulated having a first lighting channel having the characteristics shown as "4000K Ch4" in Tables 44, 46, 48, 50, 52, 53, and 56 and in FIG. 5, and a second lighting channel having the characteristics shown as "1800K Ch1" in Tables 44, 45, 47, 49, 51, 53, and 56 and in FIG. 11. The values for EML slope and EML ratio for this pair of first and second lighting channels are shown in Tables 54 and 55. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 33

A lighting system was simulated having a first lighting channel having the characteristics shown as "5000K Ch1" in Tables 44, 46, 48, 50, 52, 53, and 56 and in FIG. 12, and a second lighting channel having the characteristics shown as "1800K Ch1" in Tables 44, 45, 47, 49, 51, 53, and 56 and in FIG. 11. The values for EML slope and EML ratio for this pair of first and second lighting channels are shown in Tables 54 and 55. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof.

Example 34

A lighting system was simulated having a first lighting channel having the characteristics shown as "Exemplary 1st channels avg" in Tables 44, 46, 48, 50, 52, 53, and 56, and a second lighting channel having the characteristics shown as "Exemplary 2nd channels avg" in Tables 44, 45, 47, 49, 51, 53, and 56. The first lighting channel has a first color point at (0.3735, 0.3719) ccx, ccy coordinates. The second lighting channel has a second color point at (0.5021, 0.4137) ccx, ccy coordinates. The first lighting channel can comprise an LED having a 450 nm peak wavelength and an associated luminophoric medium having one or more phosphors, quantum dots, or a mixture thereof. The second lighting channel can comprise an LED having a 410 nm peak wavelength and an associated luminophoric medium having one or more phosphors, quantum dots, or a mixture thereof Example 35

A display system was simulated having three LED strings for use in a warm-dim operation mode. A first LED string is driven by a blue LED having peak emission wavelength of approximately 450 nm to approximately 455 nm, utilizes a recipient luminophoric medium, and generates a combined emission of a white color point with a 1931 CIE chromaticity diagram (ccx, ccy) coordinates of (0.3818, 0.3797). A second LED string is driven by a blue LED having peak emission wavelength of approximately 450 nm to approximately 455 nm, utilizes a recipient luminophoric medium, and generates a combined emission of a red color point with a 1931 CIE chromaticity diagram color point of (0.5932, 0.3903). A third LED string is driven by a blue LED having peak emission wavelength of approximately 450 nm to approximately 455 nm, utilizes a recipient luminophoric medium, and generates a combined emission of a cyan color point with a 1931 CIE chromaticity diagram color point of (0.373, 0.4978).

Tables 58 and 59 below shows the spectral power distributions for the red and cyan color points generated by the display system of this Example, with spectral power shown within wavelength ranges in nanometers from 380 nm to 780 nm, with an arbitrary reference wavelength range selected for each color range and normalized to a value of 100.0. Table 60 shows color-rendering and circadian performance characteristics of the device for a representative selection of white light color points near the Planckian locus.

Example 36

Any of the systems of Examples 1-13 and 14-35 can be modified to further include an additional lighting channel, a LRNE channel, that can be controlled to selectively provide LRNE spectral energy in the visible long-red or non-visible near infrared wavelengths ranges described herein. In some implementations, the spectral power distribution of the LRNE channel can be substantially equal to the spectral power of Long-Red Phosphor 675 nm or Long-Red Phosphor 700 nm shown in Tables 61-63. In certain implementations, the LRNE channel can have a spectral power distribution substantially equal to that of Long-Red Channel A, Long-Red Channel B, or Exemplary Long-Red Channel Average shown in Tables 7-9. One or more of the other channels in the lighting systems can have intensity reduced or turned off entirely when the LRNE channel is activated. Control methods and hardware as described elsewhere herein can be used to control the timing and amount of LRNE spectral energy provided by the systems.

TABLE 7

| | 320 < λ ≤ 340 | 340 < λ ≤ 360 | 360 < λ ≤ 380 | 380 < λ ≤ 400 | 400 < λ ≤ 420 | 420 < λ ≤ 440 | 440 < λ ≤ 460 | 460 < λ ≤ 480 | 480 < λ ≤ 500 | 500 < λ ≤ 520 | 520 < λ ≤ 540 | 540 < λ ≤ 560 |
|---|---|---|---|---|---|---|---|---|---|---|---|---|
| Red Channel 11 | 0.0 | 0.0 | 0.0 | 0.6 | 0.8 | 0.9 | 3.1 | 4.9 | 2.9 | 8.5 | 14.9 | 17.6 |
| Red Channel 3 | 0.0 | 0.0 | 0.0 | 0.0 | 0.1 | 3.9 | 14.9 | 3.4 | 0.5 | 0.8 | 2.0 | 5.8 |
| Red Channel 4 | 0.0 | 0.0 | 0.0 | 25.6 | 21.1 | 16.7 | 16.4 | 15.2 | 6.0 | 10.5 | 16.8 | 18.2 |
| Red Channel 5 | 0.0 | 0.0 | 0.0 | 0.7 | 1.0 | 12.6 | 68.4 | 23.0 | 5.5 | 16.7 | 35.7 | 43.0 |
| Red Channel 6 | 0.0 | 0.0 | 0.0 | 0.0 | 0.1 | 3.9 | 14.9 | 3.4 | 0.5 | 0.8 | 2.0 | 5.8 |
| Red Channel 7 | 0.0 | 0.0 | 0.0 | 2.0 | 15.5 | 13.4 | 2.8 | 0.9 | 1.0 | 3.2 | 5.7 | 7.8 |
| Red Channel 8 | 0.0 | 0.0 | 0.0 | 0.3 | 20.3 | 17.9 | 0.2 | 0.0 | 0.0 | 0.1 | 0.1 | 0.6 |
| Red Channel 9 | 0.0 | 0.0 | 0.0 | 0.0 | 0.0 | 0.4 | 4.1 | 5.8 | 4.0 | 7.2 | 12.7 | 18.9 |
| Red Channel 10 | 0.0 | 0.0 | 0.0 | 0.1 | 0.1 | 0.7 | 4.5 | 4.9 | 3.5 | 6.7 | 11.6 | 17.6 |
| Red Channel 1 | 0.0 | 0.0 | 0.0 | 0.0 | 0.3 | 1.4 | 1.3 | 0.4 | 0.9 | 4.2 | 9.4 | 15.3 |
| Red Channel 2 | 0.0 | 0.0 | 0.0 | 0.1 | 0.4 | 1.1 | 3.4 | 3.6 | 2.7 | 5.9 | 11.0 | 16.9 |
| Long-Red Channel A | 0.0 | 1.2 | 1.8 | 1.7 | 2.1 | 6.1 | 13.2 | 4.4 | 3.5 | 10.7 | 17.7 | 18.7 |
| Long-Red Channel B | 0.0 | 1.2 | 2.1 | 2.0 | 2.1 | 6.1 | 13.4 | 4.5 | 3.1 | 7.5 | 16.3 | 25.2 |
| Exemplary Red Channels Minimum | 0.0 | 0.0 | 0.0 | 0.0 | 0.0 | 0.4 | 0.2 | 0.0 | 0.0 | 0.1 | 0.1 | 0.6 |
| Exemplary Red Channels Average | 0.0 | 0.2 | 0.3 | 2.5 | 4.9 | 6.5 | 12.4 | 5.7 | 2.6 | 6.4 | 12.0 | 16.3 |
| Exemplary Red Channels Maximum | 0.0 | 1.2 | 2.1 | 25.6 | 21.1 | 17.9 | 68.4 | 23.0 | 6.0 | 16.7 | 35.7 | 43.0 |
| Exemplary Long-Red Channel Minimum | 0.0 | 1.2 | 1.8 | 1.7 | 2.1 | 6.1 | 13.2 | 4.4 | 3.1 | 7.5 | 16.3 | 18.7 |
| Exemplary Long-Red Channel Average | 0.0 | 1.2 | 1.9 | 1.9 | 2.1 | 6.1 | 13.3 | 4.4 | 3.3 | 9.1 | 17.0 | 21.9 |
| Exemplary Long-Red Channel Maximum | 0.0 | 1.2 | 2.1 | 2.0 | 2.1 | 6.1 | 13.4 | 4.5 | 3.5 | 10.7 | 17.7 | 25.2 |

| | 560 < λ ≤ 580 | 580 < λ ≤ 600 | 600 < λ ≤ 620 | 620 < λ ≤ 640 | 640 < λ ≤ 660 | 660 < λ ≤ 680 | 680 < λ ≤ 700 | 700 < λ ≤ 720 | 720 < λ ≤ 740 | 740 < λ ≤ 760 | 760 < λ ≤ 780 | 780 < λ ≤ 800 |
|---|---|---|---|---|---|---|---|---|---|---|---|---|
| Red Channel 11 | 21.8 | 35.7 | 63.5 | 91.4 | 100.0 | 83.9 | 58.3 | 35.6 | 20.3 | 10.8 | 5.2 | 0.0 |
| Red Channel 3 | 11.8 | 30.2 | 64.2 | 94.6 | 100.0 | 83.6 | 58.7 | 36.3 | 21.0 | 11.4 | 6.0 | 0.0 |
| Red Channel 4 | 25.8 | 93.1 | 231.0 | 215.2 | 100.0 | 27.6 | 7.1 | 2.9 | 1.9 | 1.5 | 1.8 | 0.0 |
| Red Channel 5 | 47.5 | 100.0 | 478.3 | 852.3 | 100.0 | 12.4 | 4.5 | 2.7 | 1.9 | 1.5 | 1.0 | 0.0 |
| Red Channel 6 | 11.8 | 30.2 | 64.2 | 94.6 | 100.0 | 83.6 | 58.7 | 36.3 | 21.0 | 11.4 | 6.0 | 0.0 |
| Red Channel 7 | 13.0 | 28.9 | 59.4 | 89.8 | 100.0 | 84.5 | 58.8 | 36.0 | 20.5 | 10.9 | 5.2 | 0.0 |
| Red Channel 8 | 3.2 | 15.9 | 46.4 | 79.8 | 100.0 | 94.8 | 73.4 | 50.7 | 32.9 | 20.2 | 11.1 | 0.0 |
| Red Channel 9 | 29.4 | 46.9 | 72.4 | 95.7 | 100.0 | 83.0 | 57.2 | 34.7 | 19.7 | 10.8 | 5.7 | 0.0 |
| Red Channel 10 | 30.0 | 48.9 | 67.9 | 93.5 | 100.0 | 66.0 | 33.7 | 16.5 | 7.6 | 3.2 | 1.5 | 0.0 |
| Red Channel 1 | 26.4 | 45.8 | 66.0 | 87.0 | 100.0 | 72.5 | 42.0 | 22.3 | 11.6 | 6.1 | 3.1 | 0.0 |
| Red Channel 2 | 28.1 | 46.8 | 68.9 | 92.6 | 100.0 | 73.9 | 44.5 | 24.7 | 13.1 | 6.8 | 3.5 | 0.0 |
| Long-Red Channel A | 17.4 | 17.3 | 21.6 | 43.2 | 100.0 | 182.3 | 237.5 | 229.6 | 174.5 | 112.8 | 66.3 | 36.7 |
| Long-Red Channel B | 40.3 | 69.5 | 100.8 | 111.3 | 100.0 | 86.9 | 103.1 | 162.2 | 227.8 | 248.3 | 208.2 | 144.4 |
| Exemplary Red Channels Minimum | 3.2 | 15.9 | 21.6 | 43.2 | 100.0 | 12.4 | 4.5 | 2.7 | 1.9 | 1.5 | 1.0 | 0.0 |
| Exemplary Red Channels Average | 23.6 | 46.9 | 108.0 | 157.0 | 100.0 | 79.6 | 64.4 | 53.1 | 44.1 | 35.1 | 25.0 | 13.9 |
| Exemplary Red Channels Maximum | 47.5 | 100.0 | 478.3 | 852.3 | 100.0 | 182.3 | 237.5 | 229.6 | 227.8 | 248.3 | 208.2 | 144.4 |
| Exemplary Long-Red Channel Minimum | 17.4 | 17.3 | 21.6 | 43.2 | 100.0 | 86.9 | 103.1 | 162.2 | 174.5 | 112.8 | 66.3 | 36.7 |
| Exemplary Long-Red Channel Average | 28.9 | 43.4 | 61.2 | 77.2 | 100.0 | 134.6 | 170.3 | 195.9 | 201.1 | 180.5 | 137.2 | 90.6 |
| Exemplary Long-Red Channel Maximum | 40.3 | 69.5 | 100.8 | 111.3 | 100.0 | 182.3 | 237.5 | 229.6 | 227.8 | 248.3 | 208.2 | 144.4 |

TABLE 7-continued

|  | 800 < λ ≤ 820 | 820 < λ ≤ 840 | 840 < λ ≤ 860 | 860 < λ ≤ 880 | 880 < λ ≤ 900 | 900 < λ ≤ 920 | 920 < λ ≤ 940 | 940 < λ ≤ 960 | 960 < λ ≤ 980 | 980 < λ ≤ 1000 |
| --- | --- | --- | --- | --- | --- | --- | --- | --- | --- | --- |
| Red Channel 11 | 0.0 | 0.0 | 0.0 | 0.0 | 0.0 | 0.0 | 0.0 | 0.0 | 0.0 | 0.0 |
| Red Channel 3 | 0.0 | 0.0 | 0.0 | 0.0 | 0.0 | 0.0 | 0.0 | 0.0 | 0.0 | 0.0 |
| Red Channel 4 | 0.0 | 0.0 | 0.0 | 0.0 | 0.0 | 0.0 | 0.0 | 0.0 | 0.0 | 0.0 |
| Red Channel 5 | 0.0 | 0.0 | 0.0 | 0.0 | 0.0 | 0.0 | 0.0 | 0.0 | 0.0 | 0.0 |
| Red Channel 6 | 0.0 | 0.0 | 0.0 | 0.0 | 0.0 | 0.0 | 0.0 | 0.0 | 0.0 | 0.0 |
| Red Channel 7 | 0.0 | 0.0 | 0.0 | 0.0 | 0.0 | 0.0 | 0.0 | 0.0 | 0.0 | 0.0 |
| Red Channel 8 | 0.0 | 0.0 | 0.0 | 0.0 | 0.0 | 0.0 | 0.0 | 0.0 | 0.0 | 0.0 |
| Red Channel 9 | 0.0 | 0.0 | 0.0 | 0.0 | 0.0 | 0.0 | 0.0 | 0.0 | 0.0 | 0.0 |
| Red Channel 10 | 0.0 | 0.0 | 0.0 | 0.0 | 0.0 | 0.0 | 0.0 | 0.0 | 0.0 | 0.0 |
| Red Channel 1 | 0.0 | 0.0 | 0.0 | 0.0 | 0.0 | 0.0 | 0.0 | 0.0 | 0.0 | 0.0 |
| Red Channel 2 | 0.0 | 0.0 | 0.0 | 0.0 | 0.0 | 0.0 | 0.0 | 0.0 | 0.0 | 0.0 |
| Long-Red Channel A | 18.6 | 9.3 | 2.2 | 0.0 | 0.0 | 0.0 | 0.0 | 0.0 | 0.0 | 0.0 |
| Long-Red Channel B | 90.0 | 51.3 | 27.2 | 13.6 | 6.2 | 0.0 | 0.0 | 0.0 | 0.0 | 0.0 |
| Exemplary Red Channels Minimum | 0.0 | 0.0 | 0.0 | 0.0 | 0.0 | 0.0 | 0.0 | 0.0 | 0.0 | 0.0 |
| Exemplary Red Channels Average | 8.4 | 4.7 | 2.3 | 1.0 | 0.5 | 0.0 | 0.0 | 0.0 | 0.0 | 0.0 |
| Exemplary Red Channels Maximum | 90.0 | 51.3 | 27.2 | 13.6 | 6.2 | 0.0 | 0.0 | 0.0 | 0.0 | 0.0 |
| Exemplary Long-Red Channel Minimum | 18.6 | 9.3 | 2.2 | 0.0 | 0.0 | 0.0 | 0.0 | 0.0 | 0.0 | 0.0 |
| Exemplary Long-Red Channel Average | 54.3 | 30.3 | 14.7 | 6.8 | 3.1 | 0.0 | 0.0 | 0.0 | 0.0 | 0.0 |
| Exemplary Long-Red Channel Maximum | 90.0 | 51.3 | 27.2 | 13.6 | 6.2 | 0.0 | 0.0 | 0.0 | 0.0 | 0.0 |

TABLE 8

|  | 320 < λ ≤ 380 | 380 < λ ≤ 420 | 420 < λ ≤ 460 | 460 < λ ≤ 500 | 500 < λ ≤ 540 | 540 < λ ≤ 580 | 580 < λ ≤ 620 | 620 < λ ≤ 660 |
| --- | --- | --- | --- | --- | --- | --- | --- | --- |
| Red Channel 11 | 0.0 | 0.7 | 2.1 | 4.1 | 12.2 | 20.5 | 51.8 | 100.0 |
| Red Channel 3 | 0.0 | 0.0 | 9.6 | 2.0 | 1.4 | 9.0 | 48.5 | 100.0 |
| Red Channel 4 | 0.0 | 14.8 | 10.5 | 6.7 | 8.7 | 14.0 | 102.8 | 100.0 |
| Red Channel 5 | 0.0 | 0.2 | 8.5 | 3.0 | 5.5 | 9.5 | 60.7 | 100.0 |
| Red Channel 6 | 0.0 | 0.0 | 9.6 | 2.0 | 1.4 | 9.0 | 48.5 | 100.0 |
| Red Channel 7 | 0.0 | 9.2 | 8.6 | 1.0 | 4.6 | 11.0 | 46.5 | 100.0 |
| Red Channel 8 | 0.0 | 11.5 | 10.1 | 0.1 | 0.1 | 2.1 | 34.6 | 100.0 |
| Red Channel 9 | 0.0 | 0.0 | 2.3 | 5.0 | 10.2 | 24.7 | 61.0 | 100.0 |
| Red Channel 10 | 0.0 | 0.1 | 2.7 | 4.3 | 9.5 | 24.6 | 60.4 | 100.0 |
| Long-Red Channel A | 2.1 | 2.6 | 13.5 | 5.5 | 19.8 | 25.2 | 27.2 | 100.0 |
| Long-Red Channel B | 1.6 | 2.0 | 9.2 | 3.6 | 11.3 | 31.0 | 80.6 | 100.0 |
| Red Channel 1 | 0.0 | 0.2 | 1.4 | 0.7 | 7.3 | 22.3 | 59.8 | 100.0 |
| Red Channel 2 | 0.0 | 0.3 | 2.3 | 3.3 | 8.8 | 23.4 | 60.1 | 100.0 |
| Exemplary Red Channels Minimum | 0.0 | 0.0 | 1.4 | 0.1 | 0.1 | 2.1 | 27.2 | 100.0 |
| Exemplary Red Channels Average | 0.3 | 3.2 | 7.0 | 3.2 | 7.7 | 17.4 | 57.1 | 100.0 |
| Exemplary Red Channels Maximum | 2.1 | 14.8 | 13.5 | 6.7 | 19.8 | 31.0 | 102.8 | 100.0 |
| Exemplary Long-Red Channel Minimum | 1.6 | 2.0 | 9.2 | 3.6 | 11.3 | 25.2 | 27.2 | 100.0 |
| Exemplary Long-Red Channel Average | 1.8 | 2.3 | 11.4 | 4.5 | 15.5 | 28.1 | 53.9 | 100.0 |
| Exemplary Long-Red Channel Maximum | 2.1 | 2.6 | 13.5 | 5.5 | 19.8 | 31.0 | 80.6 | 100.0 |

|  | 660 < λ ≤ 700 | 700 < λ ≤ 740 | 740 < λ ≤ 780 | 780 < λ ≤ 820 | 820 < λ ≤ 860 | 860 < λ ≤ 900 | 900 < λ ≤ 1000 |
| --- | --- | --- | --- | --- | --- | --- | --- |
| Red Channel 11 | 74.3 | 29.3 | 8.4 | 0.0 | 0.0 | 0.0 | 0.0 |
| Red Channel 3 | 73.1 | 29.5 | 9.0 | 0.0 | 0.0 | 0.0 | 0.0 |
| Red Channel 4 | 11.0 | 1.5 | 1.1 | 0.0 | 0.0 | 0.0 | 0.0 |
| Red Channel 5 | 1.8 | 0.5 | 0.3 | 0.0 | 0.0 | 0.0 | 0.0 |
| Red Channel 6 | 73.1 | 29.5 | 9.0 | 0.0 | 0.0 | 0.0 | 0.0 |
| Red Channel 7 | 75.5 | 29.8 | 8.5 | 0.0 | 0.0 | 0.0 | 0.0 |
| Red Channel 8 | 93.6 | 46.5 | 17.5 | 0.0 | 0.0 | 0.0 | 0.0 |
| Red Channel 9 | 71.7 | 27.8 | 8.4 | 0.0 | 0.0 | 0.0 | 0.0 |
| Red Channel 10 | 51.5 | 12.4 | 2.4 | 0.0 | 0.0 | 0.0 | 0.0 |
| Long-Red Channel A | 293.2 | 282.2 | 125.1 | 38.7 | 8.1 | 0.0 | 0.0 |
| Long-Red Channel B | 89.9 | 184.6 | 216.1 | 110.9 | 37.2 | 9.3 | 0.0 |
| Red Channel 1 | 61.2 | 18.1 | 4.9 | 0.0 | 0.0 | 0.0 | 0.0 |
| Red Channel 2 | 61.5 | 19.6 | 5.3 | 0.0 | 0.0 | 0.0 | 0.0 |
| Exemplary Red Channels Minimum | 1.8 | 0.5 | 0.3 | 0.0 | 0.0 | 0.0 | 0.0 |
| Exemplary Red Channels Average | 79.3 | 54.7 | 32.0 | 11.5 | 3.5 | 0.7 | 0.0 |
| Exemplary Red Channels Maximum | 293.2 | 282.2 | 216.1 | 110.9 | 37.2 | 9.3 | 0.0 |

TABLE 8-continued

| | | | | | | | |
|---|---|---|---|---|---|---|---|
| Exemplary Long-Red Channel Minimum | 89.9 | 184.6 | 125.1 | 38.7 | 8.1 | 0.0 | 0.0 |
| Exemplary Long-Red Channel Average | 191.6 | 233.4 | 170.6 | 74.8 | 22.6 | 4.7 | 0.0 |
| Exemplary Long-Red Channel Maximum | 293.2 | 282.2 | 216.1 | 110.9 | 37.2 | 9.3 | 0.0 |

TABLE 9

| | 320 < λ ≤ 400 | 400 < λ ≤ 500 | 500 < λ ≤ 600 | 600 < λ ≤ 700 | 700 < λ ≤ 800 | 800 < λ ≤ 900 | 900 < λ ≤ 1000 |
|---|---|---|---|---|---|---|---|
| Red Channel 11 | 0.2 | 3.2 | 24.8 | 100.0 | 18.1 | 0.0 | 0.0 |
| Red Channel 3 | 0.0 | 5.7 | 12.6 | 100.0 | 18.7 | 0.0 | 0.0 |
| Red Channel 4 | 4.4 | 13.0 | 28.3 | 100.0 | 1.4 | 0.0 | 0.0 |
| Red Channel 5 | 0.1 | 7.6 | 16.8 | 100.0 | 0.5 | 0.0 | 0.0 |
| Red Channel 6 | 0.0 | 5.7 | 12.6 | 100.0 | 18.7 | 0.0 | 0.0 |
| Red Channel 7 | 0.5 | 8.6 | 14.9 | 100.0 | 18.5 | 0.0 | 0.0 |
| Red Channel 8 | 0.1 | 9.8 | 5.1 | 100.0 | 29.2 | 0.0 | 0.0 |
| Red Channel 9 | 0.0 | 3.5 | 28.2 | 100.0 | 17.3 | 0.0 | 0.0 |
| Red Channel 10 | 0.0 | 3.8 | 31.8 | 100.0 | 8.0 | 0.0 | 0.0 |
| Red Channel 1 | 0.0 | 1.2 | 27.5 | 100.0 | 11.7 | 0.0 | 0.0 |
| Red Channel 2 | 0.0 | 2.9 | 28.6 | 100.0 | 12.7 | 0.0 | 0.0 |
| Long-Red Channel A | 0.8 | 5.0 | 14.0 | 100.0 | 106.0 | 5.2 | 0.0 |
| Long-Red Channel B | 1.1 | 5.8 | 31.6 | 100.0 | 197.4 | 37.5 | 0.0 |
| Exemplary Red Channels Minimum | 0.0 | 1.2 | 5.1 | 100.0 | 0.5 | 0.0 | 0.0 |
| Exemplary Red Channels Average | 0.5 | 5.8 | 21.3 | 100.0 | 35.2 | 3.3 | 0.0 |
| Exemplary Red Channels Maximum | 4.4 | 13.0 | 31.8 | 100.0 | 197.4 | 37.5 | 0.0 |
| Exemplary Long-Red Channel Minimum | 0.8 | 5.0 | 14.0 | 100.0 | 106.0 | 5.2 | 0.0 |
| Exemplary Long-Red Channel Average | 0.9 | 5.4 | 22.8 | 100.0 | 151.7 | 71.3 | 0.0 |
| Exemplary Long-Red Channel Maximum | 1.1 | 5.8 | 31.6 | 100.0 | 197.4 | 37.5 | 0.0 |

TABLE 10

| | 320 < λ ≤ 340 | 340 < λ ≤ 360 | 360 < λ ≤ 380 | 380 < λ ≤ 400 | 400 < λ ≤ 420 | 420 < λ ≤ 440 | 440 < λ ≤ 460 | 460 < λ ≤ 480 | 480 < λ ≤ 500 | 500 < λ ≤ 520 | 520 < λ ≤ 540 | 540 < λ ≤ 560 |
|---|---|---|---|---|---|---|---|---|---|---|---|---|
| Violet Channel 1 | 0.0 | 51.7 | 633.8 | 545.9 | 100.0 | 53.3 | 53.9 | 10.5 | 6.9 | 22.4 | 40.4 | 48.0 |
| Violet Channel 2 | 0.0 | 0.3 | 11.0 | 116.1 | 100.0 | 17.8 | 2.7 | 0.5 | 1.1 | 4.4 | 7.9 | 9.4 |
| Violet Channel 5 | 0.0 | 0.3 | 10.9 | 115.7 | 100.0 | 23.4 | 10.2 | 1.9 | 1.4 | 4.5 | 8.2 | 9.7 |
| Violet Channel 3 | 0.0 | 0.0 | 1.4 | 29.4 | 100.0 | 29.8 | 4.6 | 0.8 | 0.9 | 3.3 | 6.0 | 7.0 |
| Violet Channel 4 | 0.0 | 1.0 | 1.9 | 10.7 | 100.0 | 86.0 | 15.7 | 2.7 | 3.7 | 13.8 | 24.8 | 28.4 |
| Exemplary Violet Channels Minimum | 0.0 | 0.0 | 1.4 | 10.7 | 100.0 | 17.8 | 2.7 | 0.5 | 0.9 | 3.3 | 6.0 | 7.0 |
| Exemplary Violet Channels Average | 0.0 | 10.7 | 131.8 | 163.6 | 100.0 | 42.1 | 17.4 | 3.3 | 2.8 | 9.7 | 17.4 | 20.5 |
| Exemplary Violet Channels Maximum | 0.0 | 51.7 | 633.8 | 545.9 | 100.0 | 86.0 | 53.9 | 10.5 | 6.9 | 22.4 | 40.4 | 48.0 |

| | 560 < λ ≤ 580 | 580 < λ ≤ 600 | 600 < λ ≤ 620 | 620 < λ ≤ 640 | 640 < λ ≤ 660 | 660 < λ ≤ 680 | 680 < λ ≤ 700 | 700 < λ ≤ 720 | 720 < λ ≤ 740 | 740 < λ ≤ 760 | 760 < λ ≤ 780 | 780 < λ ≤ 800 |
|---|---|---|---|---|---|---|---|---|---|---|---|---|
| Violet Channel 1 | | | | | | | | | | | | |
| Violet Channel 2 | 51.7 | 54.0 | 51.2 | 41.8 | 29.8 | 19.4 | 11.6 | 6.8 | 3.7 | 2.0 | 1.1 | 0.0 |
| Violet Channel 5 | 10.0 | 10.4 | 9.8 | 8.0 | 5.7 | 3.7 | 2.2 | 1.3 | 0.7 | 0.4 | 0.2 | 0.0 |
| Violet Channel 3 | 10.6 | 11.2 | 10.8 | 8.9 | 6.3 | 4.1 | 2.5 | 1.4 | 0.8 | 0.4 | 0.2 | 0.0 |
| Violet Channel 4 | 7.3 | 7.3 | 6.7 | 5.4 | 3.8 | 2.5 | 1.5 | 0.9 | 0.5 | 0.3 | 0.1 | 0.0 |
| Exemplary Violet Channels Minimum | 28.0 | 29.9 | 32.6 | 20.3 | 10.7 | 6.5 | 3.9 | 2.4 | 1.4 | 0.8 | 0.5 | 0.0 |
| Exemplary Violet Channels Average | 7.3 | 7.3 | 6.7 | 5.4 | 3.8 | 2.5 | 1.5 | 0.9 | 0.5 | 0.3 | 0.1 | 0.0 |
| Exemplary Violet Channels Maximum | 21.5 | 22.6 | 22.2 | 16.9 | 11.3 | 7.2 | 4.3 | 2.6 | 1.4 | 0.8 | 0.5 | 0.0 |

TABLE 11

| | 320 < λ ≤ 380 | 380 < λ ≤ 420 | 420 < λ ≤ 460 | 460 < λ ≤ 500 | 500 < λ ≤ 540 | 540 < λ ≤ 580 | 580 < λ ≤ 620 | 620 < λ ≤ 660 | 660 < λ ≤ 700 | 700 < λ ≤ 740 | 740 < λ ≤ 780 |
|---|---|---|---|---|---|---|---|---|---|---|---|
| Violet Channel 1 | 106.1 | 100.0 | 16.6 | 2.7 | 9.7 | 15.4 | 16.3 | 11.1 | 4.8 | 1.6 | 0.5 |
| Violet Channel 2 | 5.2 | 100.0 | 9.5 | 0.8 | 5.7 | 9.0 | 9.3 | 6.3 | 2.7 | 0.9 | 0.3 |
| Violet Channel 5 | 5.2 | 100.0 | 15.6 | 1.5 | 5.9 | 9.4 | 10.2 | 7.1 | 3.1 | 1.0 | 0.3 |
| Violet Channel 3 | 1.1 | 100.0 | 26.6 | 1.3 | 7.1 | 11.0 | 10.8 | 7.1 | 3.0 | 1.0 | 0.3 |
| Violet Channel 4 | 2.6 | 100.0 | 91.9 | 5.8 | 34.8 | 50.9 | 56.4 | 28.0 | 9.4 | 3.4 | 1.2 |
| Exemplary Violet Channels Minimum | 1.1 | 100.0 | 9.5 | 0.8 | 5.7 | 9.0 | 9.3 | 6.3 | 2.7 | 0.9 | 0.3 |
| Exemplary Violet Channels Average | 24.1 | 100.0 | 32.0 | 2.4 | 12.6 | 19.2 | 20.6 | 11.9 | 4.6 | 1.6 | 0.5 |
| Exemplary Violet Channels Maximum | 106.1 | 100.0 | 91.9 | 5.8 | 34.8 | 50.9 | 56.4 | 28.0 | 9.4 | 3.4 | 1.2 |

TABLE 12

| | 320 < λ ≤ 400 | 400 < λ ≤ 500 | 500 < λ ≤ 600 | 600 < λ ≤ 700 | 700 < λ ≤ 780 |
|---|---|---|---|---|---|
| Violet Channel 1 | 548.2 | 100.0 | 96.4 | 68.5 | 6.1 |
| Violet Channel 2 | 104.3 | 100.0 | 34.4 | 24.0 | 2.1 |
| Violet Channel 5 | 92.7 | 100.0 | 32.3 | 23.8 | 2.1 |
| Violet Channel 3 | 22.7 | 100.0 | 22.7 | 14.5 | 1.3 |
| Violet Channel 4 | 6.5 | 100.0 | 59.9 | 35.6 | 2.5 |
| Exemplary Violet Channels Minimum | 6.5 | 100.0 | 22.7 | 14.5 | 1.3 |
| Exemplary Violet Channels Average | 154.9 | 100.0 | 49.2 | 33.3 | 2.8 |
| Exemplary Violet Channels Maximum | 548.2 | 100.0 | 96.4 | 68.5 | 6.1 |

TABLE 13

| | 320 < λ ≤ 340 | 340 < λ ≤ 360 | 360 < λ ≤ 380 | 380 < λ ≤ 400 | 400 < λ ≤ 420 | 420 < λ ≤ 440 | 440 < λ ≤ 460 | 460 < λ ≤ 480 | 480 < λ ≤ 500 | 500 < λ ≤ 520 | 520 < λ ≤ 540 | 540 < λ ≤ 560 |
|---|---|---|---|---|---|---|---|---|---|---|---|---|
| Yellow Channel 1 | 0.0 | 2.0 | 24.3 | 20.9 | 3.9 | 2.6 | 2.8 | 1.3 | 14.6 | 55.3 | 92.6 | 100.0 |
| Yellow Channel 2 | 0.0 | 0.1 | 2.3 | 24.3 | 20.9 | 3.7 | 0.6 | 1.8 | 17.7 | 55.3 | 89.8 | 100.0 |
| Yellow Channel 5 | 0.0 | 0.1 | 2.2 | 23.4 | 20.3 | 5.4 | 3.0 | 0.9 | 11.3 | 48.1 | 87.3 | 100.0 |
| Yellow Channel 3 | 0.0 | 0.0 | 0.4 | 9.2 | 31.4 | 9.4 | 1.4 | 0.6 | 11.3 | 48.2 | 87.5 | 100.0 |
| Yellow Channel 6 | 0.0 | 04 | 0.6 | 9.6 | 32.4 | 9.7 | 1.6 | 0.7 | 11.3 | 47.9 | 87.1 | 100.0 |
| Yellow Channel 4 | 0.0 | 5.0 | 8.0 | 74 | 9.4 | 7.6 | 3.6 | 2.2 | 11.8 | 48.2 | 87.2 | 100.0 |
| Exemplary Yellow Channels Minimum | 0.0 | 0.0 | 0.4 | 74 | 3.9 | 2.6 | 0.6 | 0.6 | 11.3 | 47.9 | 87.1 | 100.0 |
| Exemplary Yellow Channels Average | 0.0 | 1.2 | 6.3 | 15.8 | 19.7 | 6.4 | 2.2 | 1.3 | 13.0 | 50.5 | 88.6 | 100.0 |
| Exemplary Yellow Channels Maximum | 0.0 | 5.0 | 24.3 | 24.3 | 32.4 | 9.7 | 3.6 | 2.2 | 17.7 | 55.3 | 92.6 | 100.0 |

| | 560 < λ ≤ 580 | 580 < λ ≤ 600 | 600 < λ ≤ 620 | 620 < λ ≤ 640 | 640 < λ ≤ 660 | 660 < λ ≤ 680 | 680 < λ ≤ 700 | 700 < λ ≤ 720 | 720 < λ ≤ 740 | 740 < λ ≤ 760 | 760 < λ ≤ 780 | 780 < λ ≤ 800 |
|---|---|---|---|---|---|---|---|---|---|---|---|---|
| Yellow Channel 1 | 91.4 | 77.7 | 61.5 | 44.6 | 30.0 | 19.6 | 11.8 | 7.3 | 4.1 | 2.3 | 1.3 | 0.0 |
| Yellow Channel 2 | 94.2 | 80.8 | 63.6 | 45.9 | 30.7 | 20.0 | 12.1 | 7.5 | 4.2 | 2.4 | 1.5 | 0.0 |
| Yellow Channel 5 | 96.7 | 85.5 | 69.3 | 51.0 | 34.5 | 22.6 | 13.7 | 8.4 | 4.7 | 2.7 | 1.5 | 0.0 |
| Yellow Channel 3 | 95.8 | 83.2 | 66.2 | 47.9 | 32.2 | 21.0 | 12.8 | 7.9 | 4.5 | 2.6 | 1.5 | 0.0 |
| Yellow Channel 6 | 97.4 | 88.6 | 77.3 | 64.1 | 49.6 | 35.4 | 22.7 | 14.0 | 7.9 | 4.4 | 2.4 | 0.0 |
| Yellow Channel 4 | 99.9 | 113.9 | 134.0 | 80.5 | 39.5 | 23.2 | 13.9 | 8.6 | 5.0 | 3.0 | 2.0 | 0.0 |
| Exemplary Yellow Channels Minimum | 91.4 | 77.7 | 61.5 | 44.6 | 30.0 | 19.6 | 11.8 | 7.3 | 4.1 | 2.3 | 1.3 | 0.0 |
| Exemplary Yellow Channels Average | 95.9 | 88.3 | 78.7 | 55.7 | 36.1 | 23.6 | 14.5 | 9.0 | 5.1 | 2.9 | 1.7 | 0.0 |
| Exemplary Yellow Channels Maximum | 99.9 | 113.9 | 134.0 | 80.5 | 49.6 | 35.4 | 22.7 | 14.0 | 7.9 | 4.4 | 2.4 | 0.0 |

TABLE 14

| | 320 < λ ≤ 380 | 380 < λ ≤ 420 | 420 < λ ≤ 460 | 460 < λ ≤ 500 | 500 < λ ≤ 540 | 540 < λ ≤ 580 | 580 < λ ≤ 620 | 620 < λ ≤ 660 | 660 < λ ≤ 700 | 700 < λ ≤ 740 | 740 < λ ≤ 780 |
|---|---|---|---|---|---|---|---|---|---|---|---|
| Yellow Channel 1 | 13.7 | 12.9 | 2.8 | 8.3 | 77.2 | 100.0 | 72.7 | 39.0 | 16.4 | 5.9 | 1.9 |
| Yellow Channel 2 | 1.2 | 23.3 | 2.2 | 10.1 | 74.7 | 100.0 | 74.4 | 39.5 | 16.5 | 6.0 | 2.0 |
| Yellow Channel 5 | 1.2 | 22.2 | 4.3 | 6.2 | 68.8 | 100.0 | 78.7 | 43.5 | 18.4 | 6.7 | 2.2 |
| Yellow Channel 3 | 0.2 | 20.8 | 5.5 | 6.1 | 69.3 | 100.0 | 76.3 | 40.9 | 17.3 | 6.3 | 2.1 |
| Yellow Channel 6 | 0.3 | 21.3 | 5.7 | 6.0 | 68.4 | 100.0 | 84.1 | 57.6 | 29.5 | 11.1 | 3.4 |
| Yellow Channel 4 | 6.5 | 8.3 | 5.6 | 7.0 | 67.7 | 100.0 | 124.1 | 60.1 | 18.6 | 6.8 | 2.5 |
| Exemplary Yellow Channels Minimum | 0.2 | 8.3 | 2.2 | 6.0 | 67.7 | 100.0 | 72.7 | 39.0 | 16.4 | 5.9 | 1.9 |
| Exemplary Yellow Channels Average | 3.9 | 18.1 | 4.4 | 7.3 | 71.0 | 100.0 | 85.0 | 46.7 | 19.4 | 7.1 | 2.3 |
| Exemplary Yellow Channels Maximum | 13.7 | 23.3 | 5.7 | 10.1 | 77 | 100.0 | 124.1 | 60.1 | 29.5 | 11.1 | 3.4 |

TABLE 15

| | 320 < λ ≤ 400 | 400 < λ ≤ 500 | 500 < λ ≤ 600 | 600 < λ ≤ 700 | 700 < λ ≤ 780 |
|---|---|---|---|---|---|
| Yellow Channel 1 | 11.3 | 6.1 | 100.0 | 40.2 | 3.6 |
| Yellow Channel 2 | 6.3 | 10.7 | 100.0 | 41.0 | 3.7 |
| Yellow Channel 5 | 6.2 | 9.8 | 100.0 | 45.8 | 4.2 |
| Yellow Channel 3 | 2.3 | 13.0 | 100.0 | 43.4 | 4.0 |
| Yellow Channel 6 | 2.4 | 13.2 | 100.0 | 59.2 | 6.8 |
| Yellow Channel 4 | 4.5 | 7.7 | 100.0 | 64.8 | 4.1 |
| Exemplary Yellow Channels Minimum | 2.3 | 6.1 | 100.0 | 40.2 | 3.6 |
| Exemplary Yellow Channels Average | 5.5 | 10.1 | 100.0 | 49.1 | 4.4 |
| Exemplary Yellow Channels Maximum | 11.3 | 13.2 | 100.0 | 64.8 | 6.8 |

TABLE 16

Simulated Performance Using 4 Channels from Example 1 (highest-CRI mode)

| ccx | ccy | CCT | duv | Ra | R9 | R13 | R15 | LER | COI |
|---|---|---|---|---|---|---|---|---|---|
| 0.280 | 0.287 | 10090 | −0.41 | 95.7 | 82.9 | 96.7 | 91.0 | 253.3 | 8.9 |
| 0.284 | 0.293 | 9450 | 0.56 | 96.2 | 88.5 | 98.0 | 92.4 | 256.9 | 8.7 |
| 0.287 | 0.286 | 8998 | 0.06 | 96.2 | 85.7 | 97.4 | 92.1 | 257.7 | 8.2 |
| 0.291 | 0.300 | 8503 | −0.24 | 96.3 | 84.2 | 97.1 | 92.0 | 259.0 | 7.6 |
| 0.300 | 0.310 | 7506 | −0.35 | 96.4 | 82.5 | 96.4 | 92.0 | 262.3 | 6.4 |
| 0.306 | 0.317 | 7017 | 0.38 | 97.0 | 86.8 | 97.6 | 93.5 | 266.0 | 6.0 |
| 0.314 | 0.325 | 6480 | 0.36 | 97.3 | 87.4 | 97.7 | 94.0 | 268.5 | 5.2 |
| 0.322 | 0.331 | 5992 | −0.56 | 96.9 | 84.2 | 96.7 | 93.3 | 269.1 | 4.2 |
| 0.332 | 0.342 | 5501 | 0.4 | 97.2 | 86.6 | 96.7 | 94.2 | 271.7 | 3.2 |
| 0.345 | 0.352 | 4991 | 0.31 | 97.0 | 87.0 | 96.7 | 93.8 | 273.3 | 2.0 |
| 0.361 | 0.365 | 4509 | 0.8 | 96.8 | 86.8 | 96.2 | 94.2 | 274.7 | 0.9 |
| 0.381 | 0.378 | 3992 | 0.42 | 96.4 | 85.7 | 95.5 | 94.3 | 274.3 | 1.0 |
| 0.405 | 0.391 | 3509 | 0.1 | 95.8 | 85.9 | 94.8 | 94.4 | 271.9 | 2.7 |
| 0.438 | 0.406 | 2997 | 0.58 | 95.3 | 89.3 | 94.3 | 95.4 | 267.0 | |
| 0.460 | 0.410 | 2701 | −0.07 | 95.3 | 92.6 | 94.3 | 96.3 | 260.7 | |
| 0.487 | 0.415 | 2389 | −0.06 | 95.7 | 98.7 | 95.0 | 98.3 | 252.3 | |
| 0.517 | 0.416 | 2097 | 0.39 | 95.7 | 90.2 | 96.9 | 97.8 | 241.4 | |
| 0.549 | 0.409 | 1808 | 0.25 | 95.7 | 73.3 | 97.7 | 91.4 | 227.4 | |
| 0.571 | 0.400 | 1614 | −0.19 | 91.7 | 58.7 | 92.7 | 85.6 | 214.4 | |

TABLE 17

Simulated Performance Using the Blue, Red, and Long-Blue-Pumped Cyan Channels from Example 1 (High-EML mode)

| ccx | ccy | CCT | duv | Ra | R9 | R13 | R15 | LER | COI | CLA | CS | Rf | Rg |
|---|---|---|---|---|---|---|---|---|---|---|---|---|---|
| 0.280 | 0.288 | 10124 | 0.56 | 95.9 | 86.9 | 97.4 | 91.6 | 254.2 | 9.1 | 2236 | 0.6190 | 89 | 98 |
| 0.287 | 0.296 | 8993 | 0.58 | 95.8 | 83.3 | 96.2 | 91.1 | 256.6 | 8.0 | 2094 | 0.6130 | 90 | 99 |
| 0.295 | 0.305 | 7999 | −0.03 | 95.2 | 77.3 | 94.3 | 89.9 | 258.2 | 6.7 | 1947 | 0.6070 | 90 | 99 |
| 0.306 | 0.317 | 7026 | 0.5 | 94.3 | 76.0 | 93.2 | 89.7 | 261.3 | 5.3 | 1761 | 0.5980 | 89 | 99 |
| 0.314 | 0.325 | 6490 | 0.52 | 93.4 | 74.3 | 92.3 | 89.3 | 262.7 | 4.4 | 1643 | 0.5910 | 89 | 99 |
| 0.322 | 0.332 | 6016 | 0.08 | 92.5 | 71.9 | 91.2 | 88.5 | 263.3 | 3.4 | 1533 | 0.5830 | 89 | 99 |
| 0.332 | 0.342 | 5506 | 0.73 | 91.7 | 73.1 | 90.7 | 88.9 | 265.2 | 2.5 | 1386 | 0.5720 | 88 | 99 |
| 0.345 | 0.352 | 5000 | 0.39 | 90.1 | 71.6 | 89.8 | 87.9 | 265.6 | 1.3 | 1238 | 0.5590 | 86 | 97 |
| 0.361 | 0.364 | 4510 | 0.51 | 88.8 | 70.2 | 88.6 | 87.5 | 265.9 | 0.9 | 1070 | 0.5400 | 83 | 96 |
| 0.381 | 0.378 | 4002 | 0.66 | 87.3 | 69.5 | 87.3 | 87.2 | 265.2 | 2.0 | 877 | 0.5110 | 81 | 94 |
| 0.405 | 0.392 | 3507 | 0.48 | 85.9 | 70.1 | 86.0 | 87.1 | 262.6 | 3.6 | 1498 | 0.5810 | 79 | 93 |
| 0.438 | 0.407 | 2998 | 0.84 | 84.7 | 74.5 | 85.3 | 88.3 | 257.7 | | 1292 | 0.5640 | 75 | 89 |
| 0.460 | 0.411 | 2700 | 0.23 | 84.7 | 79.1 | 85.5 | 89.6 | 252.0 | | 1155 | 0.5500 | 73 | 87 |
| 0.482 | 0.408 | 2399 | −2.21 | 86.2 | 86.4 | 86.3 | 91.7 | 242.7 | | 1009 | 0.5320 | 77 | 90 |
| 0.508 | 0.404 | 2103 | −3.59 | 88.2 | 97.6 | 89.2 | 96.2 | 232.3 | | 831 | 0.5030 | 82 | 94 |
| 0.542 | 0.398 | 1794 | −3.34 | 91.2 | 79.1 | 96.6 | 95.0 | 219.6 | | 590 | 0.4450 | 87 | 99 |
| 0.583 | 0.392 | 1505 | −0.7 | 88.2 | 49.0 | 89.0 | 81.5 | 205.5 | | 290 | 0.3110 | 80 | 103 |

TABLE 17-continued

Simulated Performance Using the Blue, Red, and Long-Blue-Pumped Cyan Channels from Example 1
(High-EML mode)

| ccx | ccy | CCT | duv | GAI | GAI 15 | GAI_BB | circadian power [mW] | circadian flux | CER | CAF | EML | BLH |
|---|---|---|---|---|---|---|---|---|---|---|---|---|
| 0.280 | 0.288 | 10124 | 0.56 | 106.0 | 298.4 | 99.0 | 0.06 | 0.03 | 298.6 | 1.17 | 1.324 | 0.251 |
| 0.287 | 0.296 | 8993 | 0.58 | 105.2 | 293.1 | 99.2 | 0.06 | 0.03 | 287.6 | 1.12 | 1.284 | 0.257 |
| 0.295 | 0.305 | 7999 | -0.03 | 104.5 | 287.8 | 99.8 | 0.07 | 0.03 | 274.8 | 1.06 | 1.240 | 0.264 |
| 0.306 | 0.317 | 7026 | 0.5 | 101.7 | 277.0 | 99.4 | 0.07 | 0.03 | 259.6 | 0.99 | 1.188 | 0.276 |
| 0.314 | 0.325 | 6490 | 0.52 | 99.8 | 269.8 | 99.3 | 0.08 | 0.03 | 249.1 | 0.95 | 1.153 | 0.285 |
| 0.322 | 0.332 | 6016 | 0.08 | 98.0 | 263.0 | 99.6 | 0.08 | 0.03 | 238.4 | 0.90 | 1.117 | 0.293 |
| 0.332 | 0.342 | 5506 | 0.73 | 94.0 | 250.7 | 98.7 | 0.09 | 0.04 | 225.2 | 0.85 | 1.074 | 0.310 |
| 0.345 | 0.352 | 5000 | 0.39 | 90.1 | 238.4 | 98.6 | 0.10 | 0.04 | 209.9 | 0.79 | 1.024 | 0.330 |
| 0.361 | 0.364 | 4510 | 0.51 | 84.2 | 221.8 | 97.7 | 0.11 | 0.04 | 192.6 | 0.72 | 0.967 | 0.320 |
| 0.381 | 0.378 | 4002 | 0.66 | 76.0 | 199.7 | 96.1 | 0.09 | 0.03 | 171.5 | 0.65 | 0.897 | 0.245 |
| 0.405 | 0.392 | 3507 | 0.48 | 66.0 | 174.1 | 94.6 | 0.08 | 0.03 | 148.0 | 0.56 | 0.815 | 0.178 |
| 0.438 | 0.407 | 2998 | 0.84 | 51.4 | 138.2 | 90.2 | 0.06 | 0.02 | 119.4 | 0.46 | 0.711 | 0.115 |
| 0.460 | 0.411 | 2700 | 0.23 | 43.3 | 118.5 | 90.1 | 0.05 | 0.01 | 101.7 | 0.40 | 0.640 | 0.085 |
| 0.482 | 0.408 | 2399 | -2.21 | 39.4 | 109.3 | 102.3 | 0.04 | 0.01 | 85.0 | 0.35 | 0.560 | 0.066 |
| 0.508 | 0.404 | 2103 | -3.59 | 33.6 | 95.4 | 119.4 | 0.03 | 0.01 | 66.3 | 0.28 | 0.462 | 0.048 |
| 0.542 | 0.398 | 1794 | -3.34 | 24.2 | 71.4 | 142.3 | 0.02 | 0.00 | 43.4 | 0.20 | 0.330 | 0.030 |
| 0.583 | 0.392 | 1505 | -0.7 | | | | | | | | | |

TABLE 18

Simulated Performance Using the Blue, Red, and Short-Blue-Pumped Cyan Channels from Example 1
(High-CRI mode)

| ccx | ccy | CCT | duv | GAI | GAI 15 | GAI_BB | circadian power [mW] | circadian flux | CER | CAF | EML | BLH |
|---|---|---|---|---|---|---|---|---|---|---|---|---|
| 0.2795 | 0.2878 | 10154.39 | 0.45 | 105.7 | 299.6 | 99.3 | 0.1 | 0.0 | 297.7 | 1.2 | 1.287392 | 0.242465 |
| 0.2835 | 0.2927 | 9463.51 | 0.57 | 105.1 | 296.8 | 99.5 | 0.1 | 0.0 | 291.0 | 1.1 | 1.255256 | 0.243167 |
| 0.2868 | 0.2963 | 8979.72 | 0.48 | 104.8 | 294.9 | 99.8 | 0.1 | 0.0 | 285.6 | 1.1 | 1.230498 | 0.243703 |
| 0.2904 | 0.3008 | 8501.8 | 0.69 | 104.0 | 292.0 | 99.1 | 0.1 | 0.0 | 279.7 | 1.1 | 1.202935 | 0.244396 |
| 0.3006 | 0.31 | 7485.85 | -0.27 | 103.4 | 287.3 | 101.3 | 0.1 | 0.0 | 263.9 | 1.0 | 1.138359 | 0.245866 |
| 0.3064 | 0.3159 | 7006.5 | -0.29 | 102.4 | 283.1 | 101.7 | 0.1 | 0.0 | 255.1 | 1.0 | 1.101543 | 0.246923 |
| 0.3137 | 0.3232 | 6489.8 | -0.31 | 100.8 | 277.6 | 102.2 | 0.1 | 0.0 | 244.2 | 0.9 | 1.057241 | 0.24832 |
| 0.322 | 0.3308 | 6006.26 | -0.45 | 99.1 | 271.4 | 102.9 | 0.1 | 0.0 | 232.5 | 0.9 | 1.01129 | 0.2499 |
| 0.3324 | 0.3414 | 5501.95 | 0.21 | 95.8 | 261.3 | 102.9 | 0.1 | 0.0 | 218.1 | 0.8 | 0.954284 | 0.252421 |
| 0.3452 | 0.3514 | 4993.84 | -0.12 | 92.5 | 251.2 | 104.0 | 0.1 | 0.0 | 201.4 | 0.7 | 0.893796 | 0.25518 |
| 0.361 | 0.3635 | 4492.22 | -0.07 | 87.6 | 237.1 | 104.7 | 0.1 | 0.0 | 182.1 | 0.7 | 0.82457 | 0.259194 |
| 0.3806 | 0.3773 | 3999.36 | 0.24 | 80.7 | 218.2 | 105.0 | 0.1 | 0.0 | 159.8 | 0.6 | 0.746244 | 0.265169 |
| 0.4044 | 0.3896 | 3509.79 | -0.28 | 72.6 | 196.8 | 106.8 | 0.1 | 0.0 | 135.5 | 0.5 | 0.663096 | 0.198253 |
| 0.4373 | 0.4046 | 2997.87 | 0.16 | 59.3 | 162.9 | 106.3 | 0.1 | 0.0 | 105.4 | 0.4 | 0.558039 | 0.127844 |
| 0.4581 | 0.4081 | 2705 | -0.79 | 52.4 | 145.2 | 110.1 | 0.0 | 0.0 | 89.0 | 0.3 | 0.498973 | 0.097229 |
| 0.4858 | 0.4142 | 2400.92 | -0.13 | 40.5 | 114.8 | 107.3 | 0.0 | 0.0 | 68.7 | 0.3 | 0.42121 | 0.064438 |
| 0.5162 | 0.4156 | 2104.13 | 0.3 | 28.4 | 82.4 | 102.9 | 0.0 | 0.0 | 49.3 | 0.2 | 0.339504 | 0.039198 |
| 0.5487 | 0.4058 | 1789.82 | -0.69 | 19.6 | 57.8 | 116.1 | 0.0 | 0.0 | 32.4 | 0.1 | 0.252508 | 0.023439 |
| 0.5742 | 0.399 | 1593.58 | 0.05 | | | | | | | | | |

| ccx | ccy | CCT | duv | Ra | R9 | R13 | R15 | LER | COI | CLA | CS | Rf | Rg |
|---|---|---|---|---|---|---|---|---|---|---|---|---|---|
| 0.2795 | 0.2878 | 10154.39 | 0.45 | 95.77 | 95.05 | 99.27 | 93.65 | 257.2 | 9.6 | 2199 | 0.617 | 89 | 98 |
| 0.2835 | 0.2927 | 9463.51 | 0.57 | 95.91 | 95.56 | 99.15 | 94.08 | 259.63 | 9.12 | 2104 | 0.614 | 89 | 99 |
| 0.2868 | 0.2963 | 8979.72 | 0.48 | 96.05 | 94.99 | 99.24 | 94.34 | 261.19 | 8.69 | 2033 | 0.6110 | 89 | 100 |
| 0.2904 | 0.3008 | 8501.8 | 0.69 | 96.11 | 95.94 | 99.02 | 94.76 | 263.35 | 8.28 | 1952 | 0.6070 | 90 | 100 |
| 0.3006 | 0.31 | 7485.85 | -0.27 | 96.32 | 91.29 | 99.44 | 94.86 | 266.03 | 6.95 | 1774 | 0.5980 | 90 | 101 |
| 0.3064 | 0.3159 | 7006.5 | -0.29 | 96.33 | 91.45 | 99.45 | 95.26 | 268.18 | 6.3 | 1670 | 0.5920 | 91 | 101 |
| 0.3137 | 0.3232 | 6489.8 | -0.31 | 96.34 | 91.81 | 99.44 | 95.76 | 270.59 | 5.51 | 1546 | 0.5840 | 91 | 102 |
| 0.322 | 0.3308 | 6006.26 | -0.45 | 96.33 | 91.92 | 99.38 | 96.16 | 272.63 | 4.65 | 1420 | 0.5750 | 92 | 102 |
| 0.3324 | 0.3414 | 5501.95 | 0.21 | 96.39 | 95.57 | 99.13 | 97.53 | 276.11 | 3.73 | 1260 | 0.5610 | 92 | 102 |
| 0.3452 | 0.3514 | 4993.84 | -0.12 | 96.8 | 95.19 | 98.84 | 96.57 | 277.51 | 2.51 | 1100 | 0.5440 | 92 | 102 |
| 0.361 | 0.3635 | 4492.22 | -0.07 | 96.83 | 94.58 | 99.18 | 97.25 | 278.89 | 1.16 | 919 | 0.5180 | 93 | 102 |
| 0.3806 | 0.3773 | 3999.36 | 0.24 | 96.85 | 94.73 | 99.44 | 97.96 | 279.47 | 0.46 | 719 | 0.4790 | 94 | 102 |
| 0.4044 | 0.3896 | 3509.79 | -0.28 | 96.77 | 93.51 | 99.01 | 97.87 | 276.46 | 2.34 | 522 | 0.4230 | 94 | 103 |
| 0.4373 | 0.4046 | 2997.87 | 0.16 | 96.89 | 96.02 | 98.46 | 98.58 | 271.21 | | 1020 | 0.5330 | 95 | 103 |
| 0.4581 | 0.4081 | 2705 | -0.79 | 96.85 | 97.34 | 97.5 | 98.4 | 263.76 | | 906 | 0.5160 | 95 | 104 |
| 0.4858 | 0.4142 | 2400.92 | -0.13 | 97.27 | 96.43 | 97.97 | 99.32 | 255.71 | | 756 | 0.4880 | 95 | 104 |
| 0.5162 | 0.4156 | 2104.13 | 0.3 | 97.2 | 87.34 | 99.31 | 96.46 | 244.06 | | 601 | 0.4490 | 93 | 102 |
| 0.5487 | 0.4058 | 1789.82 | -0.69 | 95.09 | 72.11 | 97.24 | 91.09 | 225.81 | | 444 | 0.3930 | 87 | 104 |
| 0.5742 | 0.399 | 1593.58 | 0.05 | 91.03 | 56.48 | 91.54 | 84.56 | 213.34 | | 316 | 0.3270 | 83 | 101 |

TABLE 19

Comparison of EML Between 3-Channel Operation Modes

| Red, Blue, and Short-Blue-Pumped Cyan (High-CRI mode) | | Red, Blue, and Long-Blue-Pumped Cyan (High-EML mode) | | Change in EML between High-CRI and High-EML modes at same approximate CCT |
|---|---|---|---|---|
| CCT | EML | CCT | EML | |
| 10154.39 | 1.287392 | 10124.15 | 1.323599 | 2.8% |
| 9463.51 | 1.255256 | | | |
| 8979.72 | 1.230498 | 8993.02 | 1.284446 | 4.4% |
| 8501.8 | 1.202935 | | | |
| | | 7998.71 | 1.240274 | |
| 7485.85 | 1.138359 | | | |
| 7006.5 | 1.101543 | 7025.83 | 1.188225 | 7.9% |
| 6489.8 | 1.057241 | 6490.37 | 1.153187 | 9.1% |
| 6006.26 | 1.01129 | 6015.98 | 1.117412 | 10.5% |
| 5501.95 | 0.954284 | 5505.85 | 1.074033 | 12.5% |
| 4993.84 | 0.893796 | 4999.87 | 1.023649 | 14.5% |
| 4492.22 | 0.82457 | 4509.8 | 0.966693 | 17.2% |
| 3999.36 | 0.746244 | 4001.99 | 0.896774 | 20.2% |
| 3509.79 | 0.663096 | 3507.13 | 0.815304 | 23.0% |
| 2997.87 | 0.558039 | 2998.02 | 0.711335 | 27.5% |
| 2705 | 0.498973 | 2700.47 | 0.639906 | 28.2% |
| 2400.92 | 0.42121 | 2398.75 | 0.5596 | 32.9% |
| 2104.13 | 0.339504 | 2102.54 | 0.461974 | 36.1% |
| 1789.82 | 0.252508 | 1794.12 | 0.330184 | 30.8% |
| 1593.58 | | 1505.05 | | |

TABLE 20

Simulated Performance Using 4 Channels from Example 1
(Highest-CRI mode)
with Relative Signal Strengths Calculated for 100 Lumens Flux Output from the Device

| Blue | Red | Short-Blue-Pumped Cyan | Long-Blue-Pumped Cyan | CCT | duv | flux total | Ra | R9 | EML |
|---|---|---|---|---|---|---|---|---|---|
| 0.72 | 0.15 | 0.04 | 0.08 | 9997 | 0.99 | 100.0073 | 95.1 | 96.1 | 1.306 |
| 0.70 | 0.15 | 0.06 | 0.08 | 9501 | 0.99 | 100.0074 | 95.3 | 96.3 | 1.283 |
| 0.67 | 0.16 | 0.09 | 0.08 | 9002 | 0.99 | 100.0075 | 95.5 | 96.3 | 1.257 |
| 0.65 | 0.16 | 0.11 | 0.08 | 8501 | 0.99 | 100.0075 | 95.7 | 96.4 | 1.229 |
| 0.58 | 0.17 | 0.16 | 0.08 | 7499 | 0.99 | 100.0077 | 96.2 | 96.4 | 1.163 |
| 0.55 | 0.18 | 0.19 | 0.09 | 6999 | 0.99 | 100.0079 | 96.5 | 96.0 | 1.125 |
| 0.51 | 0.19 | 0.22 | 0.09 | 6499 | 0.99 | 100.008 | 96.8 | 95.7 | 1.082 |
| 0.46 | 0.20 | 0.25 | 0.09 | 5998 | 0.99 | 100.0082 | 97.1 | 94.8 | 1.035 |
| 0.41 | 0.22 | 0.27 | 0.10 | 5498 | 0.99 | 100.0085 | 97.5 | 93.7 | 0.983 |
| 0.35 | 0.24 | 0.30 | 0.11 | 4999 | 0.99 | 100.0089 | 97.7 | 92.3 | 0.925 |
| 0.30 | 0.26 | 0.35 | 0.09 | 4499 | 0.99 | 100.0091 | 98.0 | 92.7 | 0.848 |
| 0.24 | 0.29 | 0.38 | 0.08 | 3999 | 0.99 | 100.0096 | 97.9 | 92.2 | 0.769 |
| 0.18 | 0.34 | 0.42 | 0.07 | 3499 | 0.99 | 100.0102 | 97.7 | 92.9 | 0.675 |
| 0.11 | 0.41 | 0.44 | 0.04 | 2999 | 0.99 | 100.0111 | 97.4 | 95.6 | 0.567 |
| 0.08 | 0.46 | 0.43 | 0.03 | 2699 | 0.99 | 100.0118 | 97.5 | 98.8 | 0.495 |
| 0.04 | 0.54 | 0.40 | 0.02 | 2399 | 1.00 | 100.0127 | 97.7 | 95.7 | 0.419 |
| 0.02 | 0.64 | 0.34 | 0.01 | 2100 | 1.00 | 100.0141 | 97.4 | 86.6 | 0.337 |
| 0.00 | 0.78 | 0.19 | 0.03 | 1800 | 0.15 | 100.0161 | 95.6 | 73.0 | 0.261 |

TABLE 21

Simulated Performance Using the Blue, Red, and
Long-Blue-Pumped Cyan Channels from Example 1
(High-EML mode)
with Relative Signal Strengths Calculated for 100 Lumens Flux Output from the Device

| Blue | Red | Long-Blue-Pumped Cyan | CCT | duv | flux total | Ra | R9 | EML |
|---|---|---|---|---|---|---|---|---|
| 0.71 | 0.16 | 0.13 | 10468 | 0.77 | 99.24986 | 94.7 | 97.3 | 1.300 |
| 0.66 | 0.17 | 0.17 | 9001 | 0.99 | 100.008 | 94.9 | 90.1 | 1.285 |
| 0.59 | 0.18 | 0.23 | 7998 | 0.99 | 100.0085 | 94.5 | 86.7 | 1.242 |
| 0.51 | 0.21 | 0.29 | 6999 | 0.99 | 100.0091 | 93.8 | 82.6 | 1.187 |
| 0.46 | 0.22 | 0.32 | 6498 | 0.99 | 100.0095 | 93.1 | 80.4 | 1.154 |
| 0.41 | 0.24 | 0.35 | 5998 | 0.99 | 100.0099 | 92.3 | 78.0 | 1.116 |
| 0.36 | 0.26 | 0.39 | 5498 | 0.99 | 100.0104 | 91.3 | 75.6 | 1.073 |
| 0.29 | 0.28 | 0.43 | 4999 | 0.99 | 100.0109 | 90.2 | 73.3 | 1.023 |
| 0.23 | 0.31 | 0.46 | 4499 | 0.99 | 100.0115 | 88.8 | 71.4 | 0.965 |
| 0.18 | 0.35 | 0.47 | 3999 | −0.35 | 100.0122 | 87.3 | 68.2 | 0.897 |
| 0.11 | 0.41 | 0.48 | 3499 | −1.01 | 100.013 | 86.0 | 68.6 | 0.816 |
| 0.05 | 0.48 | 0.47 | 2999 | −1.01 | 100.014 | 85.1 | 73.3 | 0.715 |
| 0.01 | 0.53 | 0.45 | 2700 | −1.01 | 100.0146 | 85.1 | 78.7 | 0.642 |

TABLE 21-continued

Simulated Performance Using the Blue, Red, and
Long-Blue-Pumped Cyan Channels from Example 1
(High-EML mode)
with Relative Signal Strengths Calculated for 100 Lumens Flux Output from the Device

| Blue | Red | Long-Blue-Pumped Cyan | CCT | duv | flux total | Ra | R9 | EML |
|---|---|---|---|---|---|---|---|---|
| 0.02 | 0.61 | 0.37 | 2400 | −4.00 | 100.0153 | 86.5 | 85.8 | 0.564 |
| 0.01 | 0.69 | 0.30 | 2100 | −4.00 | 100.0161 | 88.2 | 97.6 | 0.462 |
| 0.00 | 0.81 | 0.19 | 1800 | −3.28 | 100.0172 | 91.2 | 79.3 | 0.333 |

TABLE 22

Simulated Performance Using the Blue, Red, and
Short-Blue-Pumped Cyan Channels from Example 1
(High-CRI mode)
with Relative Signal Strengths Calculated for
100 Lumens Flux Output from the Device

| Blue | Red | Short-Blue-Pumped Cyan | CCT | duv | flux total | Ra | R9 | EML |
|---|---|---|---|---|---|---|---|---|
| 0.75 | 0.14 | 0.11 | 10144 | 0.47 | 100 | 94.9 | 98.0 | 1.287 |
| 0.72 | 0.14 | 0.14 | 9458 | 0.59 | 100 | 95.0 | 98.0 | 1.255 |
| 0.69 | 0.15 | 0.16 | 8976 | 0.50 | 100 | 95.2 | 98.2 | 1.230 |
| 0.66 | 0.15 | 0.19 | 8498 | 0.70 | 100 | 95.2 | 97.8 | 1.203 |
| 0.61 | 0.17 | 0.23 | 7481 | −0.26 | 100 | 96.1 | 96.5 | 1.138 |
| 0.57 | 0.17 | 0.26 | 7003 | −0.28 | 100 | 96.3 | 96.4 | 1.101 |
| 0.53 | 0.18 | 0.29 | 6487 | −0.29 | 100 | 96.5 | 96.2 | 1.057 |
| 0.49 | 0.20 | 0.32 | 5989 | −0.54 | 100 | 96.8 | 94.9 | 1.010 |
| 0.43 | 0.21 | 0.36 | 5499 | 0.23 | 100 | 96.7 | 97.3 | 0.954 |
| 0.38 | 0.23 | 0.39 | 4993 | −0.12 | 100 | 96.8 | 95.4 | 0.894 |
| 0.32 | 0.25 | 0.42 | 4491 | −0.09 | 100 | 96.9 | 94.8 | 0.825 |
| 0.26 | 0.29 | 0.45 | 3999 | 0.25 | 100 | 96.9 | 95.0 | 0.746 |
| 0.20 | 0.34 | 0.46 | 3509 | −0.29 | 100 | 96.9 | 93.8 | 0.663 |
| 0.13 | 0.40 | 0.47 | 2998 | 0.18 | 100 | 97.0 | 96.3 | 0.558 |
| 0.10 | 0.46 | 0.44 | 2705 | −0.79 | 100 | 96.9 | 97.6 | 0.499 |
| 0.06 | 0.54 | 0.40 | 2401 | −0.16 | 100 | 97.3 | 96.2 | 0.421 |
| 0.02 | 0.63 | 0.34 | 2104 | 0.32 | 100 | 97.2 | 87.1 | 0.340 |
| 0.01 | 0.78 | 0.21 | 1790 | −0.70 | 100 | 95.0 | 71.9 | 0.253 |

TABLE 23

| Violet Channel 1 | Blue Channel 1 | Red Channel 1 | Yellow Channel 1 | x | y | CCT | duv | Ra | R9 | R13 | R15 | LER | COI | GAI |
|---|---|---|---|---|---|---|---|---|---|---|---|---|---|---|
| 1 | 0.4863 | 0.0275 | 0.0145 | 0.2808 | 0.2878 | 10006.64 | −0.32 | 88.93 | 56.99 | 89.55 | 90.02 | 170.08 | 13.12 | 101.1 |
| 1 | 0.4798 | 0.0307 | 0.0275 | 0.2866 | 0.2961 | 9012.09 | 0.49 | 88.11 | 52.29 | 88.39 | 88.34 | 175.4 | 12.56 | 99.5 |
| 1 | 0.4410 | 0.0339 | 0.0404 | 0.2947 | 0.3059 | 8001.65 | 0.89 | 87.29 | 48.58 | 87.25 | 86.96 | 178.35 | 11.77 | 97.8 |
| 1 | 0.3667 | 0.0371 | 0.0501 | 0.3062 | 0.3176 | 6993.76 | 0.67 | 86.47 | 46.21 | 86.2 | 85.94 | 177.6 | 10.66 | 95.9 |
| 1 | 0.3247 | 0.0404 | 0.0533 | 0.3136 | 0.3239 | 6498.08 | 0.15 | 86.23 | 46.62 | 85.94 | 85.88 | 176.16 | 9.89 | 94.9 |
| 1 | 0.2892 | 0.0468 | 0.0565 | 0.3220 | 0.3305 | 6007.62 | −0.62 | 86.21 | 48.62 | 86.01 | 86.26 | 175.26 | 8.94 | 94.0 |
| 1 | 0.2375 | 0.0468 | 0.0630 | 0.3324 | 0.3414 | 5501.83 | 0.25 | 84.55 | 41.19 | 83.93 | 83.37 | 174.38 | 8.24 | 90.5 |
| 1 | 0.2118 | 0.0630 | 0.0727 | 0.3448 | 0.3513 | 5008.33 | −0.03 | 84.47 | 43.2 | 83.93 | 83.42 | 178.14 | 6.84 | 88.0 |
| 1 | 0.1664 | 0.0727 | 0.0759 | 0.3608 | 0.3632 | 4497.73 | −0.17 | 84.23 | 45.18 | 83.67 | 83.11 | 176.16 | 5.48 | 83.7 |
| 1 | 0.0953 | 0.0727 | 0.0727 | 0.3808 | 0.3780 | 3999.57 | 0.49 | 82.44 | 40.62 | 81.71 | 80.76 | 168.6 | 4.28 | 76.8 |
| 1 | 0.0307 | 0.0727 | 0.0598 | 0.4055 | 0.3901 | 3489.48 | −0.33 | 80.86 | 39.01 | 80.4 | 79.43 | 154.51 | 3.21 | 69.4 |

| CCT | GAI 15 | GAI_BB | Circadian power [mW] | Circadian flux | CER | CAF | EML | CLA | CS | Rf | Rg | BLH | energy in 440-490/total |
|---|---|---|---|---|---|---|---|---|---|---|---|---|---|
| 10006.64 | 289.2 | 96.1 | 0.046 | 0.014 | 234.3 | 1.128 | 1.2035 | 2140 | 0.6150 | 85 | 97 | 0.1520 | 24.31% |
| 9012.09 | 283.7 | 96.0 | 0.047 | 0.014 | 227.9 | 1.069 | 1.1519 | 1987 | 0.6090 | 85 | 98 | 0.1502 | 23.42% |
| 8001.65 | 277.5 | 96.3 | 0.046 | 0.013 | 216.7 | 0.997 | 1.0863 | 1805 | 0.6000 | 84 | 97 | 0.1408 | 21.93% |
| 6993.76 | 270.4 | 97.2 | 0.042 | 0.011 | 199.5 | 0.913 | 1.0044 | 1592 | 0.5870 | 84 | 98 | 0.1231 | 19.70% |
| 6498.08 | 266.6 | 98.2 | 0.041 | 0.010 | 189.1 | 0.866 | 0.9583 | 1477 | 0.5790 | 84 | 99 | 0.1132 | 18.38% |
| 6007.62 | 262.6 | 99.6 | 0.039 | 0.009 | 178.5 | 0.818 | 0.9105 | 1358 | 0.5700 | 83 | 100 | 0.1049 | 17.06% |
| 5501.83 | 252.5 | 99.5 | 0.037 | 0.008 | 164.5 | 0.751 | 0.8453 | 1189 | 0.5540 | 82 | 100 | 0.0927 | 15.23% |
| 5008.33 | 244.2 | 100.9 | 0.037 | 0.008 | 153.2 | 0.688 | 0.7870 | 1034 | 0.5350 | 82 | 100 | 0.0883 | 13.83% |
| 4497.73 | 231.7 | 102.3 | 0.034 | 0.007 | 136.0 | 0.614 | 0.7117 | 850 | 0.5060 | 82 | 100 | 0.0762 | 11.69% |
| 3999.57 | 212.4 | 102.3 | 0.031 | 0.005 | 116.1 | 0.525 | 0.6178 | 634 | 0.4580 | 79 | 101 | 0.0604 | 8.87% |
| 3489.48 | 191.0 | 104.4 | 0.026 | 0.004 | 91.3 | 0.436 | 0.5147 | 426 | 0.3850 | 74 | 102 | 0.0444 | 5.89% |

TABLE 24

| Violet Channel 1 | Red Channel 1 | Yellow Channel 1 | x | y | CCT | duv | Ra | R9 | R13 | R15 | LER | COI | GAI |
|---|---|---|---|---|---|---|---|---|---|---|---|---|---|
| 1 | 0.01 | 0.0307 | 0.3798 | 0.3755 | 4006.89 | −0.39 | 72.72 | −1.48 | 70.29 | 67.32 | 219.13 | 7.63 | 75.0 |
| 1 | 0.0404 | 0.0436 | 0.4048 | 0.3901 | 3506.88 | −0.13 | 76.74 | 22.68 | 75.58 | 73.81 | 235.43 | 4.36 | 68.6 |
| 1 | 0.1115 | 0.0662 | 0.4373 | 0.4055 | 3004.86 | 0.51 | 81.38 | 44.89 | 81.5 | 80.41 | 258.17 | 3.08 | 57.6 |
| 1 | 0.1955 | 0.0824 | 0.4602 | 0.4109 | 2697.63 | 0.09 | 84.56 | 56.59 | 85.48 | 84.52 | 271.67 | 4.98 | 50.0 |
| 1 | 0.3603 | 0.1082 | 0.4863 | 0.415 | 2400.85 | 0.11 | 87.56 | 64.45 | 88.99 | 87.5 | 286.8 | 7.75 | 40.4 |
| 1 | 0.7124 | 0.1373 | 0.5152 | 0.4136 | 2100.63 | −0.32 | 90.1 | 67.4 | 91.71 | 89.07 | 297.99 | 11.39 | 30.5 |
| 0.4378 | 1 | 0.105 | 0.5503 | 0.4097 | 1800.92 | 0.49 | 90.94 | 62.65 | 92.01 | 87.32 | 210.12 | 16 | 17.4 |
| 0.1276 | 1 | 0.0468 | 0.5739 | 0.4011 | 1605.63 | 0.52 | 89.19 | 53.54 | 89.58 | 83.82 | 209.15 | 19.91 | |
| 0 | 1 | 0.01 | 0.5904 | 0.3926 | 1472.77 | 0.48 | 86.22 | 43.73 | 85.8 | 79 | 204.65 | 23.1 | |

| CCT | GAI 15 | GAI_BB | Circadian power [mW] | Circadian flux | CER | CAF | EML | CLA | CS | Rf | Rg | BLH | energy in 440-490/ total |
|---|---|---|---|---|---|---|---|---|---|---|---|---|---|
| 4006.89 | 209.1 | 100.7 | 0.0219 | 0.0026 | 91.2 | 0.510 | 0.5409 | 614 | 0.4520 | 66 | 99 | 0.035624 | 5.32% |
| 3506.88 | 188.7 | 102.6 | 0.0232 | 0.0028 | 83.1 | 0.429 | 0.4850 | 414 | 0.3790 | 68 | 101 | 0.036204 | 4.64% |
| 3004.86 | 157.1 | 102.3 | 0.0255 | 0.0031 | 71.3 | 0.338 | 0.4190 | 788 | 0.4940 | 71 | 103 | 0.037333 | 3.72% |
| 2697.63 | 136.1 | 103.7 | 0.0276 | 0.0034 | 62.5 | 0.287 | 0.3762 | 699 | 0.4750 | 72 | 105 | 0.038411 | 3.10% |
| 2400.85 | 110.2 | 103.1 | 0.0312 | 0.0038 | 52.1 | 0.233 | 0.3289 | 601 | 0.4480 | 74 | 105 | 0.040364 | 2.42% |
| 2100.63 | 83.9 | 105.3 | 0.0370 | 0.0045 | 40.7 | 0.181 | 0.2769 | 499 | 0.4140 | 74 | 106 | 0.04391 | 1.75% |
| 1800.92 | 47.8 | 94.0 | 0.0265 | 0.0032 | 26.8 | 0.121 | 0.2127 | 374 | 0.3600 | 77 | 103 | 0.025696 | 0.98% |
| 1605.63 | | | | | | | | 290 | 0.3110 | 77 | 100 | | 0.61% |
| 1472.77 | | | | | | | | 228 | 0.2660 | 77 | 96 | | 0.41% |

TABLE 25

| Violet Channel 2 | Blue Channel 1 | Red Channel 1 | Yellow Channel 2 | x | y | CCT | duv | Ra | R9 | R13 | R15 | LER | COI |
|---|---|---|---|---|---|---|---|---|---|---|---|---|---|
| 1 | 0.5897 | 0.0145 | 0.0533 | 0.2805 | 0.2877 | 10048.55 | −0.24 | 84.74 | 35.51 | 83.78 | 83.54 | 194.76 | 14.75 |
| 1 | 0.5669 | 0.021 | 0.0662 | 0.2872 | 0.2947 | 9004.53 | −0.61 | 84.63 | 36.9 | 83.72 | 83.62 | 198.26 | 13.89 |
| 1 | 0.5089 | 0.021 | 0.0824 | 0.2953 | 0.3043 | 8002.62 | −0.27 | 83.38 | 21.18 | 82.17 | 81.47 | 201.36 | 13.28 |
| 1 | 0.4927 | 0.0339 | 0.1082 | 0.3064 | 0.3167 | 6994.18 | 0.09 | 82.8 | 29.98 | 81.54 | 80.47 | 209.16 | 11.99 |
| 1 | 0.4637 | 0.0404 | 0.1212 | 0.3134 | 0.3249 | 6502.6 | 0.25 | 82.25 | 28.43 | 80.9 | 79.58 | 212.19 | 11.3 |
| 1 | 0.4249 | 0.0501 | 0.1341 | 0.3221 | 0.3321 | 5996.32 | 0.2 | 81.71 | 27.74 | 80.34 | 78.87 | 214.8 | 10.4 |
| 1 | 0.3893 | 0.063 | 0.1535 | 0.3326 | 0.3426 | 5491.51 | 0.71 | 80.84 | 25.11 | 79.33 | 77.43 | 219.33 | 9.4 |
| 1 | 0.3538 | 0.0889 | 0.1696 | 0.3453 | 0.3522 | 4995.38 | 0.23 | 81.06 | 29.17 | 79.63 | 77.95 | 22.48 | 7.97 |
| 1 | 0.315 | 0.1244 | 0.1955 | 0.3612 | 0.3649 | 4495.14 | 0.53 | 80.98 | 32.3 | 79.74 | 78.15 | 227.7 | 6.4 |
| 1 | 0.2342 | 0.1598 | 0.2084 | 0.3808 | 0.3783 | 4001.5 | 0.64 | 80.59 | 34.94 | 79.6 | 78.1 | 228.56 | 4.76 |
| 1 | 0.1599 | 0.2278 | 0.2213 | 0.406 | 0.3916 | 3492.72 | 0.26 | 81.11 | 41.82 | 80.74 | 79.55 | 228.66 | 2.93 |

| CCT | GAI | GAI 15 | GAI_BB | Circadian power [mW] | Circadian flux | CER | CAF | EML | CLA | CS | Rf | Rg | BLH | energy in 440-490/ total |
|---|---|---|---|---|---|---|---|---|---|---|---|---|---|---|
| 10048.55 | 99.4 | 286.8 | 95.3 | 0.06561 | 0.01832 | 227.6 | 1.15226 | 1.16343 | 2214 | 0.6180 | 82 | 98 | 0.2269 | 20.57% |
| 9004.53 | 99.0 | 284.0 | 96.1 | 0.06523 | 0.01785 | 220.1 | 1.09461 | 1.11189 | 2067 | 0.6120 | 82 | 98 | 0.2212 | 19.63% |
| 8002.62 | 97.2 | 277.5 | 96.2 | 0.06317 | 0.01659 | 209.1 | 1.02377 | 1.04507 | 1888 | 0.6040 | 80 | 98 | 0.2072 | 18.14% |
| 6994.18 | 95.1 | 269.6 | 96.9 | 0.06389 | 0.01635 | 198.6 | 0.93634 | 0.97088 | 1666 | 0.5920 | 80 | 98 | 0.2030 | 16.89% |
| 6502.6 | 93.6 | 264.4 | 97.3 | 0.06322 | 0.01576 | 190.8 | 0.88706 | 0.92605 | 1542 | 0.5840 | 79 | 98 | 0.1961 | 15.91% |
| 5996.32 | 91.9 | 258.5 | 98.0 | 0.06209 | 0.01496 | 181.2 | 0.83216 | 0.87477 | 1404 | 0.5740 | 78 | 99 | 0.1871 | 14.71% |
| 5491.51 | 89.1 | 249.5 | 98.3 | 0.06152 | 0.01428 | 170.6 | 0.76736 | 0.81655 | 1242 | 0.5590 | 77 | 99 | 0.1788 | 13.41% |
| 4995.38 | 86.7 | 241.3 | 99.8 | 0.06092 | 0.01360 | 158.8 | 0.70408 | 0.75818 | 1085 | 0.5420 | 77 | 99 | 0.1707 | 12.05% |
| 4495.14 | 82.3 | 227.8 | 100.6 | 0.06079 | 0.01292 | 144.7 | 0.62726 | 0.68922 | 895 | 0.5140 | 77 | 99 | 0.1621 | 10.45% |
| 4001.5 | 76.5 | 210.3 | 101.2 | 0.05795 | 0.01128 | 126.3 | 0.54556 | 0.60853 | 697 | 0.4740 | 75 | 100 | 0.1442 | 8.27% |
| 3492.72 | 69.0 | 187.7 | 102.4 | 0.05580 | 0.00982 | 106.1 | 0.45814 | 0.52239 | 487 | 0.4100 | 72 | 101 | 0.1282 | 6.06% |

TABLE 26

| Violet Channel 2 | Red Channel 1 | Yellow Channel 2 | x | y | CCT | duv | Ra | R9 | R13 | R15 | LER | COI |
|---|---|---|---|---|---|---|---|---|---|---|---|---|
| 1 | 0.2052 | 0.1664 | 0.4371 | 0.4039 | 2996.5 | −0.07 | 77.97 | 37.32 | 78.11 | 76.47 | 209.43 | 3.24 |
| 1 | 0.3538 | 0.1986 | 0.4592 | 0.4097 | 2702.82 | −0.25 | 81.29 | 49.05 | 82.14 | 80.83 | 217.13 | 4.6 |
| 1 | 0.6704 | 0.2536 | 0.4861 | 0.4144 | 2399.16 | −0.08 | 84.77 | 58.13 | 86.1 | 84.59 | 224.1 | 7.33 |
| 0.6898 | 1 | 0.2375 | 0.5162 | 0.4152 | 2101.05 | 0.18 | 87.89 | 62.54 | 89.28 | 86.86 | 226.74 | 10.95 |

TABLE 26-continued

| | | | | | | | | | | | | | |
|---|---|---|---|---|---|---|---|---|---|---|---|---|---|
| 0.2633 | 1 | 0.1147 | 0.5494 | 0.4075 | 1795.06 | −0.17 | 89.46 | 59.71 | 90.5 | 86.24 | 219.6 | 15.9 |
| 0 | 1 | 0.0145 | 0.5884 | 0.3941 | 1490.7 | 0.58 | 86.53 | 44.85 | 86.19 | 79.53 | 206.45 | 22.61 |

| CCT | GAI | GAI 15 | GAI_BB | Circadian power [mW] | Circadian flux | CER | CAF | EML | CLA | CS | Rf | Rg | BLH | energy in 440-490/ total |
|---|---|---|---|---|---|---|---|---|---|---|---|---|---|---|
| 2996.5 | 58.5 | 151.8 | 99.2 | 0.04468 | 0.00592 | 78.2 | 0.36760 | 0.39920 | 283 | 0.3060 | 58 | 102 | 0.0914 | 2.27% |
| 2702.82 | 51.0 | 130.9 | 99.3 | 0.04816 | 0.00634 | 68.2 | 0.31019 | 0.36006 | 686 | 0.4710 | 59 | 103 | 0.0931 | 1.94% |
| 2399.16 | 40.8 | 104.2 | 97.5 | 0.05457 | 0.00709 | 55.9 | 0.24677 | 0.31417 | 586 | 0.4440 | 61 | 103 | 0.0965 | 1.54% |
| 2101.05 | 29.4 | 75.0 | 94.0 | 0.04689 | 0.00596 | 42.1 | 0.18439 | 0.26370 | 480 | 0.4070 | 64 | 104 | 0.0723 | 1.12% |
| 1795.06 | 19.0 | 48.6 | 96.7 | 0.02750 | 0.00337 | 28.3 | 0.12835 | 0.20692 | 369 | 0.3570 | 66 | 104 | 0.0354 | 0.77% |
| 1490.7 | | | | | | | | | 234 | 0.2710 | 77 | 96 | | 0.42% |

TABLE 27

| Violet Channel 3 | Blue Channel 1 | Red Channel 1 | Yellow Channel 3 | x | y | CCT | duv | Ra | R9 | R13 | R15 | LER | COI |
|---|---|---|---|---|---|---|---|---|---|---|---|---|---|
| 1 | 0.6866 | 0 | 0.0953 | 0.2803 | 0.2888 | 10001.93 | 0.51 | 81.58 | 24.85 | 80.47 | 78.99 | 215.18 | 15.35 |
| 1 | 0.6575 | 0.0112 | 0.1082 | 0.2871 | 0.295 | 9005.05 | −0.41 | 81.96 | 30.63 | 81.18 | 80.21 | 217.66 | 14.27 |
| 1 | 0.6478 | 0.0178 | 0.1341 | 0.2952 | 0.3045 | 8002.58 | −0.17 | 81.67 | 30.4 | 80.86 | 79.7 | 223.79 | 13.26 |
| 1 | 0.609 | 0.0339 | 0.1598 | 0.3063 | 0.315 | 7019.98 | −0.75 | 81.69 | 34.05 | 81.11 | 80.14 | 228.65 | 11.8 |
| 1 | 0.609 | 0.0371 | 0.1922 | 3133 | 0.3244 | 6503.68 | 0.55 | 80.8 | 28.66 | 79.85 | 78.19 | 235.52 | 11.19 |
| 1 | 0.5606 | 0.0533 | 0.2052 | 0.3219 | 0.3313 | 6009.48 | −0.15 | 80.8 | 31.77 | 80.09 | 78.64 | 237.07 | 10.13 |
| 1 | 0.5283 | 0.0792 | 0.2278 | 0.3326 | 0.3399 | 5491.1 | −0.64 | 80.89 | 34.88 | 80.39 | 79.1 | 240.29 | 8.83 |
| 1 | 0.4507 | 0.0985 | 0.2439 | 0.3447 | 0.3496 | 5008.1 | −0.83 | 80.11 | 33.91 | 79.63 | 78.13 | 241.98 | 7.68 |
| 1 | 0.3731 | 0.1308 | 0.2666 | 0.3603 | 0.3616 | 4503.83 | −0.78 | 80.05 | 37.17 | 79.68 | 78.43 | 244.41 | 6.23 |
| 1 | 0.3053 | 0.1922 | 0.3021 | 0.3804 | 0.3756 | 3993.71 | −0.48 | 80.14 | 41.23 | 80.15 | 78.96 | 247.89 | 4.43 |
| 1 | 0.1955 | 0.2666 | 0.3212 | 0.405 | 0.3901 | 3501.05 | −0.19 | 79.95 | 44.73 | 80.49 | 79.23 | 247.8 | 2.82 |
| 1 | 0.1082 | 0.4507 | 0.3731 | 0.4379 | 0.406 | 2998.46 | 0.63 | 81.09 | 51.35 | 82.25 | 80.98 | 248.85 | 2.82 |

| CCT | GAI | GAI 15 | GAI BB | Circadian power [mW] | Circadian flux | CER | CAF | EML | CLA | CS | Rf | Rg | BLH | energy in 440-490/ total |
|---|---|---|---|---|---|---|---|---|---|---|---|---|---|---|
| 10001.93 | 98.5 | 286.4 | 95.2 | 0.0717 | 0.0223 | 249.5 | 1.1560 | 1.1337 | 2207 | 0.6170 | 78 | 98 | 0.296518 | 20.4% |
| 9005.05 | 98.9 | 285.5 | 96.6 | 0.0710 | 0.0217 | 240.9 | 1.1032 | 1.0860 | 2074 | 0.6120 | 78 | 99 | 0.289375 | 19.3% |
| 8002.58 | 97.7 | 280.0 | 97.1 | 0.0718 | 0.0215 | 231.7 | 1.0321 | 1.0280 | 1894 | 0.6040 | 78 | 99 | 0.286203 | 18.3% |
| 7019.98 | 96.7 | 274.6 | 98.6 | 0.0714 | 0.0208 | 218.5 | 0.9525 | 0.9580 | 1694 | 0.5940 | 77 | 100 | 0.276619 | 16.8% |
| 6503.68 | 94.1 | 266.3 | 98.0 | 0.0729 | 0.0208 | 211.1 | 0.8933 | 0.9122 | 1544 | 0.5840 | 76 | 99 | 0.275549 | 16.0% |
| 6009.48 | 93.3 | 262.2 | 99.4 | 0.0714 | 0.0198 | 200.8 | 0.8443 | 0.8655 | 1422 | 0.5750 | 75 | 100 | 0.264517 | 14.8% |
| 5491.1 | 91.6 | 255.6 | 100.8 | 0.0712 | 0.0193 | 189.2 | 0.7848 | 0.8128 | 1274 | 0.5620 | 75 | 101 | 0.256951 | 13.5% |
| 5008.1 | 89.0 | 246.4 | 101.8 | 0.0685 | 0.0177 | 175.3 | 0.7219 | 0.7515 | 1119 | 0.5460 | 74 | 100 | 0.239709 | 11.8% |
| 4503.83 | 84.9 | 233.1 | 102.8 | 0.0663 | 0.0162 | 158.7 | 0.6472 | 0.6808 | 936 | 0.5210 | 73 | 101 | 0.222675 | 9.8% |
| 3993.71 | 78.9 | 214.3 | 103.3 | 0.0655 | 0.0149 | 139.6 | 0.5613 | 0.6032 | 726 | 0.4810 | 71 | 102 | 0.208066 | 7.8% |
| 3501.05 | 70.8 | 188.9 | 102.8 | 0.0621 | 0.0128 | 117.2 | 0.4712 | 0.5148 | 509 | 0.4180 | 67 | 102 | 0.185032 | 5.3% |
| 2998.46 | 58.4 | 151.3 | 98.8 | 0.0624 | 0.0115 | 91.6 | 0.3666 | 0.4210 | 801 | 0.4970 | 63 | 103 | 0.168008 | 3.1% |

TABLE 28

| Violet Channel 3 | Red Channel 1 | Yellow Channel 3 | x | y | CCT | duv | Ra | R9 | R13 | R15 | LER | COI |
|---|---|---|---|---|---|---|---|---|---|---|---|---|
| 1 | 0.2892 | 0.2795 | 0.4383 | 0.4089 | 2991.9 | 0.55 | 77.14 | 41.67 | 78.4 | 76.41 | 238.03 | 3 |
| 1 | 0.5153 | 0.3376 | 0.4608 | 0.4121 | 2698.81 | 0.49 | 80.67 | 52.45 | 82.44 | 80.85 | 241.24 | 4.57 |
| 1 | 1 | 0.4313 | 0.4874 | 0.4164 | 2398.27 | 0.55 | 84.41 | 60.65 | 86.4 | 84.74 | 241.7 | 7.35 |
| 0.4701 | 1 | 0.2633 | 0.5163 | 0.4156 | 2103.15 | 0.32 | 87.78 | 64.36 | 89.6 | 87.19 | 236.56 | 10.96 |
| 0.1664 | 1 | 0.1276 | 0.5494 | 0.4087 | 1801.77 | 0.14 | 89.57 | 60.8 | 90.73 | 86.57 | 224.99 | 15.78 |
| 0 | 1 | 0.0113 | 0.5893 | 0.3932 | 1481.65 | 0.48 | 86.32 | 44.22 | 85.94 | 79.25 | 205.59 | 22.85 |

| CCT | GAI | GAI 15 | GAI BB | Circadian power [mW] | Circadian flux | CER | CAF | EML | CLA | CS | Rf | Rg | BLH | energy in 440-490/ total |
|---|---|---|---|---|---|---|---|---|---|---|---|---|---|---|
| 2991.9 | 58.3 | 144.4 | 94.5 | 0.05113 | 0.00853 | 88.24 | 0.37 | 0.3906 | 271 | 0.2980 | 53 | 102 | 0.142907 | 1.3% |
| 2698.81 | 50.2 | 122.2 | 93.0 | 0.05643 | 0.00916 | 74.82 | 0.31 | 0.3524 | 670 | 0.4670 | 55 | 104 | 0.145337 | 1.2% |
| 2398.27 | 40.0 | 96.1 | 90.0 | 0.06099 | 0.00950 | 59.56 | 0.25 | 0.3088 | 574 | 0.4400 | 57 | 103 | 0.139122 | 0.9% |
| 2103.15 | 29.5 | 70.5 | 88.2 | 0.04078 | 0.00601 | 44.32 | 0.19 | 0.2618 | 476 | 0.4060 | 59 | 104 | 0.079144 | 0.7% |
| 1801.77 | 18.5 | 44.7 | 87.8 | 0.02498 | 0.00338 | 28.98 | 0.13 | 0.2064 | 367 | 0.3560 | 63 | 103 | 0.037527 | 0.6% |
| 1481.65 | | | | | | | | | 231 | 0.2680 | 76 | 96 | | 0.4% |

TABLE 29

| Violet Channel 4 | Red Channel 1 | Yellow Channel 4 | x | y | CCT | duv | Ra | R9 | R13 | R15 | LER | COI | GAI |
|---|---|---|---|---|---|---|---|---|---|---|---|---|---|
| 1 | 0.0113 | 0.454 | 0.4049 | 0.3909 | 3509.71 | 0.17 | 70.47 | −30.68 | 71.94 | 61.99 | 302.33 | 8.76 | 67.73522 |
| 1 | 0.2827 | 0.6123 | 0.4371 | 0.4039 | 2996.02 | −0.08 | 75.95 | 0.28 | 78.09 | 70.25 | 296.34 | 5.74 | 58.16243 |
| 1 | 0.6155 | 0.7318 | 0.4588 | 0.4091 | 2702.91 | −0.47 | 79.45 | 17.36 | 81.9 | 75.09 | 287.92 | 5.74 | 51.1852 |
| 1 | 1 | 0.9192 | 0.475 | 0.415 | 2534.54 | 0.56 | 81.4 | 24.99 | 83.75 | 77.16 | 284.63 | 6.43 | 43.86021 |
| 0.7221 | 1 | 0.7124 | 0.4863 | 0.4149 | 2399.5 | 0.07 | 83.09 | 32.05 | 85.51 | 79.26 | 277.26 | 7.59 | 40.40926 |
| 0.3343 | 1 | 0.399 | 0.5143 | 0.413 | 2104.82 | −0.53 | 86.42 | 43.99 | 88.69 | 82.68 | 258.79 | 11.04 | 31.31714 |
| 0.14 | 1 | 0.2601 | 0.5386 | 0.4128 | 1903.52 | 0.5 | 88.01 | 47.93 | 89.69 | 83.3 | 246.03 | 13.97 | 21.13827 |
| 0.0889 | 1 | 0.1922 | 0.5503 | 0.4097 | 1800.78 | 0.49 | 88.42 | 48.88 | 89.79 | 83.17 | 237.3 | 15.78 | 17.44622 |
| 0.0436 | 1 | 0.1341 | 0.5629 | 0.4065 | 1700.09 | 0.75 | 88.41 | 48.52 | 89.33 | 82.48 | 228.6 | 17.73 | |
| 0.0404 | 1 | 0.0727 | 0.5723 | 0.3987 | 1603.05 | −0.23 | 87.82 | 47.4 | 88.45 | 81.62 | 217.65 | 19.94 | |

| CCT | GAI 15 | GAI BB | Circadian power [mW] | Circadian flux | CER | CAF | EML | CLA | CS | Rf | Rg | BLH | energy in 440-490/ total |
|---|---|---|---|---|---|---|---|---|---|---|---|---|---|
| 3509.71 | 176.4 | 95.8 | 0.0625 | 0.0139 | 134.9 | 0.4407 | 0.4559 | 429 | 0.3860 | 56 | 99 | 0.2220 | 3.15% |
| 2996.02 | 148.4 | 97.0 | 0.0726 | 0.0152 | 105.0 | 0.3502 | 0.3966 | 754 | 0.4870 | 58 | 102 | 0.2268 | 2.43% |
| 2702.91 | 129.3 | 98.1 | 0.0647 | 0.0129 | 86.8 | 0.2984 | 0.3591 | 674 | 0.4680 | 60 | 104 | 0.1838 | 2.00% |
| 2534.54 | 110.5 | 93.4 | 0.0572 | 0.0108 | 74.0 | 0.2575 | 0.3318 | 613 | 0.4520 | 62 | 104 | 0.1452 | 1.70% |
| 2399.5 | 101.5 | 95.0 | 0.0525 | 0.0097 | 66.0 | 0.2360 | 0.3130 | 575 | 0.4410 | 62 | 104 | 0.1262 | 1.52% |
| 2104.82 | 78.6 | 98.1 | 0.0401 | 0.0068 | 48.4 | 0.1856 | 0.2667 | 483 | 0.4080 | 64 | 105 | 0.0821 | 1.14% |
| 1903.52 | 53.5 | 88.0 | 0.0284 | 0.0043 | 34.5 | 0.1392 | 0.2263 | 401 | 0.3730 | 68 | 103 | 0.0441 | 0.83% |
| 1800.78 | 44.3 | 87.1 | 0.0237 | 0.0034 | 28.8 | 0.1208 | 0.2061 | 363 | 0.3540 | 69 | 102 | 0.0324 | 0.71% |
| 1700.09 | | | | | | | | 321 | 0.3300 | 72 | 99 | | 0.59% |
| 1603.05 | | | | | | | | 292 | 0.3120 | 69 | 104 | | 0.55% |

TABLE 30

| | High-CRI mode | | High-EML mode | | Low-EML mode | | Very-Low-EML mode | |
|---|---|---|---|---|---|---|---|---|
| Nominal CCT | EML | Circadian Stimulus (CS) | EML | Circadian Stimulus (CS) | EML | Circadian. Stimulus (CS) | EML | Circadian Stimulus (CS) |
| 10000 | 1.287392 | 0.617 | 1.323599 | 0.6190 | 1.203532 | 0.6150 | | |
| 9500 | 1.2552564 | 0.614 | | | | | | |
| 9000 | 1.230498 | 0.6110 | 1.284446 | 0.6130 | 1.151925 | 0.6090 | | |
| 8500 | 1.202935 | 0.6070 | | | | | | |
| 8000 | | | 1.240274 | 0.6070 | 1.08629 | 0.6000 | | |
| 7500 | 1.1383591 | 0.5980 | | | | | | |
| 7000 | 1.1015431 | 0.5920 | 1.188225 | 0.5980 | 1.004381 | 0.5870 | | |
| 6500 | 1.0572409 | 0.5840 | 1.153187 | 0.5910 | 0.958281 | 0.5790 | | |
| 6000 | 1.0112902 | 0.5750 | 1.117412 | 0.5830 | 0.910548 | 0.5700 | | |
| 5500 | 0.9542838 | 0.5610 | 1.074033 | 0.5720 | 0.845296 | 0.5540 | | |
| 5000 | 0.8937964 | 0.5440 | 1.023649 | 0.5590 | 0.786954 | 0.5350 | | |
| 4500 | 0.8245702 | 0.5180 | 0.966693 | 0.5400 | 0.711691 | 0.5060 | | |
| 4000 | 0.7462442 | 0.4790 | 0.896774 | 0.5110 | | | 0.540872 | 0.452 |
| 3500 | 0.6630957 | 0.4230 | 0.815304 | 0.5810 | | | 0.48499 | 0.3790 |
| 3000 | 0.5580387 | 0.5330 | 0.711335 | 0.5640 | | | 0.418977 | 0.4940 |
| 2700 | 0.4989732 | 0.5160 | 0.639906 | 0.5500 | | | 0.376181 | 0.4750 |
| 2500 | 0.44713093 | 0.497333 | 0.586369 | 0.538 | | | 0.344663 | 0.457 |
| 2400 | 0.4212098 | 0.4880 | 0.5596 | 0.5320 | | | 0.328904 | 0.4480 |
| 2100 | 0.339504 | 0.4490 | 0.461974 | 0.5030 | | | 0.276946 | 0.4140 |
| 1900 | 0.2815066 | 0.411667 | 0.374114 | 0.464333 | | | 0.234146 | 0.378 |
| 1800 | 0.2525079 | 0.3930 | 0.330184 | 0.4450 | | | 0.212746 | 0.3600 |
| 1700 | | | | | | | | |
| 1600 | | 0.3270 | | | | | | |

TABLE 31

| | EML % changes | | | CS % changes | | |
|---|---|---|---|---|---|---|
| Nominal CCT | High-EML mode to Low-EML mode | High-CRI mode to Low-EML mode and Very-Low-EML mode | High-CM mode to High-EML mode | High-EML mode to Low-EML mode | High-CRI mode to Low-EML mode and Very-Low-EML mode | High-CRI mode to High-EML mode |
| 10000 | 10.0% | 7.0% | 2.8% | 1% | 0% | 0% |
| 9500 | | | | | | |
| 9000 | 11.5% | 6.8% | 4.4% | 1% | 0% | 0% |
| 8500 | | | | | | |
| 8000 | 14.2% | | | 1% | | |
| 7500 | | | | | | |
| 7000 | 18.3% | 9.7% | 7.9% | 2% | 1% | 1% |
| 6500 | 20.3% | 10.3% | 9.1% | 2% | 1% | 1% |
| 6000 | 22.7% | 11.1% | 10.5% | 2% | 1% | 1% |
| 5500 | 27.1% | 12.9% | 12.5% | 3% | 1% | 2% |
| 5000 | 30.1% | 13.6% | 14.5% | 4% | 2% | 3% |
| 4500 | 35.8% | 15.9% | 17.2% | 7% | 2% | 4% |
| 4000 | 65.8% | 38.0% | 20.2% | 13% | 6% | 7% |
| 3500 | 68.1% | 36.7% | 23.0% | 53% | 12% | 37% |
| 3000 | 69.8% | 33.2% | 27.5% | 14% | 8% | 6% |
| 2700 | 70.1% | 32.6% | 28.2% | 16% | 9% | 7% |
| 2500 | 70.1% | 29.7% | 31.1% | 18% | 9% | 8% |
| 2400 | 70.1% | 28.1% | 32.9% | 19% | 9% | 9% |
| 2100 | 66.8% | 22.6% | 36.1% | 21% | 8% | 12% |
| 1900 | 59.8% | 20.2% | 32.9% | 23% | 9% | 13% |
| 1800 | 55.2% | 18.7% | 30.8% | 24% | 9% | 13% |
| 1700 | | | | | | |
| 1600 | | | | | | |

TABLE 32

| | High-CRI mode | | High-EML mode | | Low-EML mode | | Very-Low-EML mode | |
|---|---|---|---|---|---|---|---|---|
| Nominal CCT | EML | Circadian Stimulus (CS) | EML | Circadian Stimulus (CS) | EML | Circadian Stimulus (CS) | EML | Circadian Stimulus (CS) |
| 10000 | 1.28739 | 0.6170 | 1.32360 | 0.6190 | 1.16343 | 0.6180 | | |
| 9500 | 1.25526 | 0.6140 | | | | | | |
| 9000 | 1.23050 | 0.6110 | 1.28445 | 0.6130 | 1.11189 | 0.6120 | | |
| 8500 | 1.20294 | 0.6070 | | | | | | |
| 8000 | | | 1.24027 | 0.6070 | 1.04507 | 0.6040 | | |
| 7500 | 1.13836 | 0.5980 | | | | | | |
| 7000 | 1.10154 | 0.5920 | 1.18823 | 0.5980 | 0.97088 | 0.5920 | | |
| 6500 | 1.05724 | 0.5840 | 1.15319 | 0.5910 | 0.92605 | 0.5840 | | |
| 6000 | 1.01129 | 0.5750 | 1.11741 | 0.5830 | 0.87477 | 0.5740 | | |
| 5500 | 0.95428 | 0.5610 | 1.07403 | 0.5720 | 0.81655 | 0.5590 | | |
| 5000 | 0.89380 | 0.5440 | 1.02365 | 0.5590 | 0.75818 | 0.5420 | | |
| 4500 | 0.82457 | 0.5180 | 0.96669 | 0.5400 | 0.68922 | 0.5140 | | |
| 4000 | 0.74624 | 0.4790 | 0.89677 | 0.5110 | 0.60853 | 0.4740 | | |
| 3500 | 0.66310 | 0.4230 | 0.81530 | 0.5810 | 0.52239 | 0.4100 | | |
| 3000 | 0.55804 | 0.5330 | 0.71133 | 0.5640 | | | 0.39920 | 0.3060 |
| 2700 | 0.49897 | 0.5160 | 0.63991 | 0.5500 | | | 0.36006 | 0.4710 |
| 2500 | 0.44713 | 0.4973 | 0.58637 | 0.5380 | | | 0.32947 | 0.4530 |
| 2400 | 0.42121 | 0.4880 | 0.55960 | 0.5320 | | | 0.31417 | 0.4440 |
| 2100 | 0.33950 | 0.4490 | 0.46197 | 0.5030 | | | 0.26370 | 0.4070 |
| 1900 | 0.28151 | 0.4117 | 0.37411 | 0.4643 | | | 0.22585 | 0.3737 |
| 1800 | 0.25251 | 0.3930 | 0.33018 | 0.4450 | | | 0.20692 | 0.3570 |
| 1700 | | | | | | | | |
| 1600 | | 0.3270 | | 0.3110 | | | | 0.2710 |

TABLE 33

| | EML % changes | | | CS % changes | | |
|---|---|---|---|---|---|---|
| Nominal CCT | High-EML mode to Low-EML mode | High-CRI mode to Low-EML mode and Very-Low-EML mode | High-CRI mode to High-EML mode | High-EML mode to Low-EML mode | High-CRI mode to Low-EML mode and Very-Low-EML mode | High-CRI mode to High-EML mode |
| 10000 | 14% | 11% | 3% | 0% | 0% | 0% |
| 9500 | | | | | | |
| 9000 | 16% | 11% | 4% | 0% | 0% | 0% |
| 8500 | | | | | | |
| 8000 | 19% | | | 0% | | |
| 7500 | | | | | | |
| 7000 | 22% | 13% | 8% | 1% | 0% | 1% |
| 6500 | 25% | 14% | 9% | 1% | 0% | 1% |
| 6000 | 28% | 16% | 10% | 2% | 0% | 1% |
| 5500 | 32% | 17% | 13% | 2% | 0% | 2% |
| 5000 | 35% | 18% | 15% | 3% | 0% | 3% |
| 4500 | 40% | 20% | 17% | 5% | 1% | 4% |
| 4000 | 47% | 23% | 20% | 8% | 1% | 7% |
| 3500 | 56% | 27% | 23% | 42% | 3% | 37% |
| 3000 | 78% | 40% | 27% | 84% | 74% | 6% |
| 2700 | 78% | 39% | 28% | 17% | 10% | 7% |
| 2500 | 78% | 36% | 31% | 19% | 10% | 8% |
| 2400 | 78% | 34% | 33% | 20% | 10% | 9% |
| 2100 | 75% | 29% | 36% | 24% | 10% | 12% |
| 1900 | 66% | 25% | 33% | 24% | 10% | 13% |
| 1800 | 60% | 22% | 31% | 25% | 10% | 13% |
| 1700 | | | | | | |
| 1600 | | | | 15% | 21% | −5% |

TABLE 34

| | High-CRI mode | | High-EML mode | | Low-EML mode | | Very-Low-EML mode | |
|---|---|---|---|---|---|---|---|---|
| Nominal CCT | EML | Circadian Stimulus (CS) | EML | Circadian Stimulus (CS) | EML | Circadian Stimulus (CS) | EML | Circadian Stimulus (CS) |
| 10000 | 1.2874 | 0.617 | 1.3236 | 0.619 | 1.1337 | 0.617 | | |
| 9500 | 1.2553 | 0.614 | | | | | | |
| 9000 | 1.2305 | 0.611 | 1.2844 | 0.613 | 1.0860 | 0.612 | | |
| 8500 | 1.2029 | 0.607 | | | | | | |
| 8000 | | | 1.2403 | 0.607 | 1.0280 | 0.604 | | |
| 7500 | 1.1384 | 0.598 | | | | | | |
| 7000 | 1.1015 | 0.592 | 1.1882 | 0.598 | 0.9580 | 0.594 | | |
| 6500 | 1.0572 | 0.584 | 1.1532 | 0.591 | 0.9122 | 0.584 | | |
| 6000 | 1.0113 | 0.575 | 1.1174 | 0.583 | 0.8655 | 0.575 | | |
| 5500 | 0.9543 | 0.561 | 1.0740 | 0.572 | 0.8128 | 0.562 | | |
| 5000 | 0.8938 | 0.544 | 1.0236 | 0.559 | 0.7515 | 0.546 | | |
| 4500 | 0.8246 | 0.518 | 0.9667 | 0.540 | 0.6808 | 0.521 | | |
| 4000 | 0.7462 | 0.479 | 0.8968 | 0.511 | 0.6032 | 0.481 | | |
| 3500 | 0.6631 | 0.423 | 0.8153 | 0.581 | 0.5148 | 0.418 | | |
| 3000 | 0.5580 | 0.533 | 0.7113 | 0.564 | | | 0.3906 | 0.497 |
| 2700 | 0.4990 | 0.516 | 0.6399 | 0.550 | | | 0.3524 | 0.467 |
| 2500 | 0.4471 | 0.497 | 0.5864 | 0.538 | | | 0.3234 | 0.449 |
| 2400 | 0.4212 | 0.488 | 0.5596 | 0.532 | | | 0.3088 | 0.440 |
| 2100 | 0.3395 | 0.449 | 0.4620 | 0.503 | | | 0.2618 | 0.406 |
| 1900 | 0.2815 | 0.412 | 0.3741 | 0.464 | | | 0.2249 | 0.373 |
| 1800 | 0.2525 | 0.393 | 0.3302 | 0.445 | | | 0.2064 | 0.356 |
| 1700 | | | | | | | | |
| 1600 | | 0.327 | | | | | | 0.268 |

TABLE 35

| Nominal CCT | EML % changes | | | CS % changes | | |
|---|---|---|---|---|---|---|
| | High-EML mode to Low-EML mode | High-CRI mode to Low-EML mode and Very-Low-EML mode | High-CRI mode to High-EML mode | High-EML mode to Low-EML mode | High-CRI mode to Low-EML mode and Very-Low-EML mode | High-CRI mode to High-EML mode |
| 10000 | 16.7% | 13.6% | 2.8% | | | 0.3% |
| 9500 | | | | | | |
| 9000 | 18.3% | 13.3% | 4.4% | | | 0.3% |
| 8500 | | | | | | |
| 8000 | 20.6% | | | | | |
| 7500 | | | | | | |
| 7000 | 24.0% | 15.0% | 7.9% | 1% | −0.34% | 1.0% |
| 6500 | 26.4% | 15.9% | 9.1% | 1% | 0.00% | 1.2% |
| 6000 | 29.1% | 16.8% | 10.5% | 1% | 0.00% | 1.4% |
| 5500 | 32.1% | 17.4% | 12.5% | 2% | −0.18% | 2% |
| 5000 | 36.2% | 18.9% | 14.5% | 2% | −0.37% | 3% |
| 4500 | 42.0% | 21.1% | 17.2% | 4% | −0.58% | 4% |
| 4000 | 48.7% | 23.7% | 20.2% | 6% | −0.42% | 7% |
| 3500 | 58.4% | 28.8% | 23.0% | 39% | 1.20% | 37% |
| 3000 | 82.1% | 42.9% | 27.5% | 13% | 7% | 6% |
| 2700 | 81.6% | 41.6% | 28.2% | 18% | 10% | 7% |
| 2500 | 81.3% | 38.3% | 31.1% | 20% | 11% | 8% |
| 2400 | 81.2% | 36.4% | 32.9% | 21% | 11% | 9% |
| 2100 | 76.5% | 29.7% | 36.1% | 24% | 11% | 12% |
| 1900 | 66.4% | 25.2% | 32.9% | 25% | 10% | 13% |
| 1800 | 60.0% | 22.3% | 30.8% | 25% | 10% | 13% |
| 1700 | | | | | | |
| 1600 | | | | | 22% | |

TABLE 36

| Nominal CCT | High-CRI mode | | High-EML mode | | Very-Low-EML mode | |
|---|---|---|---|---|---|---|
| | EML | Circadian Stimulus (CS) | EML | Circadian Stimulus (CS) | EML | Circadian Stimulus (CS) |
| 10000 | 1.2874 | 0.6170 | 1.3236 | 0.6190 | | |
| 9500 | 1.2553 | 0.6140 | | | | |
| 9000 | 1.2305 | 0.6110 | 1.2844 | 0.6130 | | |
| 8500 | 1.2029 | 0.6070 | | | | |
| 8000 | | | 1.2403 | 0.6070 | | |
| 7500 | 1.1384 | 0.5980 | | | | |
| 7000 | 1.1015 | 0.5920 | 1.1882 | 0.5980 | | |
| 6500 | 1.0572 | 0.5840 | 1.1532 | 0.5910 | | |
| 6000 | 1.0113 | 0.5750 | 1.1174 | 0.5830 | | |
| 5500 | 0.9543 | 0.5610 | 1.0740 | 0.5720 | | |
| 5000 | 0.8938 | 0.5440 | 1.0236 | 0.5590 | | |
| 4500 | 0.8246 | 0.5180 | 0.9667 | 0.5400 | | |
| 4000 | 0.7462 | 0.4790 | 0.8968 | 0.5110 | | |
| 3500 | 0.6631 | 0.4230 | 0.8153 | 0.5810 | 0.4559 | 0.3860 |
| 3000 | 0.5580 | 0.5330 | 0.7113 | 0.5640 | 0.3966 | 0.4870 |
| 2700 | 0.4990 | 0.5160 | 0.6399 | 0.5500 | 0.3591 | 0.4680 |
| 2500 | 0.4471 | 0.4973 | 0.5864 | 0.5380 | 0.3284 | 0.4500 |
| 2400 | 0.4212 | 0.4880 | 0.5596 | 0.5320 | 0.3130 | 0.4410 |
| 2100 | 0.3395 | 0.4490 | 0.4620 | 0.5030 | 0.2667 | 0.4080 |
| 1900 | 0.2815 | 0.4117 | 0.3741 | 0.4643 | 0.2263 | 0.3720 |
| 1800 | 0.2525 | 0.3930 | 0.3302 | 0.4450 | 0.2061 | 0.3540 |
| 1600 | | 0.3270 | | | | |

TABLE 37

| | EML % changes | | | CS % changes | | |
|---|---|---|---|---|---|---|
| Nominal CCT | High-EML mode to Low-EML mode | High-CRI mode to Low-EML mode and Very-Low-EML mode | High-CRI mode to High-EML mode | High-EML mode to Low-EML mode | High-CRI mode to Low-EML mode and Very-Low-EML mode | High-CRI mode to High-EML mode |
| 3500 | 78.8% | 45.4% | 23.0% | 51% | 10% | 37% |
| 3000 | 79.3% | 40.7% | 27.5% | 16% | 9% | 6% |
| 2700 | 78.2% | 38.9% | 28.2% | 18% | 10% | 7% |
| 2500 | 78.6% | 36.2% | 31.1% | 20% | 11% | 8% |
| 2400 | 78.8% | 34.6% | 32.9% | 21% | 11% | 9% |
| 2100 | 73.2% | 27.3% | 36.1% | 23% | 10% | 12% |
| 1900 | 65.3% | 24.4% | 32.9% | 25% | 11% | 13% |
| 1800 | 60.2% | 22.5% | 30.8% | 26% | 11% | 13% |

TABLE 38

| | Violet Peak (Vp) $380 < \lambda \leq 460$ | | Violet Valley (Vv) $450 < \lambda \leq 510$ | | Green Peak (Gp) $500 < \lambda \leq 650$ | | Red Valley (Rv) $650 < \lambda \leq 780$ | |
|---|---|---|---|---|---|---|---|---|
| | $\lambda$ | Vp | $\lambda$ | Vv | $\lambda$ | Gp | $\lambda$ | Rv |
| Violet Channel 1 | 380 | 1 | 486 | 0.00485 | 596 | 0.05521 | 751 | 0.00218 |
| Violet Channel 2 | 400 | 1 | 476 | 0.00185 | 592 | 0.05795 | 751 | 0.00227 |
| Violet Channel 5 | 400 | 1 | 482 | 0.00525 | 596 | 0.06319 | 751 | 0.00252 |
| Violet Channel 3 | 410 | 1 | 477 | 0.00368 | 578 | 0.06123 | 751 | 0.00232 |
| Violet Channel 4 | 420 | 1 | 477 | 0.01032 | 608 | 0.22266 | 749 | 0.00519 |
| Exemplary Violet Channels Minimum | 380 | 1 | 476 | 0.00185 | 578 | 0.05521 | 749 | 0.00218 |
| Exemplary Violet Channels Average | 402 | 1 | 480 | 0.00519 | 594 | 0.09205 | 751 | 0.00290 |
| Exemplary Violet Channels Maximum | 420 | 1 | 486 | 0.01032 | 608 | 0.22266 | 751 | 0.00519 |

TABLE 39

| | Ratio | | | | |
|---|---|---|---|---|---|
| | Vp/Vv | Vp/Gp | Vp/Rv | Gp/Vv | Gp/Rv |
| Violet Channel 1 | 206.3 | 18.1 | 458.5 | 11.4 | 25.3 |
| Violet Channel 2 | 540.0 | 17.3 | 440.3 | 31.3 | 25.5 |
| Violet Channel 5 | 190.4 | 15.8 | 397.0 | 12.0 | 25.1 |
| Violet Channel 3 | 272.0 | 16.3 | 431.8 | 16.7 | 26.4 |
| Violet Channel 4 | 96.9 | 4.5 | 192.6 | 21.6 | 42.9 |
| Exemplary Violet Channels Minimum | 96.9 | 4.5 | 192.6 | 11.4 | 25.1 |
| Exemplary Violet Channels Average | 261.1 | 14.4 | 384.0 | 18.6 | 29.0 |
| Exemplary Violet Channels Maximum | 540.0 | 18.1 | 458.5 | 31.3 | 42.9 |

TABLE 40

| | Violet Peak $330 < \lambda \leq 430$ | | Violet Valley $420 < \lambda \leq 510$ | | Green Peak $500 < \lambda \leq 780$ | |
|---|---|---|---|---|---|---|
| | $\lambda$ | Vp | $\lambda$ | Vv | $\lambda$ | Gp |
| Yellow Channel 1 | 380 | 0.37195 | 470 | 0.00534 | 548 | 1 |
| Yellow Channel 2 | 400 | 0.37612 | 458 | 0.00275 | 549 | 1 |
| Yellow Channel 5 | 400 | 0.36297 | 476 | 0.00317 | 561 | 1 |
| Yellow Channel 3 | 410 | 0.37839 | 476 | 0.00139 | 547 | 1 |
| Yellow Channel 6 | 410 | 0.38876 | 476 | 0.00223 | 561 | 1 |
| Yellow Channel 4 | 419 | 0.07831 | 476 | 0.01036 | 608 | 1 |
| Exemplary Yellow Channels Minimum | 380 | 0.07831 | 458 | 0.00139 | 547 | 1 |
| Exemplary Yellow Channels Average | 403 | 0.32608 | 472 | 0.00421 | 562 | 1 |
| Exemplary Yellow Channels Maximum | 419 | 0.38876 | 476 | 0.01036 | 608 | 1 |

TABLE 41

| | Ratio | | |
|---|---|---|---|
| | Vp/Vv | Vp/Gp | Gp/Vv |
| Yellow Channel 1 | 69.7 | 0.372 | 187.3 |
| Yellow Channel 2 | 136.9 | 0.376 | 364.0 |
| Yellow Channel 5 | 114.4 | 0.363 | 315.3 |
| Yellow Channel 3 | 273.2 | 0.378 | 722.0 |
| Yellow Channel 6 | 174.3 | 0.389 | 448.2 |
| Yellow Channel 4 | 7.6 | 0.078 | 96.5 |
| Exemplary Yellow Channels Minimum | 7.559 | 0.078 | 96.525 |
| Exemplary Yellow Channels Average | 129.336 | 0.326 | 355.556 |
| Exemplary Yellow Channels Maximum | 273.202 | 0.389 | 722.022 |

TABLE 42

| | Blue Peak 380 < λ ≤ 460 | | Blue Valley 450 < λ ≤ 510 | | Red Peak 500 < λ ≤ 780 | |
|---|---|---|---|---|---|---|
| | λ | Bp | λ | Bv | λ | Rp |
| Red Channel 11 | 461 | 0.05898 | 488 | 0.02327 | 649 | 1 |
| Red Channel 3 | 449 | 0.18404 | 497 | 0.00309 | 640 | 1 |
| Red Channel 4 | 461 | 0.07759 | 495 | 0.01753 | 618 | 1 |
| Red Channel 5 | 453 | 0.07508 | 494 | 0.00374 | 628 | 1 |
| Red Channel 6 | 449 | 0.18404 | 497 | 0.00309 | 640 | 1 |
| Red Channel 9 | 461 | 0.07737 | 489 | 0.03589 | 645 | 1 |
| Red Channel 10 | 461 | 0.06982 | 489 | 0.02971 | 645 | 1 |
| Red Channel 1 | 445 | 0.01599 | 477 | 0.00353 | 649 | 1 |
| Red Channel 12 | 445 | 0.01217 | 477 | 0.00203 | 649 | 1 |
| Red Channel 13 | 451 | 0.06050 | 479 | 0.01130 | 651 | 1 |
| Red Channel 14 | 449 | 0.06020 | 485 | 0.00612 | 653 | 1 |
| Red Channel 15 | 445 | 0.02174 | 477 | 0.00326 | 649 | 1 |
| Red Channel 16 | 450 | 0.03756 | 483 | 0.00388 | 643 | 1 |
| Red Channel 17 | 450 | 0.03508 | 485 | 0.00425 | 641 | 1 |
| Exemplary Red Channels Minimum | 445 | 0.01217 | 477 | 0.00203 | 618 | 1 |
| Exemplary Red Channels Average | 452 | 0.06930 | 487 | 0.01076 | 643 | 1 |
| Exemplary Red Channels Maximum | 461 | 0.18404 | 497 | 0.03589 | 653 | 1 |

TABLE 43

| | Ratios | | |
|---|---|---|---|
| | Bp/Bv | Bp/Rp | Rp/Bv |
| Red Channel 11 | 2.5 | 0.059 | 43.0 |
| Red Channel 3 | 59.5 | 0.184 | 323.3 |
| Red Channel 4 | 4.4 | 0.078 | 57.1 |
| Red Channel 5 | 20.1 | 0.075 | 267.7 |
| Red Channel 6 | 59.5 | 0.184 | 323.3 |
| Red Channel 9 | 2.2 | 0.077 | 27.9 |
| Red Channel 10 | 2.4 | 0.070 | 33.7 |
| Red Channel 1 | 4.5 | 0.016 | 283.3 |
| Red Channel 12 | 6.0 | 0.012 | 493.0 |
| Red Channel 13 | 5.4 | 0.061 | 88.5 |
| Red Channel 14 | 9.8 | 0.060 | 163.4 |
| Red Channel 15 | 6.7 | 0.022 | 306.3 |
| Red Channel 16 | 9.7 | 0.038 | 257.7 |
| Red Channel 17 | 8.3 | 0.035 | 235.5 |
| Exemplary Red Channels Minimum | 2.156 | 0.012 | 27.864 |
| Exemplary Red Channels Average | 14.349 | 0.069 | 207.398 |
| Exemplary Red Channels Maximum | 59.501 | 0.184 | 492.975 |

TABLE 44

| | x | y | CCT | duv | Ra | R9 | R13 | R15 | LER | COI | GAI | GAI 15 | GAI_BB |
|---|---|---|---|---|---|---|---|---|---|---|---|---|---|
| 2400K Ch1 | 0.4872 | 0.4166 | 2401.7 | 0.62 | 76.39 | 50.16 | 81.3 | 61.64 | 312.32 | 10.53 | 36.61 | 89.03 | 83.17 |
| 2400K Ch2 | 0.4858 | 0.4148 | 2404.69 | 0.07 | 86.38 | 92.09 | 95.28 | 89.70 | 282.76 | 9.68 | 44.51 | 102.45 | 95.46 |
| 2400K Ch3 | 0.4852 | 0.4137 | 2403.72 | −0.29 | 80.60 | 35.83 | 84.04 | 81.58 | 282.07 | 7.79 | 41.87 | 100.73 | 93.95 |
| 1800K Ch1 | 0.5503 | 0.4097 | 1801 | 0.49 | 90.94 | 62.65 | 92.01 | 87.32 | 210.12 | 16.00 | 17.37 | 47.81 | 94.05 |
| 4000K Ch1 | 0.3807 | 0.3772 | 3995.74 | 0.16 | 91.18 | 58.05 | 90.71 | 86.30 | 292.50 | | 82.78 | 219.40 | 105.73 |
| 4000K Ch2 | 0.3803 | 0.3766 | 4003.12 | −0.02 | 88.67 | 96.86 | 89.72 | 94.57 | 274.59 | 1.2 | 76.69 | 200.10 | 96.28 |
| 4000K Ch3 | 0.3814 | 0.3758 | 3967.48 | −0.7 | 86.26 | 70.93 | 95.39 | 93.30 | 283.64 | 3.07 | 71.86 | 189.40 | 91.81 |
| 4000K Ch4 | 0.3804 | 0.3782 | 4012.69 | 0.72 | 82.45 | 79.82 | 91.17 | 92.69 | 280.02 | 2.4 | 69.51 | 182.68 | 87.72 |
| 5000K Ch1 | 0.3449 | 0.3516 | 5007 | 0.08 | 83.73 | 56.73 | 82.41 | 82.71 | 257.55 | 0.81 | 90.61 | 234.15 | 96.76 |

| | Circadian power [mW] | Circadian flux | CER (Circadian power per flux) [mW/lm] | CAF (Circadian action factor) | EML | Circadian Light (CLA) | Circadian Stimulus (CS) | Rf | Rg | BLH | Energy in 440 < λ ≤ 490 nm/ total energy 380 < λ ≤ 780 nm |
|---|---|---|---|---|---|---|---|---|---|---|---|
| 2400K Ch1 | 0.0463 | 0.0074 | 77.736 | 0.2481 | 0.30848 | 575 | 0.440 | 51 | 97 | 0.10961 | 1.04% |
| 2400K Ch2 | 0.0294 | 0.0047 | 75.434 | 0.2661 | 0.34238 | 631 | 0.457 | 56 | 109 | 0.06700 | 0.99% |
| 2400K Ch3 | 0.0442 | 0.0065 | 69.309 | 0.2453 | 0.28563 | 540 | 0.429 | 51 | 103 | 0.10573 | 0.92% |
| 1800K Ch1 | 0.0265 | 0.0032 | 26.837 | 0.1209 | 0.21275 | 374 | 0.360 | 77 | 103 | 0.02570 | 0.98% |
| 4000K Ch1 | 0.0725 | 0.0241 | 174.436 | 0.5949 | 0.79451 | 767 | 0.490 | 91 | 102 | 0.20390 | 15.87% |
| 4000K Ch2 | 0.1042 | 0.0367 | 178.778 | 0.6494 | 0.88924 | 875 | 0.511 | 85 | 96 | 0.28816 | 15.97% |
| 4000K Ch3 | 0.0930 | 0.0331 | 184.994 | 0.6516 | 0.89470 | 896 | 0.514 | 80 | 91 | 0.25199 | 18.10% |
| 4000K Ch4 | 0.0847 | 0.0307 | 188.638 | 0.6729 | 0.94619 | 938 | 0.521 | 74 | 87 | 0.22073 | 18.56% |
| 5000K Ch1 | 0.0916 | 0.0355 | 215.982 | 0.8368 | 1.10190 | 1325 | 0.567 | 81 | 97 | 0.28801 | 21.00% |

TABLE 45

|  | 320 < λ ≤ 400 | 400 < λ ≤ 500 | 500 < λ ≤ 600 | 600 < λ ≤ 700 | 700 < λ ≤ 780 |
|---|---|---|---|---|---|
| 2400K Ch3 | 9.92 | 44.53 | 83.33 | 100.00 | 7.55 |
| 2400K Ch2 | 8.59 | 39.69 | 75.82 | 100.00 | 3.09 |
| 2400K Ch1 | 11.11 | 51.02 | 105.53 | 100.00 | 4.41 |
| 1800K Ch1 | 7.61 | 4.42 | 39.66 | 100.00 | 11.52 |
| Exemplary $2^{nd}$ channels min | 7.61 | 4.42 | 39.66 | 100.00 | 3.09 |
| Exemplary $2^{nd}$ channels avg | 9.31 | 34.92 | 76.09 | 100.00 | 6.64 |
| Exemplary $2^{nd}$ channels max | 11.11 | 51.02 | 105.53 | 100.00 | 11.52 |

TABLE 46

|  | 320 < λ ≤ 400 | 400 < λ ≤ 500 | 500 < λ ≤ 600 | 600 < λ ≤ 700 | 700 < λ ≤ 780 |
|---|---|---|---|---|---|
| 4000K Ch4 | 0.29 | 67.46 | 100.00 | 96.08 | 9.60 |
| 4000K Ch2 | 0.43 | 62.49 | 100.00 | 99.55 | 12.19 |
| 4000K Ch3 | 0.24 | 64.82 | 100.00 | 93.88 | 9.61 |
| 5000K Ch1 | 0.05 | 84.60 | 100.00 | 99.73 | 10.20 |
| Exemplary $1^{st}$ channels min | 0.05 | 62.49 | 100.00 | 93.88 | 9.60 |
| Exemplary $1^{st}$ channels avg | 0.25 | 69.84 | 100.00 | 97.31 | 10.40 |
| Exemplary $1^{st}$ channels max | 0.43 | 84.60 | 100.00 | 99.73 | 12.19 |

TABLE 47

|  | 320 < λ ≤ 380 | 380 < λ ≤ 420 | 420 < λ ≤ 460 | 460 < λ ≤ 500 | 500 < λ ≤ 540 | 540 < λ ≤ 580 | 580 < λ ≤ 620 | 620 < λ ≤ 660 | 660 < λ ≤ 700 | 700 < λ ≤ 740 | 740 < λ ≤ 780 |
|---|---|---|---|---|---|---|---|---|---|---|---|
| 2400K Ch3 | 0.87 | 75.85 | 20.20 | 2.50 | 36.53 | 75.23 | 99.16 | 100.00 | 23.78 | 10.04 | 3.74 |
| 2400K Ch2 | 0.61 | 53.09 | 14.11 | 3.40 | 35.58 | 51.81 | 62.20 | 100.00 | 9.75 | 3.44 | 1.12 |
| 2400K Ch1 | 1.37 | 120.36 | 31.99 | 6.89 | 72.41 | 110.44 | 227.23 | 100.00 | 21.24 | 7.89 | 3.50 |
| 1800K Ch1 | 1.23 | 16.50 | 4.14 | 1.92 | 16.29 | 33.63 | 66.28 | 100.00 | 60.07 | 17.91 | 4.88 |
| Exemplary $2^{nd}$ channels min | 0.61 | 16.50 | 4.14 | 1.92 | 16.29 | 33.63 | 62.20 | 100.00 | 9.75 | 3.44 | 1.12 |
| Exemplary $2^{nd}$ channels avg | 1.02 | 66.45 | 17.61 | 3.68 | 40.20 | 67.78 | 113.72 | 100.00 | 28.71 | 9.82 | 3.31 |
| Exemplary $2^{nd}$ channels max | 1.37 | 120.36 | 31.99 | 6.89 | 72.41 | 110.44 | 227.23 | 100.00 | 60.07 | 17.91 | 4.88 |

TABLE 48

|  | 320 < λ ≤ 380 | 380 < λ ≤ 420 | 420 < λ ≤ 460 | 460 < λ ≤ 500 | 500 < λ ≤ 540 | 540 < λ ≤ 580 | 580 < λ ≤ 620 | 620 < λ ≤ 660 | 660 < λ ≤ 700 | 700 < λ ≤ 740 | 740 < λ ≤ 780 |
|---|---|---|---|---|---|---|---|---|---|---|---|
| 4000K Ch4 | 0.39 | 0.59 | 30.88 | 98.73 | 67.12 | 76.66 | 100.00 | 84.15 | 50.00 | 13.89 | 4.63 |
| 4000K Ch2 | 0.54 | 1.99 | 44.28 | 79.86 | 78.17 | 75.94 | 100.00 | 95.38 | 52.20 | 18.93 | 5.61 |
| 4000K Ch3 | 0.29 | 0.70 | 37.77 | 87.23 | 65.19 | 79.15 | 100.00 | 82.62 | 48.47 | 13.93 | 4.68 |
| 5000K Ch1 | 0.01 | 1.49 | 66.19 | 129.05 | 96.22 | 88.49 | 100.00 | 115.83 | 63.66 | 18.66 | 5.03 |
| Exemplary $1^{st}$ channels min | 0.01 | 0.59 | 30.88 | 79.86 | 65.19 | 75.94 | 100.00 | 82.62 | 48.47 | 13.89 | 4.63 |
| Exemplary $1^{st}$ channels avg | 0.31 | 1.19 | 44.78 | 98.72 | 76.68 | 80.06 | 100.00 | 94.49 | 53.58 | 16.35 | 4.99 |
| Exemplary $1^{st}$ channels max | 0.54 | 1.99 | 66.19 | 129.05 | 96.22 | 88.49 | 100.00 | 115.83 | 63.66 | 18.93 | 5.61 |

TABLE 49

|  | 320 < λ ≤ 340 | 340 < λ ≤ 360 | 360 < λ ≤ 380 | 380 < λ ≤ 400 | 400 < λ ≤ 420 | 420 < λ ≤ 440 |
|---|---|---|---|---|---|---|
| 2400K Ch3 | 0.00 | 0.02 | 1.13 | 22.91 | 77.86 | 23.21 |
| 2400K Ch2 | 0.00 | 0.02 | 0.72 | 14.60 | 49.67 | 14.79 |
| 2400K Ch1 | 0.00 | 0.04 | 1.83 | 37.29 | 126.84 | 37.77 |
| 1800K Ch1 | 0.00 | 0.00 | 2.61 | 29.27 | 5.68 | 4.41 |
| Exemplary 2$^{nd}$ channels min | 0.00 | 0.00 | 0.72 | 14.60 | 5.68 | 4.41 |
| Exemplary 2$^{nd}$ channels avg | 0.00 | 0.02 | 1.57 | 26.02 | 65.01 | 20.05 |
| Exemplary 2$^{nd}$ channels max | 0.00 | 0.04 | 2.61 | 37.29 | 126.84 | 37.77 |

|  | 440 < λ ≤ 460 | 460 < λ ≤ 480 | 480 < λ ≤ 500 | 500 < λ ≤ 520 | 520 < λ ≤ 540 | 540 < λ ≤ 560 |
|---|---|---|---|---|---|---|
| 2400K Ch3 | 3.62 | 0.62 | 2.70 | 13.97 | 34.57 | 48.20 |
| 2400K Ch2 | 2.29 | 0.48 | 3.64 | 15.31 | 27.77 | 31.81 |
| 2400K Ch1 | 5.84 | 1.20 | 8.20 | 35.22 | 63.53 | 73.06 |
| 1800K Ch1 | 4.36 | 1.12 | 2.94 | 11.91 | 22.59 | 30.12 |
| Exemplary 2$^{nd}$ channels min | 2.29 | 0.48 | 2.70 | 11.91 | 22.59 | 30.12 |
| Exemplary 2$^{nd}$ channels avg | 4.03 | 0.86 | 4.37 | 19.10 | 37.11 | 45.80 |
| Exemplary 2$^{nd}$ channels max | 5.84 | 1.20 | 8.20 | 35.22 | 63.53 | 73.06 |

|  | 560 < λ ≤ 580 | 580 < λ ≤ 600 | 600 < λ ≤ 620 | 620 < λ ≤ 640 | 640 < λ ≤ 660 | 660 < λ ≤ 680 |
|---|---|---|---|---|---|---|
| 2400K Ch3 | 51.74 | 53.62 | 78.10 | 100.00 | 32.85 | 18.99 |
| 2400K Ch2 | 30.90 | 29.60 | 45.70 | 100.00 | 21.06 | 7.47 |
| 2400K Ch1 | 77.56 | 122.68 | 187.19 | 100.00 | 36.37 | 18.26 |
| 1800K Ch1 | 41.10 | 60.43 | 79.94 | 100.00 | 111.79 | 80.54 |
| Exemplary 2$^{nd}$ channels min | 30.90 | 29.60 | 45.70 | 100.00 | 21.06 | 7.47 |
| Exemplary 2$^{nd}$ channels avg | 50.33 | 66.58 | 97.73 | 100.00 | 50.52 | 31.32 |
| Exemplary 2$^{nd}$ channels max | 77.56 | 122.68 | 187.19 | 100.00 | 111.79 | 80.54 |

|  | 680 < λ ≤ 700 | 700 < λ ≤ 720 | 720 < λ ≤ 740 | 740 < λ ≤ 760 | 760 < λ ≤ 780 | 780 < λ ≤ 800 |
|---|---|---|---|---|---|---|
| 2400K Ch3 | 12.60 | 8.19 | 5.15 | 3.09 | 1.87 | 0.00 |
| 2400K Ch2 | 4.33 | 2.66 | 1.50 | 0.86 | 0.50 | 0.00 |
| 2400K Ch1 | 10.70 | 6.70 | 4.06 | 2.73 | 2.05 | 0.00 |
| 1800K Ch1 | 46.67 | 24.94 | 12.99 | 6.82 | 3.52 | 0.00 |
| Exemplary 2$^{nd}$ channels min | 4.33 | 2.66 | 1.50 | 0.86 | 0.50 | 0.00 |
| Exemplary 2$^{nd}$ channels avg | 18.58 | 10.62 | 5.93 | 3.38 | 1.99 | 0.00 |
| Exemplary 2$^{nd}$ channels max | 46.67 | 24.94 | 12.99 | 6.82 | 3.52 | 0.00 |

TABLE 50

|  | 320 < λ ≤ 340 | 340 < λ ≤ 360 | 360 < λ ≤ 380 | 380 < λ ≤ 400 | 400 < λ ≤ 420 | 420 < λ ≤ 440 |
|---|---|---|---|---|---|---|
| 4000K Ch4 | 0.00 | 0.27 | 0.38 | 0.30 | 0.69 | 5.32 |
| 4000K Ch2 | 0.00 | 0.42 | 0.66 | 0.65 | 3.29 | 22.60 |
| 4000K Ch3 | 0.00 | 0.21 | 0.33 | 0.33 | 0.98 | 10.07 |
| 5000K Ch1 | 0.00 | 0.00 | 0.01 | 0.14 | 1.81 | 22.85 |
| Exemplary 1$^{st}$ channels min | 0.00 | 0.00 | 0.01 | 0.14 | 0.69 | 5.32 |
| Exemplary 1$^{st}$ channels avg | 0.00 | 0.23 | 0.34 | 0.35 | 1.69 | 15.21 |
| Exemplary 1$^{st}$ channels max | 0.00 | 0.42 | 0.66 | 0.65 | 3.29 | 22.85 |

|  | 440 < λ ≤ 460 | 460 < λ ≤ 480 | 480 < λ ≤ 500 | 500 < λ ≤ 520 | 520 < λ ≤ 540 | 540 < λ ≤ 560 |
|---|---|---|---|---|---|---|
| 4000K Ch4 | 46.45 | 65.52 | 100.00 | 61.95 | 50.58 | 58.48 |
| 4000K Ch2 | 65.24 | 58.44 | 100.00 | 82.69 | 72.40 | 71.27 |
| 4000K Ch3 | 60.41 | 62.79 | 100.00 | 64.55 | 57.10 | 67.65 |
| 5000K Ch1 | 63.41 | 68.18 | 100.00 | 67.44 | 57.95 | 57.60 |
| Exemplary 1$^{st}$ channels min | 46.45 | 58.44 | 100.00 | 61.95 | 50.58 | 57.60 |
| Exemplary 1$^{st}$ channels avg | 58.88 | 63.73 | 100.00 | 69.16 | 59.51 | 63.75 |
| Exemplary 1$^{st}$ channels max | 65.24 | 68.18 | 100.00 | 82.69 | 72.40 | 71.27 |

|  | 560 < λ ≤ 580 | 580 < λ ≤ 600 | 600 < λ ≤ 620 | 620 < λ ≤ 640 | 640 < λ ≤ 660 | 660 < λ ≤ 680 |
|---|---|---|---|---|---|---|
| 4000K Ch4 | 70.03 | 82.09 | 85.56 | 75.93 | 65.14 | 58.42 |
| 4000K Ch2 | 79.40 | 93.63 | 104.78 | 102.56 | 86.67 | 63.02 |
| 4000K Ch3 | 80.05 | 92.00 | 94.61 | 83.41 | 70.77 | 62.40 |
| 5000K Ch1 | 57.72 | 62.16 | 68.16 | 75.24 | 75.70 | 52.76 |
| Exemplary 1$^{st}$ channels min | 57.72 | 62.16 | 68.16 | 75.24 | 65.14 | 52.76 |
| Exemplary 1$^{st}$ channels avg | 71.80 | 82.47 | 88.28 | 84.29 | 74.57 | 59.15 |
| Exemplary 1$^{st}$ channels max | 80.05 | 93.63 | 104.78 | 102.56 | 86.67 | 63.02 |

|  | 680 < λ ≤ 700 | 700 < λ ≤ 720 | 720 < λ ≤ 740 | 740 < λ ≤ 760 | 760 < λ ≤ 780 | 780 < λ ≤ 800 |
|---|---|---|---|---|---|---|
| 4000K Ch4 | 25.41 | 14.66 | 8.62 | 4.90 | 2.85 | 0.00 |
| 4000K Ch2 | 40.55 | 23.98 | 13.58 | 7.34 | 3.79 | 0.00 |
| 4000K Ch3 | 28.04 | 16.34 | 9.66 | 5.52 | 3.22 | 0.00 |
| 5000K Ch1 | 30.19 | 15.99 | 8.33 | 4.35 | 2.21 | 0.00 |
| Exemplary 1$^{st}$ channels min | 25.41 | 14.66 | 8.33 | 4.35 | 2.21 | 0.00 |
| Exemplary 1$^{st}$ channels avg | 31.05 | 17.74 | 10.05 | 5.53 | 3.02 | 0.00 |
| Exemplary 1$^{st}$ channels max | 40.55 | 23.98 | 13.58 | 7.34 | 3.79 | 0.00 |

TABLE 51

|  | 320 < λ ≤ 330 | 330 < λ ≤ 340 | 340 < λ ≤ 350 | 350 < λ ≤ 360 | 360 < λ ≤ 370 | 270 < λ ≤ 380 |
|---|---|---|---|---|---|---|
| 2400K Ch3 | 0.00 | 0.00 | 0.00 | 0.04 | 0.26 | 1.62 |
| 2400K Ch2 | 0.00 | 0.00 | 0.00 | 0.03 | 0.18 | 1.16 |
| 2400K Ch1 | 0.00 | 0.00 | 0.00 | 0.06 | 0.40 | 2.52 |
| 1800K Ch1 | 0.00 | 0.00 | 0.00 | 0.00 | 0.00 | 5.56 |
| Exemplary 2$^{nd}$ channels min | 0.00 | 0.00 | 0.00 | 0.00 | 0.00 | 1.16 |
| Exemplary 2$^{nd}$ channels avg | 0.00 | 0.00 | 0.00 | 0.03 | 0.21 | 2.71 |
| Exemplary 2$^{nd}$ channels max | 0.00 | 0.00 | 0.00 | 0.06 | 0.40 | 5.56 |

|  | 380 < λ ≤ 390 | 390 < λ ≤ 400 | 400 < λ ≤ 410 | 410 < λ ≤ 420 | 420 < λ ≤ 430 | 430 < λ ≤ 440 |
|---|---|---|---|---|---|---|
| 2400K Ch3 | 7.91 | 30.16 | 70.32 | 59.07 | 27.46 | 11.12 |
| 2400K Ch2 | 5.65 | 21.61 | 50.41 | 42.34 | 19.67 | 7.95 |
| 2400K Ch1 | 12.31 | 47.07 | 109.79 | 92.21 | 42.85 | 17.31 |
| 1800K Ch1 | 42.52 | 19.80 | 8.19 | 3.91 | 3.64 | 5.74 |
| Exemplary 2$^{nd}$ channels min | 5.65 | 19.80 | 8.19 | 3.91 | 3.64 | 5.74 |
| Exemplary 2$^{nd}$ channels avg | 17.09 | 29.66 | 59.67 | 49.38 | 23.40 | 10.53 |
| Exemplary 2$^{nd}$ channels max | 42.52 | 47.07 | 109.79 | 92.21 | 42.85 | 17.31 |

TABLE 51-continued

| | 440 < λ ≤ 450 | 450 < λ ≤ 460 | 460 < λ ≤ 470 | 470 < λ ≤ 480 | 480 < λ ≤ 490 | 490 < λ ≤ 500 |
|---|---|---|---|---|---|---|
| 2400K Ch3 | 4.33 | 1.69 | 0.71 | 0.33 | 1.29 | 3.19 |
| 2400K Ch2 | 3.08 | 1.19 | 0.48 | 0.42 | 1.82 | 4.97 |
| 2400K Ch1 | 6.72 | 2.59 | 1.05 | 0.86 | 3.52 | 9.54 |
| 1800K Ch1 | 6.09 | 3.19 | 1.41 | 0.98 | 1.87 | 4.39 |
| Exemplary 2$^{nd}$ channels min | 3.08 | 1.19 | 0.48 | 0.33 | 1.29 | 3.19 |
| Exemplary 2$^{nd}$ channels avg | 5.05 | 2.16 | 0.91 | 0.65 | 2.13 | 5.52 |
| Exemplary 2$^{nd}$ channels max | 6.72 | 3.19 | 1.41 | 0.98 | 3.52 | 9.54 |

| | 500 < λ ≤ 510 | 510 < λ ≤ 520 | 520 < λ ≤ 530 | 530 < λ ≤ 540 | 540 < λ ≤ 550 | 550 < λ ≤ 560 |
|---|---|---|---|---|---|---|
| 2400K Ch3 | 7.91 | 15.30 | 24.51 | 32.93 | 38.51 | 41.59 |
| 2400K Ch2 | 10.78 | 17.80 | 24.02 | 27.83 | 29.59 | 29.81 |
| 2400K Ch1 | 21.15 | 34.93 | 46.87 | 54.30 | 57.64 | 58.70 |
| 1800K Ch1 | 9.47 | 15.90 | 21.83 | 26.26 | 30.08 | 34.05 |
| Exemplary 2$^{nd}$ channels min | 7.91 | 15.30 | 21.83 | 26.26 | 29.59 | 29.81 |
| Exemplary 2$^{nd}$ channels avg | 12.33 | 20.98 | 29.31 | 35.33 | 38.95 | 41.04 |
| Exemplary 2$^{nd}$ channels max | 21.15 | 34.93 | 46.87 | 54.30 | 57.64 | 58.70 |

| | 560 < λ ≤ 570 | 570 < λ ≤ 580 | 580 < λ ≤ 590 | 590 < λ ≤ 600 | 600 < λ ≤ 610 | 610 < λ ≤ 620 |
|---|---|---|---|---|---|---|
| 2400K Ch3 | 42.83 | 43.16 | 43.36 | 45.76 | 54.76 | 75.03 |
| 2400K Ch2 | 29.31 | 28.39 | 27.39 | 27.87 | 32.98 | 52.35 |
| 2400K Ch1 | 59.43 | 64.08 | 79.86 | 115.51 | 152.93 | 145.17 |
| 1800K Ch1 | 39.62 | 47.89 | 58.66 | 70.02 | 80.33 | 89.88 |
| Exemplary 2$^{nd}$ channels min | 29.31 | 28.39 | 27.39 | 27.87 | 32.98 | 52.35 |
| Exemplary 2$^{nd}$ channels avg | 42.80 | 45.88 | 52.32 | 64.79 | 80.25 | 90.61 |
| Exemplary 2$^{nd}$ channels max | 59.43 | 64.08 | 79.86 | 115.51 | 152.93 | 145.17 |

| | 620 < λ ≤ 630 | 630 < λ ≤ 640 | 640 < λ ≤ 650 | 650 < λ ≤ 660 | 660 < λ ≤ 670 | 670 < λ ≤ 680 |
|---|---|---|---|---|---|---|
| 2400K Ch3 | 100.00 | 66.18 | 32.55 | 22.04 | 17.39 | 14.17 |
| 2400K Ch2 | 100.00 | 86.71 | 27.42 | 11.91 | 7.93 | 6.02 |
| 2400K Ch1 | 100.00 | 59.25 | 35.20 | 22.72 | 16.72 | 12.37 |
| 1800K Ch1 | 100.00 | 112.92 | 122.48 | 115.54 | 96.01 | 75.48 |
| Exemplary 2$^{nd}$ channels min | 100.00 | 59.25 | 27.42 | 11.91 | 7.93 | 6.02 |
| Exemplary 2$^{nd}$ channels avg | 100.00 | 81.26 | 54.41 | 43.05 | 34.51 | 27.01 |
| Exemplary 2$^{nd}$ channels max | 100.00 | 112.92 | 122.48 | 115.54 | 96.01 | 75.48 |

| | 680 < λ ≤ 690 | 690 < λ ≤ 700 | 700 < λ ≤ 710 | 710 < λ ≤ 720 | 720 < λ ≤ 730 | 730 < λ ≤ 740 |
|---|---|---|---|---|---|---|
| 2400K Ch3 | 11.56 | 9.37 | 7.53 | 6.08 | 4.81 | 3.75 |
| 2400K Ch2 | 4.55 | 3.54 | 2.81 | 2.16 | 1.65 | 1.15 |
| 2400K Ch1 | 9.41 | 7.63 | 5.86 | 4.81 | 3.55 | 2.92 |
| 1800K Ch1 | 57.09 | 42.29 | 30.76 | 22.34 | 16.16 | 11.50 |
| Exemplary 2$^{nd}$ channels min | 4.55 | 3.54 | 2.81 | 2.16 | 1.65 | 1.15 |
| Exemplary 2$^{nd}$ channels avg | 20.65 | 15.71 | 11.74 | 8.85 | 6.54 | 4.83 |
| Exemplary 2$^{nd}$ channels max | 57.09 | 42.29 | 30.76 | 22.34 | 16.16 | 11.50 |

| | 740 < λ ≤ 750 | 750 < λ ≤ 760 | 760 < λ ≤ 770 | 770 < λ ≤ 780 | 780 < λ ≤ 790 | 790 < λ ≤ 800 |
|---|---|---|---|---|---|---|
| 2400K Ch3 | 2.94 | 2.20 | 1.81 | 1.30 | 0.00 | 0.00 |
| 2400K Ch2 | 0.87 | 0.74 | 0.57 | 0.37 | 0.00 | 0.00 |
| 2400K Ch1 | 2.37 | 1.97 | 2.06 | 1.20 | 0.00 | 0.00 |
| 1800K Ch1 | 8.40 | 6.13 | 4.49 | 3.01 | 0.00 | 0.00 |
| Exemplary 2$^{nd}$ channels min | 0.87 | 0.74 | 0.57 | 0.37 | 0.00 | 0.00 |
| Exemplary 2$^{nd}$ channels avg | 3.64 | 2.76 | 2.23 | 1.47 | 0.00 | 0.00 |
| Exemplary 2$^{nd}$ channels max | 8.40 | 6.13 | 4.49 | 3.01 | 0.00 | 0.00 |

TABLE 52

| | 320 < λ ≤ 330 | 330 < λ ≤ 340 | 340 < λ ≤ 350 | 350 < λ ≤ 360 | 360 < λ ≤ 370 | 370 < λ ≤ 380 |
|---|---|---|---|---|---|---|
| 4000K Ch4 | 0.00 | 0.00 | 0.05 | 0.48 | 0.41 | 0.33 |
| 4000K Ch2 | 0.00 | 0.00 | 0.08 | 0.78 | 0.70 | 0.63 |
| 4000K Ch3 | 0.00 | 0.00 | 0.04 | 0.37 | 0.34 | 0.30 |
| 5000K Ch1 | 0.00 | 0.00 | 0.00 | 0.00 | 0.00 | 0.02 |
| Exemplary 1$^{st}$ channels min | 0.00 | 0.00 | 0.00 | 0.00 | 0.00 | 0.02 |
| Exemplary 1$^{st}$ channels avg | 0.00 | 0.00 | 0.04 | 0.41 | 0.36 | 0.32 |
| Exemplary 1$^{st}$ channels max | 0.00 | 0.00 | 0.08 | 0.78 | 0.70 | 0.63 |

| | 380 < λ ≤ 390 | 390 < λ ≤ 400 | 400 < λ ≤ 410 | 410 < λ ≤ 420 | 420 < λ ≤ 430 | 430 < λ ≤ 440 |
|---|---|---|---|---|---|---|
| 4000K Ch4 | 0.28 | 0.31 | 0.46 | 0.90 | 2.35 | 8.04 |
| 4000K Ch2 | 0.60 | 0.71 | 1.61 | 5.09 | 13.75 | 32.22 |
| 4000K Ch3 | 0.29 | 0.35 | 0.58 | 1.35 | 4.22 | 15.53 |
| 5000K Ch1 | 0.17 | 0.15 | 0.35 | 1.50 | 6.59 | 25.07 |
| Exemplary 1$^{st}$ channels min | 0.17 | 0.15 | 0.35 | 0.90 | 2.35 | 8.04 |
| Exemplary 1$^{st}$ channels avg | 0.34 | 0.38 | 0.75 | 2.21 | 6.73 | 20.22 |
| Exemplary 1$^{st}$ channels max | 0.60 | 0.71 | 1.61 | 5.09 | 13.75 | 32.22 |

| | 440 < λ ≤ 450 | 450 < λ ≤ 460 | 460 < λ ≤ 470 | 470 < λ ≤ 480 | 480 < λ ≤ 490 | 490 < λ ≤ 500 |
|---|---|---|---|---|---|---|
| 4000K Ch4 | 29.43 | 61.23 | 58.55 | 69.32 | 100.00 | 95.19 |
| 4000K Ch2 | 63.32 | 69.39 | 51.86 | 67.01 | 100.00 | 103.41 |
| 4000K Ch3 | 49.12 | 69.39 | 55.36 | 67.81 | 100.00 | 96.18 |
| 5000K Ch1 | 83.73 | 95.32 | 87.91 | 118.29 | 100.00 | 89.11 |
| Exemplary 1$^{st}$ channels min | 29.43 | 61.23 | 51.86 | 67.01 | 100.00 | 89.11 |
| Exemplary 1$^{st}$ channels avg | 56.40 | 73.83 | 63.42 | 80.61 | 100.00 | 95.97 |
| Exemplary 1$^{st}$ channels max | 83.73 | 95.32 | 87.91 | 118.29 | 100.00 | 103.41 |

| | 500 < λ ≤ 510 | 510 < λ ≤ 520 | 520 < λ ≤ 530 | 530 < λ ≤ 540 | 540 < λ ≤ 550 | 550 < λ ≤ 560 |
|---|---|---|---|---|---|---|
| 4000K Ch4 | 68.51 | 52.40 | 48.14 | 50.59 | 54.63 | 59.52 |
| 4000K Ch2 | 88.51 | 79.68 | 74.88 | 72.39 | 71.61 | 73.35 |
| 4000K Ch3 | 70.57 | 56.06 | 53.84 | 58.18 | 63.52 | 69.19 |
| 5000K Ch1 | 79.33 | 76.46 | 75.98 | 76.69 | 76.73 | 75.98 |
| Exemplary 1$^{st}$ channels min | 68.51 | 52.40 | 48.14 | 50.59 | 54.63 | 59.52 |
| Exemplary 1$^{st}$ channels avg | 76.73 | 66.15 | 63.21 | 64.46 | 66.62 | 69.51 |
| Exemplary 1$^{st}$ channels max | 88.51 | 79.68 | 75.98 | 76.69 | 76.73 | 75.98 |

TABLE 52-continued

| | 560 < λ ≤ 570 | 570 < λ ≤ 580 | 580 < λ ≤ 590 | 590 < λ ≤ 600 | 600 < λ ≤ 610 | 610 < λ ≤ 620 |
|---|---|---|---|---|---|---|
| 4000K Ch4 | 65.20 | 71.49 | 77.71 | 82.52 | 84.37 | 82.62 |
| 4000K Ch2 | 77.63 | 83.86 | 91.48 | 98.97 | 105.06 | 108.06 |
| 4000K Ch3 | 75.29 | 81.76 | 87.93 | 92.55 | 94.00 | 91.61 |
| 5000K Ch1 | 74.89 | 75.31 | 77.41 | 79.89 | 82.43 | 84.24 |
| Exemplary 1st channels min | 65.20 | 71.49 | 77.41 | 79.89 | 82.43 | 82.62 |
| Exemplary 1st channels avg | 73.25 | 78.10 | 83.63 | 88.48 | 91.47 | 91.63 |
| Exemplary 1st channels max | 77.63 | 83.86 | 91.48 | 98.97 | 105.06 | 108.06 |

| | 620 < λ ≤ 630 | 630 < λ ≤ 640 | 640 < λ ≤ 650 | 650 < λ ≤ 660 | 660 < λ ≤ 670 | 670 < λ ≤ 680 |
|---|---|---|---|---|---|---|
| 4000K Ch4 | 77.44 | 70.77 | 64.70 | 62.44 | 66.81 | 47.21 |
| 4000K Ch2 | 106.77 | 101.86 | 93.61 | 82.68 | 70.31 | 57.88 |
| 4000K Ch3 | 85.60 | 78.02 | 71.00 | 67.84 | 71.44 | 50.98 |
| 5000K Ch1 | 87.47 | 94.30 | 100.45 | 94.12 | 77.38 | 60.02 |
| Exemplary 1st channels min | 77.44 | 70.77 | 64.70 | 62.44 | 66.81 | 47.21 |
| Exemplary 1st channels avg | 89.32 | 86.24 | 82.44 | 76.77 | 71.48 | 54.02 |
| Exemplary 1st channels max | 106.77 | 101.86 | 100.45 | 94.12 | 77.38 | 60.02 |

| | 680 < λ ≤ 690 | 690 < λ ≤ 700 | 700 < λ ≤ 710 | 710 < λ ≤ 720 | 720 < λ ≤ 730 | 730 < λ ≤ 740 |
|---|---|---|---|---|---|---|
| 4000K Ch4 | 28.56 | 21.04 | 16.09 | 12.52 | 9.54 | 7.29 |
| 4000K Ch2 | 46.42 | 36.07 | 27.73 | 21.05 | 15.78 | 11.85 |
| 4000K Ch3 | 31.57 | 23.45 | 18.00 | 14.05 | 10.74 | 8.22 |
| 5000K Ch1 | 45.22 | 33.23 | 24.15 | 17.38 | 12.51 | 8.98 |
| Exemplary 1st channels min | 28.56 | 21.04 | 16.09 | 12.52 | 9.54 | 7.29 |
| Exemplary 1st channels avg | 37.94 | 28.44 | 21.49 | 16.25 | 12.14 | 9.08 |
| Exemplary 1st channels max | 46.42 | 36.07 | 27.73 | 21.05 | 15.78 | 11.85 |

| | 740 < λ ≤ 750 | 750 < λ ≤ 760 | 760 < λ ≤ 770 | 770 < λ ≤ 780 | 780 < λ ≤ 790 | 790 < λ ≤ 800 |
|---|---|---|---|---|---|---|
| 4000K Ch4 | 5.50 | 4.07 | 3.17 | 2.40 | 0.00 | 0.00 |
| 4000K Ch2 | 8.63 | 6.29 | 4.50 | 3.21 | 0.00 | 0.00 |
| 4000K Ch3 | 6.22 | 4.61 | 3.61 | 2.72 | 0.00 | 0.00 |
| 5000K Ch1 | 6.52 | 4.67 | 3.43 | 2.24 | 0.00 | 0.00 |
| Exemplary 1st channels min | 5.50 | 4.07 | 3.17 | 2.24 | 0.00 | 0.00 |
| Exemplary 1st channels avg | 6.72 | 4.91 | 3.68 | 2.64 | 0.00 | 0.00 |
| Exemplary 1st channels max | 8.63 | 6.29 | 4.50 | 3.21 | 0.00 | 0.00 |

TABLE 53

| | 400 < λ ≤ 470 nm | 470 < λ ≤ 510 nm | 530 < λ ≤ 570 nm | 600 < λ ≤ 630 nm | 630 < λ ≤ 780 nm |
|---|---|---|---|---|---|
| 2400K Ch3 | 14.063 | 1.000 | 12.431 | 18.374 | 16.714 |
| 2400K Ch2 | 7.136 | 1.000 | 6.611 | 10.443 | 9.461 |
| 2400K Ch1 | 7.971 | 1.000 | 6.693 | 11.715 | 5.576 |
| 1800K Ch1 | 1.990 | 1.000 | 7.873 | 16.512 | 43.711 |
| Exemplary 2nd channels min | 1.990 | 1.000 | 6.611 | 10.443 | 5.576 |
| Exemplary 2nd channels avg | 7.790 | 1.000 | 8.402 | 14.261 | 18.866 |
| Exemplary 2nd channels max | 14.063 | 1.000 | 12.431 | 18.374 | 43.711 |

TABLE 53-continued

| | 400 < λ ≤ 470 nm | 470 < λ ≤ 510 nm | 530 < λ ≤ 570 nm | 600 < λ ≤ 630 nm | 630 < λ ≤ 780 nm |
|---|---|---|---|---|---|
| 4000K Ch4 | 0.475 | 1.000 | 0.693 | 0.746 | 1.268 |
| 4000K Ch2 | 0.652 | 1.000 | 0.830 | 0.906 | 1.643 |
| 4000K Ch3 | 0.575 | 1.000 | 0.799 | 0.825 | 1.385 |
| 5000K Ch1 | 0.634 | 1.000 | 0.652 | 0.596 | 1.493 |
| Exemplary 1st channels min | 0.475 | 1.000 | 0.652 | 0.596 | 1.268 |
| Exemplary 1st channels avg | 0.584 | 1.000 | 0.744 | 0.769 | 1.447 |
| Exemplary 1st channels max | 0.652 | 1.000 | 0.830 | 0.906 | 1.643 |

TABLE 54

EML Slope vs. CCT (per 1000K) for Pairings of Exemplary First/Second Lighting Channels

| | 4000K Ch1 | 4000K Ch2 | 4000K Ch3 | 4000K Ch4 | 5000K Ch1 |
|---|---|---|---|---|---|
| 2400K Ch1 | 0.305 | 0.363 | 0.374 | 0.396 | 0.305 |
| 2400K Ch2 | 0.284 | 0.342 | 0.353 | 0.375 | 0.292 |
| 2400K Ch3 | 0.320 | 0.377 | 0.389 | 0.411 | 0.314 |
| 1800K Ch1 | 0.265 | 0.307 | 0.315 | 0.332 | 0.277 |

TABLE 55

EML Ratio of First Lighting Channel to Second Lighting Channel for Pairings of Exemplary First/Second Lighting Channels

| | 4000K Ch1 | 4000K Ch2 | 4000K Ch3 | 4000K Ch4 | 5000K Ch1 |
|---|---|---|---|---|---|
| 2400K Ch1 | 2.6 | 2.9 | 2.9 | 3.1 | 3.6 |
| 2400K Ch2 | 2.3 | 2.6 | 2.6 | 2.8 | 3.2 |
| 2400K Ch3 | 2.8 | 3.1 | 3.1 | 3.3 | 3.9 |
| 1800K Ch1 | 3.7 | 4.2 | 4.2 | 4.4 | 5.2 |

TABLE 56

% Spectral Energy in Wavelength Range vs. Total Energy 320 nm to 800 nm

| | 400 < λ ≤ 410 | 410 < λ ≤ 420 | 420 < λ ≤ 430 | 430 < λ ≤ 440 | 440 < λ ≤ 450 | 450 < λ ≤ 460 |
|---|---|---|---|---|---|---|
| 2400K Ch3 | 7.11 | 5.97 | 2.78 | 1.12 | 0.44 | 0.17 |
| 2400K Ch2 | 6.65 | 5.59 | 2.60 | 1.05 | 0.41 | 0.16 |
| 2400K Ch1 | 7.19 | 6.04 | 2.81 | 1.13 | 0.44 | 0.17 |
| 1800K Ch1 | 0.56 | 0.27 | 0.25 | 0.39 | 0.42 | 0.22 |
| Exemplary 2nd channels min | 0.56 | 0.27 | 0.25 | 0.39 | 0.41 | 0.16 |
| Exemplary 2nd channels avg | 5.38 | 4.47 | 2.11 | 0.93 | 0.43 | 0.18 |
| Exemplary 2nd channels max | 7.19 | 6.04 | 2.81 | 1.13 | 0.44 | 0.22 |
| 4000K Ch4 | 0.03 | 0.05 | 0.14 | 0.47 | 1.71 | 3.55 |
| 4000K Ch2 | 0.07 | 0.23 | 0.62 | 1.44 | 2.84 | 3.11 |
| 4000K Ch3 | 0.03 | 0.07 | 0.22 | 0.82 | 2.58 | 3.64 |
| 5000K Ch1 | 0.02 | 0.07 | 0.30 | 1.13 | 3.78 | 4.30 |
| Exemplary 1st channels min | 0.02 | 0.05 | 0.14 | 0.47 | 1.71 | 3.11 |
| Exemplary 1st channels avg | 0.04 | 0.10 | 0.32 | 0.96 | 2.73 | 3.65 |
| Exemplary 1st channels max | 0.07 | 0.23 | 0.62 | 1.44 | 3.78 | 4.30 |

TABLE 56-continued

% Spectral Energy in Wavelength Range vs. Total Energy 320 nm to 800 nm

| | 460 < λ ≤ 470 | 470 < λ ≤ 480 | 480 < λ ≤ 490 | 490 < λ ≤ 500 | 500 < λ ≤ 510 | 510 < λ ≤ 520 |
|---|---|---|---|---|---|---|
| 2400K Ch3 | 0.071 | 0.033 | 0.13 | 0.32 | 0.80 | 1.55 |
| 2400K Ch2 | 0.064 | 0.056 | 0.24 | 0.66 | 1.42 | 2.35 |
| 2400K Ch1 | 0.069 | 0.056 | 0.23 | 0.62 | 1.38 | 2.29 |
| 1800K Ch1 | 0.097 | 0.067 | 0.13 | 0.30 | 0.65 | 1.09 |
| Exemplary 2$^{nd}$ channels min | 0.064 | 0.033 | 0.13 | 0.30 | 0.65 | 1.09 |
| Exemplary 2$^{nd}$ channels avg | 0.075 | 0.053 | 0.18 | 0.48 | 1.06 | 1.82 |
| Exemplary 2$^{nd}$ channels max | 0.097 | 0.067 | 0.24 | 0.66 | 1.42 | 2.35 |
| 4000K Ch4 | 3.40 | 4.02 | 5.80 | 5.52 | 3.97 | 3.04 |
| 4000K Ch2 | 2.32 | 3.00 | 4.48 | 4.63 | 3.97 | 3.57 |
| 4000K Ch3 | 2.91 | 3.56 | 5.25 | 5.05 | 3.71 | 2.94 |
| 5000K Ch1 | 3.97 | 5.34 | 4.51 | 4.02 | 3.58 | 3.45 |
| Exemplary 1$^{st}$ channels min | 2.32 | 3.00 | 4.48 | 4.02 | 3.58 | 2.94 |
| Exemplary 1$^{st}$ channels avg | 3.15 | 3.98 | 5.01 | 4.81 | 3.81 | 3.25 |
| Exemplary 1$^{st}$ channels max | 3.97 | 5.34 | 5.80 | 5.52 | 3.97 | 3.57 |

TABLE 57

| ANSI Nominal CCT Boundary | Center CCT | duv | Tolerance dCCT | dduv | | Center | Boundaries 1 | 2 | 3 | 4 |
|---|---|---|---|---|---|---|---|---|---|---|
| 2200 | 2238 | −0.0942 | ±102 | ±5.3 | Cx | 0.5018 | 0.4838 | 0.5046 | 0.5262 | 0.5025 |
| | | | | | Cy | 0.4153 | 0.3977 | 0.4007 | 0.4381 | 0.4348 |
| 2500 | 2470 | −0.3065 | ±109 | ±5.7 | Cx | 0.4792 | 0.4593 | 0.4838 | 0.5025 | 0.4813 |
| | | | | | Cy | 0.4131 | 0.3944 | 0.3977 | 0.4348 | 0.4319 |
| 2700 | 2725 | −0.0837 | ±145 | ±6.0 | Cx | 0.4578 | 0.4813 | 0.4562 | 0.4373 | 0.4593 |
| | | | | | Cy | 0.4101 | 0.4319 | 0.4260 | 0.3893 | 0.3944 |
| 3000 | 3045 | −0.0773 | ±175 | ±6.0 | Cx | 0.4338 | 0.4562 | 0.4299 | 0.4147 | 0.4373 |
| | | | | | Cy | 0.403 | 0.4260 | 0.4165 | 0.3814 | 0.3893 |
| 3500 | 3464 | −0.0698 | ±245 | ±6.0 | Cx | 0.4073 | 0.4299 | 0.3996 | 0.3889 | 0.4147 |
| | | | | | Cy | 0.3917 | 0.4165 | 0.4015 | 0.369 | 0.3814 |
| 4000 | 3985 | 0.9845 | ±275 | ±6.0 | Cx | 0.3818 | 0.4006 | 0.3736 | 0.3670 | 0.3898 |
| | | | | | Cy | 0.3797 | 0.4044 | 0.3874 | 0.3578 | 0.3716 |
| 5000 | 5027 | 2.0112 | ±283 | ±6.0 | Cx | 0.3447 | 0.3551 | 0.3376 | 0.3366 | 0.3515 |
| | | | | | Cy | 0.3553 | 0.376 | 0.3616 | 0.3369 | 0.3487 |
| 5700 | 5666 | 2.0235 | ±355 | ±6.0 | Cx | 0.3287 | 0.3376 | 0.3207 | 0.3222 | 0.3366 |
| | | | | | Cy | 0.3417 | 0.3616 | 0.3462 | 0.3243 | 0.3369 |
| 6500 | 6532 | 2.9989 | ±510 | ±6.0 | Cx | 0.3123 | 0.3205 | 0.3028 | 0.3068 | 0.3221 |
| | | | | | Cy | 0.3282 | 0.3481 | 0.3304 | 0.3113 | 0.3261 |

TABLE 58

| | 380 < λ ≤ 420 | 420 < λ ≤ 460 | 460 < λ ≤ 500 | 500 < λ ≤ 540 | 540 < λ ≤ 580 | 580 < λ ≤ 620 | 620 < λ ≤ 660 | 660 < λ ≤ 700 | 700 < λ ≤ 740 | 740 < λ ≤ 780 |
|---|---|---|---|---|---|---|---|---|---|---|
| Red | 0.2 | 1.4 | 0.7 | 7.3 | 22.3 | 59.8 | 100.0 | 61.2 | 18.1 | 4.9 |
| Cyan | 0.7 | 15.9 | 33.5 | 98.2 | 100.0 | 68.6 | 47.1 | 22.1 | 6.3 | 1.7 |

TABLE 59

| | 380 < λ ≤ 400 | 400 < λ ≤ 420 | 420 < λ ≤ 440 | 440 < λ ≤ 460 | 460 < λ ≤ 480 | 480 < λ ≤ 500 | 500 < λ ≤ 520 | 520 < λ ≤ 540 | 540 < λ ≤ 560 | 560 < λ ≤ 580 | 580 < λ ≤ 600 |
|---|---|---|---|---|---|---|---|---|---|---|---|
| Red | 0.0 | 0.3 | 1.4 | 1.3 | 0.4 | 0.9 | 4.2 | 9.4 | 15.3 | 26.4 | 45.8 |
| Cyan | 0.2 | 1.2 | 8.1 | 22.2 | 17.5 | 46.3 | 88.2 | 98.5 | 100.0 | 90.2 | 73.4 |

| | 600 < λ ≤ 620 | 620 < λ ≤ 640 | 640 < λ ≤ 660 | 660 < λ ≤ 680 | 680 < λ ≤ 700 | 700 < λ ≤ 720 | 720 < λ ≤ 740 | 740 < λ ≤ 760 | 760 < λ ≤ 780 | 780 < λ ≤ 800 |
|---|---|---|---|---|---|---|---|---|---|---|
| Red | 66.0 | 87.0 | 100.0 | 72.5 | 42.0 | 22.3 | 11.6 | 6.1 | 3.1 | 0.0 |
| Cyan | 57.0 | 48.1 | 41.4 | 27.0 | 15.1 | 7.9 | 4.0 | 2.1 | 1.0 | 0.0 |

TABLE 60

| CCT | duv | White Channel Relative Intensity | Cyan Channel Relative Intensity | Red Channel Relative Intensity | Ra | R9 | ccx | ccy | Rf | Rg | COI | R13 | R15 | LER | CLA | CS |
|---|---|---|---|---|---|---|---|---|---|---|---|---|---|---|---|---|
| 3200 | 0.53 | 0.57 | 0.22 | 0.21 | 89.9 | 59.6 | 0.424 | 0.4005 | 88 | 102 | 2.42 | 90.1 | 87.3 | 296.5 | 1007 | 0.531 |
| 3102 | 0.31 | 0.52 | 0.24 | 0.24 | 90.8 | 63.8 | 0.4303 | 0.4024 | 89 | 102 | 2.82 | 91.2 | 88.6 | 292.8 | 977 | 0.527 |
| 3001 | −0.04 | 0.47 | 0.26 | 0.27 | 91.7 | 67.7 | 0.4368 | 0.4039 | 89 | 102 | 3.42 | 92.2 | 89.9 | 288.9 | 946 | 0.522 |
| 2903 | 0.39 | 0.42 | 0.28 | 0.30 | 92.6 | 71.7 | 0.4446 | 0.4075 | 90 | 102 | | 93.3 | 91.0 | 285.3 | 909 | 0.516 |
| 2801 | 0.31 | 0.37 | 0.30 | 0.33 | 93.5 | 75.1 | 0.4522 | 0.4095 | 91 | 103 | | 94.3 | 92.1 | 281.1 | 873 | 0.510 |
| 2702 | 0.68 | 0.32 | 0.31 | 0.37 | 94.4 | 78.4 | 0.4609 | 0.4126 | 91 | 103 | | 95.3 | 93.0 | 276.9 | 833 | 0.503 |
| 2599 | −0.1 | 0.27 | 0.32 | 0.41 | 95.0 | 80.1 | 0.4681 | 0.412 | 91 | 104 | | 96.2 | 93.8 | 272.0 | 801 | 0.497 |
| 2509 | 0.66 | 0.23 | 0.33 | 0.44 | 95.7 | 82.5 | 0.4774 | 0.4156 | 92 | 103 | | 97.0 | 94.4 | 268.1 | 758 | 0.488 |
| 2403 | 0.46 | 0.18 | 0.33 | 0.48 | 96.3 | 83.5 | 0.4867 | 0.4161 | 92 | 103 | | 97.7 | 94.9 | 262.9 | 717 | 0.479 |
| 2296 | −0.09 | 0.14 | 0.33 | 0.52 | 96.6 | 83.4 | 0.4959 | 0.4149 | 92 | 104 | | 98.3 | 95.0 | 257.2 | 677 | 0.469 |
| 2203 | −0.18 | 0.11 | 0.33 | 0.57 | 96.7 | 82.9 | 0.5049 | 0.4146 | 91 | 104 | | 98.6 | 94.9 | 252.1 | 636 | 0.459 |
| 2099 | 0.19 | 0.07 | 0.32 | 0.61 | 96.8 | 81.9 | 0.5165 | 0.4152 | 92 | 103 | | 98.7 | 94.5 | 246.4 | 585 | 0.444 |
| 2010 | −0.28 | 0.04 | 0.30 | 0.66 | 96.4 | 79.4 | 0.525 | 0.4126 | 90 | 104 | | 98.5 | 93.8 | 241.0 | 547 | 0.431 |
| 1902 | −0.37 | 0.01 | 0.27 | 0.72 | 95.8 | 75.6 | 0.5366 | 0.4101 | 89 | 103 | | 97.7 | 92.4 | 234.3 | 494 | 0.413 |
| 1797 | −0.12 | 0.00 | 0.23 | 0.77 | 94.9 | 70.8 | 0.5493 | 0.4078 | 88 | 102 | | 96.5 | 90.5 | 227.6 | 436 | 0.389 |

TABLE 61

| | 320 < λ ≤ 400 | 400 < λ ≤ 500 | 500 < λ ≤ 600 | 600 < λ ≤ 700 | 700 < λ ≤ 800 | 800 < λ ≤ 900 | 900 < λ ≤ 1000 |
|---|---|---|---|---|---|---|---|
| Long-Red Phosphor 675 nm | 0.25 | 0.82 | 3.08 | 100.00 | 44.06 | 1.09 | 0.00 |
| Long-Red Phosphor 700 nm | 0.01 | 1.28 | 1.66 | 100.00 | 110.30 | 5.36 | 0.00 |

TABLE 62

| | 320 < λ ≤ 380 | 380 < λ ≤ 420 | 420 < λ ≤ 460 | 460 < λ ≤ 500 | 500 < λ ≤ 540 | 540 < λ ≤ 580 | 580 < λ ≤ 620 | 620 < λ ≤ 660 |
|---|---|---|---|---|---|---|---|---|
| Long-Red Phosphor 675 nm | 0.2 | 1.0 | 0.9 | 0.8 | 0.8 | 2.3 | 20.2 | 100.0 |
| Long-Red Phosphor 700 nm | 0.0 | 1.2 | 2.2 | 2.0 | 1.8 | 2.0 | 12.1 | 100.0 |

| | 660 < λ ≤ 700 | 700 < λ ≤ 740 | 740 < λ ≤ 780 | 780 < λ ≤ 820 | 820 < λ ≤ 860 | 860 < λ ≤ 900 | 900 < λ ≤ 1000 |
|---|---|---|---|---|---|---|---|
| Long-Red Phosphor 675 nm | 145.6 | 81.9 | 28.1 | 7.4 | 0.4 | 0.0 | 0.0 |
| Long-Red Phosphor 700 nm | 314.0 | 304.1 | 134.9 | 41.7 | 8.7 | 0.0 | 0.0 |

TABLE 63

| | 320 < λ ≤ 340 | 340 < λ ≤ 360 | 360 < λ ≤ 380 | 380 < λ ≤ 400 | 400 < λ ≤ 420 | 420 < λ ≤ 440 | 440 < λ ≤ 460 | 460 < λ ≤ 480 | 480 < λ ≤ 500 | 500 < λ ≤ 520 | 520 < λ ≤ 540 | 540 < λ ≤ 560 |
|---|---|---|---|---|---|---|---|---|---|---|---|---|
| Long-Red Phosphor 675 nm | 0.0 | 0.0 | 0.2 | 0.8 | 0.7 | 0.7 | 0.7 | 0.6 | 0.6 | 0.6 | 0.6 | 1.0 |
| Long-Red Phosphor 700 nm | 0.0 | 0.0 | 0.0 | 0.1 | 1.6 | 1.6 | 1.5 | 1.4 | 1.4 | 1.3 | 1.3 | 1.3 |

TABLE 63-continued

| | 560 < λ ≤ 580 | 580 < λ ≤ 600 | 600 < λ ≤ 620 | 620 < λ ≤ 640 | 640 < λ ≤ 660 | 660 < λ ≤ 680 | 680 < λ ≤ 700 | 700 < λ ≤ 720 | 720 < λ ≤ 740 | 740 < λ ≤ 760 | 760 < λ ≤ 780 | 780 < λ ≤ 800 |
|---|---|---|---|---|---|---|---|---|---|---|---|---|
| Long-Red Phosphor 675 nm | 2.7 | 7.9 | 24.2 | 58.6 | 100.0 | 121.2 | 109.6 | 79.7 | 50.2 | 28.9 | 15.7 | 7.9 |
| Long-Red Phosphor 700 nm | 1.6 | 4.3 | 12.5 | 38.2 | 100.0 | 187.6 | 246.3 | 238.7 | 181.5 | 117.4 | 69.0 | 38.2 |

| | 800 < λ ≤ 820 | 820 < λ ≤ 840 | 840 < λ ≤ 860 | 860 < λ ≤ 880 | 880 < λ ≤ 900 | 900 < λ ≤ 920 | 920 < λ ≤ 940 | 940 < λ ≤ 960 | 960 < λ ≤ 980 | 980 < λ ≤ 1000 |
|---|---|---|---|---|---|---|---|---|---|---|
| Long-Red Phosphor 675 nm | 3.9 | 0.4 | 0.2 | 0.0 | 0.0 | 0.0 | 0.0 | 0.0 | 0.0 | 0.0 |
| Long-Red Phosphor 700 nm | 19.4 | 9.7 | 2.3 | 0.0 | 0.0 | 0.0 | 0.0 | 0.0 | 0.0 | 0.0 |

TABLE 64

Relative Intensities

| 6500K White Channel | Long-Red Channel A | Lime Channel | x | y | CCT | duv | Ra | R9 | R13 | R15 | LER | COI |
|---|---|---|---|---|---|---|---|---|---|---|---|---|
| 0.8865 | 1 | 0.1293 | 0.3449 | 0.3519 | 5008.78 | 0.23 | 88.4 | 84.75 | 88.44 | 92.55 | 192.48 | 3.49 |
| 0.5303 | 1 | 0.1293 | 0.3608 | 0.3653 | 4509.54 | 0.87 | 88.54 | 89.8 | 90.42 | 96.75 | 169.13 | 2.17 |
| 0.2955 | 1 | 0.1135 | 0.3811 | 0.3787 | 3996.84 | 0.72 | 87.37 | 58.57 | 94.39 | 93.81 | 143.52 | 4.68 |
| 0.1557 | 1 | 0.095 | 0.4044 | 0.3909 | 3520.12 | 0.27 | 84.46 | 26.26 | 98.67 | 83.99 | 120.72 | 8.27 |
| 0.58 | 1 | 0.0712 | 0.4361 | 0.4018 | 2995.9 | −0.77 | 77.86 | −10.82 | 91.38 | 70.48 | 97.24 | 12.64 |

| GAI | GAI 15 | GAI_BB from Xicato | circadian power [mW] | circadian flux | CER (Circadian power per flux) [mW/lm] | CAF | EML | CLA | CS | Rf | Rg |
|---|---|---|---|---|---|---|---|---|---|---|---|
| 89.3918 | 247.7747 | 102.3761 | 200.0924 | 68.83046 | 135.0304 | 0.688305 | 0.818667 | 1036 | 0.5350 | 77 | 113 |
| 86.36168 | 237.7839 | 104.7505 | 187.755 | 61.27427 | 105.8975 | 0.612743 | 0.749807 | 845 | 0.5050 | 82 | 108 |
| 82.4943 | 224.7706 | 108.289 | 174.3035 | 53.37002 | 78.47837 | 0.5337 | 0.675682 | 647 | 0.4610 | 84 | 105 |
| 76.99131 | 207.4282 | 112.2712 | 160.6609 | 45.65426 | 56.59859 | 0.456543 | 0.601369 | 456 | 0.3980 | 85 | 102 |
| 68.36505 | 181.6168 | 118.6679 | 144.515 | 37.06582 | 37.09475 | 0.370658 | 0.514983 | 944 | 0.5220 | 85 | 100 |

| BLH | CP | MSI |
|---|---|---|
| 685.0497 | 589.8182 | 0.6360303 |
| 598.3081 | 508.7375 | 0.571554 |
| 509.4471 | 424.6709 | 0.5047331 |
| 424.4634 | 343.3108 | 0.4400915 |
| 333.168 | 254.066 | 0.3692386 |

TABLE 65

| 6500K White Channel | Long-Red Channel B | Lime Channel | x | y | CCT | duv | Ra | R9 | R13 | R15 | LER | COI |
|---|---|---|---|---|---|---|---|---|---|---|---|---|
| 1 | 0.1346 | 0.0396 | 0.3219 | 0.3314 | 6007.86 | −0.08 | 83.53 | 17.69 | 84.14 | 79.56 | 277.79 | 11.37 |
| 1 | 0.248 | 0.844 | 0.3326 | 0.3409 | 5493.5 | −0.09 | 83.69 | 21.07 | 84.14 | 79.93 | 265.75 | 9.93 |
| 1 | 0.409 | 0.1372 | 0.3448 | 0.3508 | 5006.6 | −0.28 | 83.89 | 24.77 | 84.26 | 80.42 | 251.83 | 8.37 |
| 1 | 0.6675 | 0.2296 | 0.3612 | 0.3647 | 4493.04 | 0.43 | 84.17 | 30.16 | 84.36 | 80.48 | 237.51 | 6.59 |
| 0.9156 | 1 | 0.314 | 0.3802 | 0.3778 | 4012.59 | 0.54 | 84.93 | 36.38 | 85.18 | 81.84 | 219.73 | 4.7 |
| 0.5172 | 1 | 0.2639 | 0.405 | 0.3909 | 3507.24 | 0.14 | 86.2 | 44.03 | 86.79 | 83.92 | 197.34 | 2.92 |
| 0.2612 | 1 | 0.2984 | 0.4361 | 0.4029 | 3003.81 | −0.35 | 87.59 | 50.12 | 88.69 | 85.75 | 172.6 | 3.38 |
| 0.1477 | 1 | 0.1768 | 0.4599 | 0.4104 | 2697.76 | −0.06 | 88.14 | 51.34 | 89.44 | 85.98 | 156.99 | 5.13 |
| 0.0712 | 1 | 0.1424 | 0.4847 | 0.4146 | 2416.08 | 0.03 | 88.49 | 50.71 | 89.99 | 85.57 | 141.65 | 7.51 |
| 0 | 1 | 0.1003 | 0.5189 | 0.4161 | 2083.7 | 0.52 | 87.92 | 45.4 | 89.4 | 83.48 | 122.99 | 11.29 |

TABLE 65-continued

| GAI | GAI 15 | GAI_BB from Xicato | circadian power [mW] | circadian flux | CER(Circadian power per flux) [mW/lm] | CAF (Circadian action factor | EML |
|---|---|---|---|---|---|---|---|
| 80.57328 | 223.6145 | 98.74652 | 184.8974 | 60.92392 | 150.7386 | 0.609239 | 0.73978 |
| 89.00904 | 248.8449 | 94.32858 | 219.2939 | 81.08612 | 229.4777 | 0.810861 | 0.927833 |
| 87.26652 | 243.1491 | 95.83119 | 209.1279 | 75.06076 | 204.6299 | 0.750608 | 0.872042 |
| 85.06854 | 236.2083 | 97.61831 | 198.4347 | 68.86227 | 179.2151 | 0.688623 | 0.813802 |
| 75.36568 | 209.2179 | 100.4704 | 171.0594 | 53.1747 | 122.7729 | 0.531747 | 0.665282 |
| 68.27042 | 190.0996 | 103.2834 | 155.1128 | 44.71606 | 93.63939 | 0.447161 | 0.58094 |
| 58.35771 | 164.1613 | 106.8799 | 137.1443 | 35.7349 | 66.11522 | 0.357349 | 0.487668 |
| 49.46872 | 141.1403 | 107.4254 | 124.2603 | 29.50503 | 49.96062 | 0.29505 | 0.421466 |
| 40.30136 | 116.8644 | 107.9179 | 111.5604 | 23.83105 | 36.61357 | 0.238311 | 0.35771 |
| 27.3726 | 80.81314 | 103.4908 | 94.56875 | 16.80205 | 22.55986 | 0.168021 | 0.27422 |

| CLA | Circadian Stimulus (CS) | Rf | Rg | BLH | CP | MSI |
|---|---|---|---|---|---|---|
| 1350 | 0.569 | 81 | 95 | 596.6085 | 515.0455 | 0.5634632 |
| 1199 | 0.555 | 81 | 96 | 826.8956 | 724.4693 | 0.7392685 |
| 1044 | 0.536 | 82 | 96 | 757.7669 | 661.628 | 0.6867125 |
| 845 | 0.505 | 82 | 96 | 687.2929 | 597.513 | 0.6326828 |
| 654 | 0.463 | 83 | 98 | 509.7835 | 435.9521 | 0.4959888 |
| 450 | 0.395 | 84 | 99 | 417.305 | 351.5219 | 0.4224674 |
| 901 | 0.515 | 85 | 101 | 321.9402 | 264.2208 | 0.3445643 |
| 770 | 0.491 | 85 | 102 | 256.9346 | 204.6135 | 0.2905909 |
| 647 | 0.461 | 84 | 103 | 200.3619 | 152.5087 | 0.2415826 |
| 488 | 0.41 | 81 | 103 | 133.7106 | 90.80759 | 0.1810649 |

In some implementations, with reference to FIG. 44, different combinations of lighting channels 105A-F can be present in the lighting systems of the present disclosure. Each lighting channel 105A-F can emit light at a particular color point on the 1931 CIE Chromaticity Diagram and with particular spectral power characteristics. By utilizing different combinations of lighting channels, different operational modes can be provided that can provide tunable white light between particular CCT values and with particular characteristics. In some implementations, the different operational modes can provide for substantially different circadian-stimulating energy characteristics. A first LED string 101A and a first luminophoric medium 102A together can emit a first light having a first color point within a blue color range. The combination of the first LED string 101A and the first luminophoric medium 102A are also referred to herein as a "blue channel" 105A. A second LED string 101B and a second luminophoric medium 102B together can emit a second light having a second color point within a red color range. The combination of the second LED string 101A and the second luminophoric medium 102A are also referred to herein as a "red channel" 105B. A third LED string 101C and a third luminophoric medium 102C together can emit a third light having a third color point within a short-blue-pumped cyan color range. The combination of the third LED string 101C and the third luminophoric medium 102C are also referred to herein as a "short-blue-pumped cyan channel" 105C. A fourth LED string 101D and a fourth luminophoric medium 102D together can emit a fourth light having a fourth color point within a long-blue-pumped cyan color range. The combination of the fourth LED string 101D and the fourth luminophoric medium 102D are also referred to herein as a "long-blue-pumped cyan channel" 105D. A fifth LED string 101E and a fifth luminophoric medium 102E together than emit a fifth light having a fifth color point within a yellow color range. The combination of the fifth LED string 101E and the fifth luminophoric medium 102E are also referred to herein as a "yellow channel" 105E. A sixth LED string 101E and a sixth luminophoric medium 102F together than emit a sixth light having a fifth color point within a violet color range. The combination of the sixth LED string 101F and the sixth luminophoric medium 102F are also referred to herein as a "violet channel" 105F. It should be understood that the use of the terms "blue", "red", "cyan", "yellow", and "violet" for the color ranges and channels are not meant to be limiting in terms of actual color outputs, but are used as a naming convention herein, as those of skill in the art will appreciate that color points within color ranges on the 1931 CIE Chromaticity Diagram for the channels may not have the visual appearance of what may commonly be referred to as "blue" "red", "cyan", "yellow", and "violet" by laymen, and may have the appearance of other colored light or white or near-white light, for example, in some implementations.

The first, second, third, fourth, fifth, and sixth LED strings 101A-F can be provided with independently applied on-state drive currents in order to tune the intensity of the first, second, third, and fourth unsaturated light produced by each string and luminophoric medium together. By varying the drive currents in a controlled manner, the color coordinate (ccx, ccy) of the total light that is emitted from the device 100 can be tuned. In some implementations, the device 100 can provide light at substantially the same color coordinate with different spectral power distribution profiles, which can result in different light characteristics at the same CCT. In some implementations, white light can be generated in modes that produce light from different combinations of two, three, or four of the LED strings 101A-F. In some implementations, white light is generated using only the first, second, and third LED strings, i.e. the blue, red, and short-blue-pumped cyan channels, referred to herein as "high-CRI mode". In other implementations, white light is generated using the first, second, third, and fourth LED strings, i.e., the blue, red, short-blue-pumped cyan, and long-blue-pumped cyan channels, in what is also referred to herein as a "highest—CRI mode". In further implementations, white light can be generated using the first, second, and fourth LED strings, i.e. the blue, red, and long-bluepumped cyan channels, in what is also referred to herein as a "high-EML mode". In other implementations, white light can be generated using the first, second, fifth, and sixth LED strings, i.e. the blue, red, yellow, and violet channels, in what is also referred to herein as a "low-EML mode". In yet further implementations, white light can be generated using the second, fifth, and sixth LED strings, i.e. the red, yellow, and violet channels, in what is also referred to herein as a "very-low-EML mode". In some implementations, only two of the LED strings are producing light during the generation of white light in any one of the operational modes described herein, as the other two LED strings are not necessary to generate white light at the desired color point with the desired color rendering performance. In certain implementations, substantially the same color coordinate (ccx, ccy) of total light emitted from the device can be provided in two different operational modes (different combinations of two or more of the channels), but with different color-rendering, circadian, or other performance metrics, such that the functional characteristics of the generated light can be selected as desired by users.

In some implementations, the semiconductor light emitting devices 100 of the disclosure can comprise only three, four, or five of the lighting channels described herein. FIG. 47 illustrates a device 100 having only three LED strings 101X/101Y/101Z with associated luminophoric mediums 102X/102Y/102Z. The three channels depicted can be any combination of three of lighting channels described elsewhere throughout this disclosure. In some implementations, red, blue, and long-blue-pumped cyan channels are provided. In other implementations, red, blue, and short-blue-pumped cyan channels are provided. In other implementations, red, short-blue-pumped cyan, and long-blue-pumped cyan channels are provided. In yet other implementations, blue, short-blue-pumped cyan, and long-blue-pumped cyan channels are provided. In further implementations, red, yellow, and violet channels are provided. In further implementations, one of the three, four, or five different channels of a lighting system can be duplicated as an additional channel, so that four, five, or six channels are provided, but two of the channels are duplicates of each other.

Control Systems

With respect to FIGS. 36-38, external systems can include, but are not limited to one or more computing environments, networks, local devices, remote devices, mobile devices, and wearable technology. In addition, each of those systems may provide the external input utilizable with control systems and embodiments discussed herein. For example, external inputs may include, but are not limited to audible, tactile, sensory, and user information through one or more sensors and other means, depending on the external system and its capabilities. As used herein, external systems and external information may also comprise the same types systems and information discussed below and in various embodiments herein.

In some embodiments, inputs may also include inputs from sensors associated with wearable devices 3330, such as enabling adjustment of lighting control parameters (autonomously or with remote or local control features) based on physiological factors, such as ones indicating health conditions, emotional states, moods, or the like. Inputs from wearable devices may be used in the operational feedback system, such as to measure reactions to lighting conditions (such as to enable automated adjustment of a lighting installation), as well as to measure impacts on mood, health conditions, energy, wellness factors, and the like.

In some embodiments, the platform may be configured to change settings or parameters for a lighting installation (including but not limited to panel systems of the present disclosure, such as by using a custom tuning system) based on a variety of real time data, with a view to having the lighting installation, including panel systems included therein, best suit its environment in a dynamic way. In embodiments, data may be obtained that serves as an indicator of the emotional state or the stress level of an environment, and the lighting installation may respond accordingly to that state or stress level. In embodiments, data about the environment may be collected by a wearable device 3333, such as a smartwatch, armband, or the like; for example, data may be collected on acceleration, location, ambient light characteristics, and heart rate, among other possibilities. In embodiments, the data may be provided to the platform for analysis, including using machine learning, such as to observe physiological indicators of stress, mood, or the like under given lighting conditions. The analysis may enable model-based controls (such as where a given mood or state of the users in a room are linked to a set of control parameters appropriate for that state). In embodiments, machine learning may be used; for example, over time, by variation of parameters for lighting objects and fixtures (such as color, color temperature, illumination patterns, lighting distributions, and many others), a machine learning system may, using feedback on outcomes based at least in part on physiological data and other data collected by a wearable device, select and/or promotion lighting installation parameters that improve various measures of stress, mood, satisfaction, or the like. This may occur in real time under control of a machine learning system based on the current conditions of users or the environment. In embodiments, data collected at least in part by a physiological monitor or wearable device may be used as an input to processing logic on a lighting object that changes lighting levels or other parameters to accommodate the 'emotional state' of the users in an environment where the lighting object is located. In embodiments, there is memory that retains and manages function with no appreciable drain on the battery.

In some embodiments, inputs may include systems that take data harvested from sensors 3335 in the lighting installation environment as well as sensors that reflect information about users, such as one or more of physiological sensors (including wearable devices, such as armbands, wrist bands, chest bands, glasses, clothing, and the like), sensors on various devices used by a user, ambient sensors, and the like. These may include sensing one or more of temperature, pressure, ambient lighting conditions, localized lighting conditions, lighting spectrum characteristics, humidity, UV light, sound, particles, pollutants, gases (e.g., oxygen, carbon dioxide, carbon monoxide and radon), radiation, location of objects or items, motion (e.g., speed, direction and/or acceleration). Where one or more wearable or physiological sensors are used, they may sense one or more of a person's temperature, blood pressure, heart rate, oxygen saturation, activity type, activity level, galvanic skin response, respiratory rate, cholesterol level (including HDL, LDL and triglyceride), hormone or adrenal levels (e.g., Cortisol, thyroid, adrenaline, melatonin, and others), histamine levels, immune system characteristics, blood alcohol levels, drug content, macro and micro nutrients, mood, emotional state, alertness, sleepiness, and the like.

In some embodiments, the platform may connect to or integrate with data sources of information about users, such as including social networks (Facebook™, LinkedIn™, Twitter™, and the like, sources of medical records (23&Me™ and the like), productivity, collaboration and/or calendaring software (Google™, Outlook™, scheduling apps and the like), information about web browsing and/or shopping activity, activity on media streaming services (Netflix™, Spotify™, YouTube™, Pandora™ and the like), health record information and other sources of insight about the preferences or characteristics of users of the space of a lighting installation, including psychographic, demographic and other characteristics.

In some embodiments, the platform may use information from sources that indicate patterns, such as patterns involving periods of time (daily patterns, weekly patterns, seasonal patterns, and the like), patterns involving cultural factors or norms (such as indicating usage patterns or preferences in different regions), patterns relating to personality and preferences, patterns relating to social groups (such as family and work group patterns), and the like. In embodiments, the platform may make use of the data harvested from various sources noted above to make recommendations and/or to optimize (such as automatically, under computer control) the design, ordering, fulfillment, deployment and/or operation of a lighting installation, such as based on understanding or prediction of user behavior. This may include recommendation or optimization relating to achieving optimal sleep time and duration, setting optimal mealtimes, satisfying natural light exposure requirements during the day, and maintaining tolerable artificial light exposure levels (such as during night time). In some embodiments, the platform may anticipate user needs and optimize the lighting installation to enhance productivity, alertness, emotional well-being, satisfaction, safety and/or sleep. In further embodiments, the platform may control one or more panel systems of the present disclosure in accordance with the user needs of the environment based on this information.

In some embodiments, the platform may store a space utilization data structure that indicates, over time, how people use the space of the lighting installation, such as indicating what hallways are more trafficked, and the like. This may inform understanding of a space, such as indicating what is an entry, what is a passage, what is a workspace, and the like, which may be used to suggest changes or updates to a lighting design. In embodiments, sensors may be used to collect and read where people have been in the space, such as using one or more video cameras, IR sensors, microwave sensors. LIDAR, ultrasound or the like. In embodiments, the platform may collect and read what adjustments people have made, such as task lamp activation and other activities that indicate how a lighting fixture is used by an individual in a space. By way of these examples, aggregate usage information may be used to optimize a lighting design and adjust other lighting designs. Based on these factors, a space may be dynamically adjusted, and the lighting model for an installation may be updated to reflect the actual installation.

In some embodiments, control capabilities of the panel systems may include dynamic configuration of control parameters, such as providing a dimming curve for a light source, including but not limited to a panel system of the present disclosure, that is customized to the preferences of a designer or other user. This may include a selection from one or more modes, such as ones described elsewhere herein that have desired effects on mood or aesthetic factors, that have desired health effects, that meet the functional requirements, or the like.

Bioactive thresholds may, in some instances, benefit from prolonged exposure to at least one of one of CSE and LRNE. In some instances a melanopic flux of at least 10:1 may be suitable, in other instances the melanopic flux may be 20:1, 50:1, 100:1, or a greater ratio. It will be appreciated in light of the disclosure that traditional systems simply adjust from a warm CCT to a cool CCT, which may only provide a 2:1 or 3:1 ratio of melanopic flux, which are below said threshold. In some implementations, the platform may include spectral tuning targets for panel systems of the present disclosure that may optimize this ratio based on local installation environments. These targets, in a first operational mode along with adjustments intensity of light (e.g., 4:1) may provide a higher ratio, such as a 10:1 ratio or greater, and thus provide greater melanopic flux ratios.

In a second operational mode and either in combination with the above mode or not, the platform may support an ability to shift the bias of light in a room. In embodiments, controlled variation of one or more panel systems of the present disclosure in a lighting environment can contribute to generating a lighting bias typical of being outside.

In some implementations, various other programmable modes may be provided, such as bioactive panel system settings where using different combinations of color light sources to achieve a given mixed color output may be optimized for efficacy, efficiency, color quality, health impact (e.g., circadian action and/or LRNE action), or to satisfy other requirements. In embodiments, the programmable modes may also include programmable dimming curves, color tuning curves, and the like (such as allowing various control interfaces, such as extra-low voltage (ELV) controllers or voltage-based dimmers to affect fixture colors, such as where a custom tuning curve provides a start point, an end point and a dimming and/or color tuning path in response to a level of dimming). In embodiments, programmable modes may use conventional tuning mechanisms, such as simple interpolation systems (which typically use two or three white color LEDs) are dimmable on a zero to ten-volt analog system, and have a second voltage-based input for adjusting the CCT of a fixture between warm and cool CCTs. The bioactive panel systems as described herein can provide for tunable ranges of color points at various x, y coordinates on the 1931 CIE chromaticity diagram. Because of the wide range of potential white or non-white colors produced by the panel systems, they may be controlled by the platform that may specify a particular x, y coordinate on the CIE diagram. Lighting control protocols like DMX™ and Dali 2.0™ may achieve this result.

In some implementations the control system described herein controls output of at least one CSE and LRNE. In some embodiments a programmable color curve for an LED driver may be input, such as through an interface of the platform, or through a desktop software interface, a mobile phone 3330, a tablet app, or the like, that enables a user to define a start and stop point to a color tuning curve and to specify how it will be controlled by a secondary input, such as a voltage-based input (e.g., a 0 to 10-volt input) to the fixture. These may include pre-defined curves, as well as the ability to set start, end, and waypoints to define custom curves. For example, an exemplary color curve can have a starting point around 8000K biased above the black body curve, with the color curve crossing the black body around 2700K, and finishing around 1800K below the black body curve. Similarly, another exemplary curve could be programmed such that the start was 4000K well above the black body, with the end being 4000K well below the black body. By way of these examples, any adjustment would be in hue only, not CCT. Further examples may include a curve that never produces a white color, such as starting in the purple and finishing in orange. In any of these cases, these curves may be programmed into panel systems via the interface of the platform, the desktop, mobile phone or tablet. In embodiments, the curves may be designed, saved, and then activated, such as using the secondary (supplemental) 0 to 10-volt input.

In some implementations, a three-channel warm dim operational mode may be used, such as that described more fully in U.S. Provisional Patent Application No. 62/712,182 filed Jul. 30, 2018, which is incorporated herein in its entirety for all purposes, for target applications where the "fully on" CCT falls between 3000K and 2500K. By way of these examples, as the fixture dims (via ELV control or in response to the 0 to 10-volt input) the CCT may be gradually decreased to between 2500K and 1800K. In certain embodiments, the hue adjustment may all occur below the black body curve. Alternative embodiments may use a cyan channel as described elsewhere herein, either long-blue-pumped cyan or short-blue-pumped cyan, and a red channel which may be LRNE with cyan pumped near infrared as described elsewhere herein, additionally LRNE especially in the infrared region may be produced with phosphors configured for generation of LRNE emission from a below 280 nm LED include but are not limited to: composition formula M700_rb4_lime and s_M750_rb4_M630_yag] $LiAlO_2$: $Fe^{3+}$(peak at 770 nms), CdS:$Ag+$,$Cl-$ (peak at 800 nms), ZnSbGaTe:$Cr^{3+}$,$Nd^{3+}$(peak at 845 nms), $La_3In_2Ga_3O_{12}$: $Cr^{3+}$, $Dy^{3+}$(peak at 905 nms), $BaGd_2ZnO_5$:$Yb^{3+}$(peak at 979 nms) and $Ba(GdY)_2ZnO_5$:$Yb^{3+}$(peak at 979 ns), plus a 4000K white channel as described elsewhere herein to achieve a warm dimming operational mode that allows for adjustment both above and below the black body curve. In some embodiments of the three-channel warm dim mode, the white channel can have a color point within a 7-step MacAdam ellipse around any point on the black body locus having a correlated color temperature between about 3500K and about 6500K.

In some implementations, the panel systems of the present disclosure can include a 4-channel color system as described elsewhere herein and in U.S. Provisional Patent Application No. 62/757,672 filed Nov. 8, 2018, and U.S. Provisional Application No. 62/712,191 filed Jul. 30, 2018, the contents of which are incorporated by reference herein in their entirety as if fully set forth herein, includes 3000K to 1800K CCT white color points within its range, a programmable mode may be included within the driver that adjusts color with the dimming percentage as well. In some aspects, this may be similar to a conventional control mode, except that the color control would not be on the secondary 0 to 10-volt channel, but may be activated through the primary 0 to 10-volt input channel or ELV controller. In embodiments, the "starting" color point may be the one when the fixture was "fully on." In embodiments, the "ending" color point may be the one where the fixture is maximally dimmed. It is thus possible to make full range color change, such as purple to orange, which is slaved to the 0 to 10-volt or ELV dimming signal.

In some implementations, an optimized mode may be provided. With a 4-channel color system, there are many ways to create a single x-y point on the CIE diagram. In embodiments, the maximally efficient mode may typically be one that uses the colors that have x, y coordinates closest to the target x, y coordinate. But for best color quality, utilizing a fourth channel (and thereby requiring more light from the color in the opposite "corner") may help provide a desired spectral power distribution. For the maximum melatonin suppression (for systems hoping to mimic circadian lighting), a higher cyan channel content may be required for CCTs of 3500K and above and minimizing cyan and blue content below 3500K. It will be appreciated in light of the disclosure that conventional systems either require expert users to understand the color balances necessary to achieve these effects (who then implement the color balances channel-by-channel) or are designed for maximum efficiency with color quality as a byproduct.

In some implementations, a digital power system is provided herein (including firmware-driven power conversion and LED current control) that controls a multichannel color system, such as a 4-channel color system, and allows for the inclusion of "modes" which may calculate the correct color balance between the various channels to provide optimized outputs. In embodiments, optimization may occur around one or more of efficacy, color quality, circadian effects, LRNE effects, and other factors. Other modes are possible, such as optimizing for contrast, particular display requirements. It will be appreciated in light of the disclosure that this is not an exhaustive list but is representative of potential modes that could be engaged through an interface of the platform (or of a mobile, tablet or desktop application) where a color tuning curve may be specified, such that the curve is used to specify an interface between a controller and the Digital PSU in a panel system. In embodiments, these modes may account for actual measured colors for each panel system and calculate the correct balance of for the chosen modes, such as based on algorithms loaded into the Digital PSU microprocessor.

In some implementations, machine learning may be used, such as based on various feedback measures, such as relating to mood (stated by the user or measured by one or more sensors), noise levels (such as indicating successful utilization of a space based on a desired level of noise), returns on investment (such as where panel systems are intended to promote retail merchandise), reported pain levels, measured health levels, performance levels of users (including fitness, wellness, and educational performance, among others), sleep levels, vitamin D levels, melatonin levels, and many others. In embodiments, the lighting installations including the panel systems may be operated or controlled based on external information, such as based on seasonal lighting conditions, weather, climate, collective mood indicators (such as based on stock market data, news feeds, or sentiment indices), analyses of social network data, and the like. This may include controlling a system to reflect, or influence, the mood of occupants.

FIGS. 48A-48D illustrate aspects of wearable devices whereby the user 2500 is the support for the device. Wearable devices 2602, 2604, 2605 and 2800 are configured to be support on a user's head 2502. The head supported device provides at least one illumination source 2610 and may have additional illumination sources 2610' and is configured to place the at least one illumination source within an area whereby the illumination 2612 from the illumination source reaches the users eye(s) 2503. Each illumination source may be referred to as a channel. An illumination source may be a single LED or micro-LED or it may be an array of LEDS or micro-LEDS. Channels as described herein have light characteristics associated therewith. In the below described wearable devices anon-limiting example of a two or three channel system is described. A first channel 2610 may be a LRNE channel with both visible and non-visible light emissions and the second channel 2610' may be a CSE channel. In other instances the third channel may be a non-visible LRNE light and the first channel may be a visible LRNE light.

The illumination source(s) is configured to be switched with a controller 2620 aspects of which are shown in FIG. 49. The controller 2620 being in signal communication with the illumination sources, a power supply 2630 and at least one input 2635/2637. Inputs 2635 and 2637 represent sensor data provided to the controller 2620.

Inputs may be from wearable sensors 2525 (such as an APPLE™ or FITBIT™ watch or a dedicated sensor as described previously). A smart phone 2530 associated with a user may be in signal communication with the controller and provide sensor data, the smart phone or other computing device may also provide processing for the data instead of, in addition to or in lieu of the controller. The controller may include an 802.11 chip, near field communication and/or bluetooth to communicate with sensors and/or computing device. A room, vehicle or other area sensor (as described herein) may be in signal communication with the controller and provide sensor data. The sensor data along with other data including but not limited to time or day and location, user defined settings and the like are also used by the control system as described below.

Figure 50B:
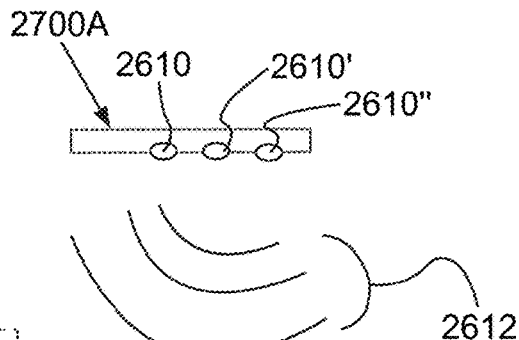
Figure 50C:
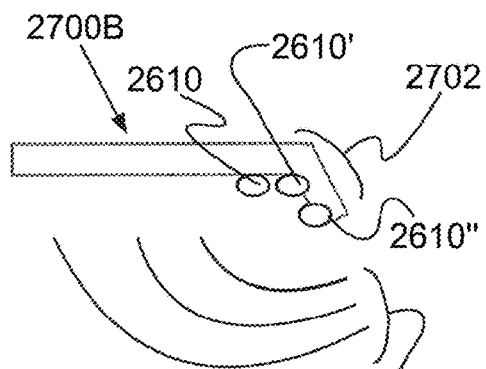

FIG. 50A shows aspects of a system and wearable device 2604 with a support 2700 which may be configured in a plethora of ways to direct illumination towards the user's eyes 2503. The support may be party of a hat or cap 2605. FIG. 50B illustrates a support region 2700A which is extended forward (in front of the user's eyes 2503). The at least one illumination source (2610, 2610' and 2610") may be a single LED, arrays of LEDS, OLEDS, micro-LEDS and the like. In some instances multiple illumination sources are provided and are positioned above the targeted eyes 2503. Such LEDS have sufficient illumination cones or angles of illumination whereby a portion of the illumination 2612 reaches a target eye 2503 or eyes.

In some instances the wearable device 2604 has a support region 2700B (FIG. 50C) which is extended forward (in front of the user's eyes 2503) and has a bent portion 2702 to position one or more of the illumination sources downward and in front of the user's eyes. The at least one illumination source (2610, 2610' and 2610") may be a single LED, arrays of LEDS, OLEDS, micro-LEDS and the like. In some instance multiple illumination sources are provided and are positioned above the targeted eyes 2503. Such LEDS have sufficient illumination cones or angles of illumination whereby a portion of the illumination 2612 reaches a target eye 2503 or eyes.

Figure 50D:
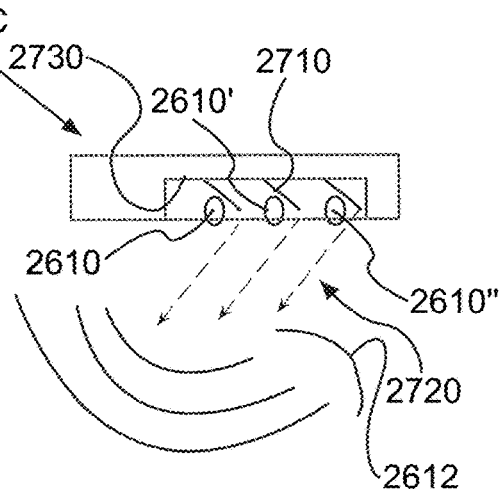
Figure 50E:
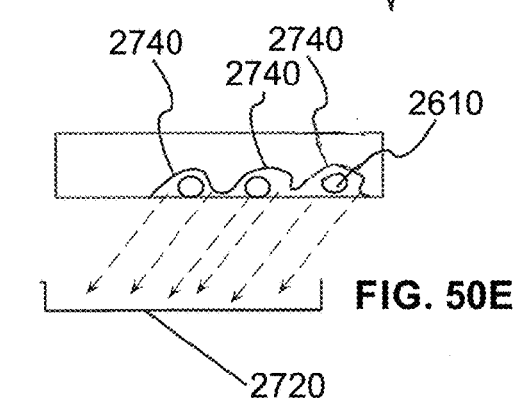
Figure 50F:
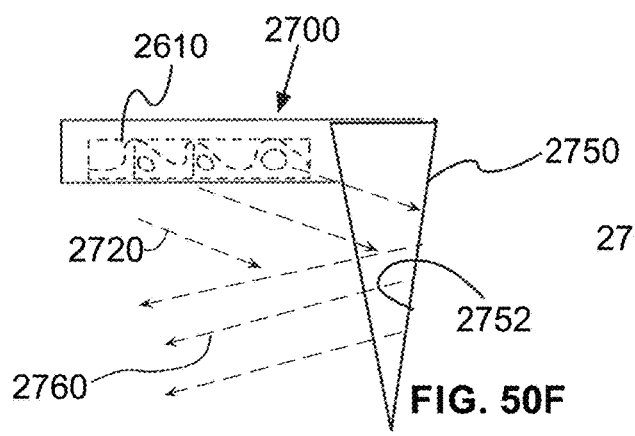

In some instances the wearable device 2604 has a illumination support region 2700C (FIG. 50D) which is extended forward (in front of the user's eyes 2503 and provides one or more reflectors 2710 positioned behind the illumination sources 2610, 2610' and 2610' configured to steer reflected illumination 2612 along the lines of arrows 2720 to direct illumination to the user's eyes. Optionally, the reflectors and illumination sources way be placed within a depression, or open cavity 2730. The depiction of the open cavity as a single cavity is not a limitation and a series of small reflective cavities 2740 shown in FIG. 50E may be used. Each reflective cavity 2740 may be shaped to optimize the direction or steering of the illumination 2612 towards the user's eyes. FIG. 50F illustrates a support region 2700 which supports illumination sources 2610 and may also support a reflector or group of reflectors as shown in FIGS. 50D and 50E. In FIG. 50F a visor or shield 2750 with an at least partially reflective inner surface 2752 is configured to attach to the support 2700 and reflect at least a portion of the reflected illumination 2720 along the lines of arrows 2760 towards the user's face and eyes.

Figure 51A:
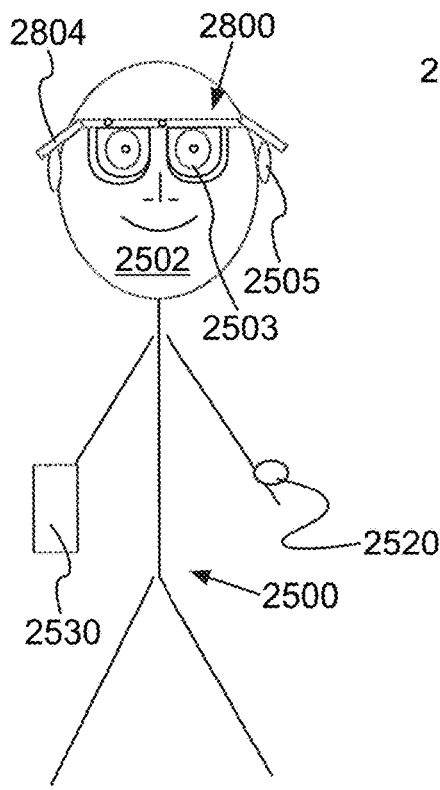

FIG. 51A illustrates aspects of wearable devices whereby the user 2500 is the support for the device. Wearable device 2800 has a frame 2802 with arms 2804 and illumination fixtures 2810. Support arms 2804 are configured to engage a user's ears 2505.

Figure 51B:
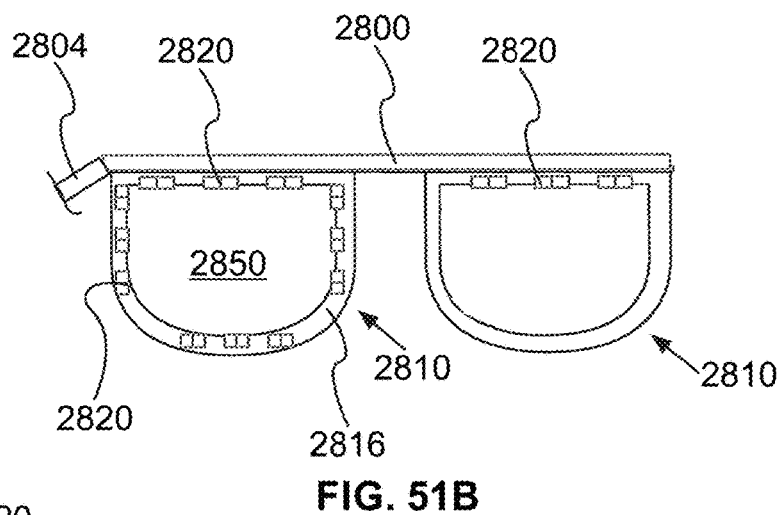
Figure 51C:
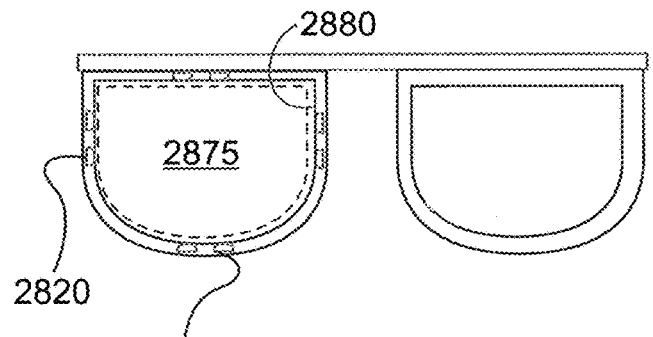
Figure 51D:
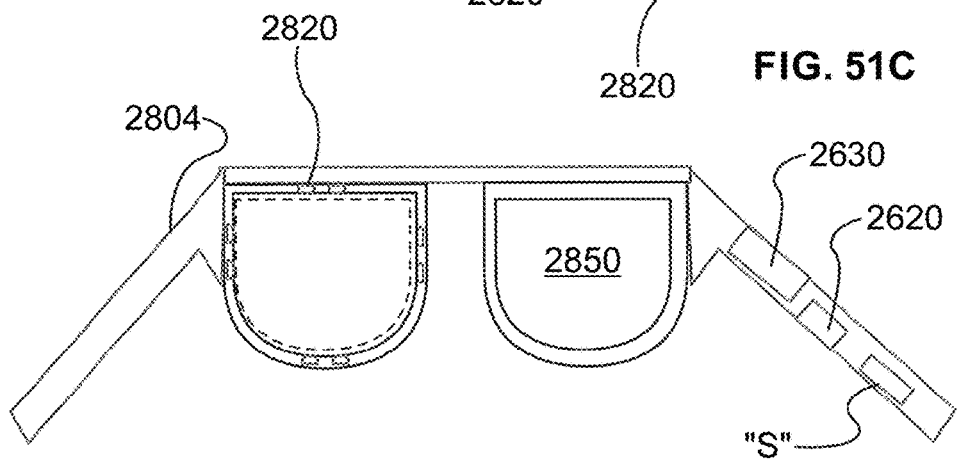

FIGS. 51B-51D show illumination sources 2820 associated with the device. In some instances the illumination sources provide illumination directed at one or both of the user's eyes and perpendicular from the back 2816 of the fixture. Optionally a clear or tinted lens 2850 may be added. In other instances the lens 2875 has an edge 2880 configured to receive illumination from illumination sources 2820 which are positioned to direct light at the edge 2880 of the lens. A reflective outer coating may be added to the lens which allows for vision through the lens but operates to allow more illumination from the illumination sources 2610 to be reflected back and to pass through the back surface of the lens 2875 towards the user's eyes. As shown in FIG. 29D, a controller 2620 and the power supply 2630 for the controller and illumination sources 2620 are be placed on the device. Optionally one or more sensors "S" may be affixed to the device. In some instance the illumination sources are configured to work cooperatively with augmented reality (AR) glasses, googles or visors as well as virtual reality (VR) glasses, googles or visors whereby the illumination 2612 is placed in the user's field of vision to be switched via the control system The above exemplars of wearable devices and systems are configured to be controlled to selectively apply aliquots of bioactive illumination.

FIG. 52 schematically shows aspects of implementations of lighting systems of the present disclosure. A first color point 605 and a second color point 601 are shown, along with respective constant CCT lines labeled with the approximate respective CCT values 4000K and 2400K of the first and second color points 605/601 for reference. As depicted, the first color point 605 has a CCT value of approximately 4000K, but in other implementations may have other CCT values as described elsewhere herein. As depicted, the second color point 601 has a CCT value of approximately 2400K, but in other implementations may have other CCT values as described elsewhere herein. The first and second color points 605/601 are depicted relative to the black body locus 150 in a portion of the 1931 CIE Chromaticity Diagram. A tie line between the first color point 605 and second color point 601 can form a predefined path of a plurality of third color points generated by the lighting system In some implementations, a first threshold point 610 can lie on the tie line and have a first threshold CCT value. In further implementations, a second threshold point 614 can lie on the tie line and have a second threshold CCT value. The third color point can have particular characteristics for points in a region 612 on the tie line between the first color point 605 and the first threshold point 610. The third color point can have particular characteristics for points in a region 616 on the tie line between the second color point 601 and the second threshold point 614.

FIG. 53 schematically shows aspects of implementations of lighting systems of the present disclosure. A first color point 805 and a second color point 801 are shown, along with respective constant CCT lines labeled with the approximate respective CCT values 4000K and 2400K of the first and second color points 805/801 for reference. As depicted, the first color point 805 has a CCT value of approximately 4000K, but in other implementations may have other CCT values as described elsewhere herein. As depicted, the second color point 801 has a CCT value of approximately 2400K but in other implementations may have other CCT values as described elsewhere herein. The first and second color points 805/801 are depicted relative to the black body locus 150 in a portion of the 1931 CIE Chromaticity Diagram. A tie line 810 between the first color point 805 and second color point 801 can form a predefined path of a plurality of third color points generated by the lighting system. In some implementations, a first threshold point 830 can lie on the tie line and have a first threshold CCT value. In further implementations, a second threshold point 820 can lie on the tie line and have a second threshold CCT value. The third color point can have particular characteristics for points in a region 825 on the tie line between the first threshold point 830 and the second threshold point 820. The third color point can have particular characteristics for points in a region on the tie line between the first color point 805 and the first threshold point 830. The third color point can have particular characteristics for points in a region on the tie line between the second color point 801 and the second threshold point 820.

FIG. 36 depicts an example computing environment 3000 suitable for implementing aspects of the embodiments of the present invention, including the control system, which can integrate one or more devices, computing, and lighting systems. As utilized herein, the phrase "computing system" generally refers to a dedicated computing device with processing power and storage memory, which supports operating software that underlies the execution of software, applications, and computer programs thereon. As used herein, an application is a small, in storage size, specialized program that is downloaded to the computing system or device. In some cases, the application is downloaded from an "App Store" such as APPLE's APP STORE or GOOGLE's ANDROID MARKET. After download, the application is generally installed on the computer system or computing device. As shown by FIG. 36, computing environment 3000 includes bus 3010 that directly or indirectly couples the following components: memory 3020, one or more processors 3030, I/O interface 3040, and network interface 3050. Bus 3010 is configured to communicate, transmit, and transfer data, controls, and commands between the various components of computing environment 3000.

Computing environment 3000 typically includes a variety of computer-readable media. Computer-readable media can be any available media that is accessible by computing environment 3000 and includes both volatile and nonvolatile media, removable and non-removable media. Computer-readable media may comprise both computer storage media and communication media. Computer storage media does not comprise, and in fact explicitly excludes, signals per se.

Computer storage media includes volatile and nonvolatile, removable and non-removable, tangible and non-transient media, implemented in any method or technology for storage of information such as computer-readable instructions, data structures, program modules or other data. Computer storage media includes RAM; ROM; EE-PROM; flash memory or other memory technology; CD-ROMs; DVDs or other optical disk storage; magnetic cassettes, magnetic tape, magnetic disk storage or other magnetic storage devices; or other mediums or computer storage devices which can be used to store the desired information and which can be accessed by computing environment 3000.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, communication media includes wired media, such as a wired network or direct-wired connection, and wireless media, such as acoustic, RF, infrared and other wireless media. Combinations of any of the above should also be included within the scope of computer-readable media.

Memory 3020 includes computer-storage media in the form of volatile and/or nonvolatile memory. The memory may be removable, non-removable, or a combination thereof. Memory 3020 may be implemented using hardware devices such as solid-state memory, hard drives, optical-disc drives, and the like. Computing environment 3000 also includes one or more processors 3030 that read data from various entities such as memory 3020, I/O interface 3040, and network interface 3050.

I/O interface 3040 enables computing environment 3000 to communicate with different input devices and output devices. Examples of input devices include a keyboard, a pointing device, a touchpad, a touchscreen, a scanner, a microphone, a joystick, and the like. Examples of output devices include a display device, an audio device (e.g., speakers), a printer, and the like. These and other I/O devices are often connected to processor 3010 through a serial port interface that is coupled to the system bus, but may be connected by other interfaces, such as a parallel port, game port, or universal serial bus (USB). A display device can also be connected to the system bus via an interface, such as a video adapter which can be part of, or connected to, a graphics processor unit. I/O interface 3040 is configured to coordinate I/O traffic between memory 3020, the one or more processors 3030, network interface 3050, and any combination of input devices and/or output devices.

Network interface 3050 enables computing environment 3000 to exchange data with other computing devices via any suitable network. In a networked environment, program modules depicted relative to computing environment 3000, or portions thereof, may be stored in a remote memory storage device accessible via network interface 3050. It will be appreciated that the network connections shown are exemplary and other means of establishing a communications link between the computers may be used.

In at least some embodiments, a server that implements a portion or all of one or more of the technologies described herein may include a general-purpose computer system that includes or is configured to access one or more computer-accessible media. FIG. 37 depicts a general-purpose computer system that includes or is configured to access one or more computer-accessible media. In the illustrated embodiment, computing device 3100 includes one or more processors 3110*a*, 3110*b*, and/or 3110*n* (which may be referred herein singularly as a processor 1010 or in the plural as the processors 3110) coupled to a system memory 3120 via an input/output ("I/O") interface 3130. Computing device 3100 further includes a network interface 3140 coupled to I/O interface 3130.

In various embodiments, computing device 3100 may be a uniprocessor system including one processor 3110 or a multiprocessor system including several processors 3110 (e.g., two, four, eight, or another suitable number). Processors 3110 may be any suitable processors capable of executing instructions. For example, in various embodiments, processors 3110 may be general-purpose or embedded processors implementing any of a variety of instruction set architectures ("ISAs"), such as the x86, PowerPC, SPARC or MIPS ISAs, or any other suitable ISA. In multiprocessor systems, each of processors 3110 may commonly, but not necessarily, implement the same ISA.

In some embodiments, a graphics processing unit ("GPU") 3112 may participate in providing graphics rendering and/or physics processing capabilities. A GPU may, for example, comprise a highly parallelized processor architecture specialized for graphical computations. In some embodiments, processors 3110 and GPU 3112 may be implemented as one or more of the same type of device.

System memory 3120 may be configured to store instructions and data accessible by processor(s) 3110. In various embodiments, system memory 3120 may be implemented using any suitable memory technology, such as static random access memory ("SRAM"), synchronous dynamic RAM ("SDRAM"), nonvolatile/Flash®-type memory, or any other type of memory. In the illustrated embodiment, program instructions and data implementing one or more desired functions, such as those methods, techniques, and data described above, are shown stored within system memory 3120 as code 3125 and data 3126.

In one embodiment, I/O interface 3130 may be configured to coordinate I/O traffic between processor 3110, system memory 3120, and any peripherals in the device, including network interface 3140 or other peripheral interfaces. In some embodiments, I/O interface 3130 may perform any necessary protocol, timing or other data transformations to convert data signals from one component (e.g., system memory 3120) into a format suitable for use by another component (e.g., processor 3110). In some embodiments, I/O interface 3130 may include support for devices attached through various types of peripheral buses, such as a variant of the Peripheral Component Interconnect ("PCI") bus standard or the Universal Serial Bus ("USB") standard, for example. In some embodiments, the function of/O interface 3130 may be split into two or more separate components, such as a north bridge and a south bridge, for example. Also, in some embodiments some or all of the functionality of I/O interface 3130, such as an interface to system memory 3120, may be incorporated directly into processor 3110.

Network interface 3140 may be configured to allow data to be exchanged between computing device 3100 and other device or devices 3160 attached to a network or networks 3150, such as other computer systems or devices, for example. In various embodiments, network interface 3140 may support communication via any suitable wired or wireless general data networks, such as types of Ethernet networks, for example. Additionally, network interface 3140 may support communication via telecommunications/telephony networks, such as analog voice networks or digital fiber communications networks, via storage area networks, such as Fibre Channel SANs (storage area networks), or via any other suitable type of network and/or protocol.

In some embodiments, system memory 3120 may be one embodiment of a computer-accessible medium configured to store program instructions and data as described above for implementing embodiments of the corresponding methods and apparatus. However, in other embodiments, program instructions and/or data may be received, sent, or stored upon different types of computer-accessible media. Generally speaking, a computer-accessible medium may include non-transitory storage media or memory media, such as magnetic or optical media, e.g., disk or DVD/CD coupled to computing device 3100 via I/O interface 3130. A non-transitory computer-accessible storage medium may also include any volatile or non-volatile media, such as RAM (e.g., SDRAM, DDR SDRAM, RDRAM, SRAM, etc.), ROM, etc., that may be included in some embodiments of computing device 3100 as system memory 3120 or another type of memory. Further, a computer-accessible medium may include transmission media or signals, such as electrical, electromagnetic or digital signals, conveyed via a communication medium, such as a network and/or a wireless link, such as those that may be implemented via network interface 3140. Portions or all of multiple computing devices, such as those illustrated in FIG. 31, may be used to implement the described functionality in various embodiments; for example, software components running on a variety of different devices and servers may collaborate to provide the functionality. In some embodiments, portions of the described functionality may be implemented using storage devices, network devices or special-purpose computer systems, in addition to or instead of being implemented using general-purpose computer systems. The term "computing device," as used herein, refers to at least all these types of devices and is not limited to these types of devices.

A compute node, which may be referred to also as a computing node, may be implemented on a wide variety of computing environments, such as tablet computers, personal computers, smartphones, game consoles, commodity-hardware computers, virtual machines, web services, computing clusters, and computing appliances. Any of these computing devices or environments may, for convenience, be described as compute nodes or as computing nodes.

A network set up by an entity, such as a company or a public sector organization, to provide one or more web services (such as various types of cloud-based computing or storage) accessible via the Internet and/or other networks to a distributed set of clients may be termed a provider network. Such a provider network may include numerous data centers hosting various resource pools, such as collections of physical and/or virtualized computer servers, storage devices, networking equipment, and the like, needed to implement and distribute the infrastructure and web services offered by the provider network. The resources may in some embodiments be offered to clients in various units related to the web service, such as an amount of storage capacity for storage, processing capability for processing, as instances, as sets of related services, and the like. A virtual computing instance may, for example, comprise one or more servers with a specified computational capacity (which may be specified by indicating the type and number of CPUs, the main memory size, and so on) and a specified software stack (e.g., a particular version of an operating system, which may in turn run on top of a hypervisor).

A number of different types of computing devices may be used singly or in combination to implement the resources of the provider network in different embodiments, including general-purpose or special-purpose computer servers, storage devices, network devices, and the like. In some embodiments a client or user may be provided direct access to a resource instance, e.g., by giving a user an administrator login and password. In other embodiments the provider network operator may allow clients to specify execution requirements for specified client applications and schedule execution of the applications on behalf of the client on execution platforms (such as application server instances, Java™ virtual machines ("JVMs"), general-purpose or special-purpose operating systems, platforms that support various interpreted or compiled programming languages, such as Ruby, Perl, Python, C, C++, and the like, or high-performance computing platforms) suitable for the applications, without, for example, requiring the client to access an instance or an execution platform directly. A given execution platform may utilize one or more resource instances in some implementations; in other implementations multiple execution platforms may be mapped to a single resource instance.

In many environments, operators of provider networks that implement different types of virtualized computing, storage and/or other network-accessible functionality may allow customers to reserve or purchase access to resources in various resource acquisition modes. The computing resource provider may provide facilities for customers to select and launch the desired computing resources, deploy application components to the computing resources, and maintain an application executing in the environment. In addition, the computing resource provider may provide further facilities for the customer to quickly and easily scale up or scale down the numbers and types of resources allocated to the application, either manually or through automatic scaling, as demand for or capacity requirements of the application change. The computing resources provided by the computing resource provider may be made available in discrete units, which may be referred to as instances. An instance may represent a physical server hardware platform, a virtual machine instance executing on a server, or some combination of the two. Various types and configurations of instances may be made available, including different sizes of resources executing different operating systems ("OS") and/or hypervisors, and with various installed software applications, runtimes, and the like. Instances may further be available in specific availability zones, representing a logical region, a fault tolerant region, a data center, or other geographic location of the underlying computing hardware, for example. Instances may be copied within an availability zone or across availability zones to improve the redundancy of the instance, and instances may be migrated within a particular availability zone or across availability zones. As one example, the latency for client communications with a particular server in an availability zone may be less than the latency for client communications with a different server. As such, an instance may be migrated from the higher latency server to the lower latency server to improve the overall client experience.

In some embodiments the provider network may be organized into a plurality of geographical regions, and each region may include one or more availability zones. An availability zone (which may also be referred to as an availability container) in turn may comprise one or more distinct locations or data centers, configured in such a way that the resources in a given availability zone may be isolated or insulated from failures in other availability zones. That is, a failure in one availability zone may not be expected to result in a failure in any other availability zone. Thus, the availability profile of a resource instance is intended to be independent of the availability profile of a resource instance in a different availability zone. Clients may be able to protect their applications from failures at a single location by launching multiple application instances in respective availability zones. At the same time, in some implementations inexpensive and low latency network connectivity may be provided between resource instances that reside within the same geographical region (and network transmissions between resources of the same availability zone may be even faster).

Each of the processes, methods, and algorithms described in the preceding sections may be embodied in, and fully or partially automated by, code modules executed by one or more computers or computer processors. The code modules may be stored on any type of non-transitory computer-readable medium or computer storage device, such as hard drives, solid state memory, optical disc, and/or the like. The processes and algorithms may be implemented partially or wholly in application-specific circuitry. The results of the disclosed processes and process steps may be stored, persistently or otherwise, in any type of non-transitory computer storage, such as, e.g., volatile or non-volatile storage.

The various features and processes described above may be used independently of one another, or may be combined in various ways. All possible combinations and sub-combinations are intended to fall within the scope of this disclosure. In addition, certain methods or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

It will also be appreciated that various items are illustrated as being stored in memory or on storage while being used, and that these items or portions thereof may be transferred between memory and other storage devices for purposes of memory management and data integrity. Alternatively, in other embodiments some or all of the software modules and/or systems may execute in memory on another device and communicate with the illustrated computing systems via inter-computer communication. Furthermore, in some embodiments, some or all of the systems and/or modules may be implemented or provided in other ways, such as at least partially in firmware and/or hardware, including, but not limited to, one or more application-specific integrated circuits ("ASICs"), standard integrated circuits, controllers (e.g., by executing appropriate instructions, and including microcontrollers and/or embedded controllers), field-programmable gate arrays ("FPGAs"), complex programmable logic devices ("CPLDs"), etc. Some or all of the modules, systems, and data structures may also be stored (e.g., as software instructions or structured data) on a computer-readable medium, such as a hard disk, a memory, a network, or a portable media article to be read by an appropriate device or via an appropriate connection. The systems, modules, and data structures may also be transmitted as generated data signals (e.g., as part of a carrier wave or other analog or digital propagated signal) on a variety of computer-readable transmission media, including wireless-based and wired/cable-based media, and may take a variety of forms (e.g., as part of a single or multiplexed analog signal, or as multiple discrete digital packets or frames). Such computer program products may also take other forms in other embodiments. Accordingly, the present invention may be practiced with other computer system configurations.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

What is claimed is:

1. A display system for displaying digital content comprising:
    a display screen;
    an array of pixels, said pixels comprising one or more lighting channels configured to generate a first light output in a first operational mode at a first circadian stimulating energy (CSE), and a second light output in a second operational mode, the second light output associated with a second CSE, wherein said first CSE is greater than said second CSE; and,
    a long red near infrared energy (LRNE) channel for emitting LRNE during at least one of said first or second operation modes, wherein said LRNE has a peak wavelength of at least one of 660 nm or greater than 700 nm.

2. The display system of claim 1, wherein the LRNE is in the visible spectrum.

3. The display system of claim 1, wherein the LRNE is in the non-visible spectrum.

4. The display system of claim 1, wherein the LRNE is in both the visible and the non-visible spectrum.

5. The display system of claim 1, wherein said array of pixels comprise as micro LED pixels or OLED pixels.

6. The display system of claim 1, wherein said LRNE channel is discrete from said display screen.

7. The display system of claim 1, wherein said LRNE channel emits light adjacent said display screen.

8. The display system of claim 1, further comprising a panel adjacent said display screen, and wherein said LRNE channel emits light from said panel.

9. The display system of claim 8, said panel is along an edge of said display screen.

10. The display system of claim 1, further comprising a backlight for said display screen, said backlight comprising said one or more lighting channels.

11. The display system of claim 10, wherein the LED-based lighting channels provide one or more white light sources for said backlight.

12. The display system of claim 11, wherein the one or more white light sources are provided as white lighting channels comprising an LED and an associated luminophoric medium that produce a combined white light at a white color point within ±7 DUV of the Planckian locus on the 1931 CIE Chromaticity Diagram.

13. The display system of claim 1, further comprising a controller configured to be in communication with said LRNE channel to selectively apply power thereto.

14. The display system of claim 13, further comprising at least one sensor for supplying data to the controller and wherein the controller is configured to process the data and adjust the switching of the LRNE channel based, at least in part, on the data supplied by the sensor.

15. The display system of claim 13, wherein the controller is in communication with one of a smartphone or a computer.

* * * * *